US007767206B2

(12) United States Patent
Tocker et al.

(10) Patent No.: US 7,767,206 B2
(45) Date of Patent: *Aug. 3, 2010

(54) NEUTRALIZING DETERMINANTS OF IL-17 RECEPTOR A AND ANTIBODIES THAT BIND THERETO

(75) Inventors: Joel Tocker, Issaquah, WA (US); Christopher Mehlin, Seattle, WA (US); Ai Ching Lim, Mercer Island, WA (US)

(73) Assignee: Amgen Inc., Thousand Oaks, CA (US)

( * ) Notice: Subject to any disclaimer, the term of this patent is extended or adjusted under 35 U.S.C. 154(b) by 82 days.

This patent is subject to a terminal disclaimer.

(21) Appl. No.: 11/906,079

(22) Filed: Sep. 27, 2007

(65) Prior Publication Data

US 2008/0221307 A1      Sep. 11, 2008

Related U.S. Application Data

(60) Provisional application No. 60/969,895, filed on Sep. 4, 2007, provisional application No. 60/873,072, filed on Dec. 5, 2006, provisional application No. 60/827,882, filed on Oct. 2, 2006.

(51) Int. Cl.
C07K 16/24      (2006.01)
(52) U.S. Cl. ............. 424/133.1; 530/387.3; 530/387.9; 530/388.22
(58) Field of Classification Search ........................ None
See application file for complete search history.

(56) References Cited

U.S. PATENT DOCUMENTS

| | | | |
|---|---|---|---|
| 5,116,964 A | 5/1992 | Capon et al. | |
| 5,703,088 A | 12/1997 | Sharpe et al. | |
| 5,716,805 A | 2/1998 | Srinivasan et al. | |
| 5,869,286 A | 2/1999 | Yao et al. | |
| 6,043,344 A | 3/2000 | Jacobs et al. | |
| 6,072,033 A | 6/2000 | Yao et al. | |
| 6,072,037 A | 6/2000 | Yao et al. | |
| 6,083,906 A | 7/2000 | Troutt | |
| 6,096,305 A | 8/2000 | Yao et al. | |
| 6,100,235 A | 8/2000 | Yao et al. | |
| 6,114,598 A | 9/2000 | Kucherlapati et al. | |
| 6,162,963 A | 12/2000 | Kucherlapati et al. | |
| 6,191,104 B1 | 2/2001 | Spriggs et al. | |
| 6,197,525 B1 | 3/2001 | Yao et al. | |
| 6,406,867 B1 | 6/2002 | Yu et al. | |
| 6,680,057 B1 | 1/2004 | Yao et al. | |
| 6,793,919 B2 | 9/2004 | Mohler | |
| 6,833,268 B1 | 12/2004 | Green et al. | |
| 7,049,426 B2 | 5/2006 | Green et al. | |
| 7,064,244 B2 | 6/2006 | Jakobovits et al. | |
| 2008/0221307 A1 | 9/2008 | Tocker et al. | |
| 2009/0074758 A1* | 3/2009 | Tocker et al. | 424/133.1 |

FOREIGN PATENT DOCUMENTS

| | | |
|---|---|---|
| WO | WO 95/18826 | 7/1995 |
| WO | WO 96/29408 | 9/1996 |
| WO | WO 97/04097 | 2/1997 |
| WO | WO 98/23284 | 6/1998 |
| WO | WO 99/14240 | 3/1999 |
| WO | WO 99/60127 | 11/1999 |
| WO | WO 00/15759 | 3/2000 |
| WO | WO 00/55204 | 9/2000 |
| WO | WO 01/68705 | 9/2001 |
| WO | WO 01/68859 | 9/2001 |
| WO | WO 2004/002519 A1 | 1/2004 |
| WO | WO 2005/063290 A3 | 7/2005 |
| WO | WO 2006/054059 | 5/2006 |
| WO | WO 2006/088925 | 8/2006 |

OTHER PUBLICATIONS

Dufner (Trends Biotechnol. 24(11):523-29 (2006)).*
Brummell et al. (Biochemistry 32:1180-1187 (1993)).*
Kobayashi et al. (Protein Engineering 12:879-844 (1999)).*
Burks et al. (PNAS 94:412-417 (1997)).*
Jang et al. (Molec. Immunol. 35:1207-1217 (1998)).*
Brorson et al. (J. Immunol. 163:6694-6701 (1999)).*
Coleman (Research in Immunol. 145:33-36 (1994)).*
Smith-Gill et al. (J. Immunol. 139:4135-4144 (1987)).*
Kumar et al. (J. Biol. Chem. 275:35129-35136 (2000)).*
Song et al. (Biochem Biophys Res Comm 268:390-394 (2000)).*
Aarvak et al., "Analysis of IL-17 and other cytokines and surface markers of RA inflammatory T cell clones," *American College of Rheumatology (ACR)* meeting, Poster 1448, Nov. 1997.
Aggarwal, S. and Gurney, A., "IL-17: prototype member of an emerging cytokine family," *J Leukocyte Biol*, 71:1-8, 2002.
Albanesi et al., "IL-17 is produced by nickel-specific T lymphocytes and regulates ICAM-1 expression and chemokine production in human keratinocytes: Synergistic or antagonist effects with IFN-γ and TNF-α," *J. Immunol.*, 162:494-502, 1999.
Albrecht et al., "Primary structure of the herpesvirus saimiri genome," *J. Virol.*, 66(8):5047-5058, 1992.
Amin, A. R. et al., "The expression and regulation of nitric oxide synthase in human osteoarthritis-affected chondrocytes: Evidence for up-regulated neuronal nitric oxide synthase," *J. Exp. Med.*, 182:2097-2102, Dec. 1995.
Ankarcrona, M. et al., "Interleukin-1β-induced nitric oxide production activates apoptosis in pancreatic RINm5F cells," *Exp Cell Rsh*, 213:172-177, 1994.
Antonysamy, M. et al., "Evidence for a role of IL-17 in organ allograft rejection: IL-17 promotes the functional differentiation of dendritic cell progenitors," *J. Immunol.*, 162:577-584, 1999.
Arend, W. et al., "Inhibition of the production and effects of interleukin-1 and tumor necrosis factor α in rheumatoid arthritis," *Arthritis & Rhem.*, 38(2):151-160, 1995.
Attur, M. G. et al., "Interleukin-17 up-regulation of nitric oxide production in human osteoarthritis cartilage," *Arthritis & Rheum.*, 40(6):1050-1053, 1997.

(Continued)

*Primary Examiner*—Lynn Bristol
(74) *Attorney, Agent, or Firm*—James E. Klaniecki

(57) ABSTRACT

The present invention relates to the identification of neutralizing determinants on IL-17 Receptor A (IL-17RA or IL-17R) and the antigen binding proteins, such as antibodies, that bind thereto and inhibit IL-17 ligand family members from binding to and activating IL-17 Receptor A or a receptor complex comprising IL-17 Receptor A.

8 Claims, 18 Drawing Sheets

OTHER PUBLICATIONS

Baragi, V. M. et al., "Transplantation of transduced chondrocytes protects articular cartilage from interleukin 1-induced extracellular matrix degradation," *J. Clin. Invest.*, 96(5):2454-2460, 1995.

Bowie et al., "Deciphering the message in protein sequences: Tolerance to amino acid substitutions," *Science*, 47:1306-1310, 1990.

Caron, J. P. et al., "Chondroprotective effect of intraarticular injections of interleukin-1 receptor antagonist in experimental osteoarthritis," *Arthritis & Rheum.*, 39(9):1535-1544, 1996.

Chabaud, M. et al., "Regulation of the effects of IL 17 on IL 6 and LIF production by RA synoviocytes," *American College of Rheumatology (ACR) meeting*, Poster 1449, Nov. 1997.

Chabaud, M. et al., "Human Interluekin-17: A T Cell-Derived Proinflammatory Cytokine Produced by the Rheumatoid Synovium," *Arthritis & Rheumatism*, 42(5):963-970, 1999.

Chabaud, M. et al., "Contribution of interleukin 17 to synovium matrix destruction in rheumatoid arthritis," *Cytokine*, 12(7):1092-1099, 2000.

Chabaud, M. et al., "Enhancing effect of IL-17 on IL-1-Induced IL-6 and leukemia inhibitory factor production by rheumatoid arthritis synoviocytes and its regulation by Th2 cytokines," *J. Immunol.*, 161:409-414, 1998.

Crystal, R., "Transfer of genes to humans: Early lessons and obstacles to success," *Sci.*, 270:404-410, 1995.

Dudler et al., "In vivo effects of murine recombinant interleukin-17 on synovial joint in mice," *American College of Rheumatology (ACR) meeting*, Poster 1450, Nov. 1997.

Fanslow et al. "Regulation of alloreactivity in vivo by a soluble form of the interleukin-1 receptor," *Science*, 248:739-742, 1990.

Fanslow et al., "Regulation of alloreactivity I vivo IL-4 and the soluble IL-4 receptor," *J. Immunol.*, 47(2):535-540, 1991.

Fossiez et al., "T cell interleukin-17 induces stromal cells to produce proinflammatory and hematopoietic cytokines," *J. Exp. Med.*, 183:2593-2603, 1996.

Fouilhoux et al., "Production of IL-17 and its regulation in rheumatoid synovium," *American College of Rheumatology (ACR) meeting*, Poster 1447, 1997.

Frömmel, C. and Holzhütter, H. G., An estimate on the effect of point mutation and natural selection on the rate of amino acid replacement in proteins, *J. Mol. Evol.*, 21:233-257, 1985.

GenBank Accession No. H55639, (pp. 1-2; Mar. 28, 1997).

GenBank Accession No. MMU31993, (pp. 1-2; Mar. 28, 1997).

Hwang, S. and Kim, H., "Expression of IL-17 homologs and their receptors in the synovial cells of rheumatoid arthritis patients," *Mol. Cells*, 19(2):180-184, 2005.

Infante-Duarte, C. et al., "Microbial lipopeptides induce the production of IL-17 in Th cells," *J. Immunol.*, 165:6107-6115, 2000.

Joosten et al., "IL-1α/β blockade prevents cartilage and bone destruction in murine type II collagen-induced arthritis, whereas TNF-α blockade only ameliorates joint inflammation," *J. Immunol.*, 163:5049-5055, 1999.

Jovanovic et al., "Stimulation of 92-kd gelatinase (matrix metalloproteinase 9) production by interleukin-17 in human monocyte/macrophages," *Arthritis Rheum.*, 43(5):1134-1144, 2000.

Jovanovic, D. et al., "IL-17 stimulates the production and expression of proinflammatory cytokines, IL-β and TNF-α, by human macrophages," *J. of Immunol.*, 160:3513-3521, 1998.

Jovanovic, D. et al., "IL-17 stimulates the secretion of proinflammatory cytokines by human macrophages," *American College of Rheumatology (ACR) meeting*, Poster 1446, Nov. 1997.

Kotake, S., "IL-17 in synovial fluids from patients with rheumatoid arthritis is a potent stimulator of osteoclastogenesis," *J. Clin. Invest.*, 103(9):1345-1352, 1999.

Kurasawa et al., "Increased interleukin-17 production in patients with systemic sclerosis," *Arthritis. Rheum.*, 43(11):2455-2463, 2000.

Lee et al., "Il-18 E42A mutant is resistant to the inhibitory effects of HPV-16 E6 and E7 oncogenes on the IL-18-mediated immune response," *Cancer Lett.*, 229:261-270, 2005.

Li et al., "Cloning and characterization of IL-17B and IL-17C, two new members of the IL-17 cytokine family," *PNAS*, 97(2):773-778, 2000.

Liew, F., "Nitric oxide in infectious and autoimmune diseases," *CIBA Foundation Symposium*, 195:234-244, 1995.

Lotz et al., IL-17 promotes cartilage degradation, *Arthritis and Rheumatism*, 39 supp. (9):S120, No. 559, 1996.

Miller, N. and Vile, R., "Targeted vectors for gene therapy," *FASEB J.*, 9:190-199, 1995.

Mosley et al., "Interleukin-17 family and IL-17 receptors," *Cytokine & Growth Factor Reviews*, 14:155-174, 2003.

Mostarica-Stojkovic, M., "The role of astrocytes in autoimmune and other inflammatory diseases of the central nervous system," Institute of Microbiology and Immunology, School of Medicine, University of Belgrade, Belgrade, Yugoslavia, p. 1 (Sep. 12, 2001).

Ngo et al., "Computational complexity, protein structure prediction, and the Levinthal Paradox," in *The Protein Folding Problem and Tertiary Structure Prediction*, Mertz and LeGrand, eds. 1994, pp. 491-495.

Nicholas et al., "Gene expression in cells infected with gammaherpesvirus saimiri: Properties of transcripts from two immediate-early genes," *Virol.*, 179:189-200, 1990.

Niederau et al., "Inflammatory mediators and acute phase proteins in patients with Crohn's disease and ulcerative colitis," *Hepato-Gastroenterol.*, 44:90-107, 1997.

Pelidou et al., "enhancement of acute phase and inhibition of chronic phase of experimental autoimmune neuritis in Lewis rats by intranasal administration of recombinant mouse interleukin 17: Potential immunoregulatory role," *Exp. Neruol.*, 163:165-172, 2000.

Rouvier et al., CTLA-8, cloned from an activated T cell, bearing AU-rich messenger RNA instability sequences, and homologous to a herpesvirus saimiri gene, *J. Immunol.*, 150(12):5445-5456, 1993.

Spriggs, M. K., "Interleukin-17 and its receptor," *J. Clin. Immunol.*, 17(5):366-369, 1997.

Sykes et al., "Xenograft Tolerance," *Immunol. Reviews*, 141:245-276, 1994.

Teunissen et al., "Interleukin-17 and interferon-γ synergize in the enhancement of proinflammatory cytokine production by human keratinocytes," *J. Invest. Dermatol.*, 111:645-649, 1998.

Torrance et al., "Inhibition of cytokine activity in collagen induced arthritis," University of Washington, Department of Immunology/Immunex Symposium, poster presentation, Mar. 7, 1997, p. 1.

Trofatter et al., "An expression-independent catalog of genes from human chromosome 22," *Genome Rsh.*, 5:214-224, 1995.

Verma, I. and Somia, N., "Gene therapy—promises, problems and prospects," *Nature*, 389:239-242, 1997.

Wong et al., "Elevation of proinflammatory cytokine (IL-18, IL-17, IL-12) and Th2 cytokine (IL-4) concentrations in patients with systemic lupus erythematosus," *Lupus*, 9:589-593, 2000.

Yao, Z. et al., "Molecular characterization of the human interleukin (IL)-17 receptor," *Cytokine*, 9(11):794-800, 1997.

Yao et al., "Complete nucleotide sequence of the mouse CTLA8 gene," *Gene*, 168:223-225 1996.

Yoo et al., "Human IL-17: A novel cytokine derived from T cells," *J. Immunol.*, 155:5483-5486, 1995.

Chabaud, M. and Miossec, P., "The combination of tumor necrosis factor α blockade with interleukin-1 and interleukin-17 blockade is more effective for controlling synovial inflammation and bone resorption in an ex vivo model," *Arthritis Rheum*, 44(6):1293-1303, 2001.

Charles et al., "Regulation of cytokines, cytokine inhibitors, and acute-phase proteins following anti-TNF-α therapy in rheumatoid arthritis," *J Immunol*, 163:1521-1528, 1999.

Cannetti et al., "IL-18 enhances collagen-induced arthritis by recruiting neutrophils via TNF-α and leukotriene $B_4$," *J Immunol*, 171:1009-1015, 2003.

Cunnane et al., "Serum amyloid A in the assessment of early inflammatory arthritis", *J. Rheumatol*, 27:58-63, 2000.

Fujino et al., "Increased expression of in terleukin 17 in inflammatory bowel disease," *Gut*, 52:65-70, 2003.

Green, L. and Jakobovits, A., "Regulation of B cell development by variable gene complexity in mice reconstituted with human immunoglobulin yeast artificial chromosomes," *J Exp Med*, 188(3):483-495, 1998.

Green et al., "Antigen-specific human monoclonal antibodies from mice engineered with huma Ig heavy and light chain YACs," *Nat Genet*, 7:13-21, 1994.

Harrington et al., "Interleukin 17-producing CD4+ effector T cells develop via a lineage distinct from the T helper type 1 and 2 lineages," *Nat Immunol*, 6(11):1123-1132, 2005.

Jia et al., "A novel method of multiplexed competitive antibody binning for the characterization of monoclonal antibodies," *J Immunol Methods*, 288:91-98, 2004.

Kauffman et al., "A phase I study evaluating the safety, pharmacokinetics, and clinical response of a human IL-12 p40 antibody in subjects with plaque psoriasis," *J Invest Dermatol*, 123:1037-1044, 2004.

Kimura, A. et al., "IL-6-dependent and -independent pathways in the development of interleukin 17-producing T helper cells," *Proc Natl Acad Sci, USA*, 104(29)12099-12104, 2007.

Kolls, J. and Linden, A., "Interleukin-17 family members and inflammation," *Immunity*, 21:467-476, 2004.

Konishi et al., "Il-18 contributes to the spontaneous development of atopic dermatitis-like inflammatory skin lesion independently of IgE/stat6 under specific pathogen-free conditions," *Proc Natl Acad Sci, USA*, 99(17):11340-11345, 2002.

Langrish et al., "IL-23 drives a pathogenic T cell population that induces autoimmune inflammation," *J Exp Med*, 201(2):233-240, 2005.

Li et al., "The expression of interleukin-17, interferon-gamma, and macrophage inflammatory protein-3 alpha mRNA in patients with psoriasis vulgaris", *J Huazhong Univ Sci Technolog Med Sci*, 24(3):294-296, 2004.

Lindén et al., "Airway neutrophils and interleukin-17," *Eur Respir J*, 15:973-977, 2000.

Lubberts et al., "IL-1-independent role of IL-17 in synovial inflammation and joint destruction during collagen-induced arthritis," *J Immunol*, 167:1004-1013, 2001.

Lubberts et al., "IL-17 promotes bone erosion in murine collagen-induced arthritis through loss of the receptor activator of NF-κB ligand/osteoprotegerin balance," *J Immunol*, 170:2655-2662, 2003.

Lubberts et al., "The role of T cell interleukin-17 in conducting destructive arthritis: lessons from animal models," *Arthritis Res Ther*, 7:29-37, 2005.

Mangan et al., "Transforming growth factor-β induces development of the $T_H17$ lineage," *Nature*, 441:231-234, 2006.

Mannon et al., "Anti-interleukin-12 antibody for active Crohn's disease," *N Engl J Med*, 351:2069-2080, 2004.

Matusevicius et al., "Interleukin-17 mRNA expression in blood and CSF mononuclear cells is augmented in multiple sclerosis", *Mult Scler*, 5:101-104, 1999.

McAllister et al., "Role of IL-17A, IL-17F, and the IL-17 receptor in regulating growth-related oncogene-α and granulocyte colony-stimulating factor in bronchial epithelium: Implications for airway inflammation in cystic fibrosis," *J Immunol*, 175:404-412, 2005.

Mendez et al., "Functional transplant of megabase human immunoglobulin loci recapitulates human antibody response in mice," *Nat Genet*, 15:146-156, 1997.

Miossec, P., "Interleukin-17 in rheumatoid arthritis," *Arthritis & Rhem*, 48(3):594-601, 2003.

Molet et al., "IL-17 is increased in asthmatic airways and induces human bronchial fibroblasts to produce cytokines," *J Allergy Clin Immunol*, 108(3):431-438, 2001.

Nakae et al., "IL-17 production from activated T cells is required for the spontaneous development of destructive arthritis in mice deficient in IL-1 receptor antagonist," *Proc Natl Acad Sci, USA*, 100(10):5986-5990, 2003.

Nakae et al., "Suppression of immune induction of collagen-induced arthritis in IL-17-deficient mice," *J Immunol*, 171:6173-6177, 2003.

Nanevicz et al., ";Mechanisms of thrombin receptor agonist specificity," *J Biol Chem*, 270(37):21619-21625, 1995.

Numasaki et al., "Regulatory roles of IL-17 and IL-17F in G-CSF production by lung microvascular endothelial cells stimulated with IL-1β and/or TNF-α," *Immunol Lett*, 95:97-104, 2004.

Oda et al., "Interleukin-17F induces pulmonary neutrophilia and amplifies antigen-induced allergic response," *Am J Respir Crit Care Med*, 171:12-18, 2005.

Park et al., "A distinct lineage of CD4 T cells regulates tissue inflammation by producing interleukin 17," *Nat Immunol*, 6(11):1133-1141, 2005.

Stemmer et al., "Single-step assembly of a gene and entire plasmid from large numbers of oligodeoxyribonucleotides," *Gene*, 164:49-53, 1995.

Toy et al., "Cutting Edge: Interleukin 17 signals through a heteromeric receptor complex," *J Immunol*, 177:36-39, 2006.

Yao et al., "Herpesvirus saimiri encodes a new cytokine, IL-17, which binds to a novel cytokine receptor," *Immunity*, 3:811-821, 1995.

Ye et al., "Requirement of interleukin 17 receptor signaling for lung CXC chemokine and granulocyte colony-stimulating factor expression, neutrophils recruitment, and host defense," *J Exp Med*, 194(4):519-527, 2001.

Yoshimoto et al., "IL-12 up-regulates IL-18 receptor expression on T cells, Th1 cells, ad B cells: Synergism with IL-18 for IFN-γ production," *J Immunol*, 161:3400-3407, 1998.

You et al., "Interleukin-17 receptor-like gene is a novel antiapoptotic gene highly expressed in androgen-independent prostate cancer," *Cancer Res*, 66(1):175-183, 2006.

Ziolkowska et al., "High levels of IL-17 in rheumatoid arthritis patients: IL-15 triggers in vitro IL-17 production via cyclosporine A-sensitive mechanism," *J Immunol*, 164:2832-2838, 2000.

Zupnick, A. and Prives, C., "Mutational analysis of the p53 core domain L1 loop," *J Biol Chem*, 281(29):20464-20473, 2006.

XP002486817, "Monoclonal anti-human IL-17 R antibody," R&D Systems, 2004.

Gaffen, S. et al., "The IL-17 cytokine family," *Vitamins and Hormones*, Academic Press, New York, NY, US, pp. 255-282, XP009086501, 2006.

About.com.arthritis (definition for "DMARDS", pp. 1-2; Jul. 2, 2009).

Dogra et al., "Biologic therapy in psoriasis," *Indian J. Dermatol. Venereol. Leprol.*, 72(4):256-265, 2006.

Janeway and Travers, Immunology, 3rd edition, p. G3, Garland Publishing Inc., New York, NY, 1997.

Nickoloff, B. and Nestle, F., "Recent insights into the immunopathogenesis of psoriasis provide new therapeutic opportunities," *J. Clin. Invest.*, 113(12):1664-1675, 2004.

Petersen, T., "In vivo pharmacological disease models for psoriasis and atopic dermatitis in drug discovery," *Basic & Clinical Pharmacology & Toxicology*, 99:104-115, 2006.

U.S. Appl. No. 12/443,962 (not yet published as a PGPub that can be cited under U.S. patent documents).

van de Kerkhof, PCM, "Consistent control of psoriasis by continuous long-term therapy: the promise of biological treatments," *JEADV*, 1468-3083:639-650, 2006.

Webmd.com (definition for "DMARDS", pp. 1-3, Jul. 2, 2009).

\* cited by examiner

| V_H DOMAINS | CDR1 | SYNTHETIC LINKER | CDR2 | SYNTHETIC LINKER | CDR3 |
|---|---|---|---|---|---|
| SEQ ID NO:24 | --SYYWS | GGGAAAAGGGAAA | RIY...PSG.RTN...YNPSLKS | GGGAAAAGGGAAA | ...E.A..Y.ELQLG...LYYYYGMDV |
| SEQ ID NO:23 | --SYYWS | GGGAAAAGGGAAA | RIY...PSG.RTN...YNPSLKS | GGGAAAAGGGAAA | ...E.A..Y.ELQLG...LYYYYGMDV |
| SEQ ID NO:5 | --SYYWS | GGGAAAAGGGAAA | RIY...PSG.NTI...YNPSLKS | GGGAAAAGGGAAA | ...E.N..YSE.SSG....LYYYYGMDV |
| SEQ ID NO:1 | --NYYWN | GGGAAAAGGGAAA | DIY...YSG.STN...YNPSLKS | GGGAAAAGGGAAA | D.GELANYY...GSGSYQFYYYGMDV |
| SEQ ID NO:2 | --GYYWS | GGGAAAAGGGAAA | EIN...HSG.RTN...YNPSLKS | GGGAAAAGGGAAA | ..GP...YYFD.SSG.Y.LYYYYGLDV |
| SEQ ID NO:25 | SGGYYWS | GGGAAAAGGGAAA | YIY...YSG.NTY...YNPSLRS | GGGAAAAGGGAAA | EAGGNSAYY............Y..GMDV |
| SEQ ID NO:10 | SGGYYWS | GGGAAAAGGGAAA | YIY...FSG.SAY...YNPSLKS | GGGAAAAGGGAAA | E......YY.D.SSG.....YPDAFDI |
| SEQ ID NO:7 | --RYGIS | GGGAAAAGGGAAA | ..WISAYNG.NTN...YAQKLQG | GGGAAAAGGGAAA | R......DYDILT.G......YYNGFDP |
| SEQ ID NO:9 | --RYGIS | GGGAAAAGGGAAA | ..WISAYNG.NTN...YAQKLQG | GGGAAAAGGGAAA | R......DYDILT.G......YYNGFDP |
| SEQ ID NO:6 | --RYGIS | GGGAAAAGGGAAA | ..WISAYNG.NTN...YAQKLQG | GGGAAAAGGGAAA | R......DYDILT.G......YYNGFDP |
| SEQ ID NO:8 | --RYGIS | GGGAAAAGGGAAA | ..WISAYNG.NTN...YAQNLQG | GGGAAAAGGGAAA | R......DYDILT.G......YYNGFDP |
| SEQ ID NO:14 | --RYGIS | GGGAAAAGGGAAA | ..WISTYSG.NTN...YAQKLQG | GGGAAAAGGGAAA | R..QLYFDY------------------ |
| SEQ ID NO:22 | --RYGIS | GGGAAAAGGGAAA | ..WISAYSG.NTN...YAQKLQG | GGGAAAAGGGAAA | R..QLYFDY------------------ |
| SEQ ID NO:16 | --SYGIS | GGGAAAAGGGAAA | ..WISAYNG.NTK...YAQKLQG | GGGAAAAGGGAAA | K..QLVFDY------------------ |
| SEQ ID NO:17 | --SYGIS | GGGAAAAGGGAAA | ..WISAYSG.NTK...YAQKLQG | GGGAAAAGGGAAA | K..QLVFDY------------------ |
| SEQ ID NO:12 | --SYGIS | GGGAAAAGGGAAA | ..WISTYKG.NTN...YAQKLQG | GGGAAAAGGGAAA | K..QLVFDY------------------ |
| SEQ ID NO:19 | --SYGIS | GGGAAAAGGGAAA | ..WISAYSG.NTK...YAQKFQG | GGGAAAAGGGAAA | R..QLALDY------------------ |
| SEQ ID NO:13 | --SYGMQ | GGGAAAAGGGAAA | VIW...YDG.NKK..YYADSVKG | GGGAAAAGGGAAA | .........GRVR.D......YYYGMDV |
| SEQ ID NO:15 | --SYGMQ | GGGAAAAGGGAAA | VIW...YDG.NKK..YYADSVKG | GGGAAAAGGGAAA | .........GRVR.D......YYYGMDV |
| SEQ ID NO:4 | --SYGMH | GGGAAAAGGGAAA | VIW...YDGSN.K..HYADSVKG | GGGAAAAGGGAAA | ...D.T....G.V..........Y----- |
| SEQ ID NO:3 | --SYGMH | GGGAAAAGGGAAA | VIW...YDGSN.K..HYADSVKG | GGGAAAAGGGAAA | ...D.T....G.V..........Y----- |
| SEQ ID NO:11 | --SYGMH | GGGAAAAGGGAAA | VIW...YDGSN.K..YYADSVKG | GGGAAAAGGGAAA | ...D.T....K.D..........Y----- |
| SEQ ID NO:21 | --SYSMN | GGGAAAAGGGAAA | II.....SSRS.SIIHYADSVKG | GGGAAAAGGGAAA | ...PKV...G..G..........GMDV |
| SEQ ID NO:20 | --SYSMN | GGGAAAAGGGAAA | FI.....SARS.STIYYADSVKG | GGGAAAAGGGAAA | ...PKV...G..G..........GMDV |
| SEQ ID NO:26 | --DYYMS | GGGAAAAGGGAAA | YI.....SS.SGGSTIYYADSVKG | GGGAAAAGGGAAA | ...DRTYYFGS.G.S......Y.EGMDV |
| SEQ ID NO:18 | --DYYMH | GGGAAAAGGGAAA | ..WMHPNSGG.TDL...AQRFQG | GGGAAAAGGGAAA | .CG......Y..CST.LSCSFYFY.FDL |

Fig. 2

| $V_L$ DOMAINS | | CDR1 | SYNTHETIC LINKER | CDR2 | SYNTHETIC LINKER | CDR3 |
|---|---|---|---|---|---|---|
| SEQ ID NO:33 | | RASQGIR.N....D.LG | GGGAAAGGGAAA | AASSLQS | GGGAAAGGGAAA | LQH.KSY...PL.T |
| SEQ ID NO:32 | | RASQGIR.N....D.LG | GGGAAAGGGAAA | AASSLQS | GGGAAAGGGAAA | LQH.KSY...PL.T |
| SEQ ID NO:34 | | RASQGIR.N....D.LG | GGGAAAGGGAAA | AASSLQS | GGGAAAGGGAAA | LQH.KSY...PL.T |
| SEQ ID NO:35 | | RASQGIR.N....D.LG | GGGAAAGGGAAA | AASSLQS | GGGAAAGGGAAA | LQH.KSY...PL.T |
| SEQ ID NO:31 | | RASQGIR.N....D.LG | GGGAAAGGGAAA | AASSFQS | GGGAAAGGGAAA | LQH.KSY...PL.T |
| SEQ ID NO:27 | | RASQGIR.N....D.LG | GGGAAAGGGAAA | AASSLQS | GGGAAAGGGAAA | LQH.NSY...PP.T |
| SEQ ID NO:49 | | RASQGII.N....D.LG | GGGAAAGGGAAA | AASSLQS | GGGAAAGGGAAA | LQH.NSN...PF.T |
| SEQ ID NO:36 | | RASQGIR.S.....WLA | GGGAAAGGGAAA | AASSLQS | GGGAAAGGGAAA | LQH.NSY...PP.T |
| SEQ ID NO:52 | | RASQAI..S....IYLA | GGGAAAGGGAAA | AASSLQS | GGGAAAGGGAAA | .Q..Q.ANNFPR.T |
| SEQ ID NO:46 | | RASQGI..S....NYLA | GGGAAAGGGAAA | AASTLQS | GGGAAAGGGAAA | .Q..Q.YSSYPR.T |
| SEQ ID NO:47 | | RASQGI..S....NYLA | GGGAAAGGGAAA | AASTLQS | GGGAAAGGGAAA | .Q..K.YNRAPF.T |
| SEQ ID NO:29 | | RASQSI..S....SYLN | GGGAAAGGGAAA | AASSLQS | GGGAAAGGGAAA | .Q..K.YNRAPF.T |
| SEQ ID NO:53 | | RASQSV.YS....N.LA | GGGAAAGGGAAA | GASTRAT | GGGAAAGGGAAA | .Q..QSYS.TPF.T |
| SEQ ID NO:30 | | RASQSV..SR...N.LA | GGGAAAGGGAAA | GASTRAT | GGGAAAGGGAAA | .Q..Q.YYNWP.WT |
| SEQ ID NO:37 | | RASQSV..SS...N.LA | GGGAAAGGGAAA | GASTRAA | GGGAAAGGGAAA | .Q..Q.YNWPTWT |
| SEQ ID NO:41 | | RASQSV..SS...N.LA | GGGAAAGGGAAA | DASTRAA | GGGAAAGGGAAA | .Q..H.YINWPKWT |
| SEQ ID NO:48 | | RASQSV..SS...N.LA | GGGAAAGGGAAA | DASTRAT | GGGAAAGGGAAA | .Q..Q.YDNWPL.T |
| SEQ ID NO:40 | | RASQSV..SS...N.LA | GGGAAAGGGAAA | DASTRAT | GGGAAAGGGAAA | .Q..Q.YDNWPL.T |
| SEQ ID NO:43 | | RASQSI..SS...N.LA | GGGAAAGGGAAA | GASTRAT | GGGAAAGGGAAA | .Q..Q.YDNWPL.T |
| SEQ ID NO:38 | | RASQSI..SS...S.LA | GGGAAAGGGAAA | GASTRAT | GGGAAAGGGAAA | .Q..Q.YDNWPL.T |
| SEQ ID NO:45 | | RASQSI..SS...N.LA | GGGAAAGGGAAA | GASTRAT | GGGAAAGGGAAA | .Q..Q.YDTWPL.T |
| SEQ ID NO:42 | | RASQSI..ST...S.LA | GGGAAAGGGAAA | GTSTRAT | GGGAAAGGGAAA | .Q..Q.YDIWPL.T |
| SEQ ID NO:28 | | RASQSV..SR...N.LV | GGGAAAGGGAAA | GASTRAN | GGGAAAGGGAAA | .Q..Q.YKSW..RT |
| SEQ ID NO:44 | | KTSQSVLYSSKNKNFLA | GGGAAAGGGAAA | WASTRES | GGGAAAGGGAAA | .Q..Q.YYSTP.FT |
| SEQ ID NO:39 | | KSSQSLLHS.DGKTYLY | GGGAAAGGGAAA | EVSTRFS | GGGAAAGGGAAA | MQSIQL....PL.T |
| SEQ ID NO:50 | | RSSQSLVYS.DGHTCLN | GGGAAAGGGAAA | KVSNWDS | GGGAAAGGGAAA | MQ....GTHWPLCS |
| SEQ ID NO:51 | | RSSQSLVYS.DGHTCLN | GGGAAAGGGAAA | KVSNWDS | GGGAAAGGGAAA | MQ....GTHWPLCS |

Fig. 3

| BIN | Bead Region mAb | 33 A | 34 B | 35 P | 36 C | 37 D | 38 E | 42 H | 43 F | 72 huIgG |
|---|---|---|---|---|---|---|---|---|---|---|
| 1 | A | -220 | 1199 | 6592 | 330 | 337 | 300 | 8643 | 345 | 84 |
| 1 | B | -326 | 453 | 5020 | 150 | 213 | 182 | 6786 | 173 | 37 |
| 1 | C | -178 | 816 | 5963 | 260 | 264 | 163 | 2948 | 239 | 54 |
| 1 | D | -233 | 684 | 5645 | 217 | 207 | 192 | 3181 | 269 | 123 |
| 1 | E | -70.5 | 447 | 3527 | 173 | 168 | 130 | 2536 | 152 | 26 |
| 1 | F | 114 | 545 | 1716 | 253 | 179 | 175 | 3971 | 187 | 140 |
| 1 | G | -162 | 1305 | 4487 | 354 | 344 | 260 | 3995 | 304 | -5 |
| 2 | H | 7507 | 1643 | 3421 | 2495 | 790 | 573 | -140 | 2805 | 74 |
| 3 | I | 3482 | 853 | 2627 | 4910 | 1636 | 1360 | 211 | 2133 | 22 |
| 3 | J | 1812 | 420 | 2258 | 2775 | 875 | 807 | -109 | 1810 | 35 |
| 3 | K | 3125 | 834 | 2605 | 4553 | 1622 | 1412 | 216 | 2124 | 100 |
| 3 | L | 2356 | 571 | 2093 | 3517 | 1084 | 890 | 64 | 1589 | 34 |
| 3 | M | 1936 | 455 | 1897 | 3040 | 888 | 765 | 73 | 1410 | 32 |
| 3 | N | 2473 | 597 | 2468 | 3975 | 1202 | 999 | 68 | 1917 | 56 |
| 3 | O | 2998 | 630 | 2536 | 4511 | 1368 | 1256 | 120 | 2223 | 95 |
| 4 | P | 12079 | 3005 | 474 | 10707 | 3369 | 3424 | 6069 | 2543 | 73 |
| 5 | Q | 9527 | 1897 | 2157 | 4766 | 1383 | 1174 | 10203 | 2201 | 28 |
| 6 | R | 6796 | 1065 | 1411 | 2994 | 783 | 666 | 8296 | 1242 | 50 |
|  | huIgG | -194 | -6 | 216 | 118 | 46 | 45 | -34 | 25.5 | 65 |

*Fig. 8A*

| Bead Region | 45 R | 46 I | 47 J | 51 K | 52 Q | 53 L | 55 G | 56 M | 61 N | 62 O | 72 huIgG |
|---|---|---|---|---|---|---|---|---|---|---|---|
| BIN mAb | | | | | | | | | | | |
| 1 A | 7064 | 5302 | 2323 | 7206 | 9649 | 3017 | 454 | 1859 | 2646 | 3800 | 84 |
| 1 B | 5885 | 3710 | 1395 | 4970 | 8280 | 1980 | 235 | 1303 | 1948 | 2638 | 37 |
| 1 C | 3954 | 6723 | 3591 | 8223 | 5497 | 3540 | 346 | 2882 | 3632 | 5517 | 54 |
| 1 D | 3552 | 6652 | 3644 | 8684 | 4686 | 4257 | 318 | 2975 | 3843 | 5545 | 123 |
| 1 E | 1655 | 4333 | 2420 | 5605 | 2394 | 2661 | 334 | 1766 | 2409 | 3313 | 26 |
| 1 F | 1120 | 3107 | 2123 | 4107 | 1650 | 1724 | 342 | 1021 | 1511 | 2626 | 140 |
| 1 G | 5109 | 6887 | 2901 | 8972 | 7846 | 3591 | 480 | 2377 | 3231 | 5377 | -5 |
| 2 H | 7525 | -5 | -51 | -111 | 9606 | -41 | 3208 | -75 | 24 | 5.5 | 74 |
| 3 I | 48 | 33 | 2 | -182 | 57 | -26 | 4909 | 13 | 56 | 16 | 22 |
| 3 J | 53.5 | -5 | 72 | -100 | 86 | -11 | 1915 | 10 | 38 | 75 | 35 |
| 3 K | 114 | 1 | -3 | -196 | 90 | -76 | 4492 | 85 | 66 | 28 | 100 |
| 3 L | 52 | 63 | 61 | -25 | 105 | 39 | 3714 | 44 | 41 | 72 | 34 |
| 3 M | 40 | 26 | 31 | -5 | 60 | 18 | 3275 | 20 | 11 | 49 | 32 |
| 3 N | 76 | 18 | 8 | -44 | 98 | -1 | 4258 | 40 | 43 | 55 | 56 |
| 4 O | 76 | 10 | 59 | -111 | 135 | 18 | 4492 | 73 | 83 | 139 | 95 |
| 5 P | 2553 | 5003 | 4475 | 6271 | 3718 | 2521 | 6001 | 1645 | 2359 | 3788 | 73 |
| 6 Q | 34 | 2.5 | 23 | -181 | 100 | -58 | 6276 | 44.5 | 39 | 175 | 28 |
| R | 25 | 58 | 26 | -29 | 60 | 15 | 4016 | 24 | 24 | 140 | 50 |
| huIgG | 31 | -72 | 42 | -235 | 64 | -36 | 216 | 27 | 3 | 20 | 65 |

*Fig. 8B*

MAIRRCWPRVVPGPALGWLLLLLNVLAPGRASPRLLDFPAPVCAQEGLSCR
VK                                              Domain A NSTCLDDSWIHPKNLTPSSPKNIYINLSVSSTQHGELVPVLHVEWTLQTDASI
LY                      Domain B LEGAELSVLQLNTNERLCVKFQFLSMLQHHRKRWRFSFSHFVVDPGQEYE
                           Domain C VTVHHLPKPIPDGDPNHKSKIIFVPDCEDSKMKMTTSCVSSGSLWDPNITV
                      Domain D ETLDTQHLRVDFTLWNESTPYQVLLESFSDSENHSCFDVVKQIFAPRQEEF
HQ Domain E                           Domain F

RANVTFTLSKFHWCCHHHVQVQPFFSSCLNDCLRHAVTVPCPVISNTTVP
KPVADYIPLW

SEQ ID NO:432

```
                    301                                                             349
Construct A  (301)  VSCPEMPDT--PEPIPDIMPLWEPRSGSSDYKDDDDKGSSHHHHHH----
Construct B  (301)  VSCPEMPDT--PEPIPDMPLWEPRSGSSDYKDDDDKGSSHHHHHH----
Construct C  (301)  VSCPEMPDT--PEPIPDMPLWEPRSGSSDYKDDDDKGSSHHHHHH----
Construct D  (301)  VSCPEMPDT--PEPIPDMPLWEPRSGSSDYKDDDDKGSSHHHHHH----
Construct E  (301)  VSCPEMPDT--PEPIPDMPLWEPRSGSSDYKDDDDKGSSHHHHHH----
Construct F  (301)  VPCPVISNTTVPKPVADYIPLWEPRSGSSDYKDDDDKGSSHHHHHH----
Construct G  (301)  VPCPVISNTTVPKPVADYIPLWEPRSGSSDYKDDDDKGSSHHHHHH----
Construct H  (301)  VSCPEMPDT--PEPIPDMPLWEPRSGSSDYKDDDDKGSSHHHHHH----
Construct I  (301)  VSCPEMPDT--PEPIPDMPLWEPRSGSSDYKDDDDKGSSHHHHHH----
Construct J  (301)  VSCPEMPDT--PEPIPDMPLWEPRSGSSDYKDDDDKGSSHHHHHH----
Construct M  (301)  VPCPVISNTTVPKPVADYIPLWEPRSGSSDYKDDDDKGSSHHHHHH----
Construct N  (301)  VPCPVISNTTVPKPVADYIPLWEPRSGSSDYKDDDDKGSSHHHHHH----
Construct K  (301)  VPCPVISNTTVPKPVADYIPLWEPRSGSSDYKDDDDKGSSHHHHHH----
Construct L  (301)  VPCPVISNTTVPKPVADYIPLWEPRSGSSDYKDDDDKGSSHHHHHH----
huIL17RFpH   (301)  VSCPEMPDT--PEPIPDMPLWEPRSGSSDYKDDDDKGSSHHHHHH----
muIL-17R     (301)  VPCPVISNTTVPKPVADYIPLW---------------------------
```

| | aa 38-51 chimera A | 75-96 B | 128-154 C | 176-197 D | 213-220 E | 229-319 F | A+E G | B+E H | C+E I | D+E J | A+F K | B+F L | C+F M | D+F N |
|---|---|---|---|---|---|---|---|---|---|---|---|---|---|---|
| BIN 1 | AM₀18/AM₀18 | 0.052 | 0.063 | 0.052 | 0.059 | 0.087 | 3105.0 | 0.052 | 0.063 | 0.059 | 0.064 | 31.310 | 0.08 | 1.551 | n.d. |
| BIN 2 | AM₀1/AM₀1 | 0.229 | 0.00 | 0.049 | 0.00 | 0.172 | 0.156 | 0.219 | 0.089 | 0.074 | 159.30 | 0.235 | 277.200 | 0.078 | n.d. |
| BIN 3 | AM₀22/AM₀22 | 0.042 | 0.064 | 0.160 | 0.00 | 0.057 | 0.041 | 0.054 | 0.093 | 0.190 | 150.50 | 0.033 | 0.056 | 0.125 | n.d. |
| BIN 3 | AM₀14/AM₀14 | 0.022 | 0.038 | 0.061 | 14.500 | 0.030 | 0.021 | 0.053 | 0.050 | 0.067 | 1.181 | 0.017 | 0.040 | 0.047 | n.d. |
| BIN 3 | AM₀19/AM₀19 | 0.566 | 0.112 | 0.092 | 51.020 | 0.075 | 0.053 | 0.076 | 0.130 | 0.131 | 149.40 | 0.043 | 0.100 | 0.092 | n.d. |
| BIN 3 | AM₀23/AM₀23 | 0.072 | 0.504 | 3.959 | 2.400 | 0.076 | 0.046 | 0.082 | 2.269 | 2.650 | 710.50 | 0.041 | 0.185 | 0.769 | n.d. |
| BIN 4 | AM₀26/AM₀26 | 0.249 | 0.201 | 0.156 | 0.145 | 0.323 | 0.00 | 0.283 | 0.410 | 0.269 | 0.234 | 0.00 | 0.096 | 0.00 | n.d. |
| BIN 5 | AM₀21/AM₀21 | 0.018 | 0.017 | 0.093 | 0.134 | 0.026 | 0.026 | 0.025 | 0.025 | 0.032 | 0.104 | 0.017 | 0.025 | 0.035 | 0.378 |
| BIN 6 | AM₀20/AM₀20 | 0.023 | 0.020 | 0.040 | 2.676 | 0.027 | 0.029 | 0.027 | 0.033 | 0.042 | 0.897 | 0.022 | 0.027 | 0.040 | 192.400 |

1    MGAARSPPSA VPGPLLGLLL LLLGVLAPGG ASLRLLDHRA LVCSQPGLNC
51   TVRNSTCLDD SWIHPRNLTP SSPKDLQIQL HFAHIQQGDL FPVAHIEWTL
101  QTDASILYLE GAELSVLQLN TNERLCVRFE FLSKLRHHHR RWRFTFSHPV
151  VDPDQEYEVT VHHLPKPIPD GDFNHQSKNF LVPDCEHARM KVTTPCMSSG
201  SLMDPNITVE TLEAHQLRVS FTLWNESTHY QILLTSFPHM EIHSCFEHMH
251  HLPAPRPERP HQRSNVTLTL RNLKGCCRHQ VQIQPFPSSC LNDCLRHSAT
301  VSCPEMPDTP EPIPDYMPLW EPRSGSSDYK DDDDKGSSHH HHHH

SEQ ID NO:431

FIG. 12

| | chimera | | arginine mutants |
|---|---|---|---|
| BIN 1 | AM$_{II}$18/AM$_{I}$18 | F: 229-319 | S220R, E226R, T228R, S236R, L270R, Q284R |
| BIN 2 | AM$_{II}$1/AM$_{I}$1 | B: 75-96<br>D: 176-197 | D152R |
| BIN 3 | AM$_{II}$22/AM$_{I}$22 | C: 128-154<br>D: 176-197 | D152R, D154R, E156R, D184R, E186R, S198R |
| | AM$_{II}$14/AM$_{I}$14 | D: 176-197 | D152R, D154R, E156R, D184R, E186R, H297R |
| | AM$_{II}$19/AM$_{I}$19 | D: 176-197 | D152R, D154R, E156R, D184R, E186R |
| | AM$_{II}$23/AM$_{I}$23 | B: 75-96<br>C: 128-154<br>D: 176-197 | E97R, D152R, D154R, E156R, Q176R, D184R, E186R, S198R, T235R, H297R |
| BIN 4 | AM$_{II}$26/AM$_{I}$26 | F: 229-319 | H138R, K166R, H215R, S220R, E226R, T228R, S236R, E241R, H243R, L270R |
| BIN 5 | AM$_{II}$21/AM$_{I}$21 | D: 176-197 | E113R, S115R, D152R, D154R, E156R, S177R, S198R |
| BIN 6 | AM$_{II}$20/AM$_{I}$20 | D: 176-197 | D152R, D154R, E156R, S177R, L270R |

FIG. 14

NEUTRALIZING DETERMINANTS OF IL-17 RECEPTOR A AND ANTIBODIES THAT BIND THERETO

CROSS REFERENCE TO RELATED APPLICATIONS

This application claims the benefit under 35 U.S.C. §119 of U.S. Provisional Application Ser. No. 60/969,895, filed Sep. 4, 2007, U.S. Provisional Application Ser. No. 60/873,072, filed Dec. 5, 2006 and U.S. Provisional Application Ser. No. 60/827,882, filed Oct. 2, 2006, which are hereby incorporated by reference.

FIELD OF THE INVENTION

The present invention relates to the identification of neutralizing determinants on IL-17 Receptor A (IL-17RA or IL-17R) and antibodies that bind thereto. Aspects of the invention also include antibodies that compete for binding with the IL-17RA neutralizing antibodies described herein.

BACKGROUND

IL-17A and IL-17F bind and activate IL-17RA. IL-17RA has been shown to be important in regulating immune responses. Activation of the IL-17RA leads to production of cytokines, chemokines, growth factors, and other proteins that contribute to the symptoms and/or pathology of numerous diseases. IL-17A is an inflammatory cytokine that induces the production of cytokines and other mediators leading to diseases and physiological effects such as inflammation, cartilage degradation, and bone resorption. IL-17A also plays a role in a number of inflammatory conditions including arthritis (rheumatoid arthritis), psoriasis, inflammatory bowel disease, multiple sclerosis, and asthma. (Li et al., 2004, *Huazhong Univ. Sci. Technolog. Med. Sci.* 24:294-296; Fujino et al., 2003, *Gut.* 52:65-70; Kauffman et al., 2004, *J. Invest. Dermatol.* 123:1037-1044; Mannon et al., 2004, *N. Engl. J Med.* 351:2069-2079; Matusevicius et al., 1999, *Mult Scler* 5, 101-104; Linden et al., *Eur Respir J.* 2000 May; 15(5):973-7; Molet et al., 2001, *J. Allergy Clin. Immunol.* 108:430-438). Recent studies have suggested that IL-17F plays a role in the induction of inflammatory responses (Oda et al., 2006, *American J. Resp. Crit. Care Medicine*, Jan. 15, 2006; Numasaki et al., 2004, *Immunol Lett.* 95:97-104).

Aspects of the invention provide for the identification of neutralizing determinants on IL-17RA that neutralizing antibodies bind and thereby inhibit IL-17 ligand family members from binding to and activating IL-17 Receptor A or a receptor complex comprising IL-17 Receptor A. Aspects of the invention also include antibodies that compete for binding with the IL-17RA neutralizing antibodies described herein

BRIEF DESCRIPTION OF THE DRAWINGS

FIG. 2 depicts an alignment of the amino acid sequences of the CDRs of the variable heavy ($V_H$) domains of various IL-17R antigen binding proteins (antibodies). The CDR1, CDR2, and CDR3 regions are highlighted.

FIG. 3 depicts an alignment of the amino acid sequences of the CDRs of the variable light ($V_L$) domains of various IL-17R antigen binding proteins (antibodies). The CDR1, CDR2, and CDR3 regions are highlighted.

FIGS. 8A and 8B show the results of multiplexed binning of IL-17RA antibodies. Shaded values indicate antibody pairs that can bind to IL-17RA simultaneously, suggesting that these antibodies bind to different neutralizing determinants. Boxed values indicate antibodies paired against themselves.

FIG. 9 shows mouse IL-17RA (SEQ ID NO:432) and the 5 domains, A, B, C, D, E, and F that replaced the counterpart domains in the human IL-17RA sequence.

Figure 10A:
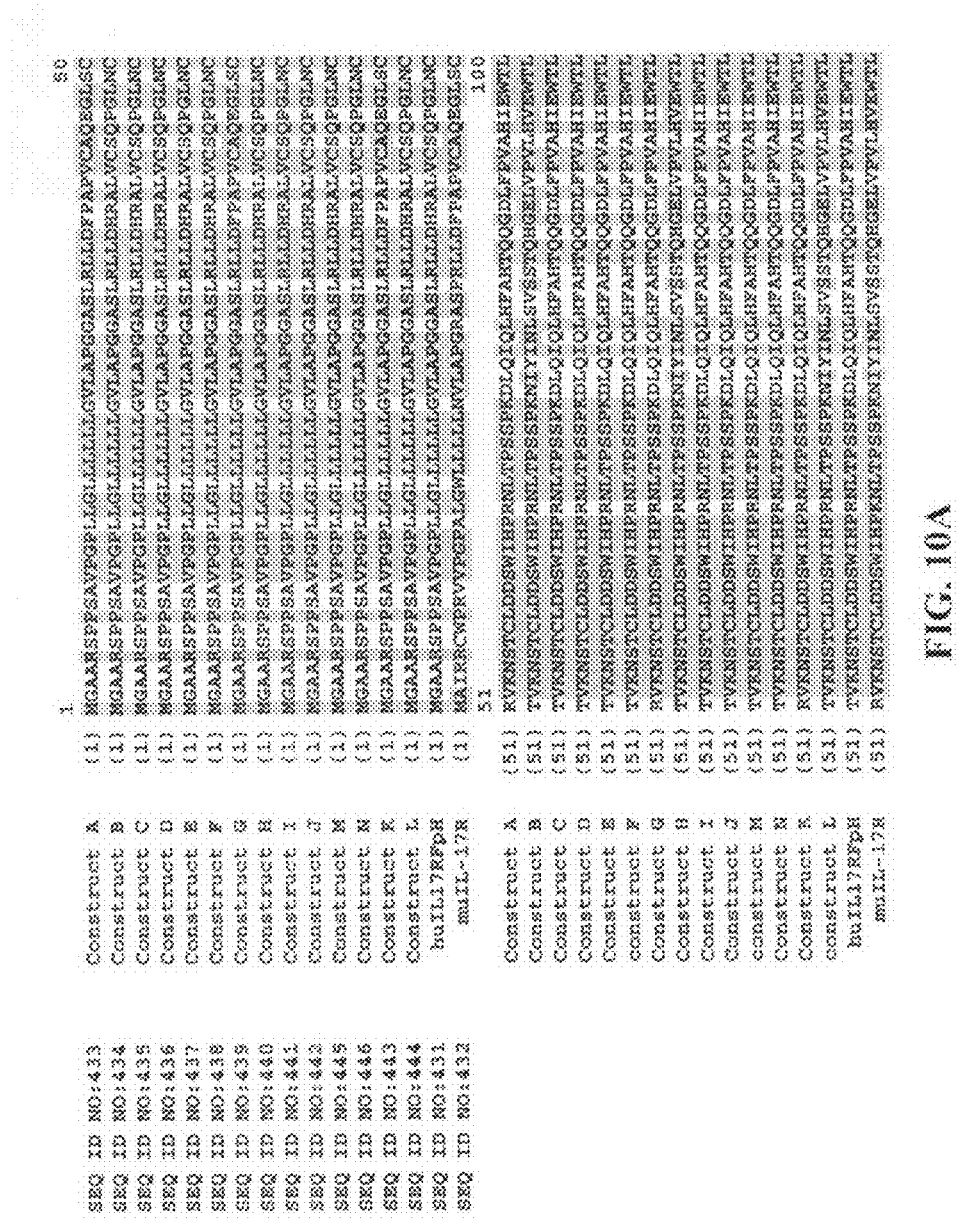
Figure 10B:
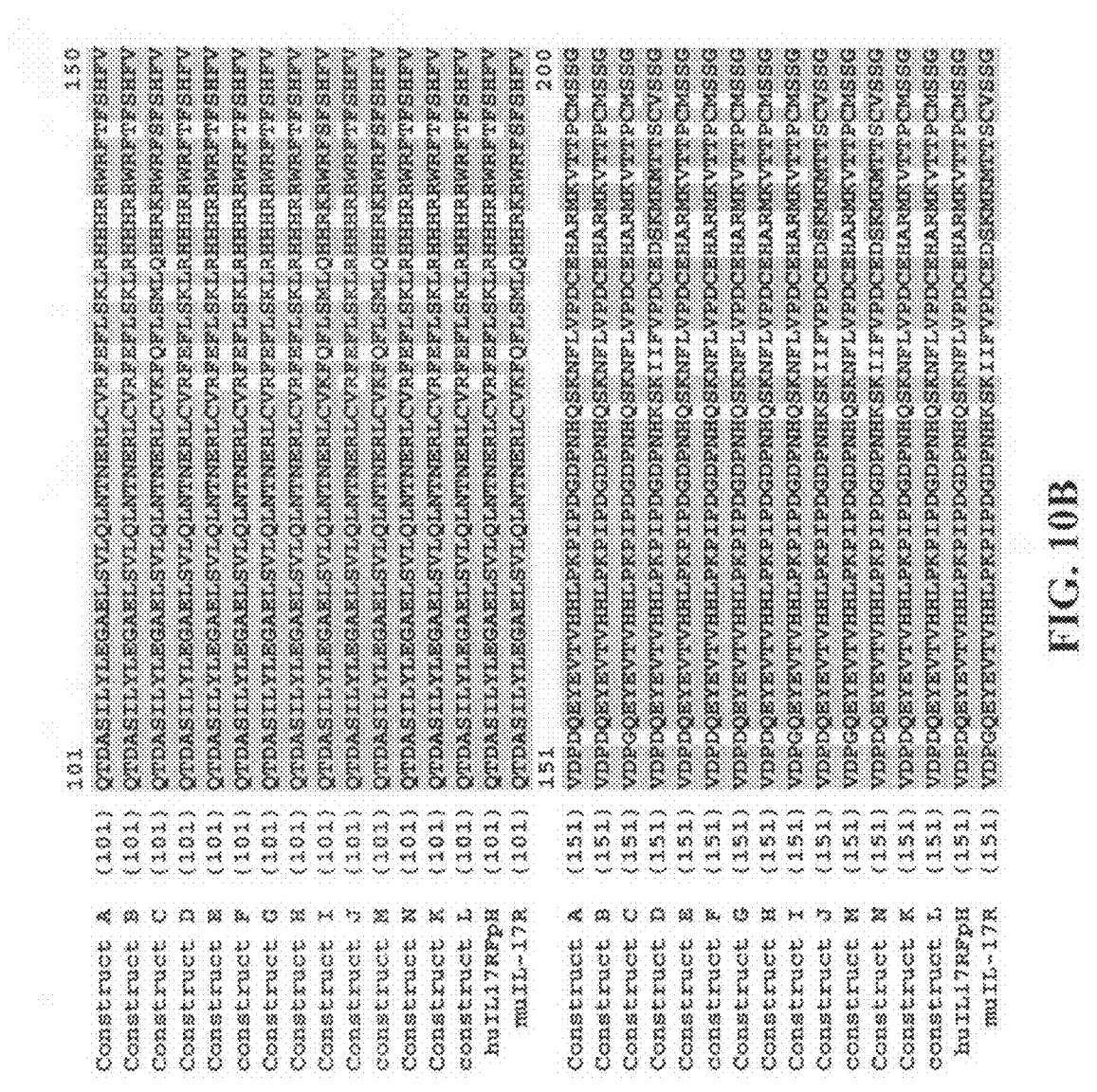
Figure 10C:
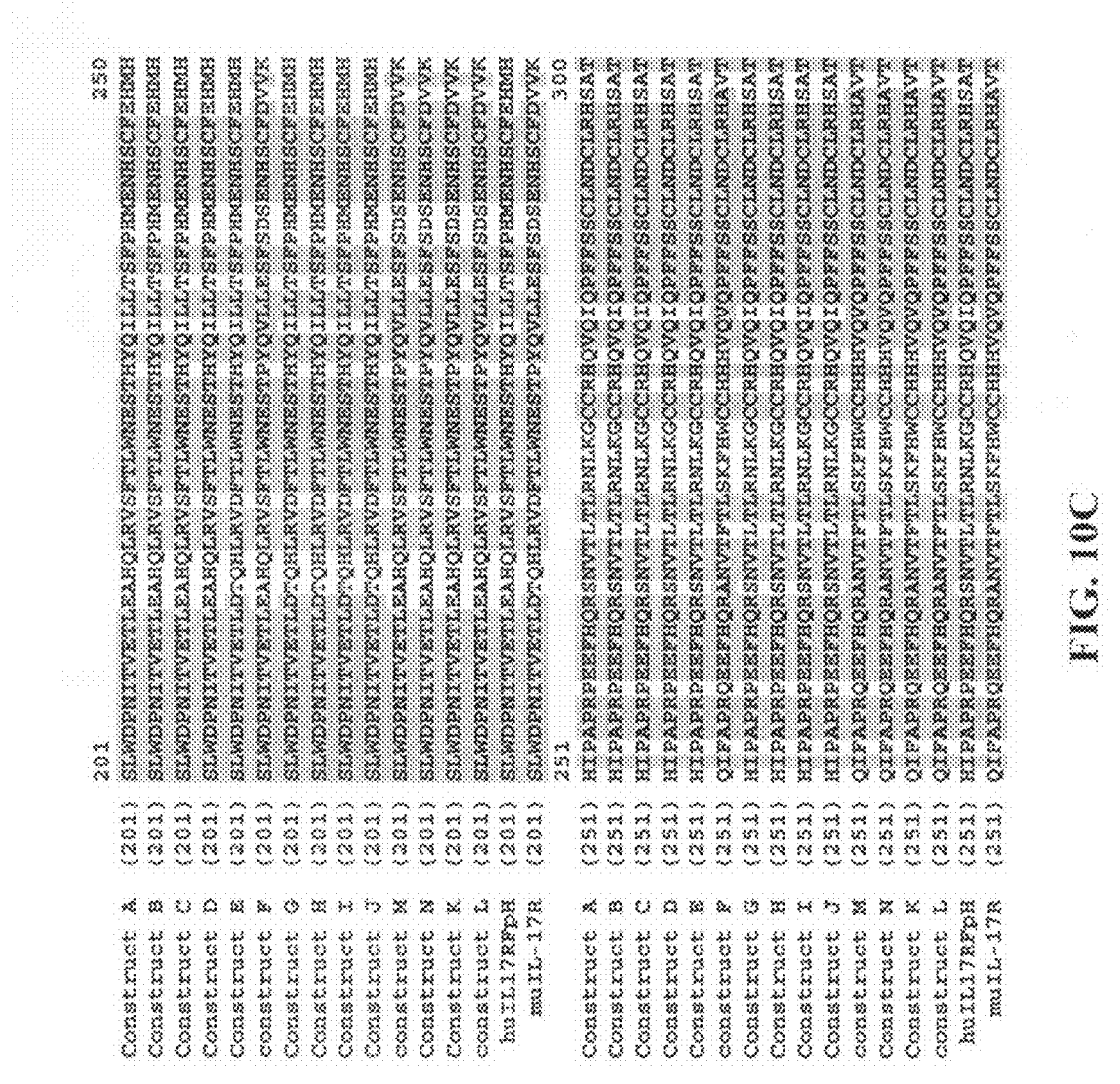

FIGS. 10A-10D shows the amino acid sequences for human and mouse IL-17RA and human/mouse chimeric IL-17RA proteins.

FIG. 11 is a table summarizing the IL-17RA mAbs capacity to bind the various chimeric proteins. Shaded values denote where the IL-17RA mAbs lost binding to that particular chimera (n.d. means not determined).

FIG. 12 depicts the amino acid residues that were replaced with an arginine residue in SEQ ID NO:431.

FIG. 14 is a summary of the arginine scan, binning, and chimera data for various IL-17RA mAbs.

DETAILED DESCRIPTION OF THE INVENTION

Figure 1:
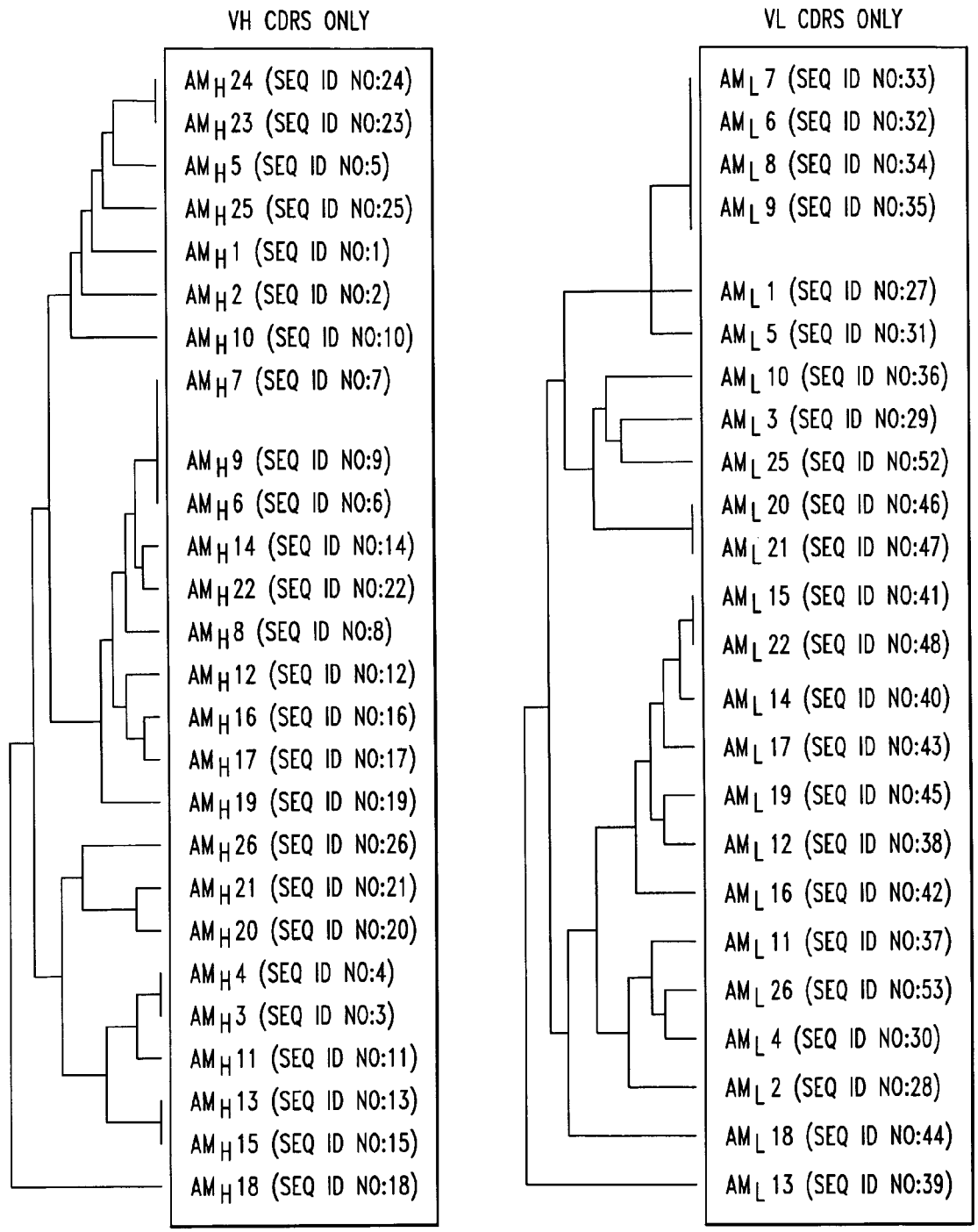
FIG. 1 shows a phylogenetic dentogram analysis of the CDRs (complementarity determining regions) of the variable heavy ($V_H$) and variable light ($V_L$) domains of various IL-17R antigen binding proteins (antibodies).

The section headings used herein are for organizational purposes only and are not to be construed as limiting the subject matter described.

Standard techniques may be used for recombinant DNA, oligonucleotide synthesis, tissue culture and transformation, protein purification etc. Enzymatic reactions and purification techniques may be performed according to the manufacturer's specifications or as commonly accomplished in the art or as described herein. The following procedures and techniques may be generally performed according to conventional methods well known in the art and as described in various general and more specific references that are cited and discussed throughout the specification. See, e.g., Sambrook et al., 2001,

*Molecular Cloning. A Laboratory Manual,* 3rd ed., Cold Spring Harbor Laboratory Press, Cold Spring Harbor, N.Y., which is incorporated herein by reference for any purpose. Unless specific definitions are provided, the nomenclature used in connection with, and the laboratory procedures and techniques of, analytical chemistry, organic chemistry, and medicinal and pharmaceutical chemistry described herein are those well known and commonly used in the art. Standard techniques may be used for chemical synthesis, chemical analyses, pharmaceutical preparation, formulation, and delivery and treatment of patients.

Aspects of the invention include, but are not limited to: Embodiment one: An isolated monoclonal antibody, or IL-17RA-binding fragment thereof, that specifically binds to IL-17RA and competes for binding with an antibody selected from the group consisting of:

A. an isolated antibody, or IL-17RA-binding fragment thereof, comprising
  a. a light chain variable domain sequence that is at least 80% identical to a light chain variable domain sequence of $AM_L2$, 3, 5, 9, 10, 12, 14-17, and 19-25 (SEQ ID NOs:28, 29, 31, 35, 36, 38, 40-43, and 45-53, respectively);
  b. a heavy chain variable domain sequence that is at least 80% identical to a heavy chain variable domain sequence of $AM_H2$, 3, 5, 9, 10, 12, 14-17, and 19-25 (SEQ ID NOs:2, 3, 5, 9, 10, 12, 14-17, and 19-25, respectively);
  c. the light chain variable domain of (a) and the heavy chain variable domain of (b); wherein said antibody specifically binds to human IL-17RA;

B. an isolated antibody, or IL-17RA-binding fragment thereof, comprising
  a. a light chain CDR1 (SEQ ID NO:188), CDR2 (SEQ ID NO:189), CDR3 (SEQ ID NO:190) and a heavy chain CDR1 (SEQ ID NO:110), CDR2 (SEQ ID NO:111), CDR3 (SEQ ID NO:112) of antibody AM-2;
  b. a light chain CDR1 (SEQ ID NO:191), CDR2 (SEQ ID NO:192), CDR3 (SEQ ID NO:193) and a heavy chain CDR1 (SEQ ID NO:113), CDR2 (SEQ ID NO:114), CDR3 (SEQ ID NO:115) of antibody AM-3;
  c. a light chain CDR1 (SEQ ID NO:197), CDR2 (SEQ ID NO:198), CDR3 (SEQ ID NO:199) and a heavy chain CDR1 (SEQ ID NO:119), CDR2 (SEQ ID NO:120), CDR3 (SEQ ID NO:121) of antibody AM-5;
  d. a light chain CDR1 (SEQ ID NO:209), CDR2 (SEQ ID NO:210), CDR3 (SEQ ID NO:211) and a heavy chain CDR1 (SEQ ID NO:131), CDR2 (SEQ ID NO:132), CDR3 (SEQ ID NO:133) of antibody AM-9;
  e. a light chain CDR1 (SEQ ID NO:212), CDR2 (SEQ ID NO:213), CDR3 (SEQ ID NO:214) and a heavy chain CDR1 (SEQ ID NO:134), CDR2 (SEQ ID NO:135), CDR3 (SEQ ID NO:136) of antibody AM-10;
  f. a light chain CDR1 (SEQ ID NO:218), CDR2 (SEQ ID NO:219), CDR3 (SEQ ID NO:220) and a heavy chain CDR1 (SEQ ID NO:140), CDR2 (SEQ ID NO:141), CDR3 (SEQ ID NO:142) of antibody AM-12;
  g. a light chain CDR1 (SEQ ID NO:224), CDR2 (SEQ ID NO:225), CDR3 (SEQ ID NO:226) and a heavy chain CDR1 (SEQ ID NO:146), CDR2 (SEQ ID NO:147), CDR3 (SEQ ID NO:148) of antibody AM-14;
  h. a light chain CDR1 (SEQ ID NO:227), CDR2 (SEQ ID NO:228), CDR3 (SEQ ID NO:229) and a heavy chain CDR1 (SEQ ID NO:149), CDR2 (SEQ ID NO:150), CDR3 (SEQ ID NO:151) of antibody AM-15;
  i. a light chain CDR1 (SEQ ID NO:230), CDR2 (SEQ ID NO:231), CDR3 (SEQ ID NO:232) and a heavy chain CDR1 (SEQ ID NO:152), CDR2 (SEQ ID NO:153), CDR3 (SEQ ID NO:154) of antibody AM-16;
  j. a light chain CDR1 (SEQ ID NO:233), CDR2 (SEQ ID NO:234), CDR3 (SEQ ID NO:235) and a heavy chain CDR1 (SEQ ID NO:155), CDR2 (SEQ ID NO:156), CDR3 (SEQ ID NO:157) of antibody AM-17;
  k. a light chain CDR1 (SEQ ID NO:239), CDR2 (SEQ ID NO:240), CDR3 (SEQ ID NO:241) and a heavy chain CDR1 (SEQ ID NO:161), CDR2 (SEQ ID NO:162), CDR3 (SEQ ID NO:163) of antibody AM-19;
  l. a light chain CDR1 (SEQ ID NO:242), CDR2 (SEQ ID NO:243), CDR3 (SEQ ID NO:244) and a heavy chain CDR1 (SEQ ID NO:164), CDR2 (SEQ ID NO:165), CDR3 (SEQ ID NO:166) of antibody AM-20;
  m. a light chain CDR1 (SEQ ID NO:245), CDR2 (SEQ ID NO:246), CDR3 (SEQ ID NO:247) and a heavy chain CDR1 (SEQ ID NO:167), CDR2 (SEQ ID NO:168), CDR3 (SEQ ID NO: 169) of antibody AM-21;
  n. a light chain CDR1 (SEQ ID NO:248), CDR2 (SEQ ID NO:249), CDR3 (SEQ ID NO:250) and a heavy chain CDR1 (SEQ ID NO:170), CDR2 (SEQ ID NO:171), CDR3 (SEQ ID NO:172) of antibody AM-22;
  o. a light chain CDR1 (SEQ ID NO:251), CDR2 (SEQ ID NO:252), CDR3 (SEQ ID NO:253) and a heavy chain CDR1 (SEQ ID NO:173), CDR2 (SEQ ID NO:174), CDR3 (SEQ ID NO:175) of antibody AM-23;
  p. a light chain CDR1 (SEQ ID NO:254), CDR2 (SEQ ID NO:255), CDR3 (SEQ ID NO:256) and a heavy chain CDR1 (SEQ ID NO:173), CDR2 (SEQ ID NO:174), CDR3 (SEQ ID NO:175) of antibody AM-23;
  q. a light chain CDR1 (SEQ ID NO:257), CDR2 (SEQ ID NO:258), CDR3 (SEQ ID NO:259) and a heavy chain CDR1 (SEQ ID NO:176), CDR2 (SEQ ID NO:177), CDR3 (SEQ ID NO:178) of antibody AM-24;
  r. a light chain CDR1 (SEQ ID NO:260), CDR2 (SEQ ID NO:261), CDR3 (SEQ ID NO:262) and a heavy chain CDR1 (SEQ ID NO:179), CDR2 (SEQ ID NO:180), CDR3 (SEQ ID NO:181) of antibody AM-25;
  wherein said antibody specifically binds to human IL-17RA; and C. an isolated antibody, or IL-17RA-binding fragment thereof, comprising
  a. a light chain variable domain and a heavy chain variable domain of $AM_L2/AM_H2$ (SEQ ID NO:28/SEQ ID NO:2);
  b. a light chain variable domain and a heavy chain variable domain of $AM_L3/AM_H3$ (SEQ ID NO:29/SEQ ID NO:3);
  c. a light chain variable domain and a heavy chain variable domain of $AM_L5/AM_H5$ (SEQ ID NO:31/SEQ ID NO:5);
  d. a light chain variable domain and a heavy chain variable domain of $AM_L9/AM_H9$ (SEQ ID NO:35/SEQ ID NO:9);

e. a light chain variable domain and a heavy chain variable domain of AM$_L$10/AM$_H$10 (SEQ ID NO:36/SEQ ID NO:10);
f. a light chain variable domain and a heavy chain variable domain of AM$_L$12/AM$_H$12 (SEQ ID NO:38/SEQ ID NO:12);
g. a light chain variable domain and a heavy chain variable domain of AM$_L$14/AM$_H$14 (SEQ ID NO:40/SEQ ID NO:14);
h. a light chain variable domain and a heavy chain variable domain of AM$_L$15/AM$_H$15 (SEQ ID NO:41/SEQ ID NO:15);
i. a light chain variable domain and a heavy chain variable domain of AM$_L$16/AM$_H$16 (SEQ ID NO:42/SEQ ID NO:16);
j. a light chain variable domain and a heavy chain variable domain of AM$_L$17/AM$_H$17 (SEQ ID NO:43/SEQ ID NO:17);
k. a light chain variable domain and a heavy chain variable domain of AM$_L$19/AM$_H$19 (SEQ ID NO:45/SEQ ID NO:19);
l. a light chain variable domain and a heavy chain variable domain of AM$_L$20/AM$_H$20 (SEQ ID NO:46/SEQ ID NO:20);
m. a light chain variable domain and a heavy chain variable domain of AM$_L$21/AM$_H$21 (SEQ ID NO:47/SEQ ID NO:21);
n. a light chain variable domain and a heavy chain variable domain of AM$_L$22/AM$_H$22 (SEQ ID NO:48/SEQ ID NO:22);
o. a light chain variable domain and a heavy chain variable domain of AM$_L$23/AM$_H$23 (SEQ ID NO:49 or SEQ ID NO:50/SEQ ID NO:23);
p. a light chain variable domain and a heavy chain variable domain of AM$_L$24/AM$_H$24 (SEQ ID NO:51/SEQ ID NO:24);
q. a light chain variable domain and a heavy chain variable domain of AM$_L$25/AM$_H$25 (SEQ ID NO:52/SEQ ID NO:25);
wherein said antibody specifically binds to human IL-17RA.

Embodiment two: the antibody of embodiment 1, wherein said antibody is selected from the group consisting of:
A. an isolated antibody, or IL-17RA-binding fragment thereof, comprising
    a. a light chain variable domain sequence that is at least 80% identical to a light chain variable domain sequence of AM$_L$9, 14, 16, 17, 19-23v2, and 26 (SEQ ID NOs:35, 40, 42, 43, 45-50, and 53, respectively);
    b. a heavy chain variable domain sequence that is at least 80% identical to a heavy chain variable domain sequence of AM$_H$9, 14, 16, 17, 19-23, and 26 (SEQ ID NOs:9, 14, 16, 17, 19-23, and 26, respectively);
    c. the light chain variable domain of (a) and the heavy chain variable domain of (b); wherein said antibody specifically binds to human IL-17RA;
B. an isolated antibody, or IL-17RA-binding fragment thereof, comprising
    a. a light chain CDR1 (SEQ ID NO:209), CDR2 (SEQ ID NO:210), CDR3 (SEQ ID NO:211) and a heavy chain CDR1 (SEQ ID NO:131), CDR2 (SEQ ID NO:132), CDR3 (SEQ ID NO:133) of antibody AM-9;
    b. a light chain CDR1 (SEQ ID NO:224), CDR2 (SEQ ID NO:225), CDR3 (SEQ ID NO:226) and a heavy chain CDR1 (SEQ ID NO:146), CDR2 (SEQ ID NO:147), CDR3 (SEQ ID NO:148) of antibody AM-14;
    c. a light chain CDR1 (SEQ ID NO:230), CDR2 (SEQ ID NO:231), CDR3 (SEQ ID NO:232) and a heavy chain CDR1 (SEQ ID NO:152), CDR2 (SEQ ID NO:153), CDR3 (SEQ ID NO:154) of antibody AM-16;
    d. a light chain CDR1 (SEQ ID NO:233), CDR2 (SEQ ID NO:234), CDR3 (SEQ ID NO:235) and a heavy chain CDR1 (SEQ ID NO:155), CDR2 (SEQ ID NO:156), CDR3 (SEQ ID NO:157) of antibody AM-17;
    e. a light chain CDR1 (SEQ ID NO:239), CDR2 (SEQ ID NO:240), CDR3 (SEQ ID NO:241) and a heavy chain CDR1 (SEQ ID NO:161), CDR2 (SEQ ID NO:162), CDR3 (SEQ ID NO:163) of antibody AM-19;
    f. a light chain CDR1 (SEQ ID NO:242), CDR2 (SEQ ID NO:243), CDR3 (SEQ ID NO:244) and a heavy chain CDR1 (SEQ ID NO:164), CDR2 (SEQ ID NO:165), CDR3 (SEQ ID NO:166) of antibody AM-20;
    g. a light chain CDR1 (SEQ ID NO:245), CDR2 (SEQ ID NO:246), CDR3 (SEQ ID NO:247) and a heavy chain CDR1 (SEQ ID NO:167), CDR2 (SEQ ID NO:168), CDR3 (SEQ ID NO:169) of antibody AM-21;
    h. a light chain CDR1 (SEQ ID NO:248), CDR2 (SEQ ID NO:249), CDR3 (SEQ ID NO:250) and a heavy chain CDR1 (SEQ ID NO:170), CDR2 (SEQ ID NO:171), CDR3 (SEQ ID NO:172) of antibody AM-22;
    i. a light chain CDR1 (SEQ ID NO:251), CDR2 (SEQ ID NO:252), CDR3 (SEQ ID NO:253) and a heavy chain CDR1 (SEQ ID NO:173), CDR2 (SEQ ID NO:174), CDR3 (SEQ ID NO:175) of antibody AM-23;
    j. a light chain CDR1 (SEQ ID NO:254), CDR2 (SEQ ID NO:255), CDR3 (SEQ ID NO:256) and a heavy chain CDR1 (SEQ ID NO:173), CDR2 (SEQ ID NO:174), CDR3 (SEQ ID NO:175) of antibody AM-23;
    k. a light chain variable domain and a heavy chain variable domain of AM$_L$26/AM$_H$26 (SEQ ID NO:53/SEQ ID NO:26);
    wherein said antibody specifically binds to human IL-17RA; and
C. an isolated antibody, or IL-17RA-binding fragment thereof, comprising
    a. a light chain variable domain and a heavy chain variable domain of AM$_L$9/AM$_H$9 (SEQ ID NO:35/SEQ ID NO:9);
    b. a light chain variable domain and a heavy chain variable domain of AM$_L$14/AM$_H$14 (SEQ ID NO:40/SEQ ID NO:14);
    c. a light chain variable domain and a heavy chain variable domain of AM$_L$16/AM$_H$16 (SEQ ID NO:42/SEQ ID NO:16);
    d. a light chain variable domain and a heavy chain variable domain of AM$_L$17/AM$_H$17 (SEQ ID NO:43/SEQ ID NO:17);
    e. a light chain variable domain and a heavy chain variable domain of AM$_L$19/AM$_H$19 (SEQ ID NO:45/SEQ ID NO:19);
    f. a light chain variable domain and a heavy chain variable domain of AM$_L$20/AM$_H$20 (SEQ ID NO:46/SEQ ID NO:20);

g. a light chain variable domain and a heavy chain variable domain of AM$_L$21/AM$_H$21 (SEQ ID NO:47/SEQ ID NO:21);
h. a light chain variable domain and a heavy chain variable domain of AM$_L$22/AM$_H$22 (SEQ ID NO:48/SEQ ID NO:22);
i. a light chain variable domain and a heavy chain variable domain of AM$_L$23/AM$_H$23 (SEQ ID NO:49 or SEQ ID NO:50/SEQ ID NO:23);
j. a light chain variable domain and a heavy chain variable domain of AM$_L$26/AM$_H$26 (SEQ ID NO:53/SEQ ID NO:26);
wherein said antibody specifically binds to human IL-17RA.

Embodiment three: the antibody of embodiment one, wherein said antibody selected from the group consisting of:
A. an isolated antibody, or IL-17RA-binding fragment thereof, comprising
 a. a light chain variable domain sequence that is at least 80% identical to a light chain variable domain sequence of AM$_L$12, 14, 16, 17, 19, and 22 (SEQ ID NOs:38, 40, 42, 43, 45, and 48 respectively);
 b. a heavy chain variable domain sequence that is at least 80% identical to a heavy chain variable domain sequence of AM$_H$12, 14, 16, 17, 19, and 22 (SEQ ID NOs:12, 14, 16, 17, 19, and 22, respectively);
 c. the light chain variable domain of (a) and the heavy chain variable domain of (b); wherein said antibody specifically binds to human IL-17RA;
B. an isolated antibody, or IL-17RA-binding fragment thereof, comprising
 a. a light chain CDR1 (SEQ ID NO:218), CDR2 (SEQ ID NO:219), CDR3 (SEQ ID NO:220) and a heavy chain CDR1 (SEQ ID NO:140), CDR2 (SEQ ID NO:141), CDR3 (SEQ ID NO:142) of antibody AM-12;
 b. a light chain CDR1 (SEQ ID NO:224), CDR2 (SEQ ID NO:225), CDR3 (SEQ ID NO:226) and a heavy chain CDR1 (SEQ ID NO:146), CDR2 (SEQ ID NO:147), CDR3 (SEQ ID NO:148) of antibody AM-14;
 c. a light chain CDR1 (SEQ ID NO:230), CDR2 (SEQ ID NO:231), CDR3 (SEQ ID NO:232) and a heavy chain CDR1 (SEQ ID NO:152), CDR2 (SEQ ID NO:153), CDR3 (SEQ ID NO:154) of antibody AM-16;
 d. a light chain CDR1 (SEQ ID NO:233), CDR2 (SEQ ID NO:234), CDR3 (SEQ ID NO:235) and a heavy chain CDR1 (SEQ ID NO:155), CDR2 (SEQ ID NO:156), CDR3 (SEQ ID NO:157) of antibody AM-17;
 e. a light chain CDR1 (SEQ ID NO:239), CDR2 (SEQ ID NO:240), CDR3 (SEQ ID NO:241) and a heavy chain CDR1 (SEQ ID NO:161), CDR2 (SEQ ID NO:162), CDR3 (SEQ ID NO:163) of antibody AM-19;
 f. a light chain CDR1 (SEQ ID NO:248), CDR2 (SEQ ID NO:249), CDR3 (SEQ ID NO:250) and a heavy chain CDR1 (SEQ ID NO:170), CDR2 (SEQ ID NO:171), CDR3 (SEQ ID NO:172) of antibody AM-22;
 wherein said antibody specifically binds to human IL-17RA; and
C. an isolated antibody, or IL-17RA-binding fragment thereof, comprising
 a. a light chain variable domain and a heavy chain variable domain of AM$_L$12/AM$_H$12 (SEQ ID NO:38/SEQ ID NO:12);
 b. a light chain variable domain and a heavy chain variable domain of AM$_L$14/AM$_H$14 (SEQ ID NO:40/SEQ ID NO:14);
 c. a light chain variable domain and a heavy chain variable domain of AM$_L$16/AM$_H$16 (SEQ ID NO:42/SEQ ID NO:16);
 d. a light chain variable domain and a heavy chain variable domain of AM$_L$17/AM$_H$17 (SEQ ID NO:43/SEQ ID NO:17);
 e. a light chain variable domain and a heavy chain variable domain of AM$_L$19/AM$_H$19 (SEQ ID NO:45/SEQ ID NO:19);
 c. a light chain variable domain and a heavy chain variable domain of AM$_L$22/AM$_H$22 (SEQ ID NO:48/SEQ ID NO:22);
 wherein said antibody specifically binds to human IL-17RA.

Embodiment four: the antibody of embodiment one, wherein said antibody is selected from the group consisting of:
A. an isolated antibody, or IL-17RA-binding fragment thereof, comprising
 a. a light chain variable domain sequence that is at least 80% identical to a light chain variable domain sequence SEQ ID NO: 40;
 b. a heavy chain variable domain sequence that is at least 80% identical to a heavy chain variable domain sequence of SEQ ID NO:14;
 c. the light chain variable domain of (a) and the heavy chain variable domain of (b); wherein said antibody specifically binds to human IL-17RA;
B. an isolated antibody, or IL-17RA-binding fragment thereof, comprising a light chain CDR1 (SEQ ID NO:224), CDR2 (SEQ ID NO:225), CDR3 (SEQ ID NO:226) and a heavy chain CDR1 (SEQ ID NO:146), CDR2 (SEQ ID NO:147), CDR3 (SEQ ID NO:148); wherein said antibody specifically binds to human IL-17RA; and
C. an isolated antibody, or IL-17RA-binding fragment thereof, comprising a light chain variable domain of SEQ ID NO:40 and a heavy chain variable domain SEQ ID NO:14; wherein said antibody specifically binds to human IL-17RA.

Embodiment five: the antibody of embodiment one, wherein said antibody is selected from the group consisting of:
a. a human antibody;
b. a humanized antibody;
c. a chimeric antibody;
d. a monoclonal antibody;
e. an antigen-binding antibody fragment;
f. a single chain antibody;
g. a diabody;
h. a triabody;
i. a tetrabody;
j. a Fab fragment;
k. a F(ab')2 fragment;
l. an IgD antibody;
m. an IgE antibody;
n. an IgM antibody;
o. an IgG1 antibody;
p. an IgG2 antibody;
q. an IgG3 antibody; and
r. an IgG4 antibody.

Embodiment six: the antibody of embodiment five, wherein said antibody inhibits human IL-17A from binding to human IL-17RA. Embodiment seven: the antibody of embodiment six, wherein said antibody inhibits human IL-17A and IL-17F from binding to human IL-17RA. Embodiment eight: the antibody of embodiment six, wherein said antibody inhibits human IL-17A or IL-17F from binding to human IL-17RA.

Embodiment nine: an isolated monoclonal antibody, or IL-17RA-binding fragment thereof, selected from the group consisting of:
 a) a monoclonal antibody that specifically binds human IL-17RA of SEQ ID NO:431 but does not specifically bind to a chimeric polypeptide consisting of SEQ ID NO:434;
 b) a monoclonal antibody that specifically binds human IL-17RA of SEQ ID NO:431 but does not specifically bind to a chimeric polypeptide consisting of SEQ ID NO:435; and
 c) a monoclonal antibody that specifically binds human IL-17RA of SEQ ID NO:431 but does not specifically bind to a chimeric polypeptide consisting of SEQ ID NO:436.

Embodiment ten: An isolated monoclonal antibody, or IL-17RA-binding fragment thereof, that specifically binds a neutralizing determinant selected from the group consisting of:
 a) a polypeptide comprising amino acids 75-96 of SEQ ID NO:431 of human IL-17RA;
 b) a polypeptide comprising amino acids 128-154 of SEQ ID NO:431 of human IL-17RA;
 c) a polypeptide comprising amino acids 176-197 of SEQ ID NO:431 of human IL-17RA;
 d) a polypeptide comprising amino acids 152-297 of SEQ ID NO:431 of human IL-17RA;
 e) a polypeptide comprising amino acids 220-284 of SEQ ID NO:431 of human IL-17RA;
 f) a polypeptide comprising amino acids 152-198 of SEQ ID NO:431 of human IL-17RA;
 g) a polypeptide comprising amino acids 152-186 of SEQ ID NO:431 of human IL-17RA;
 h) a polypeptide comprising amino acids 97-297 of SEQ ID NO:431 of human IL-17RA;
 i) a polypeptide comprising amino acids 138-270 of SEQ ID NO:431 of human IL-17RA;
 j) a polypeptide comprising amino acids 113-198 of SEQ ID NO:431 of human IL-17RA; and
 k) a polypeptide comprising amino acids 152-270 of SEQ ID NO:431 of human IL-17RA.

Embodiment eleven: an isolated monoclonal antibody, or IL-17RA-binding fragment thereof, that specifically binds human IL-17RA of SEQ ID NO:431, but does not specifically bind said IL-17RA having any one of the following amino acid substitutions E97R, E113R, S115R, H138R, D152R, D154R, E156R, K166R, Q176R, S177R, D184R, E186R, S198R, H215R, S220R, T228R, T235R, E241R, H243R, L270R, Q284R, or H297R of SEQ ID NO:431. Embodiment twelve: the antibody of embodiment eleven, wherein said antibody specifically binds human IL-17RA of SEQ ID NO:431, but does not specifically bind said IL-17RA having any one of the following amino acid substitutions D152R, D154R, E156R, D184R, E186R, or H297R of SEQ ID NO:431. Embodiment thirteen: the antibody of embodiment eleven, wherein said antibody specifically binds human IL-17RA of SEQ ID NO:431, but does not specifically bind said IL-17RA having the aspartic acid residue at position 152 of SEQ ID NO:431 substituted with an arginine. Embodiment fourteen: the antibody of embodiment eleven, wherein said antibody specifically binds an epitope defined by any one of amino acids D152, D154, E156, D184, E186, or H297 of SEQ ID NO:431.

Embodiment fifteen: the antibody of embodiment fourteen, wherein said antibody specifically binds an epitope defined by at least two of the following amino acids D152, D154, E156, D184, E186, or H297 of SEQ ID NO:431. Embodiment sixteen: the antibody of embodiment fourteen, wherein said antibody specifically binds an epitope defined by at least three of the following amino acids D152, D154, E156, D184, E186, or H297 of SEQ ID NO:431. Embodiment seventeen: the antibody of embodiment fourteen, wherein said antibody specifically binds an epitope defined by at least four of the following amino acids D152, D154, E156, D184, E186, or H297 of SEQ ID NO:431. Embodiment eighteen: the antibody of embodiment fourteen, wherein said antibody specifically binds an epitope defined by at least five of the following amino acids D152, D154, E156, D184, E186, or H297 of SEQ ID NO:431. Embodiment nineteen: the antibody of embodiment fourteen, wherein said antibody specifically binds an epitope defined by amino acids D152, D154, E156, D184, E186, H297 of SEQ ID NO:431.

Embodiment twenty: an isolated monoclonal antibody, or IL-17RA-binding fragment thereof, that specifically binds to IL-17RA and competes for binding with an antibody comprising:
 a. a heavy chain CDR1 comprising an amino acid sequence selected from the group consisting of:
  i. $X_1$YGIS, wherein $X_1$ is selected from the group consisting of R, S and G;
 b. a heavy chain CDR2 comprising an amino acid sequence selected from the group consisting of:
  i. WIS$X_1$Y$X_2$GNT$X_3$YAQ$X_4$$X_5$QG, wherein $X_1$ is selected from the group consisting of A, $X_2$ is selected from the group consisting of N, S and K, $X_3$ is selected from the group consisting of N and K, $X_4$ is selected from the group consisting of K and N, and $X_5$ is selected from the group consisting of L and F;
 c. a heavy chain CDR3 comprising an amino acid sequence selected from the group consisting of:
  i. $X_1$QL$X_2$$X_3$DY, wherein $X_1$ is selected from the group consisting of R and K, $X_2$ is selected from the group consisting of Y, V, and A, and $X_3$ is selected from the group consisting of F and L;
  ii. $X_1$QL$X_2$FDY, wherein $X_1$ is selected from the group consisting of R and K, and $X_2$ is selected from the group consisting of Y and V;
 d. a light chain CDR1 comprising an amino acid sequence selected from the group consisting of:
  i. RASQS$X_1$$X_2$$X_3$$X_4$LA, wherein $X_1$ is selected from the group consisting of V and I, $X_2$ is selected from the group consisting of I and S, $X_3$ is selected from the group consisting of S and T, $X_4$ is selected from the group consisting of N and S, and $X_5$ is selected from the group consisting of A and N;
  ii. RASQS$X_1$SSNLA, wherein $X_1$ is selected from the group consisting of V and I;
 e. a light chain CDR2 comprising an amino acid sequence selected from the group consisting of:
  i. $X_1$$X_2$STRA$X_3$, wherein $X_1$ is selected from the group consisting of G and D, $X_2$ is selected from the group consisting of A and T, and $X_3$ is selected from the group consisting of T and A;
  ii. $X_1$ASTRA$X_2$, wherein $X_1$ is selected from the group consisting of G and D, and $X_2$ is selected from the group consisting of A and T; and
 f. a light chain CDR3 comprising an amino acid sequence selected from the group consisting of:
  i. QQYD$X_1$WPLT, wherein $X_1$ is selected from the group consisting of N, T, and I.

Embodiment twenty one: the antibody of embodiment twenty, wherein said antibody comprises:
  a. a heavy chain CDR1 amino acid sequence comprising $X_1$YGIS, wherein $X_1$ is selected from the group consisting of R, S and G;
  b. a heavy chain CDR2 amino acid sequence comprising WIS$X_1$Y$X_2$GNT$X_3$YAQ$X_4X_5$QG, wherein $X_1$ is selected from the group consisting of A, $X_2$ is selected from the group consisting of N, S and K, $X_3$ is selected from the group consisting of N and K, $X_4$ is selected from the group consisting of K and N, and $X_5$ is selected from the group consisting of L and F;
  c. a heavy chain CDR3 amino acid sequence comprising $X_1$QL$X_2$FDY, wherein $X_1$ is selected from the group consisting of R and K, and $X_2$ is selected from the group consisting of Y and V;
  d. a light chain CDR1 amino acid sequence comprising RASQS$X_1$SSNLA, wherein $X_1$ is selected from the group consisting of V and I;
  e. a light chain CDR2 amino acid sequence comprising $X_1$ASTRA$X_2$, wherein $X_1$ is selected from the group consisting of G and D, and $X_2$ is selected from the group consisting of A and T; and
  f. a light chain CDR3 amino acid sequence comprising QQYD$X_1$WPLT, wherein $X_1$ is selected from the group consisting of N, T, and I.

Embodiment twenty two: the antibody of embodiment 20, wherein said antibody is selected from the group consisting of:
  a. a human antibody;
  b. a humanized antibody;
  c. a chimeric antibody;
  d. a monoclonal antibody;
  e. an antigen-binding antibody fragment;
  f. a single chain antibody;
  g. a diabody;
  h. a triabody;
  i. a tetrabody;
  j. a Fab fragment;
  k. a F(ab')2 fragment;
  l. an IgD antibody;
  m. an IgE antibody;
  n. an IgM antibody;
  o. an IgG1 antibody;
  p. an IgG2 antibody;
  q. an IgG3 antibody; and
  r. an IgG4 antibody.

Embodiment twenty three: the antibody of embodiment twenty two, wherein said antibody inhibits human IL-17A from binding to human IL-17RA. Embodiment twenty four: the antibody of embodiment twenty two, wherein said antibody inhibits human IL-17A and IL-17F from binding to human IL-17RA. Embodiment twenty five: the antibody of embodiment twenty two, wherein said antibody inhibits human IL-17A or IL-17F from binding to human IL-17RA.

IL-17A, IL-17F, and IL-17RA

"IL-17 receptor A" or "IL-17RA" (interchangeably used herein, as well as IL-17 receptor and IL-17R to refer to the same receptor) as used herein is meant the cell surface receptor and receptor complexes (such as but not limited to IL-17RA-IL-17RC complex), that bind IL-17A and IL-17F and as a result initiates a signal transduction pathway within the cell. IL-17RA proteins may also include variants. IL-17RA proteins may also include fragments, such as the extracellular domain that don't have all or part of the transmembrane and/or the intracellular domain, as well as fragments of the extracellular domain. The cloning, characterization, and preparation of IL-17RA are described, for example, in U.S. Pat. No. 6,072,033, which is incorporated herein by reference in its entirety. The amino acid sequence of the human IL-17RA is shown in SEQ ID NO:430. Soluble forms of huIL-17RA useful in the methods of the present invention include the extracellular domain or the mature form lacking the signal peptide or a fragment of the extracellular domain that retains the capacity to bind IL-17A and/or IL-17F, or a heteromeric version of IL-17A and/or IL-17F. Other forms of IL-17RA include muteins and variants that are at least between 70% and 99% homologous to the native IL-17RA of SEQ ID NO:430 and as described in U.S. Pat. No. 6,072,033, so long as the IL-17RA retains the capacity to bind IL-17A and/or IL-17F, or a heteromeric version of IL-17A and/or IL-17F. The term "IL-17RA" also includes post-translational modifications of the IL-17RA amino acid sequence. Post-translational modifications include, but is not limited to, N- and O-linked glycosylation.

IL-17RA Neutralizing Antibodies

Antibodies that specifically bind to human IL-17RA and inhibit IL-17A and/or IL-17F from binding and activating IL-17RA, or a heteromeric complex of IL-17RA and IL-17RC, are disclosed herein. Said antibodies specifically bind to human IL-17RA and may inhibit an IL-17A/IL-17F heteromer from binding and activating IL-17RA, or a heteromeric complex of IL-17RA and IL-17RC. Throughout the specification, when reference is made to inhibiting IL-17A and/or IL-17F, it is understood that this also includes inhibiting heteromers of IL-17A and IL-17F. Said antibodies that specifically bind to human IL-17RA may partially or fully inhibit IL-17RA from forming either a homomeric or heteromeric functional receptor complex, such as, but not limited to, an IL-17RA-IL-17RC complex. Said antibodies may partially or fully inhibit IL-17RA from forming either a homomeric or heteromeric functional receptor complex, such as, but not limited to IL-17RA/IL-17RC complex and do not necessarily inhibit IL-17A and/or IL-17F or an IL-17A/IL-17F heteromer from binding to IL-17RA or a IL-17RA heteromeric receptor complex.

Aspects of the invention include antibodies that compete for binding to human IL-17RA with the aforementioned IL-17RA antibodies. Aspects of the invention include antibodies that bind to the neutralizing determinants described herein. The antibodies that compete for binding to human IL-17RA with the IL-17RA antibodies described herein and the antibodies that bind to the neutralizing determinants described herein will also the same or similar functional attributes described in the previous paragraph. To be clear, antibodies that compete for binding with the IL-17RA neutralizing antibodies described herein, or antibodies that bind to the neutralizing determinants described herein are particular embodiments of the present invention.

The antibodies described herein specifically bind to IL-17RA. "Specifically binds" as used herein means that the antigen binding protein preferentially binds IL-17RA over other proteins. In some embodiments "specifically binds" means that the IL-17RA antigen binding proteins have a higher affinity for IL-17RA than for other proteins. For example, the equilibrium dissociation constant is $<10^{-7}$ to $10^{-11}$ M, or $<10^{-8}$ to $<10^{-10}$ M, or $<10^{-9}$ to $<10^{-10}$ M.

It is understood that when reference is made to the various embodiments of the IL-17RA antibodies, as well as antibodies that compete for binding to human IL-17RA with the IL-17RA neutralizing antibodies described herein, or antibodies that bind to the neutralizing determinants described herein, that it also encompasses IL-17RA-binding fragments thereof. An IL-17RA-binding fragment comprises any of the antibody fragments or domains described herein that retains the ability to specifically bind to IL-17RA. Said IL-17RA-binding fragments may be in any of the scaffolds described herein. Said IL-17RA-binding fragments also have the capacity to inhibit activation of the IL-17RA, as described throughout the specification.

One characteristic of the IL-17RA antibodies described herein, or antibodies that compete for binding with the IL-17RA antibodies described herein, or antibodies that bind to the neutralizing determinants described herein, is that they can inhibit binding of IL-17A and/or IL-17F to IL-17RA and one or more biological activities of, or mediated by, IL-17RA. Such antibodies are considered neutralizing antibodies because of their capacity to inhibit IL-17A and/or IL-17F from binding and causing IL-17RA signaling and/or biological activity. In this case, an IL-17RA neutralizing antibody or antibodies that compete for binding with the IL-17RA neutralizing antibodies described herein, or antibodies that bind to the neutralizing determinants described herein specifically binds IL-17RA and inhibits binding of IL-17A and/or IL-17F to IL-17RA from anywhere between 10 to 100%, such as by at least about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99% or more (for example by measuring binding in an in vitro competitive binding assay as described herein). An antibody that competes for binding, as described in the examples, is an antibody that inhibits the binding of another antibody to a specific target, which in this case is IL-17RA. Inhibition, in the antibody competition for binding, may be from anywhere between 10 to 100%, such as by at least about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99% or more (for example by measuring binding in an in vitro competitive binding assay as described herein). For example, IL-17RA antibodies or antibodies that compete for binding with the IL-17RA neutralizing antibodies described herein, or antibodies that bind to the neutralizing determinants described herein may be tested for neutralizing ability by testing them for the production of IL-6 in human foreskin fibroblast (HFF) assay (see for example Examples 4 and 5), or any suitable assay known in the art. Of course, this is just one example of an assay and any suitable assay known in the art may be employed to determine antibodies that fall within the scope of the claims. Further examples, for illustrative purposes only, of additional biological activity of IL-17RA (e.g., assay readouts) to test for inhibition of IL-17RA signaling and/or biological activity include in vitro and/or in vivo measurement of one or more of IL-8, CXCL1, CXCL2, GM-CSF, G-CSF, M-CSF, RANK-L, LIF, PGE2, IL-12, MMPs (such as but not limited to MMP3 and MMP9), GROα, NO, and/or C-telopeptide and the like.

Embodiments of antibodies that compete for binding to human IL-17RA with the IL-17RA neutralizing antibodies described herein, or antibodies that bind to the neutralizing determinants described herein comprise a scaffold structure, as variously define herein, with one or more complementarity determining regions (CDRs). Embodiments of antibodies that compete for binding with the IL-17RA neutralizing antibodies described herein or antibodies that bind to the neutralizing determinants described herein comprise a scaffold structure with one or more variable domains, either heavy or light.

Aspects of the invention include antibodies that compete for binding with the IL-17RA neutralizing antibodies, or antibodies that bind to the neutralizing determinants described herein, wherein said IL-17RA neutralizing antibodies comprise a light chain variable region selected from the group consisting of $AM_L1$ through $AM_L26$ (SEQ ID NO:27-53, respectively, with $AM_L23$ having two versions—SEQ ID NOs:49 and 50) and/or a heavy chain variable region selected from the group consisting of $AM_H1$ through $AM_H26$ (SEQ ID NO:1-26, respectively), as well as human IL-17R-binding fragments, derivatives, muteins, and variants thereof.

Aspects of the invention include antibodies that compete for binding with the IL-17RA neutralizing antibodies, or antibodies that bind to the neutralizing determinants described herein, wherein said IL-17RA neutralizing antibodies comprise variable light and variable heavy domains of: $AM_L1/AM_H1$ (SEQ ID NO:27/SEQ ID NO:1), $AM_L2/AM_H2$ (SEQ ID NO:28/SEQ ID NO:2), $AM_L3/AM_H3$ (SEQ ID NO:29/SEQ ID NO:3), $AM_L4/AM_H4$ (SEQ ID NO:30/SEQ ID NO:4), $AM_L5/AM_H5$ (SEQ ID NO:31/SEQ ID NO:5), $AM_L6/AM_H6$ (SEQ ID NO:32/SEQ ID NO:6), $AM_L7/AM_H7$ (SEQ ID NO:33/SEQ ID NO:7), $AM_L8/AM_H8$ (SEQ ID NO:34/SEQ ID NO:8), $AM_L9/AM_H9$ (SEQ ID NO:35/SEQ ID NO:9), $AM_L10/AM_H10$ (SEQ ID NO:36/SEQ ID NO:10), $AM_L11/AM_H11$ (SEQ ID NO:37/SEQ ID NO:11), $AM_L12/AM_H12$ (SEQ ID NO:38/SEQ ID NO:12), $AM_L13/AM_H13$ (SEQ ID NO:39/SEQ ID NO:13), $AM_L14/AM_H14$ (SEQ ID NO:40/SEQ ID NO:14), $AM_L15/AM_H15$ (SEQ ID NO:41/SEQ ID NO:15), $AM_L16/AM_H16$ (SEQ ID NO:42/SEQ ID NO:16), $AM_L17/AM_H17$ (SEQ ID NO:43/SEQ ID NO:17), $AM_L18/AM_H18$ (SEQ ID NO:44/SEQ ID NO:18), $AM_L19/AM_H19$ (SEQ ID NO:45/SEQ ID NO:19), $AM_L20/AM_H20$ (SEQ ID NO:46/SEQ ID NO:20), $AM_L21/AM_H21$ (SEQ ID NO:47/SEQ ID NO:21), $AM_L22/AM_H22$ (SEQ ID NO:48/SEQ ID NO:22), $AM_L23/AM_H23$ (SEQ ID NO:49 or SEQ ID NO:50/SEQ ID NO:23), $AM_L24/AM_H24$ (SEQ ID NO:51/SEQ ID NO:24), $AM_L25/AM_H25$ (SEQ ID NO:52/SEQ ID NO:25), $AM_L26/AM_H26$ (SEQ ID NO:53/SEQ ID NO:26), as well as IL-17RA-binding fragments thereof and combinations thereof.

Aspects of the invention include antibodies that compete for binding with the IL-17RA neutralizing antibodies, or antibodies that bind to the neutralizing determinants described herein, wherein said IL-17RA neutralizing antibodies comprise, wherein said antibodies specifically bind to human IL-17RA and inhibit IL-17A and/or IL-17F from binding and activating IL-17RA, or a heteromeric complex of IL-17RA and IL-17RC. Further embodiments include antibodies that specifically bind to human IL-17RA and inhibit an IL-17A/IL-17F heteromer from binding and activating IL-17RA, or a heteromeric complex of IL-17RA and IL-17RC. Further embodiments include antibodies that specifically bind to human IL-17RA and partially or fully inhibit IL-17RA from forming either a homomeric or heteromeric functional receptor complex, such as, but not limited to IL-17RA-IL-17RC complex. Further embodiments include antibodies that specifically bind to human IL-17RA and partially or fully inhibit IL-17RA from forming either a homomeric or heteromeric functional receptor complex, such as, but not limited to IL-17RA/IL-17RC complex and do not necessarily inhibit IL-17A and/or IL-17F or an IL-17A/IL-17F heteromer from binding to IL-17RA or a IL-17RA heteromeric receptor complex.

Aspects of the invention include antibodies that compete for binding with the IL-17RA neutralizing antibodies, or antibodies that bind to the neutralizing determinants described herein, wherein said IL-117RA neutralizing antibodies comprise at least one CDR from antibodies comprising $AM_L1/AM_H1$ (SEQ ID NO:27/SEQ ID NO:1), $AM_L2/AM_H2$ (SEQ ID NO:28/SEQ ID NO:2), $AM_L3/AM_H3$ (SEQ ID NO:29/SEQ ID NO:3), $AM_L4/AM_H4$ (SEQ ID NO:30/SEQ ID NO:4), $AM_L5/AM_H5$ (SEQ ID NO:31/SEQ ID NO:5), $AM_L6/AM_H6$ (SEQ ID NO:32/SEQ ID NO:6), $AM_L7/AM_H7$ (SEQ ID NO:33/SEQ ID NO:7), $AM_L8/AM_H8$ (SEQ ID NO:34/SEQ ID NO:8), $AM_L9/AM_H9$ (SEQ ID NO:35/SEQ ID NO:9), $AM_L10/AM_H10$ (SEQ ID NO:36/SEQ ID NO:10), $AM_L11/AM_H11$ (SEQ ID NO:37/SEQ ID NO:11), $AM_L12/AM_H12$ (SEQ ID NO:38/SEQ ID NO:12), $AM_L13/AM_H13$ (SEQ ID NO:39/SEQ ID NO:13), $AM_L14/AM_H14$ (SEQ ID NO:40/SEQ ID NO:14), $AM_L15/AM_H15$ (SEQ ID NO:41/SEQ ID NO:15), $AM_L16/AM_H16$ (SEQ ID NO:42/SEQ ID NO:16), $AM_L17/AM_H17$ (SEQ ID NO:43/SEQ ID NO:17), $AM_L18/AM_H18$ (SEQ ID NO:44/SEQ ID NO:18), $AM_L19/AM_H19$ (SEQ ID NO:45/SEQ ID NO:19), $AM_L20/AM_H20$ (SEQ ID NO:46/SEQ ID NO:20), $AM_L21/AM_H21$ (SEQ ID NO:47/SEQ ID NO:21), $AM_L22/AM_H22$ (SEQ ID NO:48/SEQ ID NO:22), $AM_L23/AM_H23$ (SEQ ID NO:49 or SEQ ID NO:50/SEQ ID NO:23), $AM_L24/AM_H24$ (SEQ ID NO:51/SEQ ID NO:24), $AM_L25/AM_H25$ (SEQ ID NO:52/SEQ ID NO:25), $AM_L26/AM_H26$ (SEQ ID NO:53/SEQ ID NO:26), as well as IL-17RA-binding fragments thereof and combinations thereof. See Table 1.

Aspects of the invention include antibodies that compete for binding with the IL-17RA neutralizing antibodies, or antibodies that bind to the neutralizing determinants described herein, wherein said IL-17RA neutralizing antibodies comprise at least one, two, or three H-CDR regions of any of SEQ ID NOs:107-184 and at least one, two, or three L-CDR region of any of SEQ ID NOs:185-265. See Table 1.

Examples 8-11 describe various studies elucidating domains on human IL-17RA that neutralizing IL-17RA mAbs bound. These domains are referred to as neutralizing determinants. A neutralizing determinant is a contiguous stretch of IL-17RA, that when mutated, negatively affects the binding of at least one of the neutralizing antibodies disclosed herein. A neutralizing determinant comprises at least one epitope. A neutralizing determinant may have primary, secondary, tertiary, and/or quarternary structural characteristics. A neutralizing antibody is any of the antibodies described herein that specifically binds human IL-17RA and inhibits binding of IL-17A and/or IL-17F and thereby inhibits IL-17RA signaling and/or biological activity. In addition, a neutralizing antibody encompasses antibodies that compete for binding to human IL-17RA with the IL-17RA antibodies described herein, as well as antibodies that bind to the neutralizing determinants described herein.

FIGS. 8A and 8B show that antibodies A: $AM_H11/AM_L11$, B: $AM_H4/AM_L4$, C: $AM_H8/AM_L8$, D: $AM_H7/AM_L7$, E: $AM_H6/AM_L6$, F: $AM_H10/AM_L10$, and G: $AM_H18/AM_L18$ competed with one another for binding to human IL-17RA and fell into a defined group (Bin 1). In general, antibodies I: $AM_H22/AM_L22$, J: $AM_H23/AM_L23$, K: $AM_H14/AM_L14$, L: $AM_H19/AM_L19$, M: $AM_H12/AM_L12$, N: $AM_H17/AM_L17$, O: $AM_H16/AM_L16$ competed with one another for binding to human IL-17RA and as a consequence fell into a different group (Bin 3). Generally speaking, the antibodies of Bin 1 did not compete with the antibodies of Bin 3. Antibody $AM_H1/AM_L1$ was unique in its competition pattern and formed Bin 2, but is most similar to Bin 3. Antibody P: $AM_H26/AM_L26$ formed Bin 4 and showed little cross-competition with any of the other antibodies, suggesting a neutralizing determinant unique to this antibody. Antibodies Q: $AM_H21/AM_L21$ and R: $AM_H20/AM_L20$ showed individually unique competition patterns, but with considerable similarities to Bin 3 antibodies, and formed Bins 5 and 6, respectively. This method identified groups of antibodies binding to different neutralizing determinants and provides evidence of several species within a subgenus of cross-competing antibodies.

Example 10 describes the use of human/mouse IL-17RA chimeric proteins to determine neutralizing determinants on human IL-17RA. FIG. 11 show that at least three neutralizing determinants were identified based on those regions affecting the binding of neutralizing IL-17RA antibodies, namely neutralizing determinant B spanning amino acids 75-96 of human IL-17RA (SEQ ID NO:431), neutralizing determinant C spanning amino acids 128-154 of human IL-17RA (SEQ ID NO:431), and neutralizing determinant D spanning amino acids 176-197 of human IL-17RA (SEQ ID NO:431). Neutralizing determinant B spanning amino acids 75-96 of human IL-17RA (SEQ ID NO:431) negatively affected the binding of neutralizing antibodies $AM_H1/AM_L1$ and $AM_H23/AM_L23$. Neutralizing determinant C spanning amino acids 128-154 of human IL-17RA (SEQ ID NO:431) negatively affected the binding of neutralizing antibodies $AM_H22/AM_L22$ and $AM_H23/AM_L23$. Neutralizing determinant D spanning amino acids 176-197 of human IL-17RA (SEQ ID NO:431) negatively affected the binding of neutralizing antibodies $AM_H1/AM_L1$, $AM_H22/AM_L22$, $AM_H14/AM_L14$, $AM_H19/AM_L19$, $AM_H23/AM_L23$, $AM_H21/AM_L21$, and $AM_H20/AM_L20$. Thus, neutralizing determinants B, C, and D are all considered neutralizing determinants.

Example 11 describes the use of arginine scan techniques to further elucidate the domains on human IL-17R that the IL-17RA neutralizing antibodies bound. A summary of the arginine scan, binning, and chimera data is presented in FIG. 11. The arginine scan methodology identified several neutralizing determinants: $AM_H18/AM_L18$ bound a domain spanning amino acids 220-284 of human IL-17RA (SEQ ID NO:431); $AM_H1/AM_L1$ bound a domain focused on amino acid residue 152 of human IL-17RA (SEQ ID NO:431); $AM_H22/AM_L22$ bound a domain spanning amino acids 152-198 of human IL-17RA (SEQ ID NO:431); $AM_H14/AM_L14$ bound a domain spanning amino acids 152-297 of human IL-17RA (SEQ ID NO:431); $AM_H19/AM_L19$ bound a domain spanning amino acids 152-186 of human IL-17RA (SEQ ID NO:431); $AM_H23/AM_L23$ bound a domain spanning amino acids 97-297 of human IL-17RA (SEQ ID NO:431); $AM_H26/AM_L26$ bound a domain spanning amino acids 138-270 of human IL-17RA (SEQ ID NO:431); $AM_H21/AM_L21$ bound a domain spanning amino acids 113-198 of human IL-17RA (SEQ ID NO:431); and $AM_H20/AM_L20$ bound a domain spanning amino acids 152-270 of human IL-17RA (SEQ ID NO:431). All of the residues shown in FIG. 14 have been shown to significantly reduce or essentially eliminate binding of a neutralizing human monoclonal antibody that specifically binds to human IL-17RA.

Embodiments include an antibody, or IL-17RA-binding fragment thereof, that specifically binds to IL-17RA and competes for binding with any one of antibodies $AM_H3/AM_L3$, $AM_H20/AM_L20$, $AM_H22/AM_L22$, $AM_H23/AM_L23$, $AM_H14/AM_L14$, $AM_H21/AM_L21$, $AM_H19/AM_L19$, $AM_H12/AM_L12$, $AM_H17/AM_L17$, or $AM_H16/AM_L16$, or any subset therein.

Embodiments include an antibody, or IL-17RA-binding fragment thereof, that specifically binds to IL-17R and competes for binding with any one of antibodies $AM_H22/AM_L22$, AM$_H$23/AM$_L$23, AM$_H$14/AM$_L$14, AM$_H$19/AM$_L$19, AM$_H$12/AM$_L$12, AM$_H$17/AM$_L$17, or AM$_H$16/AM$_L$16, or any subset therein.

Embodiments include an antibody, or IL-17RA-binding fragment thereof, that specifically binds human IL-17RA of SEQ ID NO:431 but does not specifically bind to a chimeric polypeptide consisting of SEQ ID NO:434. Embodiments include an antibody, or IL-17RA-binding fragment thereof, that specifically binds human IL-17RA of SEQ ID NO:431 but does not specifically bind to a chimeric polypeptide consisting of SEQ ID NO:435. Embodiments include an antibody, or IL-17RA-binding fragment thereof, that specifically binds human IL-17RA of SEQ ID NO:431 but does not specifically bind to a chimeric polypeptide consisting of SEQ ID NO:436.

Embodiments include an antibody, or IL-17RA-binding fragment thereof, that specifically binds a neutralizing determinant comprising amino acids 75-96 of SEQ ID NO:431 of human IL-17RA. Embodiments include an antibody, or IL-17RA-binding fragment thereof, that specifically binds a neutralizing determinant comprising amino acids 128-154 of SEQ ID NO:431 of human IL-17RA. Embodiments include an antibody, or IL-17RA-binding fragment thereof, that specifically binds a neutralizing determinant comprising amino acids 176-197 of SEQ ID NO:431 of human IL-17RA. Embodiments include an antibody, or IL-17RA-binding fragment thereof, that specifically binds a neutralizing determinant comprising amino acids 152-297 of SEQ ID NO:431 of human IL-17RA. Embodiments include an antibody, or IL-17RA-binding fragment thereof, that specifically binds a neutralizing determinant comprising amino acids 220-284 of SEQ ID NO:431 of human IL-17RA. Embodiments include an antibody, or IL-17RA-binding fragment thereof, that specifically binds a neutralizing determinant comprising amino acids 152-198 of SEQ ID NO:431 of human IL-17RA. Embodiments include an antibody, or IL-17RA-binding fragment thereof, that specifically binds a neutralizing determinant comprising amino acids 152-186 of SEQ ID NO:431 of human IL-17RA. Embodiments include an antibody, or IL-17RA-binding fragment thereof, that specifically binds a neutralizing determinant comprising amino acids 97-297 of SEQ ID NO:431 of human IL-17RA. Embodiments include an antibody, or IL-17RA-binding fragment thereof, that specifically binds a neutralizing determinant comprising amino acids 138-270 of SEQ ID NO:431 of human IL-17RA. Embodiments include an antibody, or IL-17RA-binding fragment thereof, that specifically binds a neutralizing determinant comprising amino acids 113-198 of SEQ ID NO:431 of human IL-17RA. Embodiments include an antibody, or IL-17RA-binding fragment thereof, that specifically binds a neutralizing determinant comprising amino acids 152-270 of SEQ ID NO:431 of human IL-17RA.

Further embodiments include an antibody, or IL-17RA-binding fragment thereof, that binds human IL-17RA of SEQ ID NO:431, but does not bind said IL-17RA having an amino acid substituted with arginine at any one of E97R, E113R, S115R, H138R, D152R, D154R, E156R, K166R, Q176R, S177R, D184R, E186R, S198R, H215R, S220R, T228R, T235R, E241R, H243R, L270R, Q284R, H297R of SEQ ID NO:431. Embodiments include an antibody, or IL-17RA-binding fragment thereof, that binds human IL-17RA of SEQ ID NO:431, but does not bind said IL-17RA having an amino acid substituted with arginine at any one of D152R, D154R, E156R, D184R, E186R, H297R of SEQ ID NO:431. Embodiments include an antibody, or IL-17RA-binding fragment thereof, that binds human IL-17RA of SEQ ID NO:431, but does not bind said IL-17RA having an amino acid substituted with arginine at D152R of SEQ ID NO:431.

Further embodiments include an antibody, or IL-17RA-binding fragment thereof, that specifically binds an epitope defined by any one of amino acids D152, D154, E156, D184, E186, H297 of SEQ ID NO:431. Embodiments include an antibody, or IL-17RA-binding fragment thereof, that specifically binds an epitope defined by at least two amino acids selected from the group consisting of: D152, D154, E156, D184, E186, H297 of SEQ ID NO:431. Embodiments include an antibody, or IL-17RA-binding fragment thereof, that specifically binds an epitope defined by at least three amino acids selected from the group consisting of: D152, D154, E156, D184, E186, H297 of SEQ ID NO:431. Embodiments include an antibody, or IL-17RA-binding fragment thereof, that specifically binds an epitope defined by at least four amino acids selected from the group consisting of: D152, D154, E156, D184, E186, H297 of SEQ ID NO:431. Embodiments include an antibody, or IL-17RA-binding fragment thereof, that specifically binds an epitope defined by at least five amino acids selected from the group consisting of: D152, D154, E156, D184, E186, H297 of SEQ ID NO:431. Embodiments include an antibody, or IL-17RA-binding fragment thereof, that specifically binds an epitope defined by amino acids D152, D154, E156, D184, E186, H297 of SEQ ID NO:431.

The antibodies of the invention include scaffold regions and one or more CDRs: between one and six CDRs (as typically do naturally occurring antibodies), for example, one heavy chain CDR1 ("H-CDR1"), and/or one heavy chain CDR2 ("H-CDR2"), and/or one heavy chain CDR3 ("H-CDR3"), and/or one light chain CDR1 ("L-CDR1"), and/or one light chain CDR2 ("L-CDR2"), and/or one light chain CDR3 ("L-CDR3").

The term "naturally occurring" as used throughout the specification in connection with biological materials such as peptides, polypeptides, nucleic acids, host cells, and the like, refers to materials which are found in nature. In naturally occurring antibodies, a H-CDR1 typically comprises about five (5) to about seven (7) amino acids, H-CDR2 typically comprises about sixteen (16) to about nineteen (19) amino acids, and H-CDR3 typically comprises about three (3) to about twenty five (25) amino acids. L-CDR1 typically comprises about ten (10) to about seventeen (17) amino acids, L-CDR2 typically comprises about seven (7) amino acids, and L-CDR3 typically comprises about seven (7) to about ten (10) amino acids. Specific CDRs of the IL-17RA neutralizing antibodies are provided in TABLE 1 and the Sequence Listing.

TABLE 1

| | | Corresponding Polynucleotide Sequence |
|---|---|---|
| Amino acid sequence of CDR 1 of AM$_H$1 Vh | SEQ ID NO:107 NYYWN | SEQ ID NO:266 |
| Amino acid sequence of CDR 2 of AM$_H$1 Vh | SEQ ID NO:108 DIYYSGSTNYNPS LKS | SEQ ID NO:267 |
| Amino acid sequence of CDR 3 of AM$_H$1 Vh | SEQ ID NO:109 DGELANYYGSGS YQFYYYGMDV | SEQ ID NO:268 |

TABLE 1-continued

| | | Corresponding Polynucleotide Sequence |
|---|---|---|
| Amino acid sequence of CDR 1 of AM$_H$2 Vh | SEQ ID NO:110 GYYWS | SEQ ID NO:269 |
| Amino acid sequence of CDR 2 of AM$_H$2 Vh | SEQ ID NO:111 EINHSGRTNYNPS LKS | SEQ ID NO:270 |
| Amino acid sequence of CDR 3 of AM$_H$2 Vh | SEQ ID NO:112 GPYYFDSSGYLYY YYGLDV | SEQ ID NO:271 |
| Amino acid sequence of CDR 1 of AM$_H$3 Vh | SEQ ID NO:113 SYGMH | SEQ ID NO:272 |
| Amino acid sequence of CDR 2 of AM$_H$3 Vh | SEQ ID NO:114 VIWYDGSNKHYA DSVKG | SEQ ID NO:273 |
| Amino acid sequence of CDR 3 of AM$_H$3 Vh | SEQ ID NO:115 DTGVY | SEQ ID NO:274 |
| Amino acid sequence of CDR 1 of AM$_H$4 Vh | SEQ ID NO:116 SYGMH | SEQ ID NO:275 |
| Amino acid sequence of CDR 2 of AM$_H$4 Vh | SEQ ID NO:117 VIWYDGSNKHYA DSVKG | SEQ ID NO:276 |
| Amino acid sequence of CDR 3 of AM$_H$4 Vh | SEQ ID NO:118 DTGVY | SEQ ID NO:277 |
| Amino acid sequence of CDR 1 of AM$_H$5 Vh | SEQ ID NO:119 SYYWS | SEQ ID NO:278 |
| Amino acid sequence of CDR 2 of AM$_H$5 Vh | SEQ ID NO:120 RIYRSGNTIYNPSL KS | SEQ ID NO:279 |
| Amino acid sequence of CDR 3 of AM$_H$5 Vh | SEQ ID NO:121 ENYSESSGLYYYY GMDV | SEQ ID NO:280 |
| Amino acid sequence of CDR 1 of AM$_H$6 Vh | SEQ ID NO:122 RYGIS | SEQ ID NO:281 |
| Amino acid sequence of CDR 2 of AM$_H$6 Vh | SEQ ID NO:123 WISAYNGNTNYA QKLQG | SEQ ID NO:282 |
| Amino acid sequence of CDR 3 of AM$_H$6 Vh | SEQ ID NO:124 RDYDILTGYYNGF DP | SEQ ID NO:283 |

TABLE 1-continued

| | | Corresponding Polynucleotide Sequence |
|---|---|---|
| Amino acid sequence of CDR 1 of AM$_H$7 Vh | SEQ ID NO:125 RYGIS | SEQ ID NO:284 |
| Amino acid sequence of CDR 2 of AM$_H$7 Vh | SEQ ID NO:126 WISAYNGNTNYA QKLQG | SEQ ID NO:285 |
| Amino acid sequence of CDR 3 of AM$_H$7 Vh | SEQ ID NO:127 RDYDILTGYYNGF DP | SEQ ID NO:286 |
| Amino acid sequence of CDR 1 of AM$_H$8 Vh | SEQ ID NO:128 GYGIS | SEQ ID NO:287 |
| Amino acid sequence of CDR 2 of AM$_H$8 Vh | SEQ ID NO:129 WISAYNGNTNYA QNLQG | SEQ ID NO:288 |
| Amino acid sequence of CDR 3 of AM$_H$8 Vh | SEQ ID NO:130 RDYDILTGYYNGF DP | SEQ ID NO:289 |
| Amino acid sequence of CDR 1 of AM$_H$9 Vh | SEQ ID NO:131 RYGIS | SEQ ID NO:290 |
| Amino acid sequence of CDR 2 of AM$_H$9 Vh | SEQ ID NO:132 WISAYNGNTNYA QKLQG | SEQ ID NO:291 |
| Amino acid sequence of CDR 3 of AM$_H$9 Vh | SEQ ID NO:133 RDYDILTGYYNGF DP | SEQ ID NO:292 |
| Amino acid sequence of CDR 1 of AM$_H$10 Vh | SEQ ID NO:134 SGGYYWS | SEQ ID NO:293 |
| Amino acid sequence of CDR 2 of AM$_H$10 Vh | SEQ ID NO:135 YIYFSGSAYYNPS LKS | SEQ ID NO:294 |
| Amino acid sequence of CDR 3 of AM$_H$10 Vh | SEQ ID NO:136 EYYDSSGYPDAFD I | SEQ ID NO:295 |
| Amino acid sequence of CDR 1 of AM$_H$11 Vh | SEQ ID NO:137 SYGMH | SEQ ID NO:296 |
| Amino acid sequence of CDR 2 of AM$_H$11 Vh | SEQ ID NO:138 VIWYDGSNKYYA DSVKG | SEQ ID NO:297 |
| Amino acid sequence of CDR 3 of AM$_H$11 Vh | SEQ ID NO:139 DTKDY | SEQ ID NO:298 |

TABLE 1-continued

| | | Corresponding Polynucleotide Sequence |
|---|---|---|
| Amino acid sequence of CDR 1 of AM$_H$12 Vh | SEQ ID NO:140 SYGIS | SEQ ID NO:299 |
| Amino acid sequence of CDR 2 of AM$_H$12 Vh | SEQ ID NO:141 WISTYKGNTNYAQKLQG | SEQ ID NO:300 |
| Amino acid sequence of CDR 3 of AM$_H$12 Vh | SEQ ID NO:142 KQLVFDY | SEQ ID NO:301 |
| Amino acid sequence of CDR 1 of AM$_H$13 Vh | SEQ ID NO:143 SYGMQ | SEQ ID NO:302 |
| Amino acid sequence of CDR 2 of AM$_H$13 Vh | SEQ ID NO:144 VIWYDGNKKYYADSVKG | SEQ ID NO:303 |
| Amino acid sequence of CDR 3 of AM$_H$13 Vh | SEQ ID NO:145 GRVRDYYYGMDV | SEQ ID NO:304 |
| Amino acid sequence of CDR 1 of AM$_H$14 Vh | SEQ ID NO:146 RYGIS | SEQ ID NO:305 |
| Amino acid sequence of CDR 2 of AM$_H$14 Vh | SEQ ID NO:147 WISTYSGNTNYAQKLQG | SEQ ID NO:306 |
| Amino acid sequence of CDR 3 of AM$_H$14 Vh | SEQ ID NO:148 RQLYFDY | SEQ ID NO:307 |
| Amino acid sequence of CDR 1 of AM$_H$15 Vh | SEQ ID NO:149 SYGMQ | SEQ ID NO:308 |
| Amino acid sequence of CDR 2 of AM$_H$15 Vh | SEQ ID NO:150 VIWYDGNKKYYADSVKG | SEQ ID NO:309 |
| Amino acid sequence of CDR 3 of AM$_H$15 Vh | SEQ ID NO:151 GRVRDYYYGMDV | SEQ ID NO:310 |
| Amino acid sequence of CDR 1 of AM$_H$16 Vh | SEQ ID NO:152 SYGIS | SEQ ID NO:311 |
| Amino acid sequence of CDR 2 of AM$_H$16 Vh | SEQ ID NO:153 WISAYNGNTKYAQKLQG | SEQ ID NO:312 |
| Amino acid sequence of CDR 3 of AM$_H$16 Vh | SEQ ID NO:154 KQLVFDY | SEQ ID NO:313 |

TABLE 1-continued

| | | Corresponding Polynucleotide Sequence |
|---|---|---|
| Amino acid sequence of CDR 1 of AM$_H$17 Vh | SEQ ID NO:155 SYGIS | SEQ ID NO:314 |
| Amino acid sequence of CDR 2 of AM$_H$17 Vh | SEQ ID NO:156 WISAYSGNTKYAQKLQG | SEQ ID NO:315 |
| Amino acid sequence of CDR 3 of AM$_H$17 Vh | SEQ ID NO:157 KQLVFDY | SEQ ID NO:316 |
| Amino acid sequence of CDR 1 of AM$_H$18 Vh | SEQ ID NO:158 DYYMH | SEQ ID NO:317 |
| Amino acid sequence of CDR 2 of AM$_H$18 Vh | SEQ ID NO:159 WMHPNSGGTDLAQRFQG | SEQ ID NO:318 |
| Amino acid sequence of CDR 3 of AM$_H$18 Vh | SEQ ID NO:160 GGYCSTLSCSFYWYFDL | SEQ ID NO:319 |
| Amino acid sequence of CDR 1 of AM$_H$19 Vh | SEQ ID NO:161 SYGIS | SEQ ID NO:320 |
| Amino acid sequence of CDR 2 of AM$_H$19 Vh | SEQ ID NO:162 WISAYSGNTKYAQKFQG | SEQ ID NO:321 |
| Amino acid sequence of CDR 3 of AM$_H$19 Vh | SEQ ID NO:163 RQLALDY | SEQ ID NO:322 |
| Amino acid sequence of CDR 1 of AM$_H$20 Vh | SEQ ID NO:164 SYSMN | SEQ ID NO:323 |
| Amino acid sequence of CDR 2 of AM$_H$20 Vh | SEQ ID NO:165 FISARSSTIYYADSVKG | SEQ ID NO:324 |
| Amino acid sequence of CDR 3 of AM$_H$20 Vh | SEQ ID NO:166 PKVGGGMDV | SEQ ID NO:325 |
| Amino acid sequence of CDR 1 of AM$_H$21 Vh | SEQ ID NO:167 SYSMN | SEQ ID NO:326 |
| Amino acid sequence of CDR 2 of AM$_H$21 Vh | SEQ ID NO:168 IISSRSSIIHYADSVKG | SEQ ID NO:327 |
| Amino acid sequence of CDR 3 of AM$_H$21 Vh | SEQ ID NO:169 PKVGGGMDV | SEQ ID NO:328 |

TABLE 1-continued

| | | Corresponding Polynucleotide Sequence |
|---|---|---|
| Amino acid sequence of CDR 1 of AM$_H$22 Vh | SEQ ID NO:170 RYGIS | SEQ ID NO:329 |
| Amino acid sequence of CDR 2 of AM$_H$22 Vh | SEQ ID NO:171 WISAYSGNTNYA QKLQG | SEQ ID NO:330 |
| Amino acid sequence of CDR 3 of AM$_H$22 Vh | SEQ ID NO:172 RQLYFDY | SEQ ID NO:331 |
| Amino acid sequence of CDR 1 of AM$_H$23 Vh | SEQ ID NO:173 SYYWS | SEQ ID NO:332 |
| Amino acid sequence of CDR 2 of AM$_H$23 Vh | SEQ ID NO:174 RIYPSGRTNYNPS LKS | SEQ ID NO:333 |
| Amino acid sequence of CDR 3 of AM$_H$23 Vh | SEQ ID NO:175 EAYELQLGLYYY YGMDV | SEQ ID NO:334 |
| Amino acid sequence of CDR 1 of AM$_H$24 Vh | SEQ ID NO:176 SYYWS | SEQ ID NO:335 |
| Amino acid sequence of CDR 2 of AM$_H$24 Vh | SEQ ID NO:177 RIYPSGRTNYNPS LKS | SEQ ID NO:336 |
| Amino acid sequence of CDR 3 of AM$_H$24 Vh | SEQ ID NO:178 EAYELQLGLYYY YGMDV | SEQ ID NO:337 |
| Amino acid sequence of CDR 1 of AM$_H$25 Vh | SEQ ID NO:179 SGGYYWS | SEQ ID NO:338 |
| Amino acid sequence of CDR 2 of AM$_H$25 Vh | SEQ ID NO:180 YSGNTYYNPSLRS | SEQ ID NO:339 |
| Amino acid sequence of CDR 3 of AM$_H$25 Vh | SEQ ID NO:181 EAGGNSAYYYGM DV | SEQ ID NO:340 |
| Amino acid sequence of CDR 1 of AM$_H$26 Vh | SEQ ID NO:182 DYYMS | SEQ ID NO:341 |
| Amino acid sequence of CDR 2 of AM$_H$26 Vh | SEQ ID NO:183 YISSSGSTIYYADS VKG | SEQ ID NO:342 |
| Amino acid sequence of CDR 3 of AM$_H$26 Vh | SEQ ID NO:184 DRTYYFGSGSYEG MDV | SEQ ID NO:343 |

TABLE 1-continued

| | | Corresponding Polynucleotide Sequence |
|---|---|---|
| Amino acid sequence of CDR 1 of AM$_L$1 Vl | SEQ ID NO:185 RASQGIRNDLG | SEQ ID NO:345 |
| Amino acid sequence of CDR 2 of AM$_L$1 Vl | SEQ ID NO:186 AASSLQS | SEQ ID NO:346 |
| Amino acid sequence of CDR 3 of AM$_L$1 Vl | SEQ ID NO:187 LQHNSNPFT | SEQ ID NO:347 |
| Amino acid sequence of CDR 1 of AM$_L$2 Vl | SEQ ID NO:188 RASQSVSRNLV | SEQ ID NO:348 |
| Amino acid sequence of CDR 2 of AM$_L$2 Vl | SEQ ID NO:189 GASTRAN | SEQ ID NO:349 |
| Amino acid sequence of CDR 3 of AM$_L$2 Vl | SEQ ID NO:190 QQYKSWRT | SEQ ID NO:350 |
| Amino acid sequence of CDR 1 of AM$_L$3 Vl | SEQ ID NO:191 RASQSISSYLN | SEQ ID NO:351 |
| Amino acid sequence of CDR 2 of AM$_L$3 Vl | SEQ ID NO:192 AASSLQS | SEQ ID NO:352 |
| Amino acid sequence of CDR 3 of AM$_L$3 Vl | SEQ ID NO:193 QQSYSTPFT | SEQ ID NO:353 |
| Amino acid sequence of CDR 1 of AM$_L$4 Vl | SEQ ID NO:194 RASQSVSRNLA | SEQ ID NO:354 |
| Amino acid sequence of CDR 2 of AM$_L$4 Vl | SEQ ID NO:195 GASTRAT | SEQ ID NO:355 |
| Amino acid sequence of CDR 3 of AM$_L$4 Vl | SEQ ID NO:196 QQYNNWPTWT | SEQ ID NO:356 |
| Amino acid sequence of CDR 1 of AM$_L$5 Vl | SEQ ID NO:197 RASQGIRNDLG | SEQ ID NO:357 |
| Amino acid sequence of CDR 2 of AM$_L$5 Vl | SEQ ID NO:198 AASSFQS | SEQ ID NO:358 |
| Amino acid sequence of CDR 3 of AM$_L$5 Vl | SEQ ID NO:199 LQHNSYPPT | SEQ ID NO:359 |

TABLE 1-continued

| | | Corresponding Polynucleotide Sequence |
|---|---|---|
| Amino acid sequence of CDR 1 of AM$_L$6 Vl | SEQ ID NO:200 RASQGIRNDLG | SEQ ID NO:360 |
| Amino acid sequence of CDR 2 of AM$_L$6 Vl | SEQ ID NO:201 AASSLQS | SEQ ID NO:361 |
| Amino acid sequence of CDR 3 of AM$_L$6 Vl | SEQ ID NO:202 LQHKSYPLT | SEQ ID NO:362 |
| Amino acid sequence of CDR 1 of AM$_L$7 Vl | SEQ ID NO:203 RASQGIRNDLG | SEQ ID NO:363 |
| Amino acid sequence of CDR 2 of AM$_L$7 Vl | SEQ ID NO:204 AASSLQS | SEQ ID NO:364 |
| Amino acid sequence of CDR 3 of AM$_L$7 Vl | SEQ ID NO:205 LQHKSYPLT | SEQ ID NO:365 |
| Amino acid sequence of CDR 1 of AM$_L$8 Vl | SEQ ID NO:206 RASQGIRNDLG | SEQ ID NO:366 |
| Amino acid sequence of CDR 2 of AM$_L$8 Vl | SEQ ID NO:207 AASSLQS | SEQ ID NO:367 |
| Amino acid sequence of CDR 3 of AM$_L$8 Vl | SEQ ID NO:208 LQHKSYPLT | SEQ ID NO:368 |
| Amino acid sequence of CDR 1 of AM$_L$9 Vl | SEQ ID NO:209 RASQGIRNDLG | SEQ ID NO:369 |
| Amino acid sequence of CDR 2 of AM$_L$9 Vl | SEQ ID NO:210 AASSLQS | SEQ ID NO:370 |
| Amino acid sequence of CDR 3 of AM$_L$9 Vl | SEQ ID NO:211 LQHKSYPLT | SEQ ID NO:371 |
| Amino acid sequence of CDR 1 of AM$_L$10 Vl | SEQ ID NO:212 RASQGIRSWLA | SEQ ID NO:372 |
| Amino acid sequence of CDR 2 of AM$_L$10 Vl | SEQ ID NO:213 AASSLQS | SEQ ID NO:373 |
| Amino acid sequence of CDR 3 of AM$_L$10 Vl | SEQ ID NO:214 QQANNFPRT | SEQ ID NO:374 |
| Amino acid sequence of CDR 1 of AM$_L$11 Vl | SEQ ID NO:215 RASQSVSSNLA | SEQ ID NO:375 |
| Amino acid sequence of CDR 2 of AM$_L$11 Vl | SEQ ID NO:216 GASTRAA | SEQ ID NO:376 |
| Amino acid sequence of CDR 3 of AM$_L$11 Vl | SEQ ID NO:217 QHYINWPKWT | SEQ ID NO:377 |
| Amino acid sequence of CDR 1 of AM$_L$12 Vl | SEQ ID NO:218 RASQSISSSLA | SEQ ID NO:378 |
| Amino acid sequence of CDR 2 of AM$_L$12 Vl | SEQ ID NO:219 GASTRAT | SEQ ID NO:379 |
| Amino acid sequence of CDR 3 of AM$_L$12 Vl | SEQ ID NO:220 QQYDNWPLT | SEQ ID NO:380 |
| Amino acid sequence of CDR 1 of AM$_L$13 Vl | SEQ ID NO:221 KSSQSLLHSDGKTYLY | SEQ ID NO:381 |
| Amino acid sequence of CDR 2 of AM$_L$13 Vl | SEQ ID NO:222 EVSTRFS | SEQ ID NO:382 |
| Amino acid sequence of CDR 3 of AM$_L$13 Vl | SEQ ID NO:223 MQSIQLPLT | SEQ ID NO:383 |
| Amino acid sequence of CDR 1 of AM$_L$14 Vl | SEQ ID NO:224 RASQSVSSNLA | SEQ ID NO:384 |
| Amino acid sequence of CDR 2 of AM$_L$14 Vl | SEQ ID NO:225 DASTRAT | SEQ ID NO:385 |
| Amino acid sequence of CDR 3 of AM$_L$14 Vl | SEQ ID NO:226 QQYDNWPLT | SEQ ID NO:386 |
| Amino acid sequence of CDR 1 of AM$_L$15 Vl | SEQ ID NO:227 RASQSVSSNLA | SEQ ID NO:387 |
| Amino acid sequence of CDR 2 of AM$_L$15 Vl | SEQ ID NO:228 DASTRAA | SEQ ID NO:388 |
| Amino acid sequence of CDR 3 of AM$_L$15 Vl | SEQ ID NO:229 QQYDNWPLT | SEQ ID NO:389 |

TABLE 1-continued

| | | Corresponding Polynucleotide Sequence |
|---|---|---|
| Amino acid sequence of CDR 1 of AM$_L$16 Vl | SEQ ID NO:230 RASQSISTSLA | SEQ ID NO:390 |
| Amino acid sequence of CDR 2 of AM$_L$16 Vl | SEQ ID NO:231 GTSTRAT | SEQ ID NO:391 |
| Amino acid sequence of CDR 3 of AM$_L$16 Vl | SEQ ID NO:232 QQYDIWPLT | SEQ ID NO:392 |
| Amino acid sequence of CDR 1 of AM$_L$17 Vl | SEQ ID NO:233 RASQSVSSNLA | SEQ ID NO:393 |
| Amino acid sequence of CDR 2 of AM$_L$17 Vl | SEQ ID NO:234 GASTRAT | SEQ ID NO:394 |
| Amino acid sequence of CDR 3 of AM$_L$17 Vl | SEQ ID NO:235 QQYDNWPLT | SEQ ID NO:395 |
| Amino acid sequence of CDR 1 of AM$_L$18 Vl | SEQ ID NO:236 KTSQSVLYSSKNKNFLA | SEQ ID NO:396 |
| Amino acid sequence of CDR 2 of AM$_L$18 Vl | SEQ ID NO:237 WASTRES | SEQ ID NO:397 |
| Amino acid sequence of CDR 3 of AM$_L$18 Vl | SEQ ID NO:238 QQYYSTPFT | SEQ ID NO:398 |
| Amino acid sequence of CDR 1 of AM$_L$19 Vl | SEQ ID NO:239 RASQSISSNLA | SEQ ID NO:399 |
| Amino acid sequence of CDR 2 of AM$_L$19 Vl | SEQ ID NO:240 GASTRAT | SEQ ID NO:400 |
| Amino acid sequence of CDR 3 of AM$_L$19 Vl | SEQ ID NO:241 QQYDTWPLT | SEQ ID NO:401 |
| Amino acid sequence of CDR 1 of AM$_L$20 Vl | SEQ ID NO:242 RASQGISNYLA | SEQ ID NO:402 |
| Amino acid sequence of CDR 2 of AM$_L$20 Vl | SEQ ID NO:243 AASTLQS | SEQ ID NO:403 |
| Amino acid sequence of CDR 3 of AM$_L$20 Vl | SEQ ID NO:244 QKYNRAPFT | SEQ ID NO:404 |
| Amino acid sequence of CDR 1 of AM$_L$21 Vl | SEQ ID NO:245 RASQGISNYLA | SEQ ID NO:405 |
| Amino acid sequence of CDR 2 of AM$_L$21 Vl | SEQ ID NO:246 AASTLQS | SEQ ID NO:406 |
| Amino acid sequence of CDR 3 of AM$_L$21 Vl | SEQ ID NO:247 QKYNRAPFT | SEQ ID NO:407 |
| Amino acid sequence of CDR 1 of AM$_L$22 Vl | SEQ ID NO:248 RASQSVSSNLA | SEQ ID NO:408 |
| Amino acid sequence of CDR 2 of AM$_L$22 Vl | SEQ ID NO:249 DASTRAA | SEQ ID NO:409 |
| Amino acid sequence of CDR 3 of AM$_L$22 Vl | SEQ ID NO:250 QQYDNWPLT | SEQ ID NO:410 |
| Amino acid sequence of CDR 1 of AM$_L$23 Vl version 1 | SEQ ID NO:251 RASQGIINDLG | SEQ ID NO:411 |
| Amino acid sequence of CDR 2 of AM$_L$23 Vl version 1 | SEQ ID NO:252 AASSLQS | SEQ ID NO:412 |
| Amino acid sequence of CDR 3 of AM$_L$23 Vl version 1 | SEQ ID NO:253 LQHNSYPPT | SEQ ID NO:413 |
| Amino acid sequence of CDR 1 of AM$_L$23 Vl version 2 | SEQ ID NO:254 RSSQSLVYSDGHTCLN | SEQ ID NO:414 |
| Amino acid sequence of CDR 2 of AM$_L$23 Vl version 2 | SEQ ID NO:255 KVSNWDS | SEQ ID NO:415 |
| Amino acid sequence of CDR 3 of AM$_L$23 Vl version 2 | SEQ ID NO:256 MQGTHWPLCS | SEQ ID NO:416 |
| Amino acid sequence of CDR 1 of AM$_L$24 Vl | SEQ ID NO:257 RSSQSLVYSDGHTCLN | SEQ ID NO:417 |
| Amino acid sequence of CDR 2 of AM$_L$24 Vl | SEQ ID NO:258 KVSNWDS | SEQ ID NO:418 |

TABLE 1-continued

| | | Corresponding Polynucleotide Sequence |
|---|---|---|
| Amino acid sequence of CDR 3 of AM$_L$24 V1 | SEQ ID NO:259 MQGTHWPLCS | SEQ ID NO:419 |
| Amino acid sequence of CDR 1 of AM$_L$25 V1 | SEQ ID NO:260 RASQAISIYLA | SEQ ID NO:420 |
| Amino acid sequence of CDR 2 of AM$_L$25 V1 | SEQ ID NO:261 AASSLQS | SEQ ID NO:421 |
| Amino acid sequence of CDR 3 of AM$_L$25 V1 | SEQ ID NO:262 QQYSSYPRT | SEQ ID NO:422 |
| Amino acid sequence of CDR 1 of AM$_L$26 V1 | SEQ ID NO:263 RASQSVYSNLA | SEQ ID NO:423 |
| Amino acid sequence of CDR 2 of AM$_L$26 V1 | SEQ ID NO:264 GASTRAT | SEQ ID NO:424 |
| Amino acid sequence of CDR 3 of AM$_L$26 V1 | SEQ ID NO:265 QQYYNWPWT | SEQ ID NO:425 |

As used herein, the term "antibody" refers to the various forms of monomeric or multimeric proteins comprising one or more polypeptide chains that specifically binds to an antigen, as variously described herein. In certain embodiments, antibodies are produced by recombinant DNA techniques. In additional embodiments, antibodies are produced by enzymatic or chemical cleavage of naturally occurring antibodies. In another aspect, the antibody is selected from the group consisting of: a) a human antibody; b) a humanized antibody; c) a chimeric antibody; d) a monoclonal antibody; e) a polyclonal antibody; f) a recombinant antibody; g) an antigen-binding antibody fragment; h) a single chain antibody; i) a diabody; j) a triabody; k) a tetrabody; l) a Fab fragment; m) a F(ab')$_2$ fragment; n) an IgD antibody; o) an IgE antibody; p) an IgM antibody; q) an IgA antibody; r) an IgG1 antibody; s) an IgG2 antibody; t) an IgG3 antibody; and u) an IgG4 antibody.

Traditional antibody structural units typically comprise a tetramer. Each tetramer is typically composed of two identical pairs of polypeptide chains, each pair having one "light" (typically having a molecular weight of about 25 kDa) and one "heavy" chain (typically having a molecular weight of about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa and lambda light chains. Heavy chains are classified as mu, delta, gamma, alpha, or epsilon, and define the antibody's isotype as IgM, IgD, IgG, IgA, and IgE, respectively. IgG has several subclasses, including, but not limited to, IgG1, IgG2, IgG3, and IgG4. IgM has subclasses, including, but not limited to, IgM1 and IgM2. Embodiments of the invention include all such classes of antibodies that incorporate the variable domains or the CDRs of the antigen binding proteins, as described herein.

The general structure and properties of CDRs within naturally occurring antibodies have been described in the art. Briefly, in a traditional antibody scaffold, the CDRs are embedded within a framework in the heavy and light chain variable region where they constitute the regions largely responsible for antigen binding and recognition. A variable region comprises at least three heavy or light chain CDRs (Kabat et al., 1991, *Sequences of Proteins of Immunological Interest*, Public Health Service N.I.H., Bethesda, Md.; see also Chothia and Lesk, 1987, *J. Mol. Biol.* 196:901-917; Chothia et al., 1989, *Nature* 342: 877-883), within a framework region (designated framework regions 1-4, FR1, FR2, FR3, and FR4, by Kabat et al., 1991; see also Chothia and Lesk, 1987, supra). The CDRs provided by the present invention, however, may not only be used to define the antigen binding domain of a traditional antibody structure, but may be embedded in a variety of other scaffold structures, as described herein.

Antibodies of the invention can comprise any constant region known in the art. The light chain constant region can be, for example, a kappa- or lambda-type light chain constant region, e.g., a human kappa- or lambda-type light chain constant region. The heavy chain constant region can be, for example, an alpha-, delta-, epsilon-, gamma-, or mu-type heavy chain constant regions, e.g., a human alpha-, delta-, epsilon-, gamma-, or mu-type heavy chain constant region. In one embodiment, the light or heavy chain constant region is a fragment, derivative, variant, or mutein of a naturally occurring constant region.

The CDRs of the invention also include consensus sequences derived from groups of related monoclonal antibodies. The antibodies may be related by both sequence homology and function, as shown in the Examples. As described herein, a "consensus sequence" refers to amino acid sequences having conserved amino acids common among a number of sequences and variable amino acids that vary within given amino acid sequences. The CDR consensus sequences of the invention include CDRs corresponding to each of H-CDR1, H-CDR2, H-CDR3, L-CDR1, L-CDR2 and L-CDR3.

Consensus sequences were determined using standard phylogenic analyses of the CDRs corresponding to the VH (i.e., Variable Heavy, etc.) & VL of anti-IL-17RA antibodies. Two different approaches were employed. In a first approach, the consensus sequences were determined by keeping the CDRs contiguous within the same sequence corresponding to a VH or VL. In a second approach, the consensus sequences were determined by aligning the various types of CDRs, i.e., H-CDR1, H-CDR2, H-CDR3, L-CDR1, L-CDR2 and L-CDR3 sequences of the IL-17RA antigen binding proteins disclosed herein independently.

In the first approach, briefly, amino acid sequences corresponding to the entire variable domains of either VH or VL were converted to FASTA formatting for ease in processing comparative alignments and inferring phylogenies. Next, framework regions of these sequences were replaced with an artificial linker sequence (GGGAAAGGGAAA, SEQ ID NO:448) so that examination of the CDRs alone could be performed without introducing any amino acid position weighting bias due to coincident events (e.g., such as unrelated antibodies that serendipitously share a common germline framework heritage) whilst still keeping CDRs contiguous within the same sequence corresponding to a VH or VL. VH or VL sequences of this format were then subjected to sequence similarity alignment interrogation using a program that employs a standard ClutalW-like algorithm (see, Thompson et al., 1994, *Nucleic Acids Res.* 22:4673-4680). A gap creation penalty of 8.0 was employed along with a gap extension penalty of 2.0. This program likewise generated phylograms (phylogenic tree illustrations) based on sequence similarity alignments using either UPGMA (unweighted pair group method using arithmetic averages) or Neighbor-Joining methods (see, Saitou and Nei, 1987, *Molecular Biology and Evolution* 4:406-425) to construct & illustrate similarity and distinction of sequence groups via branch length comparison and grouping. Both methods produced similar results but UPGMA-derived trees were ultimately used as the method employs a simpler and more conservative set of assumptions. UPGMA-derived trees are shown in FIG. 1 where similar groups of sequences were defined as having fewer than 15 substitutions per 100 residues (see legend in tree illustrations for scale) amongst individual sequences within the group and were used to define consensus sequence collections. The original sequence alignments generated were employed to empirically examine and document the occurrence of amino acids tolerated at each position with a consensus group and are shown in FIGS. 2 and 3. Consensus sequences for the groups of similar sequences within each CDR were then prepared. Amino acids that varied within each group were noted with the notation $X_n$ within each consensus sequence.

The H-CDR1 consensus sequences include amino acid sequences selected from the group consisting of: a) $X_1YGIS$ (SEQ ID NO:453), wherein $X_1$ is selected from the group consisting of R, S and G; b) $X_1YX_2MX_3$ (SEQ ID NO:454), wherein $X_1$ is selected from the group consisting of D and S; $X_2$ is selected from the group consisting of Y and S; and $X_3$ is selected from the group consisting of S and N; and c) $SYGMX_1$ (SEQ ID NO:455), wherein $X_1$ is selected from the group consisting of H and Q;

The H-CDR2 consensus sequences include amino acid sequence selected from the group consisting of: a) $WISX_1YX_2GNTX_3YAQX_4X_5QG$ (SEQ ID NO:456), wherein $X_1$ is selected from the group consisting of A and T; $X_2$ is selected from the group consisting of N, S and K; $X_3$ is selected from the group consisting of N and K; $X_4$ is selected from the group consisting of K and N; and $X_5$ is selected from the group consisting of L and F; b) $X_1X_2SX_3X_4X_5SX_6IX_7YADSVKG$ (SEQ ID NO:457), wherein $X_1$ is selected from the group consisting of Y, I and F; $X_2$ is selected from the group consisting of I and S; $X_3$ is selected from the group consisting of S and A; $X_4$ is selected from the group consisting of S and R; and $X_5$ is selected from the group consisting of G, S and no amino acid; $X_6$ is selected from the group consisting of T and I; and $X_7$ is selected from the group consisting of Y and H; and c) $VIWYDGX_1X_2KX_3YADSVKG$ (SEQ ID NO:458), wherein $X_1$ is selected from the group consisting of S and N; $X_2$ is selected from the group consisting of N and K; and $X_3$ is selected from the group consisting of H and Y.

The H-CDR3 consensus sequences include amino acid sequence selected from the group consisting of: a) $X_1QLX_2X_3DY$ (SEQ ID NO:459), wherein $X_1$ is selected from the group consisting of Y, V, and A, and $X_3$ is selected from the group consisting of F and L and b) $X_1QLX_2FDY$ (SEQ ID NO:460), wherein $X_1$ is selected from the group consisting of R and K, and $X_2$ is selected from the group consisting of Y and V.

The L-CDR1 consensus sequence includes an amino acid sequence selected from the group consisting of: a) $RASQX_1IX_2X_3X_4LX_5$ (SEQ ID NO:461), wherein $X_1$ is selected from the group consisting of G, S, and A; $X_2$ is selected from the group consisting of R and S; $X_3$ is selected from the group consisting of S, I and N; $X_4$ is selected from the group consisting of W and Y; and $X_5$ is selected from the group consisting of A and N; b) $RASQSX_1X_2X_3X_4LA$ (SEQ ID NO:462), wherein $X_1$ is selected from the group consisting of V and I; $X_2$ is selected from the group consisting of I and S; $X_3$ is selected from the group consisting of S and T; $X_4$ is selected from the group consisting of N and S; and $X_5$ is selected from the group consisting of A and N; and c) $RASQSVX_1X_2NLX_3$ (SEQ ID NO:463), wherein $X_1$ is selected from the group consisting of Y and S; $X_2$ is selected from the group consisting of S and R; and $X_3$ is selected from the group consisting of A and V.

The L-CDR2 consensus sequence includes an amino acid sequence selected from the group consisting of: a) $AASSX_1QS$ (SEQ ID NO:464), wherein $X_1$ is selected from the group consisting of L and F; b) $AASX_1LQS$ (SEQ ID NO:465), wherein $X_1$ is selected from the group consisting of S and T; c) $X_1X_2STRAX_3$, wherein $X_1$ is selected from the group consisting of G and D; $X_2$ is selected from the group consisting of A and T; and $X_3$ is selected from the group consisting of T and A; and d) $GASTRAX_1$ (SEQ ID NO:466), wherein $X_1$ is selected from the group consisting of A, T and N.

The L-CDR3 consensus sequences include amino acid sequences selected from the group consisting of: a) $LQHX_1SYX_2X_3T$ (SEQ ID NO:467), wherein $X_1$ is selected from the group consisting of K and N; $X_2$ is selected from the group consisting of P and N; and $X_3$ is selected from the group consisting of L, F and P; b) $QX_1X_2X_3X_4X_5PX_6T$ (SEQ ID NO:468), wherein $X_1$ is selected from the group consisting of Q and K; $X_2$ is selected from the group consisting of A, S and Y; $X_3$ is selected from the group consisting of N, Y and S; $X_4$ is selected from the group consisting of N, S and R; $X_5$ is selected from the group consisting of F, T, Y and A; and $X_6$ is selected from the group consisting of R and F; c) $QQYDX_1WPLT$ (SEQ ID NO:469), wherein $X_1$ is selected from the group consisting of N, T and I; and d) $QX_1YX_2X_3WX_4X_5X_6T$ (SEQ ID NO:470), wherein $X_1$ is selected from the group consisting of H and Q; $X_2$ is selected from the group consisting of I, Y, N and K; $X_3$ is selected from the group consisting of N and S; $X_4$ is selected from the group consisting of P and R; $X_5$ is selected from the group consisting of K, no amino acid, and T; and $X_6$ is selected from the group consisting of W and no amino acid.

FIGS. 1, 2, 3, 8A, 8B, 11, and 14 show that a clear pattern in the data exists between sequence homology in the CDR domains and the antibodies function, as determined by cross-competition binning and the determination of where the antibodies bound to IL-17RA. Thus, a structure/function relation for classes of antibodies has been established for the IL-17RA antibodies provided herein.

In a second approach CDR consensus sequences were determined for each separate CDR, independently of their contiguous context within the same sequence corresponding to a VH or VL. In this approach the consensus sequences were determined by aligning each H-CDR1, H-CDR2, H-CDR3, L-CDR1, L-CDR2, and L-CDR3 in groups, i.e., by aligning the individual H-CDR1 sequences of the IL-17RA antigen binding proteins disclosed herein to determine a H-CDR1 consensus sequence, by aligning the individual H-CDR2 sequences of the IL-17RA antigen binding proteins disclosed herein to determine a H-CDR2 consensus sequence, by aligning the individual H-CDR3 sequences of the IL-17RA antigen binding proteins disclosed herein to determine a H-CDR3 consensus sequence, by aligning the individual L-CDR1 sequences of the IL-17RA antigen binding proteins disclosed herein to determine a L-CDR1 consensus sequence, by aligning the individual L-CDR2 sequences of the IL-17RA antigen binding proteins disclosed herein to determine a L-CDR2 consensus sequence, and by aligning the individual L-CDR3 sequences of the IL-17RA antigen binding proteins disclosed herein to determine a L-CDR3 consensus sequence. Similarities between sequences within each individual CDR sequences were identified. Consensus sequences for the groups of similar sequences within each CDR were then prepared. Amino acids that varied within each group were noted with the notation $X_n$ within each consensus sequence.

Within light and heavy chains, the variable and constant regions are joined by a "J" region of about twelve (12) or more amino acids, with the heavy chain also including a "D" region of about ten (10) more amino acids. See, generally, Paul, W., ed., 1989, Fundamental Immunology Ch. 7, 2nd ed. Raven Press, N.Y. The variable regions of each light/heavy chain pair form the antibody binding site. Scaffolds of the invention include such regions.

Some naturally occurring antibodies, for example found in camels and llamas, are dimers consisting of two heavy chain and include no light chains. Muldermans et al., 2001, *J. Biotechnol.* 74:277-302; Desmyter et al., 2001, *J. Biol. Chem.* 276:26285-26290. Crystallographic studies of a camel antibody have revealed that the CDR3 regions form a surface that interacts with the antigen and thus is critical for antigen binding like in the more typical tetrameric antibodies. The invention encompasses dimeric antibodies consisting of two heavy chains, or fragments thereof, that can bind to and/or inhibit the biological activity of IL-17RA.

The variable regions of the heavy and light chains typically exhibit the same general structure of relatively conserved framework regions (FR) joined by three hypervariable regions, i.e., the complementarity determining regions or CDRs. The CDRs are the hypervariable regions of an antibody (or antigen binding protein, as outlined herein), that are responsible for antigen recognition and binding. The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with the definitions of Kabat Sequences of Proteins of Immunological Interest. Chothia et al., 1987, *J. Mol. Biol.* 196:901-917; Chothia et al., 1989, *Nature* 342:878-883. Scaffolds of the invention include such regions.

CDRs constitute the major surface contact points for antigen binding. See, e.g., Chothia and Lesk, 1987, *J. Mol. Biol.* 196:901-917. Further, CDR3 of the light chain and, especially, CDR3 of the heavy chain may constitute the most important determinants in antigen binding within the light and heavy chain variable regions. See, e.g., Chothia and Lesk, 1987, supra; Desiderio et al., 2001, *J. Mol. Biol.* 310:603-615; Xu and Davis, 2000, *Immunity* 13:37-45; Desmyter et al., 2001, *J. Biol. Chem.* 276:26285-26290; and Muyldermans, 2001, *J. Biotechnol.* 74:277-302. In some antibodies, the heavy chain CDR3 appears to constitute the major area of contact between the antigen and the antibody. Desmyter et al., 2001, supra. In vitro selection schemes in which CDR3 alone is varied can be used to vary the binding properties of an antibody. Muyldermans, 2001, supra; Desiderio et al. 2001, supra.

Naturally occurring antibodies typically include a signal sequence, which directs the antibody into the cellular pathway for protein secretion and which is not present in the mature antibody. A polynucleotide encoding an antibody of the invention may encode a naturally occurring signal sequence or a heterologous signal sequence as described below.

In some embodiments, however, the scaffold components can be a mixture from different species. As such, if the antigen binding protein is an antibody, such antibody may be a chimeric antibody and/or a humanized antibody. In general, both "chimeric antibodies" and "humanized antibodies" refer to antibodies that combine regions from more than one species. For example, "chimeric antibodies" traditionally comprise variable region(s) from a mouse (or rat, in some cases) and the constant region(s) from a human.

"Humanized antibodies" generally refer to non-human antibodies that have had the variable-domain framework regions swapped for sequences found in human antibodies. Generally, in a humanized antibody, the entire antibody, except the CDRs, is encoded by a polynucleotide of human origin or is identical to such an antibody except within its CDRs. The CDRs, some or all of which are encoded by nucleic acids originating in a non-human organism, are grafted into the beta-sheet framework of a human antibody variable region to create an antibody, the specificity of which is determined by the engrafted CDRs. The creation of such antibodies is described in, e.g., WO 92/11018, Jones, 1986, *Nature* 321:522-525, Verhoeyen et al., 1988, *Science* 239: 1534-1536. Humanized antibodies can also be generated using mice with a genetically engineered immune system. Roque et al., 2004, *Biotechnol. Prog.* 20:639-654. In the present invention, the identified CDRs are human, and thus both humanized and chimeric antibodies in this context include some non-human CDRs; for example, humanized antibodies may be generated that comprise the CDRH3 and CDRL3 regions, with one or more of the other CDR regions being of a different special origin.

In one embodiment, the antibodies of the invention are a multispecific antibody, and notably a bispecific antibody, also sometimes referred to as "diabodies". These are antibodies that bind to two (or more) different antigens. Diabodies can be manufactured in a variety of ways known in the art (Holliger and Winter, 1993, *Current Opinion Biotechnol.* 4:446-449), e.g., prepared chemically or from hybrid hybridomas.

In one embodiment, the antibody of the invention is a minibody. Minibodies are minimized antibody-like proteins comprising a scFv joined to a CH3 domain. Hu et al., 1996, *Cancer Res.* 56:3055-3061. In one embodiment, the antibody of the invention is a domain antibody; see, for example U.S. Pat. No. 6,248,516. Domain antibodies (dAbs) are functional binding domains of antibodies, corresponding to the variable regions of either the heavy (VH) or light (VL) chains of human antibodies dABs have a molecular weight of approximately 13 kDa, or less than one-tenth the size of a full antibody. dABs are well expressed in a variety of hosts including bacterial, yeast, and mammalian cell systems. In addition, dAbs are highly stable and retain activity even after being subjected to harsh conditions, such as freeze-drying or heat denaturation. See, for example, U.S. Pat. Nos. 6,291,158; 6,582,915; 6,593,081; 6,172,197; US Serial No. 2004/0110941; European Patent 0368684; U.S. Pat. No. 6,696,245, WO04/058821, WO04/003019 and WO03/002609.

In one embodiment, the antibody of the invention is an antibody fragment that retains binding specificity to IL-17RA. In various embodiments, the antibody fragments comprise, but are not limited to, a F(ab), F(ab'), F(ab')2, Fv, or a single chain Fv fragments. At a minimum, an antibody, as meant herein, comprises a polypeptide that can bind specifically to IL-17RA comprising all or part of a light or heavy chain variable region, such as one or more CDRs.

Further examples of IL-17RA-binding antibody fragments (to be clear, IL-17RA-binding antibody fragments that either compete for binding to human IL-17RA with at least one of the IL-17RA neutralizing antibodies described herein, or bind to one or more of the neutralizing determinants on IL-17RA described herein) include, but are not limited to, (i) the Fab fragment consisting of VL, VH, CL and CH1 domains, (ii) the Fd fragment consisting of the VH and CH1 domains, (iii) the Fv fragment consisting of the VL and VH domains of a single antibody; (iv) the dAb fragment (Ward et al., 1989, Nature 341:544-546) which consists of a single variable, (v) isolated CDR regions, (vi) F(ab')$_2$ fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al., 1988, Science 242:423-426, Huston et al., 1988, Proc. Natl. Acad. Sci. U.S.A. 85:5879-5883), (viii) bispecific single chain Fv dimers (PCT/US92/09965) and (ix) "diabodies" or "triabodies", multivalent or multispecific fragments constructed by gene fusion (Tomlinson et. al., 2000, Methods Enzymol. 326:461-479; WO94/13804; Holliger et al., 1993, Proc. Natl. Acad. Sci. U.S.A. 90:6444-6448). The antibody fragments may be modified. For example, the molecules may be stabilized by the incorporation of disulphide bridges linking the VH and VL domains (Reiter et al., 1996, Nature Biotech. 14:1239-1245). Aspects of the invention include embodiments wherein the non-CDR components of these fragments are human sequences.

In one embodiment, the antibody of the invention is a fully human antibody. In this embodiment, as outlined above, specific structures comprise complete heavy and light chains depicted comprising the CDR regions. Additional embodiments utilize one or more of the CDRs of the invention, with the other CDRs, framework regions, J and D regions, constant regions, etc., coming from other human antibodies. For example, the CDRs of the invention can replace the CDRs of any number of human antibodies, particularly commercially relevant antibodies Single chain antibodies may be formed by linking heavy and light chain variable domain (Fv region) fragments via an amino acid bridge (short peptide linker), resulting in a single polypeptide chain. Such single-chain Fvs (scFvs) have been prepared by fusing DNA encoding a peptide linker between DNAs encoding the two variable domain polypeptides ($V_L$ and $V_H$). The resulting polypeptides can fold back on themselves to form antigen-binding monomers, or they can form multimers (e.g., dimers, trimers, or tetramers), depending on the length of a flexible linker between the two variable domains (Kortt et al., 1997, Prot. Eng. 10:423; Kortt et al., 2001, Biomol. Eng. 18:95-108). By combining different $V_L$ and $V_H$-comprising polypeptides, one can form multimeric scFvs that bind to different epitopes (Kriangkum et al., 2001, Biomol. Eng. 18:31-40). Techniques developed for the production of single chain antibodies include those described in U.S. Pat. No. 4,946,778; Bird, 1988, Science 242:423; Huston et al., 1988, Proc. Natl. Acad. Sci. USA 85:5879; Ward et al., 1989, Nature 334:544, de Graaf et al., 2002, Methods Mol Biol. 178:379-87.

In one embodiment, the antibodies that compete for binding to human IL-17RA with the IL-17RA neutralizing antibodies described herein, or antibodies that bind to the neutralizing determinants described herein may be an antibody fusion protein (sometimes referred to herein as an "antibody conjugate"). The conjugate partner can be proteinaceous or non-proteinaceous; the latter generally being generated using functional groups on the antigen binding protein (see the discussion on covalent modifications of the antigen binding proteins) and on the conjugate partner. For example linkers are known in the art; for example, homo- or hetero-bifunctional linkers as are well known (see, 1994 Pierce Chemical Company catalog, technical section on cross-linkers, pages 155-200, incorporated herein by reference).

In one embodiment, the antibodies that compete for binding to human IL-17RA with the IL-17RA neutralizing antibodies described herein, or antibodies that hind to the neutralizing determinants described herein may be an antibody analog, sometimes referred to as "synthetic antibodies." For example, a variety of recent work utilizes either alternative protein scaffolds or artificial scaffolds with grafted CDRs. Such scaffolds include, but are not limited to, mutations introduced to stabilize the three-dimensional structure of the binding protein as well as wholly synthetic scaffolds consisting for example of biocompatible polymers. See, for example, Korndorfer et al., 2003, Proteins: Structure, Function, and Bioinformatics, Volume 53, Issue 1:121-129. Roque et al., 2004, Biotechnol. Prog. 20:639-654. In addition, peptide antibody mimetics ("PAMs") can be used, as well as work based on antibody mimetics utilizing fibronectin components as a scaffold. As it is known in the art, a number of different programs can be used to identify the degree of sequence identity or similarity a protein or nucleic acid has to a known sequence.

By "protein," as used herein, is meant at least two covalently attached amino acids, which includes proteins, polypeptides, oligopeptides and peptides. In some embodiments, the two or more covalently attached amino acids are attached by a peptide bond. The protein may be made up of naturally occurring amino acids and peptide bonds, for example when the protein is made recombinantly using expression systems and host cells, as outlined below. Alternatively, the protein may include synthetic amino acids (e.g., homophenylalanine, citrulline, ornithine, and norleucine), or peptidomimetic structures, i.e., "peptide or protein analogs", such as peptoids (see, Simon et al., 1992, Proc. Natl. Acad. Sci. U.S.A. 89:9367, incorporated by reference herein), which can be resistant to proteases or other physiological and/or storage conditions. Such synthetic amino acids may be incorporated in particular when the antigen binding protein is synthesized in vitro by conventional methods well known in the art. In addition, any combination of peptidomimetic, synthetic and naturally occurring residues/structures can be used. "Amino acid" also includes imino acid residues such as proline and hydroxyproline. The amino acid "R group" or "side chain" may be in either the (L)- or the (S)-configuration. In a specific embodiment, the amino acids are in the (L)- or (S)-configuration.

In some embodiments, the antigen binding proteins of the invention are isolated proteins or substantially pure proteins. An "isolated" protein is unaccompanied by at least some of the material with which it is normally associated in its natural state, for example constituting at least about 5%, or at least about 50% by weight of the total protein in a given sample. It is understood that the isolated protein may constitute from 5 to 99.9% by weight of the total protein content depending on the circumstances. For example, the protein may be made at a significantly higher concentration through the use of an inducible promoter or high expression promoter, such that the protein is made at increased concentration levels. The definition includes the production of an antigen binding protein in a wide variety of organisms and/or host cells that are known in the art.

For amino acid sequences, sequence identity and/or similarity is determined by using standard techniques known in the art, including, but not limited to, the local sequence identity algorithm of Smith and Waterman, 1981, *Adv. Appl. Math.* 2:482, the sequence identity alignment algorithm of Needleman and Wunsch, 1970, *J. Mol. Biol.* 48:443, the search for similarity method of Pearson and Lipman, 1988, *Proc. Nat. Acad. Sci. U.S.A.* 85:2444, computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., 1984, *Nucl. Acid Res.* 12:387-395, preferably using the default settings, or by inspection. Preferably, percent identity is calculated by FastDB based upon the following parameters: mismatch penalty of 1; gap penalty of 1; gap size penalty of 0.33; and joining penalty of 30, "Current Methods in Sequence Comparison and Analysis," Macromolecule Sequencing and Synthesis, Selected Methods and Applications, pp 127-149 (1988), Alan R. Liss, Inc. An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, 1987, *J. Mol. Evol.* 35:351-360; the method is similar to that described by Higgins and Sharp, 1989, *CABIOS* 5:151-153. Useful PILEUP parameters including a default gap weight of 3.00, a default gap length weight of 0.10, and weighted end gaps.

Another example of a useful algorithm is the BLAST algorithm, described in: Altschul et al., 1990, *J. Mol. Biol.* 215: 403-410; Altschul et al., 1997, *Nucleic Acids Res.* 25:3389-3402; and Karin et al., 1993, *Proc. Natl. Acad. Sci. U.S.A.* 90:5873-5787. A particularly useful BLAST program is the WU-BLAST-2 program which was obtained from Altschul et al., 1996, *Methods in Enzymology* 266:460-480. WU-BLAST-2 uses several search parameters, most of which are set to the default values. The adjustable parameters are set with the following values: overlap span=1, overlap fraction=0.125, word threshold (T)=II. The HSP S and HSP S2 parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul et al., 1993, *Nucl. Acids Res.* 25:3389-3402. Gapped BLAST uses BLOSUM-62 substitution scores; threshold T parameter set to 9; the two-hit method to trigger ungapped extensions, charges gap lengths of k a cost of 10+k; $X_u$ set to 16, and $X_g$ set to 40 for database search stage and to 67 for the output stage of the algorithms. Gapped alignments are triggered by a score corresponding to about 22 bits.

Amino acid substitutions are typically of single residues; insertions usually will be on the order of from about one (1) to about twenty (20) amino acid residues, although considerably larger insertions may be tolerated. Deletions range from about one (1) to about twenty (20) amino acid residues, although in some cases deletions may be much larger.

Substitutions, deletions, insertions or any combination thereof may be used to arrive at a final derivative or variant. Generally these changes are done on a few amino acids to minimize the alteration of the molecule, particularly the immunogenicity and specificity of the antigen binding protein. However, larger changes may be tolerated in certain circumstances. Conservative substitutions are generally made in accordance with the following chart depicted as TABLE 2.

TABLE 2

| Original Residue | Exemplary Substitutions |
| --- | --- |
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Substantial changes in function or immunological identity are made by selecting substitutions that are less conservative than those shown in TABLE 2. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine.

The variants typically exhibit the same qualitative biological activity and will elicit the same immune response as the naturally-occurring analogue, although variants also are selected to modify the characteristics of the antigen binding protein proteins as needed. Alternatively, the variant may be designed such that the biological activity of the antigen binding protein is altered. For example, glycosylation sites may be altered or removed as discussed herein.

Antibodies that compete for binding to human IL-17RA with the IL-17RA neutralizing antibodies described herein, or antibodies that bind to the neutralizing determinants described herein may comprise oligomers that contain one or more antibody polypeptides. Oligomers may be in the form of covalently-linked or non-covalently-linked dimers, trimers, or higher oligomers. Oligomers comprising two or more IL-17RA antibody polypeptides are contemplated for use, with one example being a homodimer. Other oligomers include heterodimers, homotrimers, heterotrimers, homotetramers, heterotetramers, etc. Such oligomers may be joined via covalent or non-covalent interactions between peptide moieties fused to the IL-17RA antibody polypeptides. Such peptides may be peptide linkers (spacers), or peptides that have the property of promoting oligomerization. Leucine zippers and certain polypeptides derived from antibodies are among the peptides that can promote oligomerization of IL-17RA antibody polypeptides attached thereto, as described in more detail below.

In one embodiment, an oligomer is prepared using polypeptides derived from immunoglobulins. Preparation of fusion proteins comprising certain heterologous polypeptides fused to various portions of antibody-derived polypeptides (including the Fc domain) has been described, e.g., by Ashkenazi et al., 1991, PNAS USA 88:10535; Byrn et al., 1990, Nature 344:677; and Hollenbaugh et al., 1992 "Construction of Immunoglobulin Fusion Proteins", in *Current Protocols in Immunology*, Suppl. 4, pages 10.19.1-10.19.11.

One embodiment is directed to a dimer comprising two fusion proteins created by fusing an IL-17RA binding fragment of an IL-17RA antibody to the Fc region of an antibody. The dimer can be made by, for example, inserting a gene fusion encoding the fusion protein into an appropriate expression vector, expressing the gene fusion in host cells transformed with the recombinant expression vector, and allowing the expressed fusion protein to assemble much like antibody molecules, whereupon interchain disulfide bonds form between the Fc moieties to yield the dimer.

The term "Fc polypeptide" as used herein includes native and mutein forms of polypeptides derived from the Fc region of an antibody. Truncated forms of such polypeptides containing the hinge region that promotes dimerization also are included. Fusion proteins comprising Fc moieties (and oligomers formed therefrom) offer the advantage of facile purification by affinity chromatography over Protein A or Protein G columns.

One suitable Fc polypeptide, described in PCT application WO 93/10151 (hereby incorporated by reference), is a single chain polypeptide extending from the N-terminal hinge region to the native C-terminus of the Fc region of a human IgG antibody. Another useful Fc polypeptide is the Fc mutein described in U.S. Pat. No. 5,457,035 and in Baum et al., 1994, *EMBO J.* 13:3992-4001. The amino acid sequence of this mutein is identical to that of the native Fc sequence presented in WO 93/10151, except that amino acid 19 has been changed from Leu to Ala, amino acid 20 has been changed from Leu to Glu, and amino acid 22 has been changed from Gly to Ala. The mutein exhibits reduced affinity for Fc receptors.

Use of Antibodies that Compete for Binding with the IL-17RA Antibodies, or Antibodies that Bind IL-17RA Neutralizing Determinants for Diagnostic and Therapeutic Purposes Antibodies that compete for binding to human IL-17RA with the IL-17RA neutralizing antibodies described herein, or antibodies that bind to the neutralizing determinants described herein can be used in diagnostic assays, e.g., binding assays to detect and/or quantify IL-17RA expressed in a tissue or cell. Said antibodies may be used in research to further investigate the role of IL-17RA in disease. Said antibodies may be used to further investigate the role of IL-17RA in forming homomeric and/or heteromeric receptor complexes and the role of said complexes in disease. Said antibodies may be used to further investigate the role of IL-17RA activation to homomeric and/or heteromeric IL-17 ligand complexes. Said antibodies may be used to further investigate the role of IL-17RA activation to homomeric mid/or heteromeric IL-17 ligand complexes and how said homomeric and/or heteromeric IL-17 ligand complexes relate to disease.

The IL-17RA neutralizing antibodies and antibodies that compete for binding to human IL-17RA with the IL-17RA neutralizing antibodies described herein, or antibodies that bind to the neutralizing determinants described herein can be used for the prevention or treatment of diseases or conditions associated with the IL-17A and/or IL-17F activity. A disease or condition associated with IL-17A and/or IL-17F means any disease, condition, or pathology whose onset in a patient is caused or exacerbated by the interaction of IL-17A and/or IL-17F with IL-17RA. The severity of the disease, condition, or pathology can also be increased or decreased by the modulating the interaction of IL-17A and/or IL-17F with IL-17RA or a heterologous complex comprising IL-17RA and IL-17RC.

Antibodies that compete for binding with the IL-17RA neutralizing antibodies described herein or antibodies that bind to the neutralizing determinants described herein may be used to reduce IL-17RA activity. Antibodies that compete for binding with the IL-17RA neutralizing antibodies described herein or antibodies that bind to the neutralizing determinants described herein may be used to inhibit binding and/or signaling of IL-17A and/or IL-17F to IL-17RA. In certain embodiments, the antibodies that compete for binding with the IL-17RA neutralizing antibodies described herein or antibodies that hind to the neutralizing determinants described herein inhibits binding and/or signaling of IL-17A and IL-17F to IL-17RA. In additional embodiments, the antibodies that compete for binding with the IL-17RA neutralizing antibodies described herein or antibodies that bind to the neutralizing determinants described herein inhibits binding and/or signaling of IL-17A but not IL-17F to IL-17RA. In other embodiments, the antibodies that compete for binding with the IL-17RA neutralizing antibodies described herein or antibodies that bind to the neutralizing determinants described herein inhibits binding and/or signaling of IL-17F and not IL-17A to IL-17RA. The antibodies that compete for binding with the IL-17RA neutralizing antibodies described herein or antibodies that bind to the neutralizing determinants described herein may be used in treating the consequences, symptoms, and/or the pathology associated with IL-17RA activity. The antibodies that compete for binding with the IL-17RA neutralizing antibodies described herein or antibodies that hind to the neutralizing determinants described herein may be used to inhibit the production of one or more of an inflammatory cytokine, chemokine, matrix metalloproteinase, or other molecule associated with IL-17RA activation. The antibodies that compete for binding with the IL-17RA neutralizing antibodies described herein or antibodies that bind to the neutralizing determinants described herein may be used in methods of inhibiting production of molecules such as but is not limited to: IL-6, IL-8, CXCL1, CXCL2, GM-CSF, G-CSF, M-CSF, IL-1β, TNFα, RANK-L, LIF, PGE2, IL-12, MMPs (such as but not limited to MMP3 and MMP9), GROα, NO, and/or C-telopeptide and the like, comprising administering an antigen binding protein. The antibodies that compete for binding with the IL-17RA neutralizing antibodies described herein or antibodies that bind to the neutralizing determinants described herein inhibit proinflammatory and proautoimmune immune responses and may be used to treat diseases associated with activity of the IL-17A and/or IL-17F/IL-17RA pathway.

Aspects of the invention include antibodies that compete for binding with the IL-17RA neutralizing antibodies described herein or antibodies that bind to the neutralizing determinants described herein that specifically bind to human IL-17RA and partially or fully inhibit IL-17RA from forming either a homomeric or heteromeric functional receptor complex, such as, but not limited to IL-17RA/IL-17RC complex and do not necessarily inhibit IL-17A and/or IL-17F or an IL-17A/IL-17F heteromer from binding to IL-17RA or a IL-17RA heteromeric receptor complex. Thus, disease states associated with IL-17RC are also associated with IL-17RA due to the fact that IL-17RC cannot signal without IL-17RA. For example, see You, Z., et al., *Cancer Res.,* 2006 Jan. 1; 66(1):175-83 and You, Z., et al., *Neoplasia,* 2007 June; 9(6): 464-70.

Antibodies that compete for binding with the IL-17RA neutralizing antibodies described herein or antibodies that bind to the neutralizing determinants described herein can be used for diagnostic purposes to detect, diagnose, or monitor diseases and/or conditions associated with IL-17A or IL-17RA. The invention provides for the detection of the presence of IL-17RA in a sample using classical immunohistological methods known to those of skill in the art (e.g., Tijssen, 1993, *Practice and Theory of Enzyme Immunoassays,* vol 15 (Eds R. H. Burdon and P. H. van Knippenberg, Elsevier, Amsterdam); Zola, 1987, *Monoclonal Antibodies: A Manual of Techniques,* pp. 147-158 (CRC Press, Inc.); Jalkanen et al., 1985, *J. Cell. Biol.* 101:976-985; Jalkanen et al., 1987, *J. Cell Biol.* 105:3087-3096). The detection of IL-17RA can be performed in vivo or in vitro.

Diagnostic applications provided herein include use of the antibodies that compete for binding with the IL-17RA neutralizing antibodies described herein or antibodies that bind to the neutralizing determinants described herein to detect expression of IL-17RA and binding of the ligands to IL-17RA. Examples of methods useful in the detection of the presence of IL-17RA include immunoassays, such as the enzyme linked immunosorbent assay (ELISA) and the radioimmunoassay (RIA).

One aspect of the invention provides for identifying a cell or cells that express IL-17RA. In a specific embodiment, the antibodies that compete for binding with the IL-17RA neutralizing antibodies described herein or antibodies that bind to the neutralizing determinants described herein is labeled with a labeling group and the binding of the labeled antigen binding protein to IL-17RA is detected.

All references cited within the body of the instant specification are hereby expressly incorporated by reference in their entirety.

EXAMPLES

The following examples, including the experiments conducted and the results achieved, are provided for illustrative purposes only and are not to be construed as limiting the invention.

Example 1

IL-17RA neutralizing antibodies were shown to reduce incidence of arthritis in a CIA (Collagen-Induced Arthritis) mouse model when administered prophylactically and therapeutically. The IL-17RA inhibition reduced clinical arthritis in both a prophylactic and therapeutic manner for several models if CIA.

Figure 4:
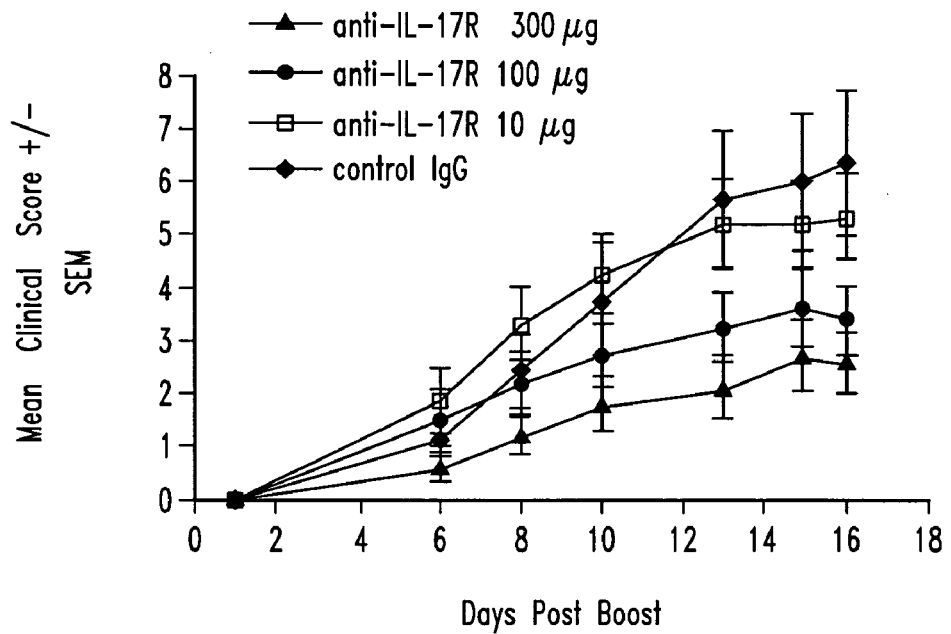
FIG. 4 shows dose-dependent inhibition by an IL-17RA mAb in a wild-type (WT) collagen-induced arthritis (CIA) model. A P<0.05 was seen when comparing IL-17RA mAb at 100 µg and 300 µg treatment groups versus control treatment group (days 13, 15 and 16).

The surrogate neutralizing mouse IL-17RA mAb administered prophylactically reduced mean clinical scores in wild-type CIA model in a dose-dependent manner. FIG. 4 shows the dose-dependent inhibition by IL-17RA mAb in wild-type CIA model. Mice were treated with either IL-17RA mAb or control Ig on a Monday, Wednesday and Friday schedule for 2.5 weeks post boost. Administration of 100 µg and 300 µg of IL-17RA antibodies resulted in a lower clinical score for 18 days post-boost than compared to isotype control Ig.

A reduction in bone loss and cartilage erosion in the joint was associated with the reduction of mean clinical scores at the 300 µg dose of the IL-17RA mAb. Histopathologic analysis and radiographic images analysis were compared to the IgG control. By both means of analysis, the ankle joint of the near paw of CBA/1 male mouse treated with an IL-18R mAb (isotype control) showed marked inflammation: subchondral bone erosion of the talus, marked joint architecture disruption of tarsal-metatarsal joints (subchondral bone and articular cartilage erosion), and reactive periosteal bone formation (osteophytosis). In stark contrast, the ankle joint of the rear paw of a DBA/1 mouse treated with 300 µg anti-IL-17RA mAb showed well-defined joint spaces, lack of edema and lack of periosteal reactive bone or lytic lesions indicated reduced bone loss and cartilage erosion.

Example 2

Figure 5:
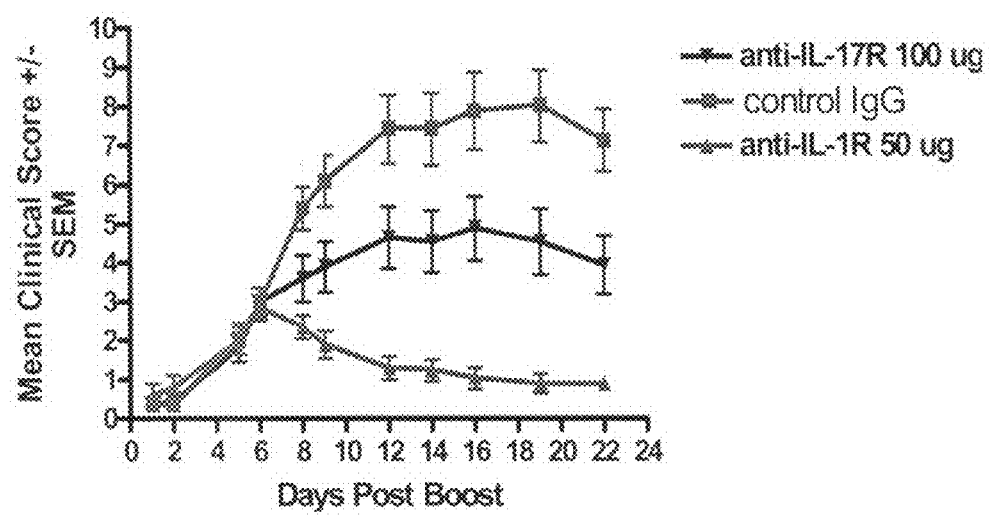
FIG. 5 shows the results of therapeutic treatment with IL-17RA mAb. The data shows stabilized mean clinical scores in wild-type mice in a standard CIA model of arthritis. These data demonstrate that IL-17RA inhibition by an IL-17RA antigen binding protein may be therapeutically useful in treating rheumatoid arthritis (RA), especially in the preservation of joint bone and cartilage.
Figure 6:
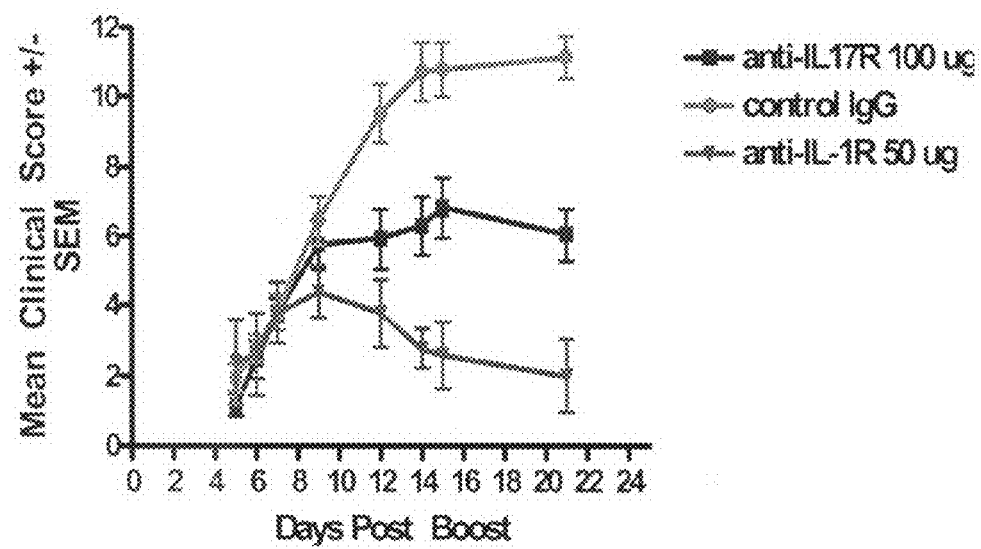
FIG. 6 shows that therapeutic treatment with IL-17RA mAb stabilized mean clinical scores in TNFR p55/p75 knockout mice in a standard CIA model of arthritis. These data show that IL-17RA inhibition by an IL-17RA antigen binding protein may be therapeutically useful in treating RA, especially in the preservation of joint bone and cartilage. Notably, IL-17RA inhibition was able to stabilize disease in a model independent of TNF signaling.

IL-17RA inhibition was also shown to be effective in a CIA model when dosing was initiated after the onset of clinical signs (i.e, therapeutic dosing protocol) in a wild-type and TNFR p55/p75 KO model. Treatment was initiated approximately 6-7 days post collagen introduction in both models. FIG. 5 shows that therapeutic treatment with IL-17RA mAb stabilized mean clinical scores in both wild-type mice. FIG. 6 shows that therapeutic treatment with IL-17RA mAb stabilized mean clinical scores in TNFR p55/p75 KO models. Mice were treated with either an IL-17RA mAb, IL-1R mAb, or control Ig on a Monday, Wednesday and Friday schedule for 2 weeks post randomization into therapeutic treatment groups. These data are representative of 2 independent experiments performed in both WT and TNFR p55/p75 KO CIA models. Administering IL-17RA mAbs showed a reduced clinical score as compared to control IgG in CIA induced wild-type mice. Surprisingly, the similar efficacy of IL-17RA mAbs in the TNF p55/p75 KO model stabilized CIA independently of TNF signaling. This data suggests IL-17RA neutralizing antibodies therapy may pick up non-responders to anti-TNF therapies. Combination therapy of an IL-17RA antigen binding protein with anti-TNF therapies may be more beneficial than either alone.

Example 3

The development of fully human monoclonal antibodies directed against human IL-17RA was carried out using Abgenix (now Amgen Fremont Inc.) XenoMouse® technology (U.S. Pat. Nos. 6,114,598; 6,162,963; 6,833,268; 7,049, 426; 7,064,244, which are incorporated herein by reference in their entirety; Green et al, 1994, *Nature Genetics* 7:13-21; Mendez et al., 1997, *Nature Genetics* 15:146-156; Green and Jakobovitis, 1998, *J. Ex. Med.* 188:483-495)). TABLE 4 shows the portions of the IL-17RA protein used as an immunogen and cell lines used to generate and screen anti-IL-17RA antibodies.

TABLE 4

| Reagent | Description |
| --- | --- |
| IL-17RA.Fc | Human IL-17RA extracellular domain with a C-terminal human Fc domain. Expressed in a stable CHO cell line. |
| IL-17RA-FLAG-polyHis (SEQ ID NO: 431) | Human IL-17RA extracellular domain with a C-terminal FLAG-polyHis tag. Expressed by transient transfection in COS PKB cells. |

TABLE 4-continued

| Reagent | Description |
| --- | --- |
| IL-17RA CHO cells | Human IL-17RA full-length expressed on the surface of CHO cells. |

IgG2 XenoMouse® mice were immunized/boosted with IL-17RA-Fc (group 1) and IL-17RA-FLAG-polyHis (group 2). Serum titers were monitored by ELISA and mice with the best titers were fused to generate hybridomas. The resulting polyclonal supernatants were screened for binding to IL-17RA by ELISA, and the positive supernatants were screened for binding to IL-17RA CHO cells by FMAT. Positive supernatants were subjected to additional screening. IgG2 XenoMouse® mice were immunized with the following immunogens: IL-17RA-Fc (group 3) and IL-17RA-FLAG-pHis (group 4) and were tested following additional immunizations.

Example 4

The IL-17RA antibodies were characterized. Non-clonal hybridoma supernatants were prepared in volumes of 1-2 mls (the Ig concentrations were not determined for these supernatants). The anti-IL-17RA non-clonal hybridoma supernatants were initially screened by FACS for their ability to inhibit biotinylated human IL-17A binding to CHO cells over-expressing human IL-17RA and another CHO cell line over-expressing cynomolgus IL-17RA. Nonclonal supernatants that were able to completely or nearly completely inhibit binding of human IL-17A to CHO-huIL-17RA and CHO-cynoIL-17RA were subsequently screened at several dilutions in an IL-17A-induced cytokine/chemokine secretion assay using a human foreskin fibroblast (HFF) cell line. Anti-IL-17RA non-clonal supernatants were incubated with HFF cells (5000 cells/well in 96 well plate) for 30 minutes at 36° C. and then stimulated overnight with either IL-17A (5 ng/ml) alone or IL-17F (20 ng/ml) and TNF-alpha (5 ng/ml). Fibroblast culture supernatants were then analyzed by ELISA for the presence of either IL-6 or GRO-alpha. Anti-IL-17RA non-clonal hybridomas were selected for sub-cloning based on their performance in the CHO-IL-17RA FACS assay and HFF bioassay. An example of the selection is shown in TABLES 5, 6, and 7.

TABLE 5

| | | | | HFF Bioassay | | Repeat assays | | |
| --- | --- | --- | --- | --- | --- | --- | --- | --- |
| | | | | 1:4 dil. | 1:32 | 1:4 | 1:32 | 1:128 |
| | | | | % inhibition of IL-6 production | | | | |
| | % positive | % positive | MFI | | | | | |
| Neg. Cntl. | 1.09 | 1.57 | 10 | | | | | |
| IL-17 biot. (500 ng/ml) | 8.85 | 10.22 | 77 | | | | | |
| Supernatant I.D. | | | | | | | | |
| 1 | 1.34 | 1.78 | 9 | 56 | 14 | | | |
| 2 (incl. $AM_H15/AM_L15$) | 0.60 | 3.77 | 6 | 80 | 72 | 98 | 91 | 81 |
| 3 | 1.04 | 1.60 | 8 | 46 | −5 | | | |
| 4 (incl. $AM_H14/AM_L14$) | 1.72 | 0.79 | 10 | 90 | 82 | 99 | 92 | 84 |
| 5 | 1.59 | 1.43 | 11 | 76 | 52 | | | |
| 6 | 1.45 | 1.93 | 14 | 82 | 79 | | | |
| 7 | 1.00 | 1.28 | 8 | 71 | 58 | | | |
| 8 | 1.43 | 1.60 | 14 | 69 | 31 | | | |
| 9 | 1.34 | 2.28 | 18 | 59 | 20 | | | |
| 10 | 0.79 | 1.96 | 11 | 58 | −2 | | | |
| 11 | 1.93 | 1.69 | 11 | 72 | 21 | | | |
| 12 | 2.23 | 1.69 | 8 | 69 | 7 | | | |
| 13 (incl. $AM_H21/AM_L21$) | 1.49 | 0.49 | 6 | 82 | 53 | | | |
| 14 | 1.01 | 1.25 | 8 | 63 | 23 | | | |
| 15 | 1.31 | 1.45 | 9 | 74 | 45 | | | |
| 16 | 1.39 | 0.72 | 8 | 58 | 4 | | | |
| 17 | 0.91 | 0.94 | 7 | 73 | 38 | | | |
| 18 | 1.37 | 2.85 | 13 | 49 | 6 | | | |
| 19 | 1.47 | 1.15 | 8 | 74 | 61 | | | |
| 20 | 1.60 | 1.20 | 7 | 72 | 46 | | | |
| 21 | 1.30 | 1.65 | 8 | 47 | 4 | | | |
| 22 | 0.93 | 1.02 | 8 | 54 | 16 | | | |
| 23 | 1.08 | 1.12 | 7 | 72 | 59 | | | |

In TABLE 5, anti-IL-17RA non-clonal hybridoma supernatants were screened for binding to IL-17RA. The first half of TABLE 5 shows the % positive and mean fluorescent intensity (MFI) in results from flow cytometry (i.e, FACS). The % positive shows inhibition of biotin-huIL-17A binding to huIL-17RA$^+$ CHO cells by the non-clonal hybridoma supernatants. The MFI column shows inhibition of biotinylated huIL-17A binding to cyno IL-17RA$^+$ CHO cells by the non-clonal hybridoma supernatants. The second half of TABLE 5 shows the HFF binding intensity for the non-clonal and mAbs as measured by the % intensity of IL-6 production. The first 2 columns show an IL-17A/HFF bioassay with non-clonal hybridoma supernatants and the last 4 columns are repeat IL-17A/HFF bioassay results with non-clonal hybridoma supernatants.

TABLE 6

| | FACS results on 293-Cyno IL-17RA-expressing Cells | | | HFF bioassay | | repeat | | | |
|---|---|---|---|---|---|---|---|---|---|
| | % positive | % positive | MFI | 1:4 dilution | 1:32 | 1:4 | 1:32 | 1:128 | 1:512 |
| | | | | % inhibition of IL-6 production | | | | | |
| Neg. Cntl | 1.09 | 1.57 | 1.0 | | | | | | |
| IL-17 biot. (500 ng/ml) | 8.85 | 10.22 | 77 | | | | | | |
| Supernatant I.D. | | | | | | | | | |
| 1 (incl. AM$_H$11/AM$_L$11) | 1.32 | 1.4 | 9 | | | | | | |
| 2 | 0.87 | 2.92 | 9 | | | | | | |
| 3 | 1.0 | 4.47 | 16 | | | | | | |
| 4 | 1.03 | 5.01 | 17 | | | | | | |
| 5 | 0.6 | 6.53 | 18 | | | | | | |
| 6 (incl. AM$_H$5/AM$_L$5) | 0.73 | 4.55 | 9 | | | | | | |
| 7 | 0.59 | 5.18 | 8 | | | | | | |
| 8 | 0.45 | 7.25 | 7 | | | | | | |
| 9 | 2.34 | 2.36 | 6 | 61 | 36 | | | | |
| 10 | 6.76 | 8.35 | 64 | 37 | 12 | | | | |
| 11 | 0.78 | 1.16 | 6 | 61 | 24 | | | | |
| 12 | 0.61 | 1.64 | 6 | 74 | 56 | 71 | 67 | 45 | 35 |
| 13 | 2.98 | 5.48 | 22 | −2 | −13 | | | | |
| 14 | 5.34 | 10.64 | 49 | 22 | 2 | 3 | 39 | 31 | 34 |
| 15 | 0.5 | 3.24 | 11 | 51 | −7 | | | | |
| 16 (incl. AM$_H$22/AM$_L$22) | 0.54 | 2.93 | 18 | 92 | 72 | 91 | 73 | 73 | 29 |
| 17 | 1.25 | 2.2 | 17 | −8 | −76 | | | | |
| 18 | 0.61 | 0.99 | 7 | 73 | 28 | | | | |
| 19 (incl. AM$_H$23) | 0.69 | 1.72 | 10 | 79 | 72 | 86 | 76 | 67 | 50 |
| 20 | 1.53 | 1.94 | 31 | 5 | −31 | | | | |
| 21 | 6.66 | 9.63 | 66 | −15 | 4 | | | | |
| 22 | 6.33 | 10.32 | 71 | 1 | 14 | | | | |
| 23 | 0.3 | 2.55 | 7 | 50 | 35 | | | | |
| 24 | 0.24 | 4.11 | 6 | 34 | 15 | | | | |
| 25 | 0.81 | 0.99 | 8 | −49 | 11 | | | | |
| 26 | 0.43 | 1.31 | 7 | 67 | 48 | | | | |
| 27 | 0.7 | 1.23 | 11 | 50 | 26 | | | | |
| 28 | 0.58 | 1.32 | 9 | 56 | 47 | | | | |
| 29 (incl. AM$_H$1/AM$_L$1) | 0.8 | 1.85 | 11 | 77 | 76 | 90 | 87 | 79 | 66 |
| 30 | 0.69 | 1.55 | 11 | 40 | 16 | | | | |
| 31 | 0.56 | 1.96 | 12 | 12 | −11 | | | | |
| 32 | 0.21 | 1.11 | 8 | 46 | 7 | | | | |
| 33 | 1.24 | 1.15 | 13 | 68 | 43 | | | | |
| 34 | 0.74 | 0.81 | 11 | 36 | 8 | | | | |
| 35 | 0.71 | 1.37 | 9 | 65 | 21 | | | | |
| 36 | 0.57 | 1.21 | 7 | 78 | 32 | | | | |
| 37 | 0.59 | 1.0 | 8 | 71 | 3 | | | | |
| 38 | 0.65 | 1.43 | 8 | 63 | −38 | | | | |
| 39 | 0.28 | 1.23 | 7 | 43 | −21 | | | | |
| 40 | 0.35 | 2.48 | 9 | 50 | −39 | | | | |
| 41 | 0.64 | 1.61 | 8 | 49 | −19 | | | | |
| 42 | 0.12 | 1.04 | 8 | 87 | 68 | 96 | 92 | 80 | 66 |
| 43 | 0.21 | 1.12 | 11 | 79 | 34 | | | | |
| 44 | 0.32 | 1.33 | 8 | 68 | −3 | | | | |
| 45 | 0.74 | 1.68 | 10 | 40 | −16 | | | | |
| 46 | 0.58 | 1.74 | 10 | 64 | 7 | | | | |

TABLE 6 shows IL-17RA non-clonal hybridoma supernatant screening data. The % positive and MFI columns show results from flow cytometry (FACS). The % positive columns show inhibition of biotin-huIL-17A binding to huIL-17RA$^+$ CHO cells by the non-clonal hybridoma supernatants. The MFI column shows inhibition of biotinylated huIL-17A binding to cyno IL-17RA$^+$ CHO cells by the non-clonal hybridoma supernatants. The first 2 HFF bioassay columns are IL-17A/HFF bioassay with non-clonal hybridoma supernatants and the last 4 bioassay columns are repeat IL-17A/HFF bioassay results with selected non-clonal hybridoma supernatants. A number of supernatants were selected for subcloning.

TABLE 7

| | % positive | | MFI | HFF bioassay 1:4 | 1:32 | 1:128 |
|---|---|---|---|---|---|---|
| | | | | % inhibition of IL-6 Production | | |
| Neg. Cntl | 1.09 | 1.57 | 10 | | | |
| IL-17 biot. (500 ng/ml) | 8.85 | 10.22 | 77 | | | |
| Supernatant I.D. | | | | | | |
| 1 | 1.85 | 1.33 | 10 | 29 | 9 | 21 |
| 2 | 1.08 | 1.46 | 16 | 90 | 61 | 50 |
| 3 | 1.29 | 1.39 | 22 | 33 | 10 | 4 |
| 4 | 1.55 | 1.33 | 18 | 53 | 66 | 58 |
| 5 | 1.69 | 0.7 | 8 | 76 | 46 | 30 |
| 6 (incl. $AM_H13/AM_L13$) | 1.52 | 0.89 | 6 | 73 | 78 | 75 |
| 7 | 1.54 | 0.98 | 7 | 79 | 71 | 45 |
| 8 | 1.78 | 3.44 | 34 | 73 | 63 | 30 |
| 9 | 6.34 | 8.45 | 53 | 57 | 48 | 34 |
| 10 | 1.23 | 1.58 | 10 | 82 | 71 | 31 |
| 11 | 1.62 | 2.1 | 28 | −10 | −6 | −10 |
| 12 | 1.15 | 1.04 | 16 | 71 | 63 | 37 |
| 13 | 2.43 | 1.67 | 12 | 58 | 23 | −4 |
| 14 | 1.43 | 1.03 | 13 | 42 | 17 | 18 |
| 15 | 1.62 | 1.59 | 18 | 67 | 59 | 31 |
| 16 | 1.79 | 2.2 | 25 | 61 | 57 | 45 |
| 17 | 0.91 | 1.85 | 10 | 49 | 54 | 23 |
| 18 (incl. $AM_H12/AM_L12$) | 1 | 1.36 | 6 | 75 | 82 | 61 |
| 19 (incl. $AM_H17/AM_L17$) | 1.75 | 1.23 | 8 | 90 | 81 | 73 |
| 20 | 2.31 | 0.49 | 9 | 35 | 20 | 38 |
| 21 (incl. $AM_H16/AM_L16$) | 1.84 | 0.76 | 6 | 86 | 90 | 71 |

TABLE 7 shows anti-IL-17RA non-clonal hybridoma supernatant screening data. The first two columns are flow cytometry data (FACS). The % positive columns show inhibition of biotin-huIL-17A binding to huIL-17RA$^+$ CHO cells by the non-clonal hybridoma supernatants. The MFI column shows inhibition of biotinylated huIL-17A binding to cynomolgus IL-17RA$^-$ CHO cells by the non-clonal hybridoma supernatants. The final three columns show IL-17A/HFF bioassay results with non-clonal hybridoma supernatants. Supernatants 6, 18, 19 and 21 were selected for subcloning.

TABLE 8

| Sub-clone ID | IL-17A/HFF bioassay $IC_{50}$ (nM) | Low resolution BIAcore $K_D$(nM) |
|---|---|---|
| 1. Subclone of ($AM_H14/AM_L14$) | 0.12 | 0.69 |
| 2. Subclone of ($AM_H14/AM_L14$)2 | 0.20 | ND |
| 3. Subelone of ($AM_H14/AM_L14$)3 | 0.075 | ND |
| 4. Subclone of ($AM_H21/AM_L21$) | 2.3 | ND |
| 5. Subclone of ($AM_H21/AM_L21$) | 3.1 | ND |
| 6. Subclone of ($AM_H21/AM_L21$) | 3.3 | 16.7 |
| 7. Subclone of ($AM_H20/AM_L20$) | 8.1 | ND |
| 8. Subclone of ($AM_H20/AM_L20$) | 6.6 | ND |
| 9. Subclone of ($AM_H20/AM_L20$) | 6.7 | 11.6 |
| 10. Subclone of ($AM_H19/AM_L19$) | 0.22 | 3.1 |
| 11. Subclone of ($AM_H19/AM_L19$) | 1.1 | ND |
| 12. Subclone of ($AM_H19/AM_L19$) | 0.50 | ND |
| 13. Subclone of ($AM_H13/AM_L13$) | >10 | 7.6 |
| 14. Subclone of ($AM_H18/AM_L18$) | 0.44 | ND |
| 15. Subclone of ($AM_H18/AM_L18$) | 0.40 | ND |
| 16. Subclone of ($AM_H18/AM_L18$) | 0.17 | 14.9 |
| 17. Subclone of ($AM_H12/AM_L12$) | 3.5 | ND |
| 18. Subclone of ($AM_H12/AM_L12$) | 3.7 | 8.2 |
| 20. Subclone of ($AM_H12/AM_L12$) | 5.5 | ND |
| 21. Subclone of ($AM_H17/AM_L17$) | 2.5 | 8.2 |
| 22. Subclone of ($AM_H17/AM_L17$) | 5.3 | ND |

TABLE 8-continued

| Sub-clone ID | IL-17A/HFF bioassay $IC_{50}$ (nM) | Low resolution BIAcore $K_D$(nM) |
|---|---|---|
| 23. Subclone of ($AM_H17/AM_L17$) | 0.57 | ND |
| 24. Subclone of ($AM_H16/AM_L16$) | 1.6 | ND |
| 25. Subclone of ($AM_H16/AM_L16$) | 2.3 | 6.2 |
| 26. Subclone of ($AM_H16/AM_L16$) | 1.4 | ND |
| 27. Subclone of ($AM_H22/AM_L22$) | 0.046 | 1.5 |
| 28. Subclone of ($AM_H22/AM_L22$) | 0.09 | ND |
| 29. Subclone of ($AM_H22/AM_L22$) | 0.07 | ND |

ND = not determined

TABLE 8 shows IL-17A/HFF bioassay IC50 values and low resolution BIAcore® $K_D$ values for subcloned hybridomas. Lower IC50 and $K_D$ values in the IL-17A/HFF IL-17RA binding assays showed that the IL-17RA mAbs inhibited binding of IL-17A to IL-17 receptor A. Antibodies were selected for further characterization based on low $K_D$ values for inhibiting IL-17A binding to human IL-17RA.

Example 5

IL-17RA human mAb clones having the heavy and light chain sequences ($AM_H22/AM_L22$), ($AM_H19/AM_L19$), ($AM_H18/AM_L18$) and ($AM_H14/AM_L14$) were selected for further bioassay characterization. TABLE 9 below shows IC50 values for the selected Abs in the HFF bioassay and a primary lung fibroblast bioassay against both IL-17A and IL-17F.

TABLE 9

| IL-17RA mAb | IL-17A/HFF IC50 (nM) | IL-17F/HFF IC50(nM) | IL-17A/lung fibroblast IC50(nM) |
|---|---|---|---|
| ($AM_H14/AM_L14$) | 0.13 | 0.067 | 0.04 |
| ($AM_H22/AM_L22$) | 0.10 | 0.033 | 0.14 |
| ($AM_H19/AM_L19$) | 0.20 | 0.087 | 0.22 |
| ($AM_H18/AM_L18$) | 0.33 | 0.073 | 0.081 |

The selected human mAbs inhibited IL-17A binding to IL-17RA. In addition to the lower IC50 values observed for IL-17A binding to IL-17RA, the selected human mAbs exhibited reduced IC50 values inhibiting the binding of IL-17F to IL-17RA (second column). Therefore, the selected human mAbs inhibit both IL-17A-IL-17RA binding and IL-17F-IL-17RA binding.

Example 6

Figure 7:
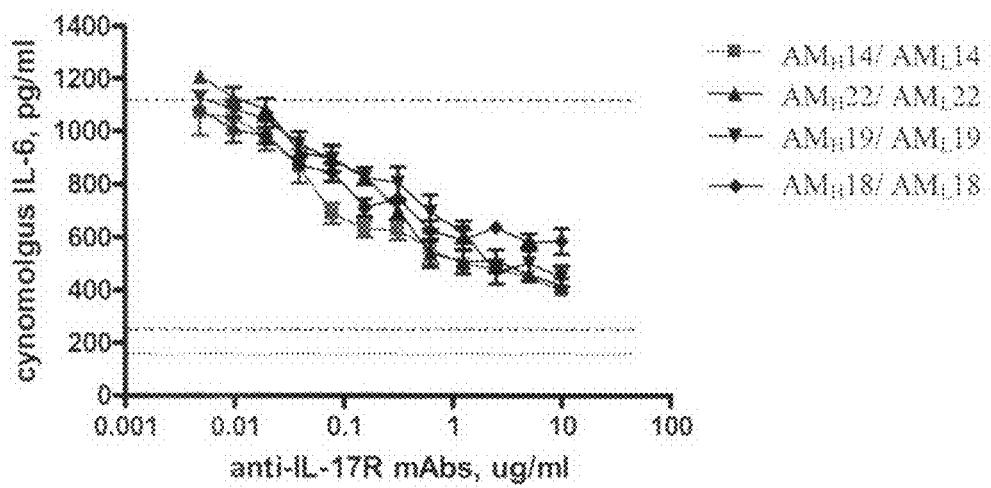
FIG. 7 shows exemplary IL-17RA human mAbs ($AM_H14/AM_L14$, $AM_H22/AM_L22$, $AM_H19/AM_L19$, and $AM_H18/AM_L18$) were able to inhibit cynomolgus IL-17-induced IL-6 production from JTC-12 cells (cynomolgus kidney cell line). The (----) line depicts the positive control value of cynomolgus IL-17 in combination with TNF-alpha. The (-.-.-) line depicts the positive control value of cynomolgus TNF-alpha. The (...) line depicts the media control value.

Exemplary IL-17RA human mAbs were tested in a cynomolgus bioassay utilizing the cynomolgus-derived kidney epithelial cell line JTC-12 stimulated with cynomolgus IL-17A. FIG. 4 shows IL-17RA mAbs having the heavy and light chain sequences ($AM_H22/AM_L22$), ($AM_H19/AM_L19$), ($AM_H18/AM_L18$) and ($AM_H14/AM_L14$) in the inhibition of cynomolgus IL-17A-induced IL-6 production from JTC-12 cells. The (----) line depicts the positive control value of cynomolgus IL-17 in combination with TNF-alpha. The (-.-.-) line depicts the positive control value of cynomolgus TNF-alpha. The (....) line depicts the media control value. JTC-12 cells were preincubated for 30 mins with anti-IL-17RA mAbs and then stimulated overnight with cynomolgus IL-17A (5 ng/ml) and human TNF-alpha (5 ng/ml). FIG. 7 shows that each antibody was able to inhibit cynomolgus IL-17A from binding IL-17RA and inhibit IL-17RA activation, as determined by IL-6 production from JTC-12 cells. The IL-17RA antibody (AM$_H$14/AM$_L$14) was able to antagonize cynomolgus IL-17A-induced IL-6 production from JTC-12 cells with an IC50 of approximately 1.2 nM.

Example 7

In vitro binding of IL-17RA mAbs was assayed. The binding affinities of IL-17RA antibodies were measured by surface plasmon resonance using a Biacore 3000® instrument by standard methods known in the art. Antibody candidates were captured on CM4 chips derivatized with goat anti-human IgG (H+L) antibody (Jackson Immuno Research, Bar Harbor, Me.). A CM4 chip coated with goat anti-human IgG (H+L) antibody but without captured antibody was used as a reference. Soluble huIL-17RA-FLAG-polyHis (SEQ ID NO:431) at a concentration range of 0.46-1000 nM was flowed over the chips for 2 minutes (association phase) followed by a 15-30 minute disassociation phase. FLAG peptide, Asp-Tyr-Lys-Asp-Asp-Asp-Asp-Lys (DYKDDDDK) (SEQ ID NO:447) as described in Hopp et al., *Bio/Technology* 6:1204, 1988, and U.S. Pat. No. 5,011,912 enables rapid assay and facile purification of expressed recombinant protein. Reagents useful for preparing fusion proteins in which the FLAG peptide is fused to a given polypeptide are commercially available (Sigma, St. Louis, Mo.).

Experiments were conducted at 25° C. using a 50 uL/min flow rate. Data was fit to a 1:1 Model+Local Rmax using BIAeval Software® (v4.1).

TABLE 10

| Human Antibody | k$_a$ (1/Ms) | K$_D$ (1/s) | K$_A$ (1/M) | K$_D$ (M) |
|---|---|---|---|---|
| (AM$_H$14/AM$_L$14) | 2.60 × 10$^5$ | 6.22 × 10$^{-5}$ | 4.18 × 10$^9$ | 2.39 × 10$^{-10}$ |
| (AM$_H$22/AM$_L$22) | 2.35 × 10$^5$ | 1.17 × 10$^{-4}$ | 2.01 × 10$^9$ | 4.98 × 10$^{-10}$ |
| (AM$_H$19/AM$_L$19) | 1.42 × 10$^5$ | 1.14 × 10$^{-4}$ | 1.25 × 10$^9$ | 8.02 × 10$^{-10}$ |
| (AM$_H$18/AM$_L$18) | 1.02 × 10$^5$ | 1.01 × 10$^{-3}$ | 1.01 × 10$^8$ | 9.88 × 10$^{-9}$ |

TABLE 10 shows the K$_D$ of the human mAb clones was on the order of 10$^{-10}$ to 10$^{-9}$, with the clone having the heavy and light chain sequences (AM$_H$14/AM$_L$14) having the highest affinity. Each of the human monoclonal antibodies' kinetic data was consistent with the equilibrium data. The antibody with the heavy and light chain variable sequences (AM$_H$14/AM$_L$14; SEQ ID NO:14 and SEQ ID NO:40, respectively) had the highest affinity for IL-17RA, as well as the slowest off-rate.

Example 8

Studies were conducted to determine where the various IL-17RA neutralizing antibodies bound on human IL-17RA. The ForteBio™ Octet System is one of several systems and techniques available for measuring antibody binding. The methods used for screening antibody binding essentially followed the manufacturer's recommendations. For more information see www.fortebio.com. In brief, streptavidin sensors (ForteBio™) were presoaked for 10 minutes in PBSAT (1% BSA/PBS+0.05% Tween20® (polyoxyethylene sorbitan monolaurate). Biotinylated AM$_H$14/AM$_L$14 at 10 ug/mL in PBSAT was loaded onto the sensors for 900 seconds. A new baseline was run for 600 seconds in PBSAT. Wild-type IL-17RA-FLAG-polyHis (SEC ID NO:431) at 10 ug/mL in PBSAT was then bound to the sensors for 900 seconds. A new baseline was established for 600 seconds in PBSAT. 200 nM of the following mAbs AM$_H$22/AM$_L$22, AM$_H$19/AM$_L$19, and AM$_H$18/AM$_L$18 were associated for 900 seconds, followed by dissociation for 900 seconds in PBSAT. The data showed that AM$_H$18/AM$_L$18 did not compete with AM$_H$14/AM$_L$14 for binding, showing that AM$_H$14/AM$_L$14 and AM$_H$18/AM$_L$18 bind to different neutralizing determinants. AM$_H$22/AM$_L$22 and AM$_H$19/AM$_L$19 did not bind in the presence of AM$_H$14/AM$_L$14, suggesting that all three of these antibodies bind to the same or to a similar neutralizing determinant and therefore are considered to bin together.

Example 9

Cross-competition studies were performed to determine IL-17RA binding characteristics of exemplary IL-17RA neutralizing antibodies. A modification of the multiplexed binning method described by Jia, et al. was used (see Jia, et al., *J. Immun. Meth.*, 2004, 288:91-98). The method employed the Bio-Plex Workstation and software (BioRad, Hercules, Calif.), as well as reagents from Luminex® Corp. (Austin, Tex.). The manufacturers' basic protocols were followed except where noted below (see www.bio-rad.com and www.luminexcorp.com for details). Each bead code of streptavidin-coated Luminex® beads (Luminex®, #L100-LIXX-01, where "XX" specifies the bead code) were incubated in 150 ul of 50 ug/ml biotinylated monovalent mouse-anti-human IgG capture antibody (BD Pharmingen, Becton Dickinson, Franklin Lakes, N.J., product #555785) for 1 hour at room temperature in the dark and then washed 3 times with PBSAT. The mouse-anti-human IgG coating was evaluated and the beads quantified by FACS. Each bead code was separately incubated with 10 ul of anti-IL-17RA antibody for 1 hour at room temperature and then washed. The beads were pooled and then dispensed to a 96-well filter plate (Millipore, Billerica, Mass., product #MSBVN1250). 80 ul of 2 ug/ml IL-17RA (SEQ ID NO:431) was added to half the wells and buffer to the other half and incubated at room temperature for 1 hour then washed with PBSAT. 10 ul of an anti-IL-17RA antibody was added to one well with IL-17RA (SEQ ID NO:431) and one well without IL-17RA and incubated at room temperature for 1 hour then washed with PBSAT. An irrelevant human-IgG (Jackson Labs., Bar Harbor, Me., product #009-000-003) was included as a negative control. 50 ul PE-conjugated monovalent mouse-anti-human IgG (BD Pharmingen, Becton Dickinson, Franklin Lakes, N.J., #555787) was added to each well and incubated at room temperature for 1 hour and then washed with PBSAT. The PE-tagged monovalent antibody will detect the presence of the second mAb added to the well, but not the first mAb captured by the monovalent mouse-anti-human IgG antibody. Beads were resuspended in 120 ul PBSAT and at least 100 events/bead code were collected on the Bio-Plex workstation as per the manufacturer's recommended protocol.

Median Fluorescent Intensity (MFI) of the antibody pair without IL-17RA was subtracted from the MFI signal of the corresponding reaction containing IL-17RA to normalize for background noise. The criteria for determining if two antibodies cross-competed with each other and therefore "binned" together was a matter of determining the degree to which the second antibody was detectable. If the normalized MFI was higher than the highest of any of the following three values, then the anti-IL-17RA antibodies were considered to be simultaneously bound to IL-17RA and were considered to be in different bins (i.e., the antibodies did not cross-compete): the normalized MFI is greater than 3 times the MFI value of the antibody paired with itself, or 3 times the MFI value of the antibody paired with a huIgG control, or a MFI of 300. Generally speaking, antibodies assigned to different bins bind different parts of IL-17RA and antibodies assigned to the same bin(s) bind similar parts of IL-17RA.

FIGS. 8A and 8B show the results of multiplexed binning of anti-IL-17RA antibodies. Shaded values indicate antibody pairs that bind to IL-17RA simultaneously, suggesting that these antibodies bind to different neutralizing determinants. Boxed values indicate antibodies paired against themselves and cross-compete. The following monoclonal human antibodies containing the ascribed heavy and light variable domains were tested: A: $AM_H11/AM_L11$, B: $AM_H4/AM_L4$, C: $AM_H8/AM_L8$, D: $AM_H7/AM_L7$, E: $AM_H6/AM_L6$, F: $AM_H10/AM_L10$, G: $AM_H18/AM_L18$, H: $AM_H1/AM_L1$, I: $AM_H22/AM_L22$, J: $AM_H23/AM_L23$, K: $AM_H14/AM_L14$, L: $AM_H19/AM_L19$, M: $AM_H12/AM_L12$, N: $AM_H17/AM_L17$, O: $AM_H16/AM_L16$, P: $AM_H26/AM_L26$, Q: $AM_H21/AM_L21$, and R: $AM_H20/AM_L20$.

FIGS. 8A and 8B also show that antibodies A: $AM_H11/AM_L11$, B: $AM_H4/AM_L4$, C: $AM_H8/AM_L8$, D: $AM_H7/AM_L7$, E: $AM_H6/AM_L6$, F: $AM_H10/AM_L10$, and G: $AM_H18/AM_L18$ competed with one another for binding to human IL-17RA and as a consequence fell into a defined group (Bin 1). In general, antibodies I: $AM_H22/AM_L22$, J: $AM_H23/AM_L23$, K: $AM_H14/AM_L14$, L: $AM_H19/AM_L19$, M: $AM_H12/AM_L12$, N: $AM_H17/AM_L17$, O: $AM_H16/AM_L16$ competed with one another for binding to human IL-17RA and as a consequence fell into a defined group (Bin 3). Generally speaking, the antibodies of Bin 1 did not compete with the antibodies of Bin 3.

Antibody H: $AM_H1/AM_L1$ was unique in its competition pattern and formed Bin 2, but is most similar to Bin 3. Antibody P: $AM_H26/AM_L26$ formed Bin 4 and showed little cross-competition with any of the other antibodies, suggesting a neutralizing determinant unique to this antibody. Antibodies Q: $AM_H21/AM_L21$ and R: $AM_H20/AM_L20$, showed individually unique competition patterns, but with considerable similarities to Bin 3 antibodies, and formed Bins 5 and 6, respectively. This data provides evidence of several species within a subgenus of cross-competing antibodies.

Example 10

As described above, antibodies that bind human IL-17RA and inhibit, or neutralize, the binding of IL-17A and/or IL-17F were created and characterized. To determine the neutralizing determinants on human IL-17RA that these various IL-17RA antibodies bound, a number of chimeric human/mouse IL-17RA proteins were constructed. This method takes advantage of the non-cross reactivity of the various IL-17RA antibodies with mouse IL-17RA. For each chimera, one or two regions of human IL-17RA extracellular domain (SEQ ID NO:431) was/were replaced with the corresponding region(s) of mouse IL-17RA (SEQ ID NO:432). FIG. 9 shows mouse IL-17RA (SEQ ID NO:432) and the 5 domains, A, B, C, D, E, and F that replaced the counterpart domains in the human IL-17RA sequence. Such techniques are known in the art, see for example Stemmer, W. P. C. et al., 1995 *Gene* 164:49-53.

Six single-region and 8 double-region chimeras were constructed in pTT5 vectors. Chimeric constructs A through F (single region chimeras) were made synthetically by PCR annealing of 65-mer sense and antisense oligonucleotides which span the protein from a Sal1 site 5' of the initiation codon to a Not1 site 3' of the termination codon. The template used in the first round of PCR was a mix of oligos (sense and antisense) spanning the region from the Sal1 site to the Not1 site. PCR was done in 2 steps as follows:

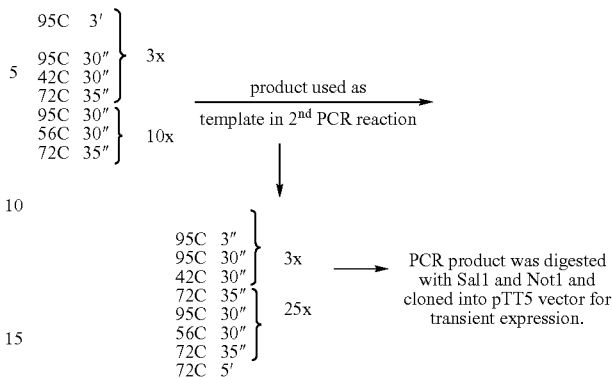

Double chimeric constructs were made by digestion of single chimeras A through D with Sal1 and Sac1 restriction enzymes and a 3-way ligation with Sac1 and Not1 digested chimeras E and F using pTT5 as the expression vector. The chimeras, huIL-17RA-FLAG-polyHis (SEQ ID NO:431), and muIL-17RA-FLAG-polyHis (SEQ ID NO:432) were expressed transiently using 2936-E cells (available from the National Research Council of Canada (NRCC); see NRCC document L-11565 for further information) as host cells in roller bottles. Such transient expression techniques are well known in the art, see for example Durocher, Y. et al., 2002 *Nucleic Acids Res. Janurary* 15; 30(2):E9. The supernatants were purified using a HisTrap™ HP column as per the manufacturer's general guidelines (GE Healthcare, Piscataway N.J.) and eluted using a standard imidazole gradient (see manufacturer's recommended protocols). Purified protein was desalted into PBS, pH 7.2.

The chimeras were aligned using standard analysis tools, such as ClustalW (EMBL-EBI). The resulting chimeric proteins are shown in FIGS. 10A-10D. With reference to FIGS. 9 and 10A-10D, Chimera A (SEQ ID NO:433) is human IL-17RA extracellular domain with mouse Domain A; Chimera B (SEQ ID NO:434) is human IL-17RA extracellular domain with mouse Domain B; Chimera C (SEQ ID NO:435) is human IL-17RA extracellular domain with mouse Domain C; Chimera D (SEQ ID NO:436) is human IL-17RA extracellular domain with mouse Domain D; Chimera E (SEQ ID NO:437) is human IL-17RA extracellular domain with mouse Domain E; Chimera F (SEQ ID NO:438) is human IL-17RA extracellular domain with mouse Domain F; Chimera G (SEQ ID NO:439) is human IL-17RA extracellular domain with mouse Domains A and E; Chimera H (SEQ ID NO:440) is human IL-17RA extracellular domain with mouse Domains B and E; Chimera I (SEQ ID NO:441) is human IL-17RA extracellular domain with mouse Domains C and E; Chimera J (SEQ ID NO:442) is human IL-17RA extracellular domain with mouse Domains D and E; Chimera K (SEQ ID NO:443) is human IL-17RA extracellular domain with mouse Domains A and F; Chimera L (SEQ ID NO:444) is human IL-17RA extracellular domain with mouse Domains B and F; Chimera M (SEQ ID NO:445) is human IL-17RA extracellular domain with mouse Domains C and F; and Chimera N (SEQ ID NO:446) is human IL-17RA extracellular domain with mouse Domains D and F.

Using methods similar to those described in Example 9, multiplex analysis using the Bio-Plex Workstation and software (BioRad, Hercules, Calif.) was performed to determine neutralizing determinants on human IL-17RA by analyzing exemplary human IL-17RA mAbs differential binding to chimeric versus wild-type IL-17RA proteins. Twelve bead codes of pentaHis-coated beads (Qiagen, Valencia, Calif.; see www1.qiagen.com) were used to capture histidine-tagged protein. The 12 bead codes allowed the multiplexing of 11 chimeric and the wild type human IL-17RA.

To prepare the beads, 100 ul of wild-type IL-17RA supernatant from transient expression culture and 100 ul of 2.5 ug/ml chimeric protein were bound to penta-His-coated beads overnight at 4° C. or 2 hours at room temperature with vigorous shaking. The beads were washed as per the manufacturer's protocol and the 12 bead set was pooled and aliquoted into 2 or 3 columns of a 96-well filter plate (Millipore, Billerica, Mass., product #MSBVN1250) for duplicate or triplicate assay points, respectively. 100 ul anti-IL-17RA antibodies in 4-fold dilutions were added to the wells, incubated for 1 hour at room temperature, and washed. 100 ul of a 1:100 dilution of PE-conjugated anti-human IgG Fc (Jackson Labs., Bar Harbor, Me., product #109-116-170) was added to each well, incubated for 1 hour at room temperature and washed. Beads were resuspended in 1% BSA, shaken for 3 minutes, and read on the Bio-Plex workstation. Antibody binding to IL-17RA chimeric protein was compared to antibody binding to the human IL-17RA wild-type from the same pool. A titration of antibody over approximately a 5 log scale was performed. Median Fluorescence Intensity (MFI) of chimeric proteins was graphed as a percent of maximum wild-type human IL-17RA signal. Mutations (i.e., mouse domains) that increase the EC50 (expressed in nM) for the IL-17RA mAb by 3-fold or greater (as calculated by GraphPad Prism®) were considered to have negatively affected IL-17RA mAb binding. Through these methods, neutralizing determinants for various IL-17RA antibodies were elucidated.

FIG. 11 is a table summarizing the IL-17RA mAbs capacity to bind the various chimeric proteins. Shaded values denote where the IL-17RA mAb did not meet the criteria for binding to that particular chimeric protein ("n.d.," i.e., "not determined" means that the chimera was not assayed). As described above, EC50 values are provided. A zero value indicates that antibody binding was ablated. The underlined value was assigned an EC50 value by the GraphPad Prism® even though the titration curve was essentially flat. TABLE 11 shows the control values in nM for the assay.

TABLE 11

| mAb | mu WT | huWT ctrl | 3 × wt ctrl | 2 × wt ctrl |
|---|---|---|---|---|
| AM$_H$18/AM$_L$18 | 0.000 | 0.061 | 0.182 | 0.121 |
| AM$_H$1/AM$_L$1 | 1.879 | 0.134 | 0.403 | 0.269 |
| AM$_H$22/AM$_L$22 | 0.000 | 0.043 | 0.128 | 0.085 |
| AM$_H$14/AM$_L$14 | 3416.000 | 0.027 | 0.082 | 0.055 |
| AM$_H$19/AM$_L$19 | 770.100 | 0.062 | 0.187 | 0.125 |
| AM$_H$23/AM$_L$23 | 0.000 | 0.053 | 0.158 | 0.106 |
| AM$_H$26/AM$_L$26 | 0.000 | 0.281 | 0.843 | 0.562 |
| AM$_H$21/AM$_L$21 | 0.196 | 0.018 | 0.055 | 0.037 |
| AM$_H$20/AM$_L$20 | 1.333 | 0.022 | 0.066 | 0.044 |

As can be seen in FIG. 11, at least three neutralizing determinants were identified based on those regions affecting the binding of neutralizing IL-17RA antibodies, namely Domain B spanning amino acids 75-96 of human IL-17RA (SEQ ID NO:431), Domain C spanning amino acids 128-154 of human IL-17RA (SEQ ID NO:431), and Domain D spanning amino acids 176-197 of human IL-17RA (SEQ ID NO:431). Domain B spanning amino acids 75-96 of human IL-17RA (SEQ ID NO:431) negatively affected the binding of neutralizing antibodies AM$_H$1/AM$_L$1 and AM$_H$23/AM$_L$23. Domain C spanning amino acids 128-154 of human IL-17RA (SEQ ID NO:431) negatively affected the binding of neutralizing antibodies AM$_H$22/AM$_L$22 and AM$_H$23/AM$_L$23. Domain D spanning amino acids 176-197 of human IL-17RA (SEQ ID NO:431) negatively affected the binding of neutralizing antibodies AM$_H$1/AM$_L$1, AM$_H$22/AM$_L$22, AM$_H$14/AM$_L$14, AM$_H$19/AM$_L$19, AM$_H$23/AM$_L$23, AM$_H$21/AM$_L$21, and AM$_H$20/AM$_L$20. The binding characteristics of the IL-17RA antibodies in relation to where the antibodies bound on human IL-17RA was confirmed by the double chimeras. Thus. Domain B, C, and D are considered neutralizing determinants.

Example 11

As described above, antibodies that bind human IL-17RA and inhibit, or neutralize, the binding of IL-17A and/or IL-17F were created and characterized. To determine the neutralizing determinants on human IL-17RA that these various IL-17RA antibodies bound, a number of mutant IL-17RA proteins were constructed having arginine substitutions at select amino acid residues of human IL-17RA. Arginine scanning is an art-recognized method of evaluating where antibodies, or other proteins, bind to another protein, see for example Nanevicz, T., et al., 1995, J. Biol. Chem., 270:37, 21619-21625 and Zupnick, A., et al., 2006, J. Biol. Chem., 281:29, 20464-20473. In general, the arginine sidechain is positively charged and relatively bulky as compared to other amino acids, which may disrupt antibody binding to a region of the antigen where the mutation is introduced. Arginine scanning is a method that determines if a residue is part of a neutralizing determinant and/or an epitope.

95 amino acids distributed throughout the human IL-17RA extracellular domain were selected for mutation to arginine. The selection was biased towards charged or polar amino acids to maximize the possibility of the residue being on the surface and reduce the likelihood of the mutation resulting in misfolded protein. FIG. 12 depicts the amino acid residues that were replaced with an arginine residue in SEQ ID NO:431. Using standard techniques known in the art, sense and anti-sense oligonucleotides containing the mutated residues were designed based on criteria provided by Stratagene Quickchange® II protocol kit (Stratagene/Agilent, Santa Clara, Calif.). Mutagenesis of the wild-type (WT) HuIL-17RA-Flag-pHis was performed using a Quickchange® II kit (Stratagene). All chimeric constructs were constructed to encode a FLAG-histidine tag (six histidines) on the carboxy terminus of the extracellular domain to facilitate purification via the poly-His tag.

Multiplex analysis using the Bio-Plex Workstation and software (BioRad, Hercules, Calif.) was performed to determine neutralizing determinants on human IL-17RA by analyzing exemplary human IL-17RA mAbs differential binding to arginine mutants versus wild-type IL-17RA proteins. Twelve bead codes of pentaHis-coated beads (Qiagen, Valencia, Calif.; see www1.qiagen.com) were used to capture histidine-tagged protein. The 12 bead codes allowed the multiplexing of 11 IL-17RA arginine mutants and wild-type human IL-17RA (SEQ ID NO:431).

To prepare the beads, 100 ul of wild-type IL-17RA and IL-17RA arginine mutant supernatants from transient expression culture were bound to penta-His-coated beads overnight at 4° C. or 2 hours at room temperature with vigorous shaking. The beads were washed as per the manufacturer's protocol and the 12 bead set was pooled and aliquoted into 2 or 3 columns of a 96-well filter plate (Millipore, Bellerica, Mass., product #MSBVN1250) for duplicate or triplicate assay points, respectively. 100 ul anti-IL-17RA antibodies in 4-fold dilutions were added to the wells, incubated for 1 hour at room temperature, and washed. 100 ul of a 1:100 dilution of PE-conjugated anti-human IgG Fc (Jackson Labs., Bar Harbor, Me., product #109-116-170) was added to each well, incubated for 1 hour at room temperature and washed. Beads were resuspended in 1% BSA, shaken for 3 minutes, and read on the Bio-Plex workstation. Antibody binding to IL-17RA arginine mutant protein was compared to antibody binding to the human IL-17RA wild-type from the same pool. A titration of antibody over approximately a 5 log scale was performed. Median Fluorescence Intensity (MWI) of IL-17RA arginine mutant proteins was graphed as a percent of maximum wild-type human IL-17RA signal. Those mutants for which signal from all the antibodies are below 30% of wild-type IL-17RA were deemed to be either of too low a protein concentration on the head due to poor expression in the transient culture or possibly misfolded and were excluded from analysis: these were T51R, K53R, S55R, H64R, D75R, E110R, Q118R, T121, E123R, S147R, H148R, E158R, T160R, H163R, K191R, T193R, E213R, H251R, T269R, H279R, and D293R of SEQ ID NO:431. Mutations (i.e., arginine substitutions) that increase the EC50 for the IL-17RA mAb by 3-fold or greater (as calculated by GraphPad Prism®) were considered to have negatively affected IL-17RA mAb binding. Through these methods, neutralizing determinants and epitopes for various IL-17RA antibodies were elucidated.

Figure 13:
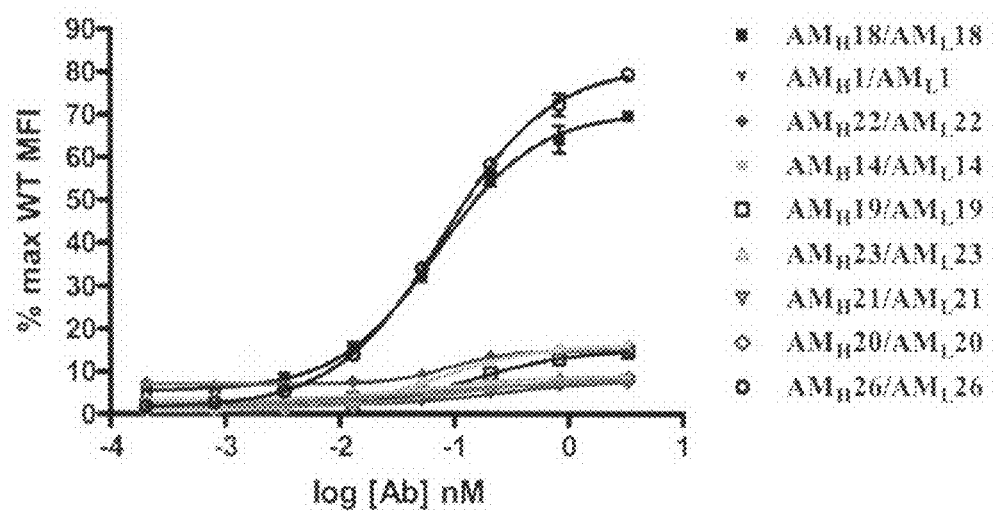
FIG. 13 illustrates titration curves of various IL-17RA mAbs binding to the D152R IL-17RA mutant.

FIG. 13 illustrates titration curves of various IL-17RA mAbs binding to the D152R IL-17RA mutant (i.e., the aspartic acid at position 152 of SEQ ID NO:431 was mutagenized to be an arginine). Antibodies $AM_H1/AM_L1$, $AM_H22/AM_L22$, $AM_H14/AM_L14$, $AM_H19/AM_L19$, $AM_H23/AM_L23$, $AM_H21/AM_L21$, and $AM_H20/AM_L20$ lost the capacity to bind the D152R IL-17RA mutant. Antibodies $AM_H18/AM_L18$ and $AM_H26/AM_L26$ were only marginally affected but did not meet the cutoff criteria.

A summary of the arginine scan, binning, and chimera data is presented in FIG. 14. The arginine scan methodology identified several neutralizing determinants: $AM_H18/AM_L18$ bound a domain spanning amino acids 220-284 of human IL-17RA (SEQ ID NO:431); $AM_H1/AM_L1$ bound a domain focused on amino acid residue 152 of human IL-17RA (SEQ ID NO:431); $AM_H22/AM_L22$ bound a domain spanning amino acids 152-198 of human IL-17RA (SEQ ID NO:431); $AM_H14/AM_L14$ bound a domain spanning amino acids 152-297 of human IL-17RA (SEQ ID NO:431); $AM_H19/AM_L19$ bound a domain spanning amino acids 152-186 of human IL-17RA (SEQ ID NO:431); $AM_H23/AM_L23$ bound a domain spanning amino acids 97-297 of human IL-17RA (SEQ ID NO:431); $AM_H26/AM_L26$ bound a domain spanning amino acids 138-270 of human IL-17RA (SEQ ID NO:431); $AM_H21/AM_L21$ bound a domain spanning amino acids 113-198 of human IL-17RA (SEQ ID NO:431); and $AM_H20/AM_L20$ bound a domain spanning amino acids 152-270 of human IL-17RA (SEQ ID NO:431).

All of the residues shown in FIG. 14 have been shown to reduce binding of a neutralizing human monoclonal antibody that specifically binds to human IL-17RA.

What is claimed is:

1. An isolated monoclonal antibody, comprising a first isolated monoclonal antibody, or IL-17RA-binding fragment thereof, that specifically binds to IL-17RA and competes for binding with a second isolated monoclonal antibody, wherein said second isolated monoclonal antibody, or IL-17RA-binding fragment thereof, comprises a light chain CDR1 (SEQ ID NO:224), CDR2 (SEQ ID NO:225), CDR3 (SEQ ID NO:226) and a heavy chain CDR1 (SEQ ID NO:146), CDR2 (SEQ ID NO:147), CDR3 (SEQ ID NO:148).

2. The first isolated monoclonal antibody of claim 1, wherein said first isolated monoclonal antibody is selected from the group consisting of:
   a. a human antibody;
   b. a humanized antibody;
   c. a chimeric antibody;
   d. a single chain antibody;
   e. a diabody;
   f. a triabody;
   g. a tetrabody;
   h. a Fab fragment;
   i. a F(ab')2 fragment;
   j. an IgD antibody;
   k. an IgE antibody;
   l. an IgM antibody;
   m. an IgG1 antibody;
   n. an IgG2 antibody;
   o. an IgG3 antibody; and
   p. an IgG4 antibody.

3. The first isolated monoclonal antibody of claim 2, wherein said antibody inhibits human IL-17A from binding to human IL-17RA.

4. The first isolated monoclonal antibody of claim 3, wherein said antibody inhibits human IL-17A and human IL-17F from binding to human IL-17RA.

5. The first isolated monoclonal antibody of claim 2, wherein said antibody inhibits human IL-17A or human IL-17F from binding to human IL-17RA.

6. An isolated monoclonal antibody, comprising a first isolated monoclonal antibody, or IL-17RA-binding fragment thereof, that specifically binds to IL-17RA and competes for binding with a second isolated monoclonal antibody, wherein said second isolated monoclonal antibody, or IL-17RA-binding fragment thereof, comprises a light chain variable domain sequence comprising SEQ ID NO:40 and a heavy chain variable domain sequence comprising SEQ ID NO:14.

7. An isolated monoclonal antibody, comprising a first isolated monoclonal antibody, or IL-17RA-binding fragment thereof, that specifically binds to IL-17RA and competes for binding with a second isolated monoclonal antibody, wherein said second isolated monoclonal antibody, or IL-17RA-binding fragment thereof, comprises a light chain sequence comprising SEQ ID NO:429 and a heavy chain sequence comprising SEQ ID NO:427.

8. An isolated monoclonal antibody, comprising a first isolated monoclonal antibody, or IL-17RA-binding fragment thereof, that specifically binds to IL-17RA and competes for binding with a second isolated monoclonal antibody, wherein said second isolated monoclonal antibody, or IL-17RA-binding fragment thereof, comprises at least two light chain sequences comprising SEQ ID NO:429 and at least two heavy chain sequences comprising SEQ ID NO:427.

* * * * *

SEQUENCE LISTING

```
<160> NUMBER OF SEQ ID NOS: 470

<210> SEQ ID NO 1
<211> LENGTH: 131
<212> TYPE: PRT
<213> ORGANISM: Homo sapiens

<400> SEQUENCE: 1

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Asn Tyr
            20                  25                  30

Tyr Trp Asn Trp Ile Arg Gln Ser Pro Gly Lys Gly Leu Glu Trp Ile
        35                  40                  45

Gly Asp Ile Tyr Tyr Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Thr Ala Asp Thr Ala Val Tyr Tyr Cys Ala
                85                  90                  95

Arg Asp Gly Glu Leu Ala Asn Tyr Tyr Gly Ser Gly Ser Tyr Gln Phe
            100                 105                 110

Tyr Tyr Tyr Tyr Gly Met Asp Val Trp Gly Gln Gly Thr Thr Val Thr
        115                 120                 125

Val Ser Ser
    130

<210> SEQ ID NO 2
<211> LENGTH: 127
```

```
<212> TYPE: PRT
<213> ORGANISM: Homo sapiens

<400> SEQUENCE: 2

Gln Val Gln Leu Gln Gln Trp Gly Ala Gly Leu Leu Lys Pro Ser Glu
1               5                   10                  15

Thr Leu Ser Leu Thr Cys Ala Val Ser Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Arg Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Pro Tyr Tyr Phe Asp Ser Ser Gly Tyr Leu Tyr Tyr Tyr Tyr
            100                 105                 110

Gly Leu Asp Val Trp Gly Gln Gly Thr Thr Val Thr Val Ser Ser
        115                 120                 125

<210> SEQ ID NO 3
<211> LENGTH: 114
<212> TYPE: PRT
<213> ORGANISM: Homo sapiens

<400> SEQUENCE: 3

Gln Val Gln Leu Val Glu Ser Gly Gly Gly Val Val Gln Pro Gly Arg
1               5                   10                  15

Ser Leu Arg Leu Ser Cys Ala Ala Ser Gly Ile Asn Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Thr Gly Val Tyr Trp Gly Gln Gly Thr Leu Val Thr Val
            100                 105                 110

Ser Ser

<210> SEQ ID NO 4
<211> LENGTH: 114
<212> TYPE: PRT
<213> ORGANISM: Homo sapiens

<400> SEQUENCE: 4

Gln Val Gln Leu Val Glu Ser Gly Gly Gly Val Val Gln Pro Gly Arg
1               5                   10                  15

Ser Leu Arg Leu Ser Cys Ala Ala Ser Gly Ile Asn Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys His Tyr Ala Asp Ser Val
    50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Thr Gly Val Tyr Trp Gly Gln Gly Thr Leu Val Thr Val
            100                 105                 110

Ser Ser

<210> SEQ ID NO 5
<211> LENGTH: 125
<212> TYPE: PRT
<213> ORGANISM: Homo sapiens

<400> SEQUENCE: 5

Gln Val Gln Leu Gln Glu Ser Gly Pro Gly Leu Val Lys Pro Ser Glu
 1               5                  10                  15

Thr Leu Pro Leu Thr Cys Thr Val Ser Gly Gly Ser Ile Arg Ser Tyr
                20                  25                  30

Tyr Trp Ser Trp Ile Arg Gln Pro Ala Gly Lys Gly Leu Glu Trp Ile
            35                  40                  45

Gly Arg Ile Tyr Arg Ser Gly Asn Thr Ile Tyr Asn Pro Ser Leu Lys
        50                  55                  60

Ser Arg Val Thr Met Ser Ile Asp Thr Ser Lys Asn Gln Phe Ser Leu
 65                  70                  75                  80

Thr Leu Ser Ser Val Thr Ala Ala Asp Thr Ala Val Tyr Tyr Cys Ala
                 85                  90                  95

Arg Glu Asn Tyr Ser Glu Ser Ser Gly Leu Tyr Tyr Tyr Tyr Gly Met
            100                 105                 110

Asp Val Trp Gly Gln Gly Thr Thr Val Thr Val Ser Ser
        115                 120                 125

<210> SEQ ID NO 6
<211> LENGTH: 124
<212> TYPE: PRT
<213> ORGANISM: Homo sapiens

<400> SEQUENCE: 6

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Leu Thr Arg Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
        50                  55                  60

Gln Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Arg Asp Tyr Asp Ile Leu Thr Gly Tyr Tyr Asn Gly Phe Asp
            100                 105                 110

Pro Trp Gly Gln Gly Thr Leu Val Thr Val Ser Ser
        115                 120

<210> SEQ ID NO 7
<211> LENGTH: 124
```

```
<212> TYPE: PRT
<213> ORGANISM: Homo sapiens

<400> SEQUENCE: 7

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Thr Arg Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Arg Asp Tyr Asp Ile Leu Thr Gly Tyr Tyr Asn Gly Phe Asp
                100                 105                 110

Pro Trp Gly Gln Gly Thr Leu Val Thr Val Ser Ser
            115                 120

<210> SEQ ID NO 8
<211> LENGTH: 124
<212> TYPE: PRT
<213> ORGANISM: Homo sapiens

<400> SEQUENCE: 8

Gln Val Gln Leu Val Gln Ser Gly Ala Glu Val Lys Lys Pro Gly Ala
1               5                   10                  15

Ser Val Lys Val Ser Cys Lys Ala Ser Gly Asn Thr Phe Thr Gly Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Asn Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Arg Asp Tyr Asp Ile Leu Thr Gly Tyr Tyr Asn Gly Phe Asp
                100                 105                 110

Pro Trp Gly Gln Gly Thr Leu Val Thr Val Ser Ser
            115                 120

<210> SEQ ID NO 9
<211> LENGTH: 124
<212> TYPE: PRT
<213> ORGANISM: Homo sapiens

<400> SEQUENCE: 9

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Leu Thr Arg Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
```

```
                 50                  55                  60
Gln Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Arg Asp Tyr Asp Ile Leu Thr Gly Tyr Tyr Asn Gly Phe Asp
                100                 105                 110

Pro Trp Gly Gln Gly Thr Leu Val Thr Val Ser Ser
                115                 120

<210> SEQ ID NO 10
<211> LENGTH: 124
<212> TYPE: PRT
<213> ORGANISM: Homo sapiens

<400> SEQUENCE: 10

Gln Val Gln Leu Gln Glu Ser Gly Pro Gly Leu Val Lys Pro Ser Gln
  1               5                  10                  15

Thr Leu Ser Leu Thr Cys Thr Val Ser Gly Gly Ser Ile Ser Ser Gly
                 20                  25                  30

Gly Tyr Tyr Trp Ser Trp Ile Arg Gln His Pro Gly Lys Gly Leu Glu
                 35                  40                  45

Trp Ile Gly Tyr Ile Tyr Phe Ser Gly Ser Ala Tyr Tyr Asn Pro Ser
 50                  55                  60

Leu Lys Ser Arg Val Ala Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Glu Tyr Tyr Asp Ser Ser Gly Tyr Pro Asp Ala Phe Asp
                100                 105                 110

Ile Trp Gly Gln Gly Thr Met Val Thr Val Ser Ser
                115                 120

<210> SEQ ID NO 11
<211> LENGTH: 114
<212> TYPE: PRT
<213> ORGANISM: Homo sapiens

<400> SEQUENCE: 11

Gln Val Gln Leu Val Glu Ser Gly Gly Gly Val Val Gln Pro Gly Arg
  1               5                  10                  15

Ser Leu Arg Leu Ser Cys Ala Thr Ser Gly Ile Thr Phe Ser Ser Tyr
                 20                  25                  30

Gly Met His Trp Val Arg Gln Ala Pro Gly Lys Gly Leu Glu Trp Val
                 35                  40                  45

Ala Val Ile Trp Tyr Asp Gly Ser Asn Lys Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Thr Lys Asp Tyr Trp Gly Gln Gly Thr Leu Val Thr Val
                100                 105                 110

Ser Ser

<210> SEQ ID NO 12
```

<211> LENGTH: 116
<212> TYPE: PRT
<213> ORGANISM: Homo sapiens

<400> SEQUENCE: 12

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Thr Ser Tyr
            20                  25                  30

Gly Ile Ser Trp Val Arg Gln Ala Pro Gly Gln Gly Leu Glu Trp Met
        35                  40                  45

Gly Trp Ile Ser Thr Tyr Lys Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Lys Gln Leu Val Phe Asp Tyr Trp Gly Gln Gly Thr Leu Val
            100                 105                 110

Thr Val Ser Ser
        115

<210> SEQ ID NO 13
<211> LENGTH: 121
<212> TYPE: PRT
<213> ORGANISM: Homo sapiens

<400> SEQUENCE: 13

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met Gln Trp Val Arg Gln Ala Pro Gly Lys Gly Leu Glu Trp Val
        35                  40                  45

Ala Val Ile Trp Tyr Asp Gly Asn Lys Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Arg Val Arg Asp Tyr Tyr Tyr Gly Met Asp Val Trp Gly
            100                 105                 110

Gln Gly Thr Thr Val Thr Val Ser Ser
        115                 120

<210> SEQ ID NO 14
<211> LENGTH: 116
<212> TYPE: PRT
<213> ORGANISM: Homo sapiens

<400> SEQUENCE: 14

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
            20                  25                  30

Gly Ile Ser Trp Val Arg Gln Ala Pro Gly Gln Gly Leu Glu Trp Met
        35                  40                  45

```
Gly Trp Ile Ser Thr Tyr Ser Gly Asn Thr Asn Tyr Ala Gln Lys Leu
            50                  55                  60

Gln Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Arg Gln Leu Tyr Phe Asp Tyr Trp Gly Gln Gly Thr Leu Val
            100                 105                 110

Thr Val Ser Ser
        115

<210> SEQ ID NO 15
<211> LENGTH: 121
<212> TYPE: PRT
<213> ORGANISM: Homo sapiens

<400> SEQUENCE: 15

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
             20                  25                  30

Gly Met Gln Trp Val Arg Gln Ala Pro Gly Lys Gly Leu Glu Trp Val
         35                  40                  45

Ala Val Ile Trp Tyr Asp Gly Asn Lys Lys Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Arg Val Arg Asp Tyr Tyr Tyr Gly Met Asp Val Trp Gly
            100                 105                 110

Gln Gly Thr Thr Val Thr Val Ser Ser
            115                 120

<210> SEQ ID NO 16
<211> LENGTH: 116
<212> TYPE: PRT
<213> ORGANISM: Homo sapiens

<400> SEQUENCE: 16

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
             20                  25                  30

Gly Ile Ser Trp Val Arg Gln Ala Pro Gly Gln Gly Leu Glu Trp Met
         35                  40                  45

Gly Trp Ile Ser Ala Tyr Asn Gly Asn Thr Lys Tyr Ala Gln Lys Leu
     50                  55                  60

Gln Gly Arg Val Thr Met Thr Thr Asp Thr Ser Thr Ser Thr Val Tyr
 65                  70                  75                  80

Met Glu Leu Arg Ser Leu Arg Ser Asp Asp Thr Ala Val Tyr Tyr Cys
                 85                  90                  95

Ala Arg Lys Gln Leu Val Phe Asp Tyr Trp Gly Gln Gly Thr Leu Val
            100                 105                 110

Thr Val Ser Ser
        115
```

<210> SEQ ID NO 17
<211> LENGTH: 116
<212> TYPE: PRT
<213> ORGANISM: Homo sapiens

<400> SEQUENCE: 17

Gln Val Gln Leu Val Gln Ser Gly Ala Glu Val Lys Lys Pro Gly Ala
1               5                   10                  15

Ala Val Lys Val Ser Cys Lys Ala Thr Gly Tyr Thr Leu Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Ser Gly Asn Thr Lys Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Lys Gln Leu Val Phe Asp Tyr Trp Gly Gln Gly Thr Leu Val
            100                 105                 110

Thr Val Ser Ser
        115

<210> SEQ ID NO 18
<211> LENGTH: 126
<212> TYPE: PRT
<213> ORGANISM: Homo sapiens

<400> SEQUENCE: 18

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

Tyr Met His Trp Val Arg Gln Ala Pro Gly Gln Gly Leu Glu Trp Met
        35                  40                  45

Gly Trp Met His Pro Asn Ser Gly Gly Thr Asp Leu Ala Gln Arg Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Gly Tyr Cys Ser Thr Leu Ser Cys Ser Phe Tyr Trp Tyr
            100                 105                 110

Phe Asp Leu Trp Gly Arg Gly Thr Leu Val Thr Val Ser Ser
        115                 120                 125

<210> SEQ ID NO 19
<211> LENGTH: 116
<212> TYPE: PRT
<213> ORGANISM: Homo sapiens

<400> SEQUENCE: 19

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Thr Ser Tyr
            20                  25                  30

Gly Ile Ser Trp Val Arg Gln Ala Pro Gly Gln Gly Leu Glu Trp Met

```
                35                  40                  45
Gly Trp Ile Ser Ala Tyr Ser Gly Asn Thr Lys Tyr Ala Gln Lys Phe
 50                  55                  60
Gln Gly Arg Val Thr Met Thr Thr Asp Thr Ser Thr Ser Thr Ala Tyr
 65                  70                  75                  80
Met Glu Leu Arg Ser Leu Arg Ser Asp Asp Thr Ala Val Tyr Tyr Cys
                 85                  90                  95
Ala Arg Arg Gln Leu Ala Leu Asp Tyr Trp Gly Gln Gly Thr Leu Val
                100                 105                 110
Thr Val Ser Ser
        115

<210> SEQ ID NO 20
<211> LENGTH: 118
<212> TYPE: PRT
<213> ORGANISM: Homo sapiens

<400> SEQUENCE: 20

Glu Val Gln Leu Val Glu Ser Gly Gly Gly Leu Val Gln Pro Gly Gly
 1               5                  10                  15
Ser Leu Arg Leu Ser Cys Ala Ala Ser Gly Phe Thr Phe Ser Ser Tyr
                20                  25                  30
Ser Met Asn Trp Val Arg Gln Ala Pro Gly Lys Gly Leu Glu Trp Val
                35                  40                  45
Ser Phe Ile Ser Ala Arg Ser Ser Thr Ile Tyr Tyr Ala Asp Ser Val
 50                  55                  60
Lys Gly Arg Phe Thr Ile Ser Arg Asp Asn Ala Lys Asn Ser Leu Tyr
 65                  70                  75                  80
Leu Gln Met Asn Ser Leu Arg Asp Glu Asp Thr Ala Val Tyr Tyr Cys
                 85                  90                  95
Ala Arg Pro Lys Val Gly Gly Gly Met Asp Val Trp Gly Gln Gly Thr
                100                 105                 110
Thr Val Thr Val Ser Ser
        115

<210> SEQ ID NO 21
<211> LENGTH: 118
<212> TYPE: PRT
<213> ORGANISM: Homo sapiens

<400> SEQUENCE: 21

Glu Val Gln Leu Val Glu Ser Gly Gly Gly Ser Val Gln Pro Gly Gly
 1               5                  10                  15
Ser Leu Arg Leu Ser Cys Ala Ala Ser Gly Phe Thr Phe Ser Ser Tyr
                20                  25                  30
Ser Met Asn Trp Val Arg Gln Ala Pro Gly Lys Gly Leu Glu Trp Val
                35                  40                  45
Ser Ile Ile Ser Ser Arg Ser Ser Ile Ile His Tyr Ala Asp Ser Val
 50                  55                  60
Lys Gly Arg Phe Thr Ile Ser Arg Asp Asn Ala Lys Asn Ser Leu Tyr
 65                  70                  75                  80
Leu Gln Met Asn Ser Leu Arg Asp Glu Asp Thr Ala Val Tyr Tyr Cys
                 85                  90                  95
Ala Arg Pro Lys Val Gly Gly Gly Met Asp Val Trp Gly Gln Gly Thr
                100                 105                 110
Thr Val Thr Val Ser Ser
```

<210> SEQ ID NO 22
<211> LENGTH: 116
<212> TYPE: PRT
<213> ORGANISM: Homo sapiens

<400> SEQUENCE: 22

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Ser Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Arg Gln Leu Tyr Phe Asp Tyr Trp Gly Gln Gly Thr Leu Val
            100                 105                 110

Thr Val Ser Ser
        115

<210> SEQ ID NO 23
<211> LENGTH: 125
<212> TYPE: PRT
<213> ORGANISM: Homo sapiens

<400> SEQUENCE: 23

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Ala Gly Lys Arg Leu Glu Trp Ile
        35                  40                  45

Gly Arg Ile Tyr Pro Ser Gly Arg Thr Asn Tyr Asn Pro Ser Leu Lys
    50                  55                  60

Ser Arg Val Thr Met Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Ala Tyr Glu Leu Gln Leu Gly Leu Tyr Tyr Tyr Tyr Gly Met
            100                 105                 110

Asp Val Trp Gly Gln Gly Thr Pro Val Thr Val Ser Ser
        115                 120                 125

<210> SEQ ID NO 24
<211> LENGTH: 125
<212> TYPE: PRT
<213> ORGANISM: Homo sapiens

<400> SEQUENCE: 24

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

```
Tyr Trp Ser Trp Ile Arg Gln Ala Ala Gly Lys Arg Leu Glu Trp Ile
         35                  40                  45

Gly Arg Ile Tyr Pro Ser Gly Arg Thr Asn Tyr Asn Pro Ser Leu Lys
 50                  55                  60

Ser Arg Val Thr Met Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Glu Ala Tyr Glu Leu Gln Leu Gly Leu Tyr Tyr Tyr Gly Met
             100                 105                 110

Asp Val Trp Gly Gln Gly Thr Pro Val Thr Val Ser Ser
             115                 120                 125

<210> SEQ ID NO 25
<211> LENGTH: 124
<212> TYPE: PRT
<213> ORGANISM: Homo sapiens

<400> SEQUENCE: 25

Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Ser Ser Gly
                 20                  25                  30

Gly Tyr Tyr Trp Ser Trp Ile Arg Gln His Pro Gly Lys Gly Leu Glu
             35                  40                  45

Trp Ile Gly Tyr Ile Tyr Tyr Ser Gly Asn Thr Tyr Tyr Asn Pro Ser
 50                  55                  60

Leu Arg Ser Arg Val Thr Ile Ser Val Asp Thr Ser Lys Asn Gln Phe
 65                  70                  75                  80

Ser Leu Lys Leu Asn Ser Val Thr Ala Ala Asp Thr Ala Val Tyr Tyr
                 85                  90                  95

Cys Ala Arg Glu Ala Gly Gly Asn Ser Ala Tyr Tyr Tyr Gly Met Asp
             100                 105                 110

Val Trp Gly Gln Gly Thr Thr Val Thr Val Ser Ser
             115                 120

<210> SEQ ID NO 26
<211> LENGTH: 125
<212> TYPE: PRT
<213> ORGANISM: Homo sapiens

<400> SEQUENCE: 26

Gln Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asp Tyr
                 20                  25                  30

Tyr Met Ser Trp Ile Arg Gln Ala Pro Gly Lys Gly Leu Glu Trp Val
             35                  40                  45

Ser Tyr Ile Ser Ser Ser Gly Ser Thr Ile Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Arg Thr Tyr Tyr Phe Gly Ser Gly Ser Tyr Glu Gly Met
             100                 105                 110
```

```
Asp Val Trp Gly Gln Gly Thr Thr Val Thr Val Ser Ser
        115                 120                 125
```

<210> SEQ ID NO 27
<211> LENGTH: 107
<212> TYPE: PRT
<213> ORGANISM: Homo sapiens

<400> SEQUENCE: 27

```
Asp Ile Leu Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Asn Pro Phe
                85                  90                  95

Thr Phe Gly Pro Gly Thr Lys Val Asp Ile Lys
            100                 105
```

<210> SEQ ID NO 28
<211> LENGTH: 106
<212> TYPE: PRT
<213> ORGANISM: Homo sapiens

<400> SEQUENCE: 28

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Arg Asn
            20                  25                  30

Leu Val Trp Tyr Gln Gln Arg Pro Gly Gln Ala Pro Arg Leu Leu Ile
        35                  40                  45

Tyr Gly Ala Ser Thr Arg Ala Asn Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Lys Ser Trp Arg Thr
                85                  90                  95

Phe Gly Gln Gly Ser Lys Val Glu Ile Lys
            100                 105
```

<210> SEQ ID NO 29
<211> LENGTH: 107
<212> TYPE: PRT
<213> ORGANISM: Homo sapiens

<400> SEQUENCE: 29

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45
```

```
Tyr Ala Ala Ser Ser Leu Gln Ser Gly Val Pro Ser Arg Phe Ser Gly
            50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Lys Ser Tyr Pro Leu
                 85                  90                  95

Thr Phe Gly Gly Gly Thr Lys Val Glu Ile Lys
                100                 105

<210> SEQ ID NO 30
<211> LENGTH: 108
<212> TYPE: PRT
<213> ORGANISM: Homo sapiens

<400> SEQUENCE: 30

Glu Ile Val Met Thr Gln Ser Pro Ala Thr Leu Ser Val Ser Pro Gly
 1               5                  10                  15

Glu Arg Ala Thr Leu Ser Cys Arg Ala Ser Gln Ser Val Ser Arg Asn
                20                  25                  30

Leu Ala Trp Tyr Gln Gln Lys Pro Gly Gln Ala Pro Arg Leu Leu Ile
            35                  40                  45

Tyr Gly Ala Ser Thr Arg Ala Thr Gly Ile Pro Ala Arg Phe Ser Gly
        50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Tyr Asn Asn Trp Pro Thr
                 85                  90                  95

Trp Thr Phe Gly Gln Gly Thr Lys Val Glu Ile Lys
                100                 105

<210> SEQ ID NO 31
<211> LENGTH: 107
<212> TYPE: PRT
<213> ORGANISM: Homo sapiens

<400> SEQUENCE: 31

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asp
                20                  25                  30

Leu Gly Trp Tyr Gln Gln Lys Pro Gly Lys Ala Pro Lys Arg Leu Ile
            35                  40                  45

Tyr Ala Ala Ser Ser Phe Gln Ser Gly Val Pro Ser Arg Phe Ser Gly
        50                  55                  60

Ser Gly Ser Gly Thr Gly Phe Thr Leu Thr Ile Ser Ser Leu Gln Pro
 65                  70                  75                  80

Glu Asp Phe Ala Thr Tyr Tyr Cys Leu Gln His Asn Ser Tyr Pro Pro
                 85                  90                  95

Thr Phe Gly Gln Gly Thr Lys Val Glu Ile Lys
                100                 105

<210> SEQ ID NO 32
<211> LENGTH: 107
<212> TYPE: PRT
<213> ORGANISM: Homo sapiens

<400> SEQUENCE: 32

Asp Ile Gln Met Thr Gln Ser Pro Ser Ser Leu Ser Ala Ser Val Gly
```

```
                1               5                  10                 15
Asp Arg Val Thr Ile Thr Cys Arg Ala Ser Gln Gly Ile Arg Asn Asp
                20                  25                  30

Leu Gly Trp Tyr Gln Gln Lys Pro Gly Lys Ala Pro Lys Arg Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Lys Ser Tyr Pro Leu
                85                  90                  95

Thr Phe Gly Gly Gly Thr Lys Val Glu Ile Lys
            100                 105

<210> SEQ ID NO 33
<211> LENGTH: 107
<212> TYPE: PRT
<213> ORGANISM: Homo sapiens

<400> SEQUENCE: 33

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
                20                  25                  30

Leu Gly Trp Tyr Gln Gln Lys Pro Gly Lys Ala Pro Lys Arg Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Lys Ser Tyr Pro Leu
                85                  90                  95

Thr Phe Gly Gly Gly Thr Lys Val Glu Ile Lys
            100                 105

<210> SEQ ID NO 34
<211> LENGTH: 107
<212> TYPE: PRT
<213> ORGANISM: Homo sapiens

<400> SEQUENCE: 34

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
                20                  25                  30

Leu Gly Trp Tyr Gln Gln Lys Pro Gly Lys Ala Pro Lys Arg Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Lys Ser Tyr Pro Leu
                85                  90                  95

Thr Phe Gly Gly Gly Thr Lys Val Glu Ile Lys
            100                 105
```

```
<210> SEQ ID NO 35
<211> LENGTH: 107
<212> TYPE: PRT
<213> ORGANISM: Homo sapiens

<400> SEQUENCE: 35

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Lys Ser Tyr Pro Leu
                85                  90                  95

Thr Phe Gly Gly Gly Thr Lys Val Glu Ile Lys
            100                 105

<210> SEQ ID NO 36
<211> LENGTH: 107
<212> TYPE: PRT
<213> ORGANISM: Homo sapiens

<400> SEQUENCE: 36

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Arg Ser Trp
            20                  25                  30

Leu Ala Trp Tyr Gln Gln Lys Pro Gly Lys Ala Pro Lys Leu Leu Ile
        35                  40                  45

Phe Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Ala Asn Asn Phe Pro Arg
                85                  90                  95

Thr Phe Gly Gln Gly Thr Lys Val Glu Ile Lys
            100                 105

<210> SEQ ID NO 37
<211> LENGTH: 108
<212> TYPE: PRT
<213> ORGANISM: Homo sapiens

<400> SEQUENCE: 37

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Ala Gly Ile Pro Ala Arg Phe Ser Gly
    50                  55                  60

Gly Gly Ser Gly Thr Ala Phe Thr Leu Thr Ile Ser Asn Leu Gln Ser
65                  70                  75                  80
```

Glu Asp Phe Ala Val Tyr Tyr Cys Gln His Tyr Ile Asn Trp Pro Lys
                85                  90                  95

Trp Thr Phe Gly Gln Gly Thr Lys Val Asp Ile Lys
            100                 105

<210> SEQ ID NO 38
<211> LENGTH: 107
<212> TYPE: PRT
<213> ORGANISM: Homo sapiens

<400> SEQUENCE: 38

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Ser Ser Ser
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asn Phe Ala Val Tyr Tyr Cys Gln Gln Tyr Asp Asn Trp Pro Leu
                85                  90                  95

Thr Phe Gly Gly Gly Thr Lys Val Glu Ile Lys
            100                 105

<210> SEQ ID NO 39
<211> LENGTH: 112
<212> TYPE: PRT
<213> ORGANISM: Homo sapiens

<400> SEQUENCE: 39

Asp Ile Val Met Thr Gln Thr Pro Leu Ser Leu Ser Val Thr Pro Gly
1               5                   10                  15

Gln Pro Ala Ser Ile Ala Cys Lys Ser Ser Gln Ser Leu Leu His Ser
            20                  25                  30

Asp Gly Lys Thr Tyr Leu Tyr Trp Tyr Leu Gln Lys Pro Gly Gln Pro
        35                  40                  45

Pro Gln Leu Leu Ile Tyr Glu Val Ser Thr Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Phe Tyr Cys Met Gln Ser
                85                  90                  95

Ile Gln Leu Pro Leu Thr Phe Gly Gly Gly Thr Lys Val Glu Ile Lys
            100                 105                 110

<210> SEQ ID NO 40
<211> LENGTH: 107
<212> TYPE: PRT
<213> ORGANISM: Homo sapiens

<400> SEQUENCE: 40

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

```
Leu Ala Trp Phe Gln Gln Lys Pro Gly Gln Ala Pro Arg Pro Leu Ile
        35                  40                  45

Tyr Asp Ala Ser Thr Arg Ala Thr Gly Val Pro Ala Arg Phe Ser Gly
 50                  55                  60

Ser Gly Ser Gly Thr Asp Phe Thr Leu Thr Ile Ser Ser Leu Gln Ser
 65                  70                  75                  80

Glu Asp Phe Ala Val Tyr Tyr Cys Gln Gln Tyr Asp Asn Trp Pro Leu
                 85                  90                  95

Thr Phe Gly Gly Gly Thr Lys Val Glu Ile Lys
            100                 105
```

<210> SEQ ID NO 41
<211> LENGTH: 107
<212> TYPE: PRT
<213> ORGANISM: Homo sapiens

<400> SEQUENCE: 41

```
Glu Ile Val Met Thr Gln Ser Pro Ala Thr Leu Ser Val Ser Pro Gly
 1               5                  10                  15

Glu Arg Val Thr Leu Ser Cys Arg Ala Ser Gln Ser Val Ser Ser Asn
             20                  25                  30

Leu Ala Trp Phe Gln Gln Lys Pro Gly Gln Ala Pro Arg Pro Leu Ile
        35                  40                  45

Tyr Asp Ala Ser Thr Arg Ala Ala Gly Ile Pro Ala Arg Phe Ser Gly
 50                  55                  60

Ser Gly Ser Gly Thr Asp Phe Thr Leu Thr Ile Ser Ser Leu Gln Ser
 65                  70                  75                  80

Glu Asp Phe Ala Val Tyr Tyr Cys Gln Gln Tyr Asp Asn Trp Pro Leu
                 85                  90                  95

Thr Phe Gly Gly Gly Thr Lys Val Glu Ile Lys
            100                 105
```

<210> SEQ ID NO 42
<211> LENGTH: 107
<212> TYPE: PRT
<213> ORGANISM: Homo sapiens

<400> SEQUENCE: 42

```
Glu Ile Val Met Thr Gln Ser Pro Ala Thr Leu Ser Val Ser Pro Gly
 1               5                  10                  15

Glu Arg Ala Thr Leu Ser Cys Arg Ala Ser Gln Ser Ile Ser Thr Ser
             20                  25                  30

Leu Ala Trp Tyr Gln Gln Lys Pro Gly Gln Ala Pro Arg Leu Leu Ile
        35                  40                  45

Tyr Gly Thr Ser Thr Arg Ala Thr Gly Ile Pro Ala Arg Phe Ser Gly
 50                  55                  60

Ser Gly Ser Gly Thr Glu Phe Thr Leu Thr Ile Ser Ser Leu Gln Ser
 65                  70                  75                  80

Glu Asp Phe Ala Val Tyr Phe Cys Gln Gln Tyr Asp Ile Trp Pro Leu
                 85                  90                  95

Thr Phe Gly Gly Gly Thr Lys Val Glu Ile Lys
            100                 105
```

<210> SEQ ID NO 43
<211> LENGTH: 107
<212> TYPE: PRT
<213> ORGANISM: Homo sapiens

```
<400> SEQUENCE: 43

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Ser Cys Gln Gln Tyr Asp Asn Trp Pro Leu
                85                  90                  95

Thr Phe Gly Gly Gly Thr Lys Val Glu Ile Lys
                100                 105

<210> SEQ ID NO 44
<211> LENGTH: 113
<212> TYPE: PRT
<213> ORGANISM: Homo sapiens

<400> SEQUENCE: 44

Asp Ile Val Met Thr Gln Ser Pro Asp Ser Leu Ala Val Ser Leu Gly
1               5                   10                  15

Glu Arg Ala Thr Ile Asn Cys Lys Thr Ser Gln Ser Val Leu Tyr Ser
            20                  25                  30

Ser Lys Asn Lys Asn Phe Leu Ala Trp Tyr Gln Gln Lys Pro Gly Gln
        35                  40                  45

Pro Leu Asn Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Phe Thr Phe Gly Pro Gly Thr Lys Val Asp Ile
                100                 105                 110

Lys

<210> SEQ ID NO 45
<211> LENGTH: 107
<212> TYPE: PRT
<213> ORGANISM: Homo sapiens

<400> SEQUENCE: 45

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Asp
50                  55                  60

Asn Gly Ser Gly Thr Glu Phe Thr Leu Thr Ile Ser Ser Leu Gln Ser
65                  70                  75                  80

Glu Asp Phe Ala Val Tyr Phe Cys Gln Gln Tyr Asp Thr Trp Pro Leu
                85                  90                  95
```

Thr Phe Gly Gly Gly Thr Lys Val Glu Ile Lys
            100                 105

<210> SEQ ID NO 46
<211> LENGTH: 107
<212> TYPE: PRT
<213> ORGANISM: Homo sapiens

<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Phe Pro Glu Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Arg Ala Pro Phe
                85                  90                  95

Thr Phe Gly Pro Gly Thr Lys Val Asp Ile Lys
            100                 105

<210> SEQ ID NO 47
<211> LENGTH: 107
<212> TYPE: PRT
<213> ORGANISM: Homo sapiens

<400> SEQUENCE: 47

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Phe Pro Glu Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Arg Ala Pro Phe
                85                  90                  95

Thr Phe Gly Pro Gly Thr Lys Val Asp Ile Lys
            100                 105

<210> SEQ ID NO 48
<211> LENGTH: 107
<212> TYPE: PRT
<213> ORGANISM: Homo sapiens

<400> SEQUENCE: 48

Glu Ile Val Met Thr Gln Ser Pro Ala Thr Leu Ser Val Ser Pro Gly
1               5                   10                  15

Glu Arg Val Thr Leu Ser Cys Arg Ala Ser Gln Ser Val Ser Ser Asn
            20                  25                  30

Leu Ala Trp Phe Gln Gln Lys Pro Gly Gln Ala Pro Arg Pro Leu Ile
        35                  40                  45

```
Tyr Asp Ala Ser Thr Arg Ala Ala Gly Ile Pro Ala Arg Phe Ser Gly
        50                  55                  60

Ser Gly Ser Gly Thr Asp Phe Thr Leu Thr Ile Ser Ser Leu Gln Ser
65                  70                  75                  80

Glu Asp Phe Ala Val Tyr Tyr Cys Gln Gln Tyr Asp Asn Trp Pro Leu
                85                  90                  95

Thr Phe Gly Gly Gly Thr Lys Val Glu Ile Lys
            100                 105

<210> SEQ ID NO 49
<211> LENGTH: 107
<212> TYPE: PRT
<213> ORGANISM: Homo sapiens

<400> SEQUENCE: 49

Asp Ile Gln Met Thr Gln Ser Pro Ser Ser Leu Ser Ala Ser Val Gly
1               5                   10                  15

Asp Arg Val Thr Ile Ser Cys Arg Ala Ser Gln Gly Ile Ile Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
        50                  55                  60

Ser Gly Ser Gly Thr Glu Phe Thr Phe Thr Ile Ser Ser Leu Gln Pro
65                  70                  75                  80

Glu Asp Phe Ala Thr Tyr Tyr Cys Leu Gln His Asn Ser Tyr Pro Pro
                85                  90                  95

Thr Phe Gly Gln Gly Thr Lys Val Glu Ile Lys
            100                 105

<210> SEQ ID NO 50
<211> LENGTH: 113
<212> TYPE: PRT
<213> ORGANISM: Homo sapiens

<400> SEQUENCE: 50

Asp Ile Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly His Thr Cys Leu Asn Trp Phe Gln Gln Arg Pro Gly Gln Ser
        35                  40                  45

Pro Arg Arg Leu Ile Tyr Lys Val Ser Asn Trp Asp Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Asp Asp Val Gly Val Tyr Tyr Cys Met Gln Gly
                85                  90                  95

Thr His Trp Pro Leu Cys Ser Phe Gly Gln Gly Thr Lys Leu Glu Ile
            100                 105                 110

Lys

<210> SEQ ID NO 51
<211> LENGTH: 113
<212> TYPE: PRT
<213> ORGANISM: Homo sapiens

<400> SEQUENCE: 51
```

Asp Ile Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly His Thr Cys Leu Asn Trp Phe Gln Gln Arg Pro Gly Gln Ser
        35                  40                  45

Pro Arg Arg Leu Ile Tyr Lys Val Ser Asn Trp Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Asp Asp Val Gly Val Tyr Tyr Cys Met Gln Gly
                85                  90                  95

Thr His Trp Pro Leu Cys Ser Phe Gly Gln Gly Thr Lys Leu Glu Ile
            100                 105                 110

Lys

<210> SEQ ID NO 52
<211> LENGTH: 107
<212> TYPE: PRT
<213> ORGANISM: Homo sapiens

<400> SEQUENCE: 52

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ala Ile Ser Ile Tyr
            20                  25                  30

Leu Ala Trp Phe Gln Gln Lys Pro Gly Lys Ala Pro Lys Ser Leu Ile
        35                  40                  45

Tyr Ala Ala Ser Ser Leu Gln Ser Gly Val Pro Ser Lys Phe Ser Gly
    50                  55                  60

Ser Val Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Tyr Pro Arg
                85                  90                  95

Thr Phe Gly Gln Gly Thr Lys Val Glu Ile Lys
            100                 105

<210> SEQ ID NO 53
<211> LENGTH: 107
<212> TYPE: PRT
<213> ORGANISM: Homo sapiens

<400> SEQUENCE: 53

Glu Ile Leu Met Thr Gln Ser Pro Ala Thr Leu Ser Val Ser Pro Gly
1               5                   10                  15

Glu Arg Ala Thr Leu Ser Cys Ala Ser Gln Ser Val Tyr Ser Asn
            20                  25                  30

Leu Ala Trp Tyr Gln Gln Lys Pro Gly Gln Ala Pro Arg Leu Leu Ile
        35                  40                  45

Ser Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Tyr Asn Trp Pro Trp
                85                  90                  95

Thr Phe Gly Gln Gly Thr Lys Val Glu Ile Lys
            100                 105

<210> SEQ ID NO 54
<211> LENGTH: 393
<212> TYPE: DNA
<213> ORGANISM: Homo sapiens

<400> SEQUENCE: 54
caggtgcagc tgcaggagtc gggcccagga ctggtgaagc cttcggagac cctgtccctc    60
acctgcactg tctcaggtgg ctccatcagt aattactact ggaactggat ccggcagtcc   120
ccagggaagg gactggagtg gattggggat atctattaca gtgggagcac caactacaac   180
ccctccctca gagtcgagt caccatatca gtagacacgt ccaagaacca gttctccctg   240
aagctgagct ctgtgaccac tgcggacacg gccgtgtatt actgtgcgag agatggggaa   300
ctcgccaatt actatggttc ggggagttat cagttctact actactacgg tatggacgtc   360
tggggccaag ggaccacggt caccgtctcc tca                                393

<210> SEQ ID NO 55
<211> LENGTH: 381
<212> TYPE: DNA
<213> ORGANISM: Homo sapiens

<400> SEQUENCE: 55
caggtgcagc tacagcagtg gggcgcagga ctgttgaagc cttcggagac cctgtccctc    60
acctgcgctg tctctggtgg gtccttcagt ggttactact ggagctggat ccgccagccc   120
ccagggaagg ggctggaatg gattggggaa atcaatcata gtggacgcac caattacaac   180
ccgtccctca gagtcgagt caccatatca gtagacacgt ccaagaacca gttctccctg   240
aagctgagct ctgtgaccgc cgcggacacg gctgtttatt actgtgcgag aggcccttat   300
tactttgata gtagtggtta cctttactac tactacggtt ggacgtctg gggccaaggg   360 accacggtca ccgtctcctc a                                             381

<210> SEQ ID NO 56
<211> LENGTH: 342
<212> TYPE: DNA
<213> ORGANISM: Homo sapiens

<400> SEQUENCE: 56
caggtgcagc tggtggagtc tgggggaggc gtggtccagc ctgggaggtc cctgagactc    60
tcctgtgcag cgtctggaat caacttcagt agctatggca tgcactgggt ccgccaggct   120
ccaggcaagg ggctggagtg ggtggcagtt atatggtatg atggaagtaa taaacactat   180
gcagactccg tgaagggccg attcaccatc tccagagaca attccaagaa cacgctgtat   240
ctgcaaatga acagcctgag agccgaggac acggctgtgt attactgtgc gagagatact   300
ggggtctact ggggccaggg aaccctggtc accgtctcct ca                      342

<210> SEQ ID NO 57
<211> LENGTH: 342
<212> TYPE: DNA
<213> ORGANISM: Homo sapiens

<400> SEQUENCE: 57
caggtgcagc tggtggagtc tgggggaggc gtggtccagc ctgggaggtc cctgagactc    60
tcctgtgcag cgtctggaat caacttcagt agctatggca tgcactgggt ccgccaggct   120

```
ccaggcaagg ggctggagtg ggtggcagtt atatggtatg atggaagtaa taaacactat    180
gcagactccg tgaagggccg attcaccatc tccagagaca attccaagaa cacgctgtat    240
ctgcaaatga acagcctgag agccgaggac acggctgtgt attactgtgc gagagatact    300
ggggtctact ggggccaggg aaccctggtc accgtctcct ca                       342

<210> SEQ ID NO 58
<211> LENGTH: 375
<212> TYPE: DNA
<213> ORGANISM: Homo sapiens

<400> SEQUENCE: 58
caggtgcagc tgcaggagtc gggcccagga ctggtgaagc cttcggagac cctgcccctc     60
acctgcactg tctctggtgg ctccatcaga agttactact ggagctggat ccggcagccc    120
gccgggaagg gactggagtg gattgggcgt atctatcgca gtgggaacac catctacaac    180
ccctccctca agagtcgagt caccatgtca atagacacgt ccaagaacca gttctccctg    240
acgctgagtt ctgtgaccgc cgcggacacg gccgtgtatt actgtgcgag agaattac     300 tctgagagta gtggtctcta ctactactac ggtatggacg tctggggcca agggaccacg    360
gtcaccgtct cctca                                                    375

<210> SEQ ID NO 59
<211> LENGTH: 372
<212> TYPE: DNA
<213> ORGANISM: Homo sapiens

<400> SEQUENCE: 59
caggttcagc tggtgcagtc tggagctgag gtgaagaagc ctggggcctc agtgaaggtc     60
tcctgcaagg cttctggtta caccttaacc agatatggta tcagctgggt gcgacaggcc    120
cctggacaag gcttgagtg gatgggttgg atcagcgctt acaatggtaa cacaaactat    180
gcacagaagc tccagggcag agtcaccatg accacagaca cgtccacgag cacagcctac    240
atggagctga ggagcctgag atctgacgac acggccgtgt attactgtgc gagaagggat    300
tacgatattt tgactggtta ttataacggg ttcgacccct ggggccaggg aaccctggtc    360
accgtctcct ca                                                        372

<210> SEQ ID NO 60
<211> LENGTH: 372
<212> TYPE: DNA
<213> ORGANISM: Homo sapiens

<400> SEQUENCE: 60
caggttcagc tggtgcagtc tggagctgag gtgaagaagc ctggggcctc agtgaaggtc     60
tcctgcaagg cttctggtta caccttaacc agatatggta tcagctgggt gcgacaggcc    120
cctggacaag gcttgagtg gatgggttgg atcagcgctt acaatggtaa cacaaactat    180
gcacagaagc tccagggcag agtcaccatg accacagaca cgtccacgag cacagcctac    240
atggagctga ggagcctgag atctgacgac acggccgtgt attactgtgc gagaagggat    300
tacgatattt tgactggtta ttataacggg ttcgacccct ggggccaggg aaccctggtc    360
accgtctcct ca                                                        372

<210> SEQ ID NO 61
<211> LENGTH: 372
<212> TYPE: DNA
<213> ORGANISM: Homo sapiens
```

<400> SEQUENCE: 61

```
caggttcagc tggtgcagtc tggagctgag gtgaagaagc ctggggcctc agtgaaggtc      60
tcctgcaagg cttctggtaa cacctttacc ggctatggta tcagctgggt gcgacaggcc     120
cctggacaag ggcttgagtg gatgggatgg atcagcgctt acaatggtaa cacaaactat     180
gcacagaacc tccagggcag agtcaccatg accacagaca catccacgag cacagcctac     240
atggagctga ggagcctgag atctgacgac acggccgtgt attactgtgc gagaagggat     300
tacgatattt tgactggtta ttataacggg ttcgacccct ggggccaggg aaccctggtc     360
accgtctcct ca                                                         372
```

<210> SEQ ID NO 62
<211> LENGTH: 372
<212> TYPE: DNA
<213> ORGANISM: Homo sapiens

<400> SEQUENCE: 62

```
caggttcagc tggtgcagtc tggagttgag gtgaagaagc ctggggcctc agtgaaggtc      60
tcctgcaagg cttctggtta caccttaacc agatatggta tcagctgggt gcgacaggcc     120
cctggacaag ggcttgagtg gatgggttgg atcagcgctt acaatggtaa cacaaactat     180
gcacagaagc tccagggcag agtcaccatg accacagaca catccacgag cacagcctac     240
atggagctga ggagcctgag atctgacgac acggccgtgt attactgtgc gagaagggat     300
tacgatattt tgactggtta ttataacggg ttcgacccct ggggccaggg aaccctggtc     360
accgtctcct ca                                                         372
```

<210> SEQ ID NO 63
<211> LENGTH: 372
<212> TYPE: DNA
<213> ORGANISM: Homo sapiens

<400> SEQUENCE: 63

```
caggtgcagc tgcaggagtc gggcccagga ctggtgaagc cttcacagac cctgtccctc      60
acctgcactg tctctggtgg ctccatcagc agtggtggtt actactggag ctggatccgc     120
cagcaccccg ggaagggcct ggagtggatt gggtacatct atttcagtgg gagcgcctac     180
tacaacccgt ccctcaagag tcgagtcgcc atatcagtgg acacgtctaa gaaccagttc     240
tccctgaagc tgagctctgt gactgccgcg gacacggccg tatattactg tgcgagagaa     300
tactatgata gtagtggtta ccccgatgct tttgatatct ggggccaagg gacaatggtc     360
accgtctcct ca                                                         372
```

<210> SEQ ID NO 64
<211> LENGTH: 342
<212> TYPE: DNA
<213> ORGANISM: Homo sapiens

<400> SEQUENCE: 64

```
caggtgcaac tggtggagtc tgggggaggc gtggtccagc ctgggaggtc cctgagactc      60
tcctgtgcaa cgtccggaat cacctttcagt agctatggca tgcactgggt ccgccaggct     120
ccaggcaagg ggctggagtg ggtggcagtt atatggtatg atggaagtaa taatattat     180
gcagactccg tgaagggccg attcaccatc tccagagaca attccaagaa cacgctgtat     240
ctgcaaatga acagcctgag agccgaggac acggctgtgt attactgtgc gagagatacg     300
```

-continued

```
aaggactact ggggccaggg aaccctggtc accgtctcct ca                342
```

<210> SEQ ID NO 65
<211> LENGTH: 348
<212> TYPE: DNA
<213> ORGANISM: Homo sapiens

<400> SEQUENCE: 65

```
caggttcagc tggtgcagtc tggagctgag gtgaagaagc ctggggcctc agtgaaggtc   60
tcctgcaagg cttctggtta caccctcacc agctatggta tcagctgggt gcgacaggcc  120
cctggacaag gacttgagtg gatgggatgg atcagcactt acaaaggtaa cacaaactat  180
gcacagaagc tccagggcag agtcaccatg accacagaca catccacgag cacagcctac  240
atggaactga ggagcctgag atctgacgac acggccgtgt attactgtgc gagaaagcag  300
ctcgtctttg actactgggg tcagggaacc ctggtcaccg tctcctca              348
```

<210> SEQ ID NO 66
<211> LENGTH: 363
<212> TYPE: DNA
<213> ORGANISM: Homo sapiens

<400> SEQUENCE: 66

```
caggtgcagc tggtggagtc tgggggaggc gtggtccagc ctgggaggtc cctgagactc   60
tcctgtgcag cgtctggatt caccttcagt agctatggca tgcagtgggt ccgccaggct  120
ccaggcaagg ggctggagtg ggtggcagtt atatggtatg atggaaataa gaaatactat  180
gcagactccg tgaagggccg attcaccatc tccagagaca attccaagaa cacgctgtat  240
ctgcaaatga acagcctgag agccgaggac acggctgtgt attactgtgc gagaggacgt  300
gttagggact actactacgg tatggacgtc tggggccaag gaccacggt caccgtctcc  360
tca                                                                363
```

<210> SEQ ID NO 67
<211> LENGTH: 350
<212> TYPE: DNA
<213> ORGANISM: Homo sapiens

<400> SEQUENCE: 67

```
caggttcagc tggtgcagtc tggagctgag gtgaagaagc ctggggcctc agtgaaggtc   60
tcctgcaagg cttctggtta cacctttacc agatatggta tcagctgggt gcgacaggcc  120
cctggacaag ggcttgagtg gatgggatgg atcagcactt acagtggtaa cacaaactat  180
gcacagaagc tccagggcag agtcaccatg accacagaca catccacgag cacagcctac  240
atggagctga ggagcctgag atctgacgac acggccgtgt attactgtgc gagacggcag  300
ctttactttg actactgggg ccagggaacc ctggtcaccg tctcctcagc              350
```

<210> SEQ ID NO 68
<211> LENGTH: 363
<212> TYPE: DNA
<213> ORGANISM: Homo sapiens

<400> SEQUENCE: 68

```
caggtgcagc tggtggagtc tgggggaggc gtggtccagc ctgggaggtc cctgagactc   60
tcctgtgcag cgtctggatt caccttcagt agctatggca tgcagtgggt ccgccaggct  120
ccaggcaagg ggctggagtg ggtggcagtt atatggtatg atggaaataa gaaatactat  180
gcagactccg tgaagggccg attcaccatc tccagagaca attccaagaa cacgctgtat  240
```

```
ctgcaaatga acagcctgag agccgaggac acggctgtgt attactgtgc gagaggacgt      300
gttagggact actactacgg tatggacgtc tggggccaag ggaccacggt caccgtctcc      360
tca                                                                    363
```

<210> SEQ ID NO 69
<211> LENGTH: 348
<212> TYPE: DNA
<213> ORGANISM: Homo sapiens

<400> SEQUENCE: 69

```
caggttcagc tggtgcagtc tggagctgag gtgaagaagc ctggggcctc agtgaaggtc       60
tcctgcaagg cttctggtta ccctttacc agctatggta tcagctgggt gcgacaggcc      120
cctggacaag gcttgagtg gatgggatgg atcagcgctt acaatggtaa cacaaagtat      180
gcacagaagc tccagggcag agtcaccatg accacagaca catccacgag cacagtctac      240
atggagctga ggagcctgag atctgacgac acggccgtgt attactgtgc gagaaagcag      300
ctcgtctttg actactgggg ccagggaacc ctggtcaccg tctcctca                  348
```

<210> SEQ ID NO 70
<211> LENGTH: 348
<212> TYPE: DNA
<213> ORGANISM: Homo sapiens

<400> SEQUENCE: 70

```
caggttcagc tggtgcagtc tggagctgag gtgaagaagc ctggggccgc agtgaaggtc       60
tcctgcaagg ctactggtta caccttgacc agctatggta tcagctgggt gcgacaggcc      120
cctggacaag gcttgagtg gatgggatgg atcagcgctt acagtggtaa tacaaagtat      180
gcacagaagc tccagggcag agtcaccatg accacagaca catccacgag cacagcctac      240
atggagctga ggagcctgag atctgacgac acggccgtgt attactgtgc gagaaagcag      300
ctcgtctttg actactgggg ccagggaacc ctggtcaccg tctcctca                  348
```

<210> SEQ ID NO 71
<211> LENGTH: 378
<212> TYPE: DNA
<213> ORGANISM: Homo sapiens

<400> SEQUENCE: 71

```
caggtgcagc tggtgcagtc tggggctgag gtgaagaagc ctggggcctc agtgaaggtc       60
tcctgcaagg cttctggata tcccttcacc gactactaca tgcactgggt gcgacaggcc      120
cctggacaag gacttgagtg gatgggatgg atgcaccccta acagtggtgg cacagactta     180
gcacagaggt ttcagggcag ggtcaccatg accagggaca cgtccatcag cacagcctac      240
atggagctga gcaggctgag atctgacgac acggccgtgt attactgtgc gagaggggga     300
tattgtagta ctttgagctg ctccttctac tggtacttcg atctctgggg ccgtggcacc      360
ctggtcactg tctcctca                                                   378
```

<210> SEQ ID NO 72
<211> LENGTH: 348
<212> TYPE: DNA
<213> ORGANISM: Homo sapiens

<400> SEQUENCE: 72

```
caggttcagc tggtgcagtc tggagctgag gtgaagaagc ctggggcctc agtgaaggtc       60
```

```
tcctgcaagg cttctggtta caccttgacc agctatggaa tcagtttggt gcgacaggcc    120
cctggacaag ggcttgagtg gatgggatgg atcagcgctt acagtggtaa cacaaagtat    180
gcacagaagt tccagggcag agtcaccatg accacagaca catccacgag cacagcctac    240
atggagctga ggagcctgag atctgacgac acggccgtgt attactgtgc gagaaggcag    300
ctcgcgttgg actactgggg ccagggaacc ctggtcaccg tctcctca                 348
```

```
<210> SEQ ID NO 73
<211> LENGTH: 354
<212> TYPE: DNA
<213> ORGANISM: Homo sapiens

<400> SEQUENCE: 73
gaggtgcagc tggtggagtc tgggggaggc ttggtacagc ctggggggtc cctgagactc    60
tcctgtgcag cctctggatt caccttcagc agctatagca tgaactgggt ccgccaggct    120
ccagggaagg ggctggagtg ggtttcattc attagtgcta aagtagtac catatactac    180 gcagactctg tgaagggccg attcaccatc tccagagaca atgccaagaa ctcactgtat    240
ctgcaaatga acagcctgag agacgaggac acggctgtgt attactgtgc gagacctaaa    300
gtggggggcg gtatggacgt ctggggccaa ggaaccacgg tcaccgtctc ctca          354
```

```
<210> SEQ ID NO 74
<211> LENGTH: 354
<212> TYPE: DNA
<213> ORGANISM: Homo sapiens

<400> SEQUENCE: 74
gaggtgcagt tggtggagtc tgggggaggc tcggtacagc ctggggggtc cctgagactc    60
tcctgtgcag cctctggatt caccttcagt agctatagca tgaactgggt ccgccaggct    120
ccagggaagg ggctggagtg ggtttcaatc attagtagta aagtagtat catacactac    180 gcagactctg tgaagggccg attcaccatc tccagagaca atgccaagaa ctcactgtat    240
ctgcaaatga acagcctgag agacgaggac acggctgtgt attactgtgc gagacctaaa    300
gtggggggcg gtatggacgt ctggggccaa gggaccacgg tcaccgtctc ctca          354
```

```
<210> SEQ ID NO 75
<211> LENGTH: 348
<212> TYPE: DNA
<213> ORGANISM: Homo sapiens

<400> SEQUENCE: 75
caggttcagc tggtgcagtc tggagctgag gtgaagaagc ctggggcctc agtgaaggtc    60
tcctgcaagg cttctggtta cacctttacc agatatggta tcagctgggt gcgacaggcc    120
cctggacaag ggcttgagtg gatgggatgg atcagcgctt acagtggtaa cacaaactat    180
gcacagaagc tccagggcag agtcaccatg accacagaca catccacgag cacagcctac    240
atggagctga ggagcctgag atctgacgac acggccgtgt attactgtgc gagacggcag    300
ctttactttg actactgggg ccagggaacc ctggtcaccg tctcctca                 348
```

```
<210> SEQ ID NO 76
<211> LENGTH: 375
<212> TYPE: DNA
<213> ORGANISM: Homo sapiens

<400> SEQUENCE: 76
caggtgcagc tgcaggagtc gggcccagga ctggtgaagc cttcggagac cctgtccctc    60
```

```
acctgcactg tcactggtgg ctccatcagg agttactact ggagctggat ccggcagccc    120
gccgggaaga gactggagtg gattgggcgt atctatccca gtgggagaac caactacaac    180
ccctccctca agagtcgagt caccatgtca gtagacacgt ccaagaacca gttctccctg    240
aagctgagct ctgtgaccgc cgcggacacg gccgtgtatt actgtgcgag agaggcatat    300
gagctgcaac tgggcctcta ctactactac ggtatggacg tctggggcca agggaccccg    360
gtcaccgtct cctca                                                    375

<210> SEQ ID NO 77
<211> LENGTH: 375
<212> TYPE: DNA
<213> ORGANISM: Homo sapiens

<400> SEQUENCE: 77
caggtgcagc tgcaggagtc gggcccagga ctggtgaagc cttcggagac cctgtccctc    60
acctgcactg tcactggtgg ctccatcagg agttactact ggagctggat ccggcaggcc    120
gccgggaaga gactggagtg gattgggcgt atctatccca gtgggagaac caactacaac    180
ccctccctca agagtcgagt caccatgtca gtagacacgt ccaagaacca gttctccctg    240
aagctgagct ctgtgaccgc cgcggacacg gccgtgtatt actgtgcgag agaggcatat    300
gagctgcaac tgggcctcta ctactactac ggtatggacg tctggggcca agggaccccg    360
gtcaccgtct cctca                                                    375

<210> SEQ ID NO 78
<211> LENGTH: 372
<212> TYPE: DNA
<213> ORGANISM: Homo sapiens

<400> SEQUENCE: 78
caggtgcagc tgcaggagtc gggcccagga ctggtgaagc cttcacagac cctgtccctc    60
acctgcactg tctctggtgg ctccatcagc agtggtggtt actactggag ctggatccgc    120
cagcacccag ggaagggcct ggagtggatt gggtacatct attacagtgg gaacacctac    180
tacaacccgt ccctcaggag tcgagttacc atatcagttg acacgtctaa gaaccagttc    240
tccctgaagc tgaactctgt gactgccgcg gacacggccg tgtattactg tgcgagagag    300
gccggtggta actccgccta ctactacggt atggacgtct ggggccaagg gaccacggtc    360
accgtctcct ca                                                       372

<210> SEQ ID NO 79
<211> LENGTH: 375
<212> TYPE: DNA
<213> ORGANISM: Homo sapiens

<400> SEQUENCE: 79
caggtgcagc tggtggagtc tggggggaggc ttggtcaagc ctggagggtc cctgagactc    60
tcctgtgcag cctctggatt caccttcagt gactactaca tgagctggat ccgccaggct    120
ccagggaagg ggctggagtg ggtttcatac attagtagta gtggtagtac catatactac    180
gcagactctg tgaagggccg attcaccatc tccagggaca cgccaagaa ctcactgtat    240 ctgcaaatga acagcctgag agccgaggac acggccgtgt attactgtgc gagagatcgc    300
acgtattact ttggttcggg gagttatgaa gggatggacg tctggggcca agggaccacg    360
gtcaccgtct cctca                                                    375
```

<210> SEQ ID NO 80
<211> LENGTH: 321
<212> TYPE: DNA
<213> ORGANISM: Homo sapiens

<400> SEQUENCE: 80

| | | | | | |
|---|---|---|---|---|---|
| gacatcctga | tgacccagtc | tccatcctcc | ctgtctgcat | ctgtcggaga | cagagtcacc | 60 |
| atcacttgcc | gggcaagtca | gggcattaga | aatgatttag | gctggtatca | gcagaaacca | 120 |
| gggaaagccc | ctaagcgcct | gatctatgct | gcatccagtt | tgcaaagtgg | ggtcccatcc | 180 |
| aggttcagcg | gcagtggctc | tgggacagaa | ttcactctca | caatcagcag | cctgcagcct | 240 |
| gaagattttg | caacttatta | ctgtctacag | cataatagta | acccattcac | tttcggccct | 300 |
| gggaccaaag | tggatatcaa | a | | | | 321 |

<210> SEQ ID NO 81
<211> LENGTH: 318
<212> TYPE: DNA
<213> ORGANISM: Homo sapiens

<400> SEQUENCE: 81

| | | | | | |
|---|---|---|---|---|---|
| gaaatagtga | tgacgcagtc | tccagccacc | ctgtctgtgt | ctccagggga | aagagccacc | 60 |
| ctctcctgca | gggccagtca | gagtgttagc | agaaacttag | cctggtacca | gcagagacct | 120 |
| ggccaggctc | ccaggctcct | catctatggg | gcatccacta | gggccaatgg | tatcccagcc | 180 |
| aggttcagtg | gcagtgggtc | agggacagaa | ttcactctca | ccatcagcag | cctgcagtct | 240 |
| gaagattttg | cagtttatta | ctgtcagcag | tataaaagct | ggcggacgtt | cggccaaggg | 300 |
| tccaaggtgg | aaatcaaa | | | | | 318 |

<210> SEQ ID NO 82
<211> LENGTH: 321
<212> TYPE: DNA
<213> ORGANISM: Homo sapiens

<400> SEQUENCE: 82

| | | | | | |
|---|---|---|---|---|---|
| gacatccaga | tgacccagtc | tccatcctcc | ctgtctgcat | ctgtaggaga | cagagtcacc | 60 |
| atcacttgcc | gggcaagtca | gagcattagc | agctatttaa | attggtatca | gcagaaacca | 120 |
| gggaaagccc | ctaagctcct | gatctatgct | gcatccagtt | tgcaaagtgg | ggtcccatca | 180 |
| aggttcagtg | gcagtggatc | tgggacagat | ttcactctca | ccatcagcag | tctgcaacct | 240 |
| gaagattttg | caacttacta | ctgtcaacag | agttacagta | ccccattcac | tttcggccct | 300 |
| gggaccaaag | tggatatcaa | a | | | | 321 |

<210> SEQ ID NO 83
<211> LENGTH: 324
<212> TYPE: DNA
<213> ORGANISM: Homo sapiens

<400> SEQUENCE: 83

| | | | | | |
|---|---|---|---|---|---|
| gaaatagtga | tgacgcagtc | tccagccacc | ctgtctgtgt | ctccagggga | aagagccacc | 60 |
| ctctcctgca | gggccagtca | gagtgttagt | aggaatttag | cctggtacca | gcagaaacct | 120 |
| ggccaggctc | ccaggctcct | catctatggt | gcatccacca | gggccactgg | tatcccagcc | 180 |
| aggttcagtg | gcagtgggtc | tgggacagag | ttcactctca | ccatcagcag | cctgcagtct | 240 |
| gaagattttg | cagtttatta | ctgtcagcag | tataataact | ggcccacgtg | gacgttcggc | 300 |
| caagggacca | aggtggaaat | caaa | | | | 324 |

<210> SEQ ID NO 84
<211> LENGTH: 321
<212> TYPE: DNA
<213> ORGANISM: Homo sapiens

<400> SEQUENCE: 84

```
gacatccaga tgacccagtc tccatcctcc ctgtctgcat ctgtaggaga cagagtcacc    60
atcacttgcc gggcaagtca gggcattaga aatgatttag gctggtatca gcagaagcca   120
gggaaagccc ctaaacgcct gatctatgct gcatccagtt tccaaagtgg ggtcccatca   180
aggttcagcg gcagtggatc tgggacagga ttcactctca caatcagcag cctgcagcct   240
gaagattttg caacttatta ctgtctacag cataatagtt accctccgac gttcggccaa   300
gggaccaagg tggaaatcaa a                                              321
```

<210> SEQ ID NO 85
<211> LENGTH: 321
<212> TYPE: DNA
<213> ORGANISM: Homo sapiens

<400> SEQUENCE: 85

```
gacatccaga tgacccagtc tccatcctcc ctgtctgcat ctgtaggaga cagagtcacc    60
atcacttgcc gggcaagtca gggcattaga aatgatttag gctggtatca gcagaaacca   120
gggaaagccc ctaagcgcct gatctatgct gcatccagtt tgcaaagtgg ggtcccatca   180
aggttcagcg gcagtggatc tgggacagaa ttcactctca caatcagcag cctgcagcct   240
gaagattttg caacttatta ctgtctacag cataaaagtt acccgctcac tttcggcgga   300
gggaccaagg tggagatcaa a                                              321
```

<210> SEQ ID NO 86
<211> LENGTH: 321
<212> TYPE: DNA
<213> ORGANISM: Homo sapiens

<400> SEQUENCE: 86

```
gacatccaga tgacccagtc tccatcctcc ctgtctgcat ctgtaggaga cagagtcacc    60
atcacttgcc gggcaagtca gggcattaga aatgatttag gctggtatca gcagaaacca   120
gggaaagccc ctaagcgcct gatctatgct gcatccagtt tgcaaagtgg ggtcccatca   180
aggttcagcg gcagtggatc tgggacagaa ttcactctca caatcagcag cctgcagcct   240
gaagattttg caacttatta ctgtctacag cataaaagtt acccgctcac tttcggcgga   300
gggaccaagg tggagatcaa a                                              321
```

<210> SEQ ID NO 87
<211> LENGTH: 321
<212> TYPE: DNA
<213> ORGANISM: Homo sapiens

<400> SEQUENCE: 87

```
gacatccaga tgacccagtc tccatcctcc ctgtctgcat ctgtaggaga cagagtcacc    60
atcacttgcc gggcaagtca gggcattaga aatgatttag gctggtatca gcagaaacca   120
gggaaagccc ctaagcgcct gatctatgct gcatccagtt tgcaaagtgg ggtcccatca   180
aggttcagcg gcagtggatc tgggacagaa ttcactctca caatcagcag cctgcagcct   240
gaagattttg caacttatta ctgtctacag cataagagtt acccgctcac tttcggcgga   300
```

```
gggaccaagg tggagatcaa a                                              321
```

<210> SEQ ID NO 88
<211> LENGTH: 321
<212> TYPE: DNA
<213> ORGANISM: Homo sapiens

<400> SEQUENCE: 88

```
gacatccaga tgacccagtc tccatcctcc ctgtctgcat ctgtaggaga cagagtcacc     60
atcacttgcc gggcaagtca gggcattaga aatgatttag ctggtatca gcagaaacca    120
gggaaagccc ctaagcgcct gatctacgct gcatccagtt tgcaaagtgg ggtcccatca   180
aggttcagcg gcagtggatc tgggacagaa ttcactctca caatcagcag cctgcagcct   240
gaagattttg caacttatta ctgtctacag cataaaagtt acccgctcac tttcggcgga   300
gggaccaagg tggagatcaa a                                              321
```

<210> SEQ ID NO 89
<211> LENGTH: 321
<212> TYPE: DNA
<213> ORGANISM: Homo sapiens

<400> SEQUENCE: 89

```
gacatccaga tgacccagtc tccatcttcc gtgtctgcat ctgtaggaga cagagtcacc     60
atcacttgtc gggcgagtca gggtattagg agctggttag cctggtatca gcagaaacca   120
gggaaagccc ctaagctcct gatctttgct gcatccagtt tgcaaagtgg ggtcccatca   180
aggttcagcg gcagtggatc tgggacagaa ttcactctca ccatcagcag cctgcagcct   240
gaagattttg caacttacta ttgtcaacag gctaacaatt tccctcggac gttcggccaa   300
gggaccaagg tggaaatcaa a                                              321
```

<210> SEQ ID NO 90
<211> LENGTH: 324
<212> TYPE: DNA
<213> ORGANISM: Homo sapiens

<400> SEQUENCE: 90

```
gaaatagtga tgacgcagtc tccagccacc ctgtctgtgt ctccagggga aagagccacc     60
ctctcctgca gggccagtca gagtgttagc agcaacttag cctggtacca gcagaaacct   120
ggccaggctc ccaggctcct catctatggt gcatccacca gggccgctgg tatcccagcc   180
aggttcagtg gcggtgggtc tgggacagcg ttcactctca ccatcagcaa cctacagtct   240
gaagattttg cagtttatta ctgtcagcac tatataaact ggcctaagtg acgttcggc    300
caagggacca aggtggacat caaa                                           324
```

<210> SEQ ID NO 91
<211> LENGTH: 321
<212> TYPE: DNA
<213> ORGANISM: Homo sapiens

<400> SEQUENCE: 91

```
gaaatagtaa tgacgcagtc tccagccacc ctgtctgtgt ctccagggga aagagccacc     60
ctctcctgca gggccagtca gagtattagc agcagcttag cctggtacca gcagaaacct   120
ggccaggctc ccaggctcct catctatggt gcatccacca gggccactgg tatcccagcc   180
aggttcagtg gcagtgggtc tgggacagag ttcactctca ccatcagcag cctgcagtct   240
gaaaattttg cagtttatta ctgtcagcaa tatgataact ggccgctcac tttcggcgga   300
```

```
gggaccaagg tggagatcaa a                                              321

<210> SEQ ID NO 92
<211> LENGTH: 336
<212> TYPE: DNA
<213> ORGANISM: Homo sapiens

<400> SEQUENCE: 92
gatattgtga tgacccagac tccactctct ctgtccgtca cccctggaca gccggcctcc     60
atcgcctgca agtctagtca gagcctcctg catagtgatg gaaagaccta tttgtattgg    120
tacctgcaga agccaggcca gcctccacag ctcctgatct atgaagtttc cacccggttc    180
tctggagtgc cagataggtt cagtggcagc gggtcaggga cagatttcac actgaaaatc    240
agccgggtgg aggctgagga tgttggggtt ttttactgca tgcaaagtat acagcttccg    300
ctcactttcg gcggagggac caaggtggag atcaaa                              336

<210> SEQ ID NO 93
<211> LENGTH: 321
<212> TYPE: DNA
<213> ORGANISM: Homo sapiens

<400> SEQUENCE: 93
gaaatagtga tgacgcagtc tccagccacc ctgtctgtgt ctcctgggga aagagccacc     60
ctctcctgca gggccagtca gagtgttagc agcaacttag cctggttcca gcagaaacct    120
ggccaggctc ccaggcccct catctatgat gcatccacca gggccactgg tgtcccagcc    180
aggttcagtg gcagtgggtc tgggacagac ttcactctca ccatcagcag cctgcagtct    240
gaagattttg cagtttatta ctgtcagcag tatgataact ggccgctcac tttcggcgga    300
gggaccaagg tggagatcaa a                                              321

<210> SEQ ID NO 94
<211> LENGTH: 321
<212> TYPE: DNA
<213> ORGANISM: Homo sapiens

<400> SEQUENCE: 94
gaaatagtga tgacgcagtc tccagccacc ctgtctgtgt ctccagggga aagagtcacc     60
ctctcctgca gggccagtca gagtgttagc agcaacttag cctggttcca gcagaaacct    120
ggccaggctc ccaggcccct catctatgat gcatccacca gggccgctgg tatcccagcc    180
aggttcagtg gcagtgggtc tgggacagac ttcactctca ccatcagcag cctgcagtct    240
gaagattttg cagtttatta ctgtcagcag tatgataact ggccgctcac tttcggcgga    300
gggaccaagg tggagatcaa a                                              321

<210> SEQ ID NO 95
<211> LENGTH: 324
<212> TYPE: DNA
<213> ORGANISM: Homo sapiens

<400> SEQUENCE: 95
gaaatagtga tgacgcagtc tccagccacc ctgtctgtgt ctccagggga aagagccacc     60
ctctcctgca gggccagtca gagtgttagc agcagcttag cctggtacca gcagaaacct    120
ggccaggctc ccaggctcct catctatggt acatccacca gggccactgg tatcccagcc    180
aggttcagtg gcagtgggtc tgggacagag ttcactctca ccatcagcag cctgcagtct    240
```

```
gaagattttg cagtttattt ctgtcaacag tatgatatct ggccgctcac tttcggcgga      300
gggaccaagg tggagatcaa acga                                             324
```

<210> SEQ ID NO 96
<211> LENGTH: 321
<212> TYPE: DNA
<213> ORGANISM: Homo sapiens

<400> SEQUENCE: 96

```
gaaatagtga tgacgcagtc tccagccacc ctgtctgtgt ctccagggga aagagccacc       60
ctctcctgca gggccagtca gagtgttagc agcaacttag cctggtacca gcagaaacct      120
ggccaggctc ccaggctcct catctatggt gcatccacca gggccactgg tatcccagcc      180
aggttcagtg gcagtgggtc tgggacagag ttcactctca ccatcagcag cctgcagtct      240
gaagattttg cagtttattc ctgtcagcag tatgataact ggccgctcac tttcggcgga      300
gggaccaagg tggagatcaa a                                                321
```

<210> SEQ ID NO 97
<211> LENGTH: 339
<212> TYPE: DNA
<213> ORGANISM: Homo sapiens

<400> SEQUENCE: 97

```
gacatcgtga tgacccagtc tccagactcc ctggctgtgt ctctgggcga gagggccacc       60
atcaactgca agaccagcca gagtgtttta tacagctcca aaaacaagaa cttcttagct      120
tggtatcagc agaaaccagg acagcctctt aacctgctca tttactgggc atctacccgg      180
gaatccgggg tccctgaccg attcagtggc agcgggtctg ggacagattt cactctcacc      240
atcagcagcc tgcaggctga agatgtggca gtttattact gtcagcaata ttatagtact      300
ccattcactt tcggccctgg gaccaaagtg gatatcaaa                             339
```

<210> SEQ ID NO 98
<211> LENGTH: 321
<212> TYPE: DNA
<213> ORGANISM: Homo sapiens

<400> SEQUENCE: 98

```
gaaatagtga tgacgcagtc tccagccacc ctgtctgtgt ctccagggga aagagccacc       60
ctctcctgca gggccagtca gagtattagc agcaacttag cctggtacca gcagaaacct      120
ggccaggctc ccaggctcct catctatggt gcatccacca gggccactgg tatcccagcc      180
aggttcagtg acaatgggtc tgggacagag ttcactctca ccatcagcag cctgcagtct      240
gaagattttg cagtttattt ctgtcagcag tatgatacct ggcctctcac tttcggcggc      300
gggaccaagg tggagatcaa a                                                321
```

<210> SEQ ID NO 99
<211> LENGTH: 321
<212> TYPE: DNA
<213> ORGANISM: Homo sapiens

<400> SEQUENCE: 99

```
gacatccaga tgacccagtc tccatcctcc ctgtctgcat ctgtaggaga cagagtcacc       60
atcacttgcc gggcgagtca gggcattagc aattatttag cctggtatca gcagaaacca      120
gggaaatttc ctgagctcct gatctatgct gcatccactt tacaatcagg gtcccatct       180 cggttcagtg gcagtggatc tgggacagat ttcactctca ccatcagcag cctgcagcct      240
```

```
gaagatgttg caacttatta ctgtcaaaag tataaccgtg ccccattcac tttcggccct    300
gggaccaaag tggatatcaa a                                              321

<210> SEQ ID NO 100
<211> LENGTH: 321
<212> TYPE: DNA
<213> ORGANISM: Homo sapiens

<400> SEQUENCE: 100
gacatccaga tgacccagtc tccatcctcc ctgtctgcat ctgtaggaga cagagtcacc    60
atcacttgcc gggcgagtca gggcattagc aattatttag cctggtatca gcagaaacca   120
gggaaatttc ctgagctcct gatctatgct gcatccactt tgcaatcagg ggtcccatct   180
cggttcagtg gcagtggatc tgggacagat ttcactctca ccatcagcag cctgcagcct   240
gaagatgttg caacttatta ctgtcaaaag tataaccgtg ccccattcac tttcggccct   300
gggaccaaag tggatatcaa a                                             321

<210> SEQ ID NO 101
<211> LENGTH: 321
<212> TYPE: DNA
<213> ORGANISM: Homo sapiens

<400> SEQUENCE: 101
gaaatagtga tgacgcagtc tccagccacc ctgtctgtgt ctccagggga aagagtcacc    60
ctctcctgca gggccagtca gagtgttagc agcaacttag cctggttcca gcagaaacct   120
ggccaggctc ccaggcccct catctatgat gcatccacca gggccgctgg tatcccagcc   180
aggttcagtg gcagtgggtc tgggacagac ttcactctca ccatcagcag cctgcagtct   240
gaagattttg cagtttatta ctgtcagcag tatgataact ggccgctcac tttcggcgga   300
gggaccaagg tggagatcaa a                                             321

<210> SEQ ID NO 102
<211> LENGTH: 321
<212> TYPE: DNA
<213> ORGANISM: Homo sapiens

<400> SEQUENCE: 102
gacatccaga tgacccagtc tccatcctcc ctgtctgcat ctgttggaga cagagtcacc    60
atctcttgcc gggcaagtca gggcattata aatgatttag gctggtatca gcagaaacca   120
gggaaagccc ctaagcgcct gatctatgct gcatccagtt tgcaaagtgg ggtcccatca   180
aggttcagcg gcagtggatc tgggacagaa ttcacttttca caatcagcag cctgcagcct   240
gaagattttg caacttatta ctgtctacag cataatagtt accctccgac gttcggccaa   300
gggaccaagg tggaaatcaa a                                             321

<210> SEQ ID NO 103
<211> LENGTH: 339
<212> TYPE: DNA
<213> ORGANISM: Homo sapiens

<400> SEQUENCE: 103
gatattgtga tgactcagtc tccactctcc ctgcccgtca cccttggaca gccggcctcc    60
atctcctgca ggtctagtca aagcctcgta tatagtgatg gacacacctg cttgaattgg   120
tttcagcaga ggccaggcca atctccaagg cgcctaattt ataaggtttc taactgggac   180
```

```
tctggggtcc cagacagatt cagcggcagt gggtcaggca ctgatttcac actgaaaatc    240
agcagggtgg aggctgacga tgttgggggtt tattactgca tgcaaggtac acactggcct    300
```


```
tctggggtcc cagacagatt cagcggcagt gggtcaggca ctgatttcac actgaaaatc    240
agcagggtgg aggctgacga tgttgggggtt tattactgca tgcaaggtac acactggcct    300
ctgtgcagtt ttggccaggg gaccaagctg gagatcaaa                           339
```

<210> SEQ ID NO 104
<211> LENGTH: 339
<212> TYPE: DNA
<213> ORGANISM: Homo sapiens

<400> SEQUENCE: 104

```
gatattgtga tgactcagtc tccactctcc ctgcccgtca cccttggaca gccggcctcc     60
atctcctgca ggtctagtca aagcctcgta tatagtgatg gacacacctg cttgaattgg    120
tttcagcaga ggccaggcca atctccaagg cgcctaattt ataaggtttc taactgggac    180
tctggggtcc cagacagatt cagcggcagt gggtcaggca ctgatttcac actgaaaatc    240
agcagggtgg aggctgacga tgttggggtt tattactgca tgcaaggtac acactggcct    300
ctgtgcagtt ttggccaggg gaccaagctg gagatcaaa                           339
```

<210> SEQ ID NO 105
<211> LENGTH: 321
<212> TYPE: DNA
<213> ORGANISM: Homo sapiens

<400> SEQUENCE: 105

```
gacatccaga tgacccagtc tccatcctca ctgtctgcat ctgtaggaga cagagtcacc     60
atcacttgtc gggcgagtca ggccattagc atttatttag cctggtttca gcagaaacca    120
gggaaagccc ctaagtccct gatctatgct gcatccagtt tgcaaagtgg ggtcccatca    180
aagttcagcg gcagtgtatc tgggacagat ttcactctca ccatcagcag cctgcagcct    240
gaagattttg caacttatta ctgccaacag tatagtagtt accctcggac gttcggccaa    300
gggaccaagg tggaaatcaa a                                               321
```

<210> SEQ ID NO 106
<211> LENGTH: 321
<212> TYPE: DNA
<213> ORGANISM: Homo sapiens

<400> SEQUENCE: 106

```
gaaatattga tgacgcagtc tccagccacc ctgtctgtgt ctccagggga aagagccacc     60
ctctcctgca gggccagtca gagtgtttac agcaacttag cctggtacca gcagaaacct    120
ggccaggctc ccagactcct catctctggt gcttccacca gggccactgg tatcccagcc    180
aggttcagtg gcagtgggtc tgggacagag ttcactctca ccatcagcag cctgcagtct    240
gaagattttg cagtttatta ctgtcagcag tattataact ggccgtggac gttcggccaa    300
gggaccaagg tggaaatcaa a                                               321
```

<210> SEQ ID NO 107
<211> LENGTH: 5
<212> TYPE: PRT
<213> ORGANISM: Homo sapiens

<400> SEQUENCE: 107

Asn Tyr Tyr Trp Asn
1               5

<210> SEQ ID NO 108

```
<211> LENGTH: 16
<212> TYPE: PRT
<213> ORGANISM: Homo sapiens

<400> SEQUENCE: 108

Asp Ile Tyr Tyr Ser Gly Ser Thr Asn Tyr Asn Pro Ser Leu Lys Ser
1               5                   10                  15

<210> SEQ ID NO 109
<211> LENGTH: 23
<212> TYPE: PRT
<213> ORGANISM: Homo sapiens

<400> SEQUENCE: 109

Asp Gly Glu Leu Ala Asn Tyr Tyr Gly Ser Gly Ser Tyr Gln Phe Tyr
1               5                   10                  15

Tyr Tyr Tyr Gly Met Asp Val
            20

<210> SEQ ID NO 110
<211> LENGTH: 5
<212> TYPE: PRT
<213> ORGANISM: Homo sapiens

<400> SEQUENCE: 110

Gly Tyr Tyr Trp Ser
1               5

<210> SEQ ID NO 111
<211> LENGTH: 16
<212> TYPE: PRT
<213> ORGANISM: Homo sapiens

<400> SEQUENCE: 111

Glu Ile Asn His Ser Gly Arg Thr Asn Tyr Asn Pro Ser Leu Lys Ser
1               5                   10                  15

<210> SEQ ID NO 112
<211> LENGTH: 19
<212> TYPE: PRT
<213> ORGANISM: Homo sapiens

<400> SEQUENCE: 112

Gly Pro Tyr Tyr Phe Asp Ser Ser Gly Tyr Leu Tyr Tyr Tyr Tyr Gly
1               5                   10                  15

Leu Asp Val

<210> SEQ ID NO 113
<211> LENGTH: 5
<212> TYPE: PRT
<213> ORGANISM: Homo sapiens

<400> SEQUENCE: 113

Ser Tyr Gly Met His
1               5

<210> SEQ ID NO 114
<211> LENGTH: 17
<212> TYPE: PRT
<213> ORGANISM: Homo sapiens

<400> SEQUENCE: 114

Val Ile Trp Tyr Asp Gly Ser Asn Lys His Tyr Ala Asp Ser Val Lys
1               5                   10                  15
```

Gly

<210> SEQ ID NO 115
<211> LENGTH: 5
<212> TYPE: PRT
<213> ORGANISM: Homo sapiens

<400> SEQUENCE: 115

Asp Thr Gly Val Tyr
1               5

<210> SEQ ID NO 116
<211> LENGTH: 5
<212> TYPE: PRT
<213> ORGANISM: Homo sapiens

<400> SEQUENCE: 116

Ser Tyr Gly Met His
1               5

<210> SEQ ID NO 117
<211> LENGTH: 17
<212> TYPE: PRT
<213> ORGANISM: Homo sapiens

<400> SEQUENCE: 117

Val Ile Trp Tyr Asp Gly Ser Asn Lys His Tyr Ala Asp Ser Val Lys
1               5                   10                  15
Gly

<210> SEQ ID NO 118
<211> LENGTH: 5
<212> TYPE: PRT
<213> ORGANISM: Homo sapiens

<400> SEQUENCE: 118

Asp Thr Gly Val Tyr
1               5

<210> SEQ ID NO 119
<211> LENGTH: 5
<212> TYPE: PRT
<213> ORGANISM: Homo sapiens

<400> SEQUENCE: 119

Ser Tyr Tyr Trp Ser
1               5

<210> SEQ ID NO 120
<211> LENGTH: 16
<212> TYPE: PRT
<213> ORGANISM: Homo sapiens

<400> SEQUENCE: 120

Arg Ile Tyr Arg Ser Gly Asn Thr Ile Tyr Asn Pro Ser Leu Lys Ser
1               5                   10                  15

<210> SEQ ID NO 121
<211> LENGTH: 17
<212> TYPE: PRT
<213> ORGANISM: Homo sapiens

<400> SEQUENCE: 121

-continued

Glu Asn Tyr Ser Glu Ser Ser Gly Leu Tyr Tyr Tyr Gly Met Asp
1               5                   10                  15

Val

<210> SEQ ID NO 122
<211> LENGTH: 5
<212> TYPE: PRT
<213> ORGANISM: Homo sapiens

<400> SEQUENCE: 122

Arg Tyr Gly Ile Ser
1               5

<210> SEQ ID NO 123
<211> LENGTH: 17
<212> TYPE: PRT
<213> ORGANISM: Homo sapiens

<400> SEQUENCE: 123

Trp Ile Ser Ala Tyr Asn Gly Asn Thr Asn Tyr Ala Gln Lys Leu Gln
1               5                   10                  15

Gly

<210> SEQ ID NO 124
<211> LENGTH: 15
<212> TYPE: PRT
<213> ORGANISM: Homo sapiens

<400> SEQUENCE: 124

Arg Asp Tyr Asp Ile Leu Thr Gly Tyr Tyr Asn Gly Phe Asp Pro
1               5                   10                  15

<210> SEQ ID NO 125
<211> LENGTH: 5
<212> TYPE: PRT
<213> ORGANISM: Homo sapiens

<400> SEQUENCE: 125

Arg Tyr Gly Ile Ser
1               5

<210> SEQ ID NO 126
<211> LENGTH: 17
<212> TYPE: PRT
<213> ORGANISM: Homo sapiens

<400> SEQUENCE: 126

Trp Ile Ser Ala Tyr Asn Gly Asn Thr Asn Tyr Ala Gln Lys Leu Gln
1               5                   10                  15

Gly

<210> SEQ ID NO 127
<211> LENGTH: 15
<212> TYPE: PRT
<213> ORGANISM: Homo sapiens

<400> SEQUENCE: 127

Arg Asp Tyr Asp Ile Leu Thr Gly Tyr Tyr Asn Gly Phe Asp Pro
1               5                   10                  15

<210> SEQ ID NO 128
<211> LENGTH: 5
<212> TYPE: PRT

<213> ORGANISM: Homo sapiens

<400> SEQUENCE: 128

Gly Tyr Gly Ile Ser
1               5

<210> SEQ ID NO 129
<211> LENGTH: 17
<212> TYPE: PRT
<213> ORGANISM: Homo sapiens

<400> SEQUENCE: 129

Trp Ile Ser Ala Tyr Asn Gly Asn Thr Asn Tyr Ala Gln Asn Leu Gln
1               5                   10                  15

Gly

<210> SEQ ID NO 130
<211> LENGTH: 15
<212> TYPE: PRT
<213> ORGANISM: Homo sapiens

<400> SEQUENCE: 130

Arg Asp Tyr Asp Ile Leu Thr Gly Tyr Tyr Asn Gly Phe Asp Pro
1               5                   10                  15

<210> SEQ ID NO 131
<211> LENGTH: 5
<212> TYPE: PRT
<213> ORGANISM: Homo sapiens

<400> SEQUENCE: 131

Arg Tyr Gly Ile Ser
1               5

<210> SEQ ID NO 132
<211> LENGTH: 17
<212> TYPE: PRT
<213> ORGANISM: Homo sapiens

<400> SEQUENCE: 132

Trp Ile Ser Ala Tyr Asn Gly Asn Thr Asn Tyr Ala Gln Lys Leu Gln
1               5                   10                  15

Gly

<210> SEQ ID NO 133
<211> LENGTH: 15
<212> TYPE: PRT
<213> ORGANISM: Homo sapiens

<400> SEQUENCE: 133

Arg Asp Tyr Asp Ile Leu Thr Gly Tyr Tyr Asn Gly Phe Asp Pro
1               5                   10                  15

<210> SEQ ID NO 134
<211> LENGTH: 7
<212> TYPE: PRT
<213> ORGANISM: Homo sapiens

<400> SEQUENCE: 134

Ser Gly Gly Tyr Tyr Trp Ser
1               5

<210> SEQ ID NO 135

```
<211> LENGTH: 16
<212> TYPE: PRT
<213> ORGANISM: Homo sapiens

<400> SEQUENCE: 135

Tyr Ile Tyr Phe Ser Gly Ser Ala Tyr Tyr Asn Pro Ser Leu Lys Ser
1               5                   10                  15

<210> SEQ ID NO 136
<211> LENGTH: 14
<212> TYPE: PRT
<213> ORGANISM: Homo sapiens

<400> SEQUENCE: 136

Glu Tyr Tyr Asp Ser Ser Gly Tyr Pro Asp Ala Phe Asp Ile
1               5                   10

<210> SEQ ID NO 137
<211> LENGTH: 5
<212> TYPE: PRT
<213> ORGANISM: Homo sapiens

<400> SEQUENCE: 137

Ser Tyr Gly Met His
1               5

<210> SEQ ID NO 138
<211> LENGTH: 17
<212> TYPE: PRT
<213> ORGANISM: Homo sapiens

<400> SEQUENCE: 138

Val Ile Trp Tyr Asp Gly Ser Asn Lys Tyr Tyr Ala Asp Ser Val Lys
1               5                   10                  15

Gly

<210> SEQ ID NO 139
<211> LENGTH: 5
<212> TYPE: PRT
<213> ORGANISM: Homo sapiens

<400> SEQUENCE: 139

Asp Thr Lys Asp Tyr
1               5

<210> SEQ ID NO 140
<211> LENGTH: 5
<212> TYPE: PRT
<213> ORGANISM: Homo sapiens

<400> SEQUENCE: 140

Ser Tyr Gly Ile Ser
1               5

<210> SEQ ID NO 141
<211> LENGTH: 17
<212> TYPE: PRT
<213> ORGANISM: Homo sapiens

<400> SEQUENCE: 141

Trp Ile Ser Thr Tyr Lys Gly Asn Thr Asn Tyr Ala Gln Lys Leu Gln
1               5                   10                  15

Gly
```

```
<210> SEQ ID NO 142
<211> LENGTH: 7
<212> TYPE: PRT
<213> ORGANISM: Homo sapiens

<400> SEQUENCE: 142

Lys Gln Leu Val Phe Asp Tyr
1               5

<210> SEQ ID NO 143
<211> LENGTH: 5
<212> TYPE: PRT
<213> ORGANISM: Homo sapiens

<400> SEQUENCE: 143

Ser Tyr Gly Met Gln
1               5

<210> SEQ ID NO 144
<211> LENGTH: 17
<212> TYPE: PRT
<213> ORGANISM: Homo sapiens

<400> SEQUENCE: 144

Val Ile Trp Tyr Asp Gly Asn Lys Lys Tyr Tyr Ala Asp Ser Val Lys
1               5                   10                  15

Gly

<210> SEQ ID NO 145
<211> LENGTH: 12
<212> TYPE: PRT
<213> ORGANISM: Homo sapiens

<400> SEQUENCE: 145

Gly Arg Val Arg Asp Tyr Tyr Tyr Gly Met Asp Val
1               5                   10

<210> SEQ ID NO 146
<211> LENGTH: 5
<212> TYPE: PRT
<213> ORGANISM: Homo sapiens

<400> SEQUENCE: 146

Arg Tyr Gly Ile Ser
1               5

<210> SEQ ID NO 147
<211> LENGTH: 17
<212> TYPE: PRT
<213> ORGANISM: Homo sapiens

<400> SEQUENCE: 147

Trp Ile Ser Thr Tyr Ser Gly Asn Thr Asn Tyr Ala Gln Lys Leu Gln
1               5                   10                  15

Gly

<210> SEQ ID NO 148
<211> LENGTH: 7
<212> TYPE: PRT
<213> ORGANISM: Homo sapiens

<400> SEQUENCE: 148

Arg Gln Leu Tyr Phe Asp Tyr
```

```
1               5

<210> SEQ ID NO 149
<211> LENGTH: 5
<212> TYPE: PRT
<213> ORGANISM: Homo sapiens

<400> SEQUENCE: 149

Ser Tyr Gly Met Gln
1               5

<210> SEQ ID NO 150
<211> LENGTH: 17
<212> TYPE: PRT
<213> ORGANISM: Homo sapiens

<400> SEQUENCE: 150

Val Ile Trp Tyr Asp Gly Asn Lys Lys Tyr Tyr Ala Asp Ser Val Lys
1               5                   10                  15

Gly

<210> SEQ ID NO 151
<211> LENGTH: 12
<212> TYPE: PRT
<213> ORGANISM: Homo sapiens

<400> SEQUENCE: 151

Gly Arg Val Arg Asp Tyr Tyr Tyr Gly Met Asp Val
1               5                   10

<210> SEQ ID NO 152
<211> LENGTH: 5
<212> TYPE: PRT
<213> ORGANISM: Homo sapiens

<400> SEQUENCE: 152

Ser Tyr Gly Ile Ser
1               5

<210> SEQ ID NO 153
<211> LENGTH: 17
<212> TYPE: PRT
<213> ORGANISM: Homo sapiens

<400> SEQUENCE: 153

Trp Ile Ser Ala Tyr Asn Gly Asn Thr Lys Tyr Ala Gln Lys Leu Gln
1               5                   10                  15

Gly

<210> SEQ ID NO 154
<211> LENGTH: 7
<212> TYPE: PRT
<213> ORGANISM: Homo sapiens

<400> SEQUENCE: 154

Lys Gln Leu Val Phe Asp Tyr
1               5

<210> SEQ ID NO 155
<211> LENGTH: 5
<212> TYPE: PRT
<213> ORGANISM: Homo sapiens

<400> SEQUENCE: 155
```

```
Ser Tyr Gly Ile Ser
1               5

<210> SEQ ID NO 156
<211> LENGTH: 17
<212> TYPE: PRT
<213> ORGANISM: Homo sapiens

<400> SEQUENCE: 156

Trp Ile Ser Ala Tyr Ser Gly Asn Thr Lys Tyr Ala Gln Lys Leu Gln
1               5                   10                  15

Gly

<210> SEQ ID NO 157
<211> LENGTH: 7
<212> TYPE: PRT
<213> ORGANISM: Homo sapiens

<400> SEQUENCE: 157

Lys Gln Leu Val Phe Asp Tyr
1               5

<210> SEQ ID NO 158
<211> LENGTH: 5
<212> TYPE: PRT
<213> ORGANISM: Homo sapiens

<400> SEQUENCE: 158

Asp Tyr Tyr Met His
1               5

<210> SEQ ID NO 159
<211> LENGTH: 17
<212> TYPE: PRT
<213> ORGANISM: Homo sapiens

<400> SEQUENCE: 159

Trp Met His Pro Asn Ser Gly Gly Thr Asp Leu Ala Gln Arg Phe Gln
1               5                   10                  15

Gly

<210> SEQ ID NO 160
<211> LENGTH: 17
<212> TYPE: PRT
<213> ORGANISM: Homo sapiens

<400> SEQUENCE: 160

Gly Gly Tyr Cys Ser Thr Leu Ser Cys Ser Phe Tyr Trp Tyr Phe Asp
1               5                   10                  15

Leu

<210> SEQ ID NO 161
<211> LENGTH: 5
<212> TYPE: PRT
<213> ORGANISM: Homo sapiens

<400> SEQUENCE: 161

Ser Tyr Gly Ile Ser
1               5

<210> SEQ ID NO 162
<211> LENGTH: 17
```

```
<212> TYPE: PRT
<213> ORGANISM: Homo sapiens

<400> SEQUENCE: 162

Trp Ile Ser Ala Tyr Ser Gly Asn Thr Lys Tyr Ala Gln Lys Phe Gln
1               5                   10                  15

Gly

<210> SEQ ID NO 163
<211> LENGTH: 7
<212> TYPE: PRT
<213> ORGANISM: Homo sapiens

<400> SEQUENCE: 163

Arg Gln Leu Ala Leu Asp Tyr
1               5

<210> SEQ ID NO 164
<211> LENGTH: 5
<212> TYPE: PRT
<213> ORGANISM: Homo sapiens

<400> SEQUENCE: 164

Ser Tyr Ser Met Asn
1               5

<210> SEQ ID NO 165
<211> LENGTH: 17
<212> TYPE: PRT
<213> ORGANISM: Homo sapiens

<400> SEQUENCE: 165

Phe Ile Ser Ala Arg Ser Ser Thr Ile Tyr Tyr Ala Asp Ser Val Lys
1               5                   10                  15

Gly

<210> SEQ ID NO 166
<211> LENGTH: 9
<212> TYPE: PRT
<213> ORGANISM: Homo sapiens

<400> SEQUENCE: 166

Pro Lys Val Gly Gly Gly Met Asp Val
1               5

<210> SEQ ID NO 167
<211> LENGTH: 5
<212> TYPE: PRT
<213> ORGANISM: Homo sapiens

<400> SEQUENCE: 167

Ser Tyr Ser Met Asn
1               5

<210> SEQ ID NO 168
<211> LENGTH: 17
<212> TYPE: PRT
<213> ORGANISM: Homo sapiens

<400> SEQUENCE: 168

Ile Ile Ser Ser Arg Ser Ser Ile Ile His Tyr Ala Asp Ser Val Lys
1               5                   10                  15

Gly
```

```
<210> SEQ ID NO 169
<211> LENGTH: 9
<212> TYPE: PRT
<213> ORGANISM: Homo sapiens

<400> SEQUENCE: 169

Pro Lys Val Gly Gly Gly Met Asp Val
1               5

<210> SEQ ID NO 170
<211> LENGTH: 5
<212> TYPE: PRT
<213> ORGANISM: Homo sapiens

<400> SEQUENCE: 170

Arg Tyr Gly Ile Ser
1               5

<210> SEQ ID NO 171
<211> LENGTH: 17
<212> TYPE: PRT
<213> ORGANISM: Homo sapiens

<400> SEQUENCE: 171

Trp Ile Ser Ala Tyr Ser Gly Asn Thr Asn Tyr Ala Gln Lys Leu Gln
1               5                   10                  15

Gly

<210> SEQ ID NO 172
<211> LENGTH: 7
<212> TYPE: PRT
<213> ORGANISM: Homo sapiens

<400> SEQUENCE: 172

Arg Gln Leu Tyr Phe Asp Tyr
1               5

<210> SEQ ID NO 173
<211> LENGTH: 5
<212> TYPE: PRT
<213> ORGANISM: Homo sapiens

<400> SEQUENCE: 173

Ser Tyr Tyr Trp Ser
1               5

<210> SEQ ID NO 174
<211> LENGTH: 16
<212> TYPE: PRT
<213> ORGANISM: Homo sapiens

<400> SEQUENCE: 174

Arg Ile Tyr Pro Ser Gly Arg Thr Asn Tyr Asn Pro Ser Leu Lys Ser
1               5                   10                  15

<210> SEQ ID NO 175
<211> LENGTH: 17
<212> TYPE: PRT
<213> ORGANISM: Homo sapiens

<400> SEQUENCE: 175

Glu Ala Tyr Glu Leu Gln Leu Gly Leu Tyr Tyr Tyr Tyr Gly Met Asp
1               5                   10                  15
```

Val

<210> SEQ ID NO 176
<211> LENGTH: 5
<212> TYPE: PRT
<213> ORGANISM: Homo sapiens

<400> SEQUENCE: 176

Ser Tyr Tyr Trp Ser
1               5

<210> SEQ ID NO 177
<211> LENGTH: 16
<212> TYPE: PRT
<213> ORGANISM: Homo sapiens

<400> SEQUENCE: 177

Arg Ile Tyr Pro Ser Gly Arg Thr Asn Tyr Asn Pro Ser Leu Lys Ser
1               5                   10                  15

<210> SEQ ID NO 178
<211> LENGTH: 17
<212> TYPE: PRT
<213> ORGANISM: Homo sapiens

<400> SEQUENCE: 178

Glu Ala Tyr Glu Leu Gln Leu Gly Leu Tyr Tyr Tyr Gly Met Asp
1               5                   10                  15
Val

<210> SEQ ID NO 179
<211> LENGTH: 7
<212> TYPE: PRT
<213> ORGANISM: Homo sapiens

<400> SEQUENCE: 179

Ser Gly Gly Tyr Tyr Trp Ser
1               5

<210> SEQ ID NO 180
<211> LENGTH: 13
<212> TYPE: PRT
<213> ORGANISM: Homo sapiens

<400> SEQUENCE: 180

Tyr Ser Gly Asn Thr Tyr Tyr Asn Pro Ser Leu Arg Ser
1               5                   10

<210> SEQ ID NO 181
<211> LENGTH: 14
<212> TYPE: PRT
<213> ORGANISM: Homo sapiens

<400> SEQUENCE: 181

Glu Ala Gly Gly Asn Ser Ala Tyr Tyr Tyr Gly Met Asp Val
1               5                   10

<210> SEQ ID NO 182
<211> LENGTH: 5
<212> TYPE: PRT
<213> ORGANISM: Homo sapiens

<400> SEQUENCE: 182

```
Asp Tyr Tyr Met Ser
1               5
```

<210> SEQ ID NO 183
<211> LENGTH: 17
<212> TYPE: PRT
<213> ORGANISM: Homo sapiens

<400> SEQUENCE: 183

```
Tyr Ile Ser Ser Ser Gly Ser Thr Ile Tyr Tyr Ala Asp Ser Val Lys
1               5                   10                  15
Gly
```

<210> SEQ ID NO 184
<211> LENGTH: 16
<212> TYPE: PRT
<213> ORGANISM: Homo sapiens

<400> SEQUENCE: 184

```
Asp Arg Thr Tyr Tyr Phe Gly Ser Gly Ser Tyr Glu Gly Met Asp Val
1               5                   10                  15
```

<210> SEQ ID NO 185
<211> LENGTH: 11
<212> TYPE: PRT
<213> ORGANISM: Homo sapiens

<400> SEQUENCE: 185

```
Arg Ala Ser Gln Gly Ile Arg Asn Asp Leu Gly
1               5                   10
```

<210> SEQ ID NO 186
<211> LENGTH: 7
<212> TYPE: PRT
<213> ORGANISM: Homo sapiens

<400> SEQUENCE: 186

```
Ala Ala Ser Ser Leu Gln Ser
1               5
```

<210> SEQ ID NO 187
<211> LENGTH: 9
<212> TYPE: PRT
<213> ORGANISM: Homo sapiens

<400> SEQUENCE: 187

```
Leu Gln His Asn Ser Asn Pro Phe Thr
1               5
```

<210> SEQ ID NO 188
<211> LENGTH: 11
<212> TYPE: PRT
<213> ORGANISM: Homo sapiens

<400> SEQUENCE: 188

```
Arg Ala Ser Gln Ser Val Ser Arg Asn Leu Val
1               5                   10
```

<210> SEQ ID NO 189
<211> LENGTH: 7
<212> TYPE: PRT
<213> ORGANISM: Homo sapiens

<400> SEQUENCE: 189

```
Gly Ala Ser Thr Arg Ala Asn
1               5

<210> SEQ ID NO 190
<211> LENGTH: 8
<212> TYPE: PRT
<213> ORGANISM: Homo sapiens

<400> SEQUENCE: 190

Gln Gln Tyr Lys Ser Trp Arg Thr
1               5

<210> SEQ ID NO 191
<211> LENGTH: 11
<212> TYPE: PRT
<213> ORGANISM: Homo sapiens

<400> SEQUENCE: 191

Arg Ala Ser Gln Ser Ile Ser Ser Tyr Leu Asn
1               5                   10

<210> SEQ ID NO 192
<211> LENGTH: 7
<212> TYPE: PRT
<213> ORGANISM: Homo sapiens

<400> SEQUENCE: 192

Ala Ala Ser Ser Leu Gln Ser
1               5

<210> SEQ ID NO 193
<211> LENGTH: 9
<212> TYPE: PRT
<213> ORGANISM: Homo sapiens

<400> SEQUENCE: 193

Gln Gln Ser Tyr Ser Thr Pro Phe Thr
1               5

<210> SEQ ID NO 194
<211> LENGTH: 11
<212> TYPE: PRT
<213> ORGANISM: Homo sapiens

<400> SEQUENCE: 194

Arg Ala Ser Gln Ser Val Ser Arg Asn Leu Ala
1               5                   10

<210> SEQ ID NO 195
<211> LENGTH: 7
<212> TYPE: PRT
<213> ORGANISM: Homo sapiens

<400> SEQUENCE: 195

Gly Ala Ser Thr Arg Ala Thr
1               5

<210> SEQ ID NO 196
<211> LENGTH: 10
<212> TYPE: PRT
<213> ORGANISM: Homo sapiens

<400> SEQUENCE: 196

Gln Gln Tyr Asn Asn Trp Pro Thr Trp Thr
1               5                   10
```

```
<210> SEQ ID NO 197
<211> LENGTH: 11
<212> TYPE: PRT
<213> ORGANISM: Homo sapiens

<400> SEQUENCE: 197

Arg Ala Ser Gln Gly Ile Arg Asn Asp Leu Gly
1               5                   10

<210> SEQ ID NO 198
<211> LENGTH: 7
<212> TYPE: PRT
<213> ORGANISM: Homo sapiens

<400> SEQUENCE: 198

Ala Ala Ser Ser Phe Gln Ser
1               5

<210> SEQ ID NO 199
<211> LENGTH: 9
<212> TYPE: PRT
<213> ORGANISM: Homo sapiens

<400> SEQUENCE: 199

Leu Gln His Asn Ser Tyr Pro Pro Thr
1               5

<210> SEQ ID NO 200
<211> LENGTH: 11
<212> TYPE: PRT
<213> ORGANISM: Homo sapiens

<400> SEQUENCE: 200

Arg Ala Ser Gln Gly Ile Arg Asn Asp Leu Gly
1               5                   10

<210> SEQ ID NO 201
<211> LENGTH: 7
<212> TYPE: PRT
<213> ORGANISM: Homo sapiens

<400> SEQUENCE: 201

Ala Ala Ser Ser Leu Gln Ser
1               5

<210> SEQ ID NO 202
<211> LENGTH: 9
<212> TYPE: PRT
<213> ORGANISM: Homo sapiens

<400> SEQUENCE: 202

Leu Gln His Lys Ser Tyr Pro Leu Thr
1               5

<210> SEQ ID NO 203
<211> LENGTH: 11
<212> TYPE: PRT
<213> ORGANISM: Homo sapiens

<400> SEQUENCE: 203

Arg Ala Ser Gln Gly Ile Arg Asn Asp Leu Gly
1               5                   10
```

<210> SEQ ID NO 204
<211> LENGTH: 7
<212> TYPE: PRT
<213> ORGANISM: Homo sapiens

<400> SEQUENCE: 204

Ala Ala Ser Ser Leu Gln Ser
1               5

<210> SEQ ID NO 205
<211> LENGTH: 9
<212> TYPE: PRT
<213> ORGANISM: Homo sapiens

<400> SEQUENCE: 205

Leu Gln His Lys Ser Tyr Pro Leu Thr
1               5

<210> SEQ ID NO 206
<211> LENGTH: 11
<212> TYPE: PRT
<213> ORGANISM: Homo sapiens

<400> SEQUENCE: 206

Arg Ala Ser Gln Gly Ile Arg Asn Asp Leu Gly
1               5                   10

<210> SEQ ID NO 207
<211> LENGTH: 7
<212> TYPE: PRT
<213> ORGANISM: Homo sapiens

<400> SEQUENCE: 207

Ala Ala Ser Ser Leu Gln Ser
1               5

<210> SEQ ID NO 208
<211> LENGTH: 9
<212> TYPE: PRT
<213> ORGANISM: Homo sapiens

<400> SEQUENCE: 208

Leu Gln His Lys Ser Tyr Pro Leu Thr
1               5

<210> SEQ ID NO 209
<211> LENGTH: 11
<212> TYPE: PRT
<213> ORGANISM: Homo sapiens

<400> SEQUENCE: 209

Arg Ala Ser Gln Gly Ile Arg Asn Asp Leu Gly
1               5                   10

<210> SEQ ID NO 210
<211> LENGTH: 7
<212> TYPE: PRT
<213> ORGANISM: Homo sapiens

<400> SEQUENCE: 210

Ala Ala Ser Ser Leu Gln Ser
1               5

<210> SEQ ID NO 211
<211> LENGTH: 9

```
<212> TYPE: PRT
<213> ORGANISM: Homo sapiens

<400> SEQUENCE: 211

Leu Gln His Lys Ser Tyr Pro Leu Thr
1               5

<210> SEQ ID NO 212
<211> LENGTH: 11
<212> TYPE: PRT
<213> ORGANISM: Homo sapiens

<400> SEQUENCE: 212

Arg Ala Ser Gln Gly Ile Arg Ser Trp Leu Ala
1               5                   10

<210> SEQ ID NO 213
<211> LENGTH: 7
<212> TYPE: PRT
<213> ORGANISM: Homo sapiens

<400> SEQUENCE: 213

Ala Ala Ser Ser Leu Gln Ser
1               5

<210> SEQ ID NO 214
<211> LENGTH: 9
<212> TYPE: PRT
<213> ORGANISM: Homo sapiens

<400> SEQUENCE: 214

Gln Gln Ala Asn Asn Phe Pro Arg Thr
1               5

<210> SEQ ID NO 215
<211> LENGTH: 11
<212> TYPE: PRT
<213> ORGANISM: Homo sapiens

<400> SEQUENCE: 215

Arg Ala Ser Gln Ser Val Ser Ser Asn Leu Ala
1               5                   10

<210> SEQ ID NO 216
<211> LENGTH: 7
<212> TYPE: PRT
<213> ORGANISM: Homo sapiens

<400> SEQUENCE: 216

Gly Ala Ser Thr Arg Ala Ala
1               5

<210> SEQ ID NO 217
<211> LENGTH: 10
<212> TYPE: PRT
<213> ORGANISM: Homo sapiens

<400> SEQUENCE: 217

Gln His Tyr Ile Asn Trp Pro Lys Trp Thr
1               5                   10

<210> SEQ ID NO 218
<211> LENGTH: 11
<212> TYPE: PRT
<213> ORGANISM: Homo sapiens
```

```
<400> SEQUENCE: 218

Arg Ala Ser Gln Ser Ile Ser Ser Ser Leu Ala
1               5                   10

<210> SEQ ID NO 219
<211> LENGTH: 7
<212> TYPE: PRT
<213> ORGANISM: Homo sapiens

<400> SEQUENCE: 219

Gly Ala Ser Thr Arg Ala Thr
1               5

<210> SEQ ID NO 220
<211> LENGTH: 9
<212> TYPE: PRT
<213> ORGANISM: Homo sapiens

<400> SEQUENCE: 220

Gln Gln Tyr Asp Asn Trp Pro Leu Thr
1               5

<210> SEQ ID NO 221
<211> LENGTH: 16
<212> TYPE: PRT
<213> ORGANISM: Homo sapiens

<400> SEQUENCE: 221

Lys Ser Ser Gln Ser Leu Leu His Ser Asp Gly Lys Thr Tyr Leu Tyr
1               5                   10                  15

<210> SEQ ID NO 222
<211> LENGTH: 7
<212> TYPE: PRT
<213> ORGANISM: Homo sapiens

<400> SEQUENCE: 222

Glu Val Ser Thr Arg Phe Ser
1               5

<210> SEQ ID NO 223
<211> LENGTH: 9
<212> TYPE: PRT
<213> ORGANISM: Homo sapiens

<400> SEQUENCE: 223

Met Gln Ser Ile Gln Leu Pro Leu Thr
1               5

<210> SEQ ID NO 224
<211> LENGTH: 11
<212> TYPE: PRT
<213> ORGANISM: Homo sapiens

<400> SEQUENCE: 224

Arg Ala Ser Gln Ser Val Ser Ser Asn Leu Ala
1               5                   10

<210> SEQ ID NO 225
<211> LENGTH: 7
<212> TYPE: PRT
<213> ORGANISM: Homo sapiens

<400> SEQUENCE: 225
```

Asp Ala Ser Thr Arg Ala Thr
1               5

<210> SEQ ID NO 226
<211> LENGTH: 9
<212> TYPE: PRT
<213> ORGANISM: Homo sapiens

<400> SEQUENCE: 226

Gln Gln Tyr Asp Asn Trp Pro Leu Thr
1               5

<210> SEQ ID NO 227
<211> LENGTH: 11
<212> TYPE: PRT
<213> ORGANISM: Homo sapiens

<400> SEQUENCE: 227

Arg Ala Ser Gln Ser Val Ser Ser Asn Leu Ala
1               5                   10

<210> SEQ ID NO 228
<211> LENGTH: 7
<212> TYPE: PRT
<213> ORGANISM: Homo sapiens

<400> SEQUENCE: 228

Asp Ala Ser Thr Arg Ala Ala
1               5

<210> SEQ ID NO 229
<211> LENGTH: 9
<212> TYPE: PRT
<213> ORGANISM: Homo sapiens

<400> SEQUENCE: 229

Gln Gln Tyr Asp Asn Trp Pro Leu Thr
1               5

<210> SEQ ID NO 230
<211> LENGTH: 11
<212> TYPE: PRT
<213> ORGANISM: Homo sapiens

<400> SEQUENCE: 230

Arg Ala Ser Gln Ser Ile Ser Thr Ser Leu Ala
1               5                   10

<210> SEQ ID NO 231
<211> LENGTH: 7
<212> TYPE: PRT
<213> ORGANISM: Homo sapiens

<400> SEQUENCE: 231

Gly Thr Ser Thr Arg Ala Thr
1               5

<210> SEQ ID NO 232
<211> LENGTH: 9
<212> TYPE: PRT
<213> ORGANISM: Homo sapiens

<400> SEQUENCE: 232

Gln Gln Tyr Asp Ile Trp Pro Leu Thr

```
<210> SEQ ID NO 233
<211> LENGTH: 11
<212> TYPE: PRT
<213> ORGANISM: Homo sapiens

<400> SEQUENCE: 233

Arg Ala Ser Gln Ser Val Ser Ser Asn Leu Ala
1               5                   10

<210> SEQ ID NO 234
<211> LENGTH: 7
<212> TYPE: PRT
<213> ORGANISM: Homo sapiens

<400> SEQUENCE: 234

Gly Ala Ser Thr Arg Ala Thr
1               5

<210> SEQ ID NO 235
<211> LENGTH: 9
<212> TYPE: PRT
<213> ORGANISM: Homo sapiens

<400> SEQUENCE: 235

Gln Gln Tyr Asp Asn Trp Pro Leu Thr
1               5

<210> SEQ ID NO 236
<211> LENGTH: 17
<212> TYPE: PRT
<213> ORGANISM: Homo sapiens

<400> SEQUENCE: 236

Lys Thr Ser Gln Ser Val Leu Tyr Ser Ser Lys Asn Lys Asn Phe Leu
1               5                   10                  15

Ala

<210> SEQ ID NO 237
<211> LENGTH: 7
<212> TYPE: PRT
<213> ORGANISM: Homo sapiens

<400> SEQUENCE: 237

Trp Ala Ser Thr Arg Glu Ser
1               5

<210> SEQ ID NO 238
<211> LENGTH: 9
<212> TYPE: PRT
<213> ORGANISM: Homo sapiens

<400> SEQUENCE: 238

Gln Gln Tyr Tyr Ser Thr Pro Phe Thr
1               5

<210> SEQ ID NO 239
<211> LENGTH: 11
<212> TYPE: PRT
<213> ORGANISM: Homo sapiens

<400> SEQUENCE: 239

Arg Ala Ser Gln Ser Ile Ser Ser Asn Leu Ala
```

```
<210> SEQ ID NO 240
<211> LENGTH: 7
<212> TYPE: PRT
<213> ORGANISM: Homo sapiens

<400> SEQUENCE: 240

Gly Ala Ser Thr Arg Ala Thr
1               5

<210> SEQ ID NO 241
<211> LENGTH: 9
<212> TYPE: PRT
<213> ORGANISM: Homo sapiens

<400> SEQUENCE: 241

Gln Gln Tyr Asp Thr Trp Pro Leu Thr
1               5

<210> SEQ ID NO 242
<211> LENGTH: 11
<212> TYPE: PRT
<213> ORGANISM: Homo sapiens

<400> SEQUENCE: 242

Arg Ala Ser Gln Gly Ile Ser Asn Tyr Leu Ala
1               5                   10

<210> SEQ ID NO 243
<211> LENGTH: 7
<212> TYPE: PRT
<213> ORGANISM: Homo sapiens

<400> SEQUENCE: 243

Ala Ala Ser Thr Leu Gln Ser
1               5

<210> SEQ ID NO 244
<211> LENGTH: 9
<212> TYPE: PRT
<213> ORGANISM: Homo sapiens

<400> SEQUENCE: 244

Gln Lys Tyr Asn Arg Ala Pro Phe Thr
1               5

<210> SEQ ID NO 245
<211> LENGTH: 11
<212> TYPE: PRT
<213> ORGANISM: Homo sapiens

<400> SEQUENCE: 245

Arg Ala Ser Gln Gly Ile Ser Asn Tyr Leu Ala
1               5                   10

<210> SEQ ID NO 246
<211> LENGTH: 7
<212> TYPE: PRT
<213> ORGANISM: Homo sapiens

<400> SEQUENCE: 246

Ala Ala Ser Thr Leu Gln Ser
1               5
```

```
<210> SEQ ID NO 247
<211> LENGTH: 9
<212> TYPE: PRT
<213> ORGANISM: Homo sapiens

<400> SEQUENCE: 247

Gln Lys Tyr Asn Arg Ala Pro Phe Thr
1               5

<210> SEQ ID NO 248
<211> LENGTH: 11
<212> TYPE: PRT
<213> ORGANISM: Homo sapiens

<400> SEQUENCE: 248

Arg Ala Ser Gln Ser Val Ser Ser Asn Leu Ala
1               5                   10

<210> SEQ ID NO 249
<211> LENGTH: 7
<212> TYPE: PRT
<213> ORGANISM: Homo sapiens

<400> SEQUENCE: 249

Asp Ala Ser Thr Arg Ala Ala
1               5

<210> SEQ ID NO 250
<211> LENGTH: 9
<212> TYPE: PRT
<213> ORGANISM: Homo sapiens

<400> SEQUENCE: 250

Gln Gln Tyr Asp Asn Trp Pro Leu Thr
1               5

<210> SEQ ID NO 251
<211> LENGTH: 11
<212> TYPE: PRT
<213> ORGANISM: Homo sapiens

<400> SEQUENCE: 251

Arg Ala Ser Gln Gly Ile Ile Asn Asp Leu Gly
1               5                   10

<210> SEQ ID NO 252
<211> LENGTH: 7
<212> TYPE: PRT
<213> ORGANISM: Homo sapiens

<400> SEQUENCE: 252

Ala Ala Ser Ser Leu Gln Ser
1               5

<210> SEQ ID NO 253
<211> LENGTH: 9
<212> TYPE: PRT
<213> ORGANISM: Homo sapiens

<400> SEQUENCE: 253

Leu Gln His Asn Ser Tyr Pro Pro Thr
1               5

<210> SEQ ID NO 254
```

```
<211> LENGTH: 16
<212> TYPE: PRT
<213> ORGANISM: Homo sapiens

<400> SEQUENCE: 254

Arg Ser Ser Gln Ser Leu Val Tyr Ser Asp Gly His Thr Cys Leu Asn
1               5                   10                  15

<210> SEQ ID NO 255
<211> LENGTH: 7
<212> TYPE: PRT
<213> ORGANISM: Homo sapiens

<400> SEQUENCE: 255

Lys Val Ser Asn Trp Asp Ser
1               5

<210> SEQ ID NO 256
<211> LENGTH: 10
<212> TYPE: PRT
<213> ORGANISM: Homo sapiens

<400> SEQUENCE: 256

Met Gln Gly Thr His Trp Pro Leu Cys Ser
1               5                   10

<210> SEQ ID NO 257
<211> LENGTH: 16
<212> TYPE: PRT
<213> ORGANISM: Homo sapiens

<400> SEQUENCE: 257

Arg Ser Ser Gln Ser Leu Val Tyr Ser Asp Gly His Thr Cys Leu Asn
1               5                   10                  15

<210> SEQ ID NO 258
<211> LENGTH: 7
<212> TYPE: PRT
<213> ORGANISM: Homo sapiens

<400> SEQUENCE: 258

Lys Val Ser Asn Trp Asp Ser
1               5

<210> SEQ ID NO 259
<211> LENGTH: 10
<212> TYPE: PRT
<213> ORGANISM: Homo sapiens

<400> SEQUENCE: 259

Met Gln Gly Thr His Trp Pro Leu Cys Ser
1               5                   10

<210> SEQ ID NO 260
<211> LENGTH: 11
<212> TYPE: PRT
<213> ORGANISM: Homo sapiens

<400> SEQUENCE: 260

Arg Ala Ser Gln Ala Ile Ser Ile Tyr Leu Ala
1               5                   10

<210> SEQ ID NO 261
<211> LENGTH: 7
<212> TYPE: PRT
```

<213> ORGANISM: Homo sapiens

<400> SEQUENCE: 261

Ala Ala Ser Ser Leu Gln Ser
1               5

<210> SEQ ID NO 262
<211> LENGTH: 9
<212> TYPE: PRT
<213> ORGANISM: Homo sapiens

<400> SEQUENCE: 262

Gln Gln Tyr Ser Ser Tyr Pro Arg Thr
1               5

<210> SEQ ID NO 263
<211> LENGTH: 11
<212> TYPE: PRT
<213> ORGANISM: Homo sapiens

<400> SEQUENCE: 263

Arg Ala Ser Gln Ser Val Tyr Ser Asn Leu Ala
1               5                   10

<210> SEQ ID NO 264
<211> LENGTH: 7
<212> TYPE: PRT
<213> ORGANISM: Homo sapiens

<400> SEQUENCE: 264

Gly Ala Ser Thr Arg Ala Thr
1               5

<210> SEQ ID NO 265
<211> LENGTH: 9
<212> TYPE: PRT
<213> ORGANISM: Homo sapiens

<400> SEQUENCE: 265

Gln Gln Tyr Tyr Asn Trp Pro Trp Thr
1               5

<210> SEQ ID NO 266
<211> LENGTH: 15
<212> TYPE: DNA
<213> ORGANISM: Homo sapiens

<400> SEQUENCE: 266
aattactact ggaac                                                   15

<210> SEQ ID NO 267
<211> LENGTH: 75
<212> TYPE: DNA
<213> ORGANISM: Homo sapiens

<400> SEQUENCE: 267
ccagggaagg gactggagtg gattggggat atctattaca gtgggagcac caactacaac   60
ccctccctca agagt                                                   75

<210> SEQ ID NO 268
<211> LENGTH: 69
<212> TYPE: DNA
<213> ORGANISM: Homo sapiens

```
<400> SEQUENCE: 268
gatggggaac tcgccaatta ctatggttcg gggagttatc agttctacta ctactacggt      60
atggacgtc                                                              69

<210> SEQ ID NO 269
<211> LENGTH: 15
<212> TYPE: DNA
<213> ORGANISM: Homo sapiens

<400> SEQUENCE: 269
ggttactact ggagc                                                       15

<210> SEQ ID NO 270
<211> LENGTH: 48
<212> TYPE: DNA
<213> ORGANISM: Homo sapiens

<400> SEQUENCE: 270
gaaatcaatc atagtggacg caccaattac aacccgtccc tcaagagt                   48

<210> SEQ ID NO 271
<211> LENGTH: 57
<212> TYPE: DNA
<213> ORGANISM: Homo sapiens

<400> SEQUENCE: 271
ggcccttatt actttgatag tagtggttac ctttactact actacggttt ggacgtc         57

<210> SEQ ID NO 272
<211> LENGTH: 15
<212> TYPE: DNA
<213> ORGANISM: Homo sapiens

<400> SEQUENCE: 272
agctatggca tgcac                                                       15

<210> SEQ ID NO 273
<211> LENGTH: 51
<212> TYPE: DNA
<213> ORGANISM: Homo sapiens

<400> SEQUENCE: 273
gttatatggt atgatggaag taataaacac tatgcagact ccgtgaaggg c               51

<210> SEQ ID NO 274
<211> LENGTH: 15
<212> TYPE: DNA
<213> ORGANISM: Homo sapiens

<400> SEQUENCE: 274
gatactgggg tctac                                                       15

<210> SEQ ID NO 275
<211> LENGTH: 15
<212> TYPE: DNA
<213> ORGANISM: Homo sapiens

<400> SEQUENCE: 275
agctatggca tgcac                                                       15

<210> SEQ ID NO 276
<211> LENGTH: 51
```

```
<212> TYPE: DNA
<213> ORGANISM: Homo sapiens

<400> SEQUENCE: 276
gttatatggt atgatggaag taataaacac tatgcagact ccgtgaaggg c          51

<210> SEQ ID NO 277
<211> LENGTH: 15
<212> TYPE: DNA
<213> ORGANISM: Homo sapiens

<400> SEQUENCE: 277
gatactgggg tctac                                                  15

<210> SEQ ID NO 278
<211> LENGTH: 15
<212> TYPE: DNA
<213> ORGANISM: Homo sapiens

<400> SEQUENCE: 278
agttactact ggagc                                                  15

<210> SEQ ID NO 279
<211> LENGTH: 48
<212> TYPE: DNA
<213> ORGANISM: Homo sapiens

<400> SEQUENCE: 279
cgtatctatc gcagtgggaa caccatctac aacccctccc tcaagagt              48

<210> SEQ ID NO 280
<211> LENGTH: 51
<212> TYPE: DNA
<213> ORGANISM: Homo sapiens

<400> SEQUENCE: 280
gagaattact ctgagagtag tggtctctac tactactacg gtatggacgt c          51

<210> SEQ ID NO 281
<211> LENGTH: 15
<212> TYPE: DNA
<213> ORGANISM: Homo sapiens

<400> SEQUENCE: 281
agatatggta tcagc                                                  15

<210> SEQ ID NO 282
<211> LENGTH: 51
<212> TYPE: DNA
<213> ORGANISM: Homo sapiens

<400> SEQUENCE: 282
tggatcagcg cttacaatgg taacacaaac tatgcacaga agctccaggg c          51

<210> SEQ ID NO 283
<211> LENGTH: 45
<212> TYPE: DNA
<213> ORGANISM: Homo sapiens

<400> SEQUENCE: 283
agggattacg atattttgac tggttattat aacgggttcg acccc                 45

<210> SEQ ID NO 284
```

```
<211> LENGTH: 15
<212> TYPE: DNA
<213> ORGANISM: Homo sapiens

<400> SEQUENCE: 284
agatatggta tcagc                                                    15

<210> SEQ ID NO 285
<211> LENGTH: 51
<212> TYPE: DNA
<213> ORGANISM: Homo sapiens

<400> SEQUENCE: 285
tggatcagcg cttacaatgg taacacaaac tatgcacaga agctccaggg c             51

<210> SEQ ID NO 286
<211> LENGTH: 45
<212> TYPE: DNA
<213> ORGANISM: Homo sapiens

<400> SEQUENCE: 286
agggattacg atattttgac tggttattat aacgggttcg acccc                   45

<210> SEQ ID NO 287
<211> LENGTH: 15
<212> TYPE: DNA
<213> ORGANISM: Homo sapiens

<400> SEQUENCE: 287
ggctatggta tcagc                                                    15

<210> SEQ ID NO 288
<211> LENGTH: 51
<212> TYPE: DNA
<213> ORGANISM: Homo sapiens

<400> SEQUENCE: 288
tggatcagcg cttacaatgg taacacaaac tatgcacaga acctccaggg c             51

<210> SEQ ID NO 289
<211> LENGTH: 45
<212> TYPE: DNA
<213> ORGANISM: Homo sapiens

<400> SEQUENCE: 289
agggattacg atattttgac tggttattat aacgggttcg acccc                   45

<210> SEQ ID NO 290
<211> LENGTH: 15
<212> TYPE: DNA
<213> ORGANISM: Homo sapiens

<400> SEQUENCE: 290
agatatggta tcagc                                                    15

<210> SEQ ID NO 291
<211> LENGTH: 50
<212> TYPE: DNA
<213> ORGANISM: Homo sapiens

<400> SEQUENCE: 291
tggatcagcg cttacaatgg taacacaaac tatgcacaga agctccaggg               50
```

-continued

```
<210> SEQ ID NO 292
<211> LENGTH: 45
<212> TYPE: DNA
<213> ORGANISM: Homo sapiens

<400> SEQUENCE: 292
agggattacg atattttgac tggttattat aacgggttcg acccc              45

<210> SEQ ID NO 293
<211> LENGTH: 21
<212> TYPE: DNA
<213> ORGANISM: Homo sapiens

<400> SEQUENCE: 293
agtggtggtt actactggag c                                        21

<210> SEQ ID NO 294
<211> LENGTH: 48
<212> TYPE: DNA
<213> ORGANISM: Homo sapiens

<400> SEQUENCE: 294
tacatctatt tcagtgggag cgcctactac aacccgtccc tcaagagt           48

<210> SEQ ID NO 295
<211> LENGTH: 42
<212> TYPE: DNA
<213> ORGANISM: Homo sapiens

<400> SEQUENCE: 295
gaatactatg atagtagtgg ttaccccgat gcttttgata tc                 42

<210> SEQ ID NO 296
<211> LENGTH: 15
<212> TYPE: DNA
<213> ORGANISM: Homo sapiens

<400> SEQUENCE: 296
agctatggca tgcac                                               15

<210> SEQ ID NO 297
<211> LENGTH: 51
<212> TYPE: DNA
<213> ORGANISM: Homo sapiens

<400> SEQUENCE: 297
gttatatggt atgatggaag taataaatat tatgcagact ccgtgaaggg c       51

<210> SEQ ID NO 298
<211> LENGTH: 15
<212> TYPE: DNA
<213> ORGANISM: Homo sapiens

<400> SEQUENCE: 298
gatacgaagg actac                                               15

<210> SEQ ID NO 299
<211> LENGTH: 15
<212> TYPE: DNA
<213> ORGANISM: Homo sapiens

<400> SEQUENCE: 299
agctatggta tcagc                                               15
```

```
<210> SEQ ID NO 300
<211> LENGTH: 51
<212> TYPE: DNA
<213> ORGANISM: Homo sapiens

<400> SEQUENCE: 300
tggatcagca cttacaaagg taacacaaac tatgcacaga agctccaggg c          51

<210> SEQ ID NO 301
<211> LENGTH: 21
<212> TYPE: DNA
<213> ORGANISM: Homo sapiens

<400> SEQUENCE: 301
aagcagctcg tctttgacta c                                           21

<210> SEQ ID NO 302
<211> LENGTH: 15
<212> TYPE: DNA
<213> ORGANISM: Homo sapiens

<400> SEQUENCE: 302
agctatggca tgcag                                                  15

<210> SEQ ID NO 303
<211> LENGTH: 51
<212> TYPE: DNA
<213> ORGANISM: Homo sapiens

<400> SEQUENCE: 303
gttatatggt atgatggaaa taagaaatac tatgcagact ccgtgaaggg c          51

<210> SEQ ID NO 304
<211> LENGTH: 36
<212> TYPE: DNA
<213> ORGANISM: Homo sapiens

<400> SEQUENCE: 304
ggacgtgtta gggactacta ctacggtatg gacgtc                           36

<210> SEQ ID NO 305
<211> LENGTH: 15
<212> TYPE: DNA
<213> ORGANISM: Homo sapiens

<400> SEQUENCE: 305
agatatggta tcagc                                                  15

<210> SEQ ID NO 306
<211> LENGTH: 51
<212> TYPE: DNA
<213> ORGANISM: Homo sapiens

<400> SEQUENCE: 306
tggatcagca cttacagtgg taacacaaac tatgcacaga agctccaggg c          51

<210> SEQ ID NO 307
<211> LENGTH: 21
<212> TYPE: DNA
<213> ORGANISM: Homo sapiens

<400> SEQUENCE: 307
cggcagcttt actttgacta c                                           21
```

<210> SEQ ID NO 308
<211> LENGTH: 15
<212> TYPE: DNA
<213> ORGANISM: Homo sapiens
<400> SEQUENCE: 308
agctatggca tgcag                                                    15

<210> SEQ ID NO 309
<211> LENGTH: 51
<212> TYPE: DNA
<213> ORGANISM: Homo sapiens
<400> SEQUENCE: 309
gttatatggt atgatggaaa taagaaatac tatgcagact ccgtgaaggg c             51

<210> SEQ ID NO 310
<211> LENGTH: 36
<212> TYPE: DNA
<213> ORGANISM: Homo sapiens
<400> SEQUENCE: 310
ggacgtgtta gggactacta ctacggtatg gacgtc                             36

<210> SEQ ID NO 311
<211> LENGTH: 15
<212> TYPE: DNA
<213> ORGANISM: Homo sapiens
<400> SEQUENCE: 311
agctatggta tcagc                                                    15

<210> SEQ ID NO 312
<211> LENGTH: 51
<212> TYPE: DNA
<213> ORGANISM: Homo sapiens
<400> SEQUENCE: 312
tggatcagcg cttacaatgg taacacaaag tatgcacaga agctccaggg c             51

<210> SEQ ID NO 313
<211> LENGTH: 21
<212> TYPE: DNA
<213> ORGANISM: Homo sapiens
<400> SEQUENCE: 313
aagcagctcg tctttgacta c                                             21

<210> SEQ ID NO 314
<211> LENGTH: 15
<212> TYPE: DNA
<213> ORGANISM: Homo sapiens
<400> SEQUENCE: 314
agctatggta tcagc                                                    15

<210> SEQ ID NO 315
<211> LENGTH: 51
<212> TYPE: DNA
<213> ORGANISM: Homo sapiens
<400> SEQUENCE: 315

-continued tggatcagcg cttacagtgg taatacaaag tatgcacaga agctccaggg c        51

<210> SEQ ID NO 316
<211> LENGTH: 21
<212> TYPE: DNA
<213> ORGANISM: Homo sapiens

<400> SEQUENCE: 316
aagcagctcg tctttgacta c        21

<210> SEQ ID NO 317
<211> LENGTH: 15
<212> TYPE: DNA
<213> ORGANISM: Homo sapiens

<400> SEQUENCE: 317
gactactaca tgcac        15

<210> SEQ ID NO 318
<211> LENGTH: 51
<212> TYPE: DNA
<213> ORGANISM: Homo sapiens

<400> SEQUENCE: 318
tggatgcacc ctaacagtgg tggcacagac ttagcacaga ggtttcaggg c        51

<210> SEQ ID NO 319
<211> LENGTH: 51
<212> TYPE: DNA
<213> ORGANISM: Homo sapiens

<400> SEQUENCE: 319
gggggatatt gtagtacttt gagctgctcc ttctactggt acttcgatct c        51

<210> SEQ ID NO 320
<211> LENGTH: 15
<212> TYPE: DNA
<213> ORGANISM: Homo sapiens

<400> SEQUENCE: 320
agctatggaa tcagt        15

<210> SEQ ID NO 321
<211> LENGTH: 51
<212> TYPE: DNA
<213> ORGANISM: Homo sapiens

<400> SEQUENCE: 321
tggatcagcg cttacagtgg taacacaaag tatgcacaga agttccaggg c        51

<210> SEQ ID NO 322
<211> LENGTH: 21
<212> TYPE: DNA
<213> ORGANISM: Homo sapiens

<400> SEQUENCE: 322
aggcagctcg cgttggacta c        21

<210> SEQ ID NO 323
<211> LENGTH: 15
<212> TYPE: DNA
<213> ORGANISM: Homo sapiens

<400> SEQUENCE: 323
agctatagca tgaac                                                          15

<210> SEQ ID NO 324
<211> LENGTH: 51
<212> TYPE: DNA
<213> ORGANISM: Homo sapiens

<400> SEQUENCE: 324
ttcattagtg ctagaagtag taccatatac tacgcagact ctgtgaaggg c                  51

<210> SEQ ID NO 325
<211> LENGTH: 27
<212> TYPE: DNA
<213> ORGANISM: Homo sapiens

<400> SEQUENCE: 325
cctaaagtgg ggggcggtat ggacgtc                                             27

<210> SEQ ID NO 326
<211> LENGTH: 15
<212> TYPE: DNA
<213> ORGANISM: Homo sapiens

<400> SEQUENCE: 326
agctatagca tgaac                                                          15

<210> SEQ ID NO 327
<211> LENGTH: 51
<212> TYPE: DNA
<213> ORGANISM: Homo sapiens

<400> SEQUENCE: 327
atcattagta gtagaagtag tatcatacac tacgcagact ctgtgaaggg c                  51

<210> SEQ ID NO 328
<211> LENGTH: 27
<212> TYPE: DNA
<213> ORGANISM: Homo sapiens

<400> SEQUENCE: 328
cctaaagtgg ggggcggtat ggacgtc                                             27

<210> SEQ ID NO 329
<211> LENGTH: 15
<212> TYPE: DNA
<213> ORGANISM: Homo sapiens

<400> SEQUENCE: 329
agatatggta tcagc                                                          15

<210> SEQ ID NO 330
<211> LENGTH: 51
<212> TYPE: DNA
<213> ORGANISM: Homo sapiens

<400> SEQUENCE: 330
tggatcagcg cttacagtgg taacacaaac tatgcacaga agctccaggg c                  51

<210> SEQ ID NO 331
<211> LENGTH: 21
<212> TYPE: DNA
<213> ORGANISM: Homo sapiens -continued

```
<400> SEQUENCE: 331
cggcagcttt actttgacta c                                              21

<210> SEQ ID NO 332
<211> LENGTH: 15
<212> TYPE: DNA
<213> ORGANISM: Homo sapiens

<400> SEQUENCE: 332
agttactact ggagc                                                     15

<210> SEQ ID NO 333
<211> LENGTH: 48
<212> TYPE: DNA
<213> ORGANISM: Homo sapiens

<400> SEQUENCE: 333
cgtatctatc ccagtgggag aaccaactac aacccctccc tcaagagt                 48

<210> SEQ ID NO 334
<211> LENGTH: 51
<212> TYPE: DNA
<213> ORGANISM: Homo sapiens

<400> SEQUENCE: 334
gaggcatatg agctgcaact gggcctctac tactactacg gtatggacgt c             51

<210> SEQ ID NO 335
<211> LENGTH: 15
<212> TYPE: DNA
<213> ORGANISM: Homo sapiens

<400> SEQUENCE: 335
agttactact ggagc                                                     15

<210> SEQ ID NO 336
<211> LENGTH: 48
<212> TYPE: DNA
<213> ORGANISM: Homo sapiens

<400> SEQUENCE: 336
cgtatctatc ccagtgggag aaccaactac aacccctccc tcaagagt                 48

<210> SEQ ID NO 337
<211> LENGTH: 51
<212> TYPE: DNA
<213> ORGANISM: Homo sapiens

<400> SEQUENCE: 337
gaggcatatg agctgcaact gggcctctac tactactacg gtatggacgt c             51

<210> SEQ ID NO 338
<211> LENGTH: 21
<212> TYPE: DNA
<213> ORGANISM: Homo sapiens

<400> SEQUENCE: 338
agtggtggtt actactggag c                                              21

<210> SEQ ID NO 339
<211> LENGTH: 39
<212> TYPE: DNA
<213> ORGANISM: Homo sapiens
```

```
<400> SEQUENCE: 339
tacagtggga acacctacta caacccgtcc ctcaggagt                                39

<210> SEQ ID NO 340
<211> LENGTH: 42
<212> TYPE: DNA
<213> ORGANISM: Homo sapiens

<400> SEQUENCE: 340
gaggccggtg gtaactccgc ctactactac ggtatggacg tc                           42

<210> SEQ ID NO 341
<211> LENGTH: 15
<212> TYPE: DNA
<213> ORGANISM: Homo sapiens

<400> SEQUENCE: 341
gactactaca tgagc                                                         15

<210> SEQ ID NO 342
<211> LENGTH: 51
<212> TYPE: DNA
<213> ORGANISM: Homo sapiens

<400> SEQUENCE: 342
tacattagta gtagtcgtag taccatatac tacgcagact ctgtgaaggg c                 51

<210> SEQ ID NO 343
<211> LENGTH: 48
<212> TYPE: DNA
<213> ORGANISM: Homo sapiens

<400> SEQUENCE: 343
gatcgcacgt attactttgg ttcggggagt tatgaaggga tggacgtc                     48

<210> SEQ ID NO 344
<211> LENGTH: 88
<212> TYPE: PRT
<213> ORGANISM: Homo sapiens

<400> SEQUENCE: 344

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Phe Gln Gln Lys Pro Gly Gln Ala Pro Arg Pro Leu Ile
        35                  40                  45

Tyr Asp Ala Ser Thr Arg Ala Thr Gly Val Pro Ala Arg Phe Ser Gly
    50                  55                  60

Ser Gly Ser Gly Thr Asp Phe Thr Leu Thr Ile Ser Ser Leu Gln Ser
65                  70                  75                  80

Glu Asp Phe Ala Val Tyr Tyr Cys
                85

<210> SEQ ID NO 345
<211> LENGTH: 33
<212> TYPE: DNA
<213> ORGANISM: Homo sapiens

<400> SEQUENCE: 345
```

| | |
|---|---|
| cgggcaagtc agggcattag aaatgattta ggc | 33 |

<210> SEQ ID NO 346
<211> LENGTH: 21
<212> TYPE: DNA
<213> ORGANISM: Homo sapiens

<400> SEQUENCE: 346

| | |
|---|---|
| gctgcatcca gtttgcaaag t | 21 |

<210> SEQ ID NO 347
<211> LENGTH: 27
<212> TYPE: DNA
<213> ORGANISM: Homo sapiens

<400> SEQUENCE: 347

| | |
|---|---|
| ctacagcata atagtaaccc attcact | 27 |

<210> SEQ ID NO 348
<211> LENGTH: 33
<212> TYPE: DNA
<213> ORGANISM: Homo sapiens

<400> SEQUENCE: 348

| | |
|---|---|
| agggccagtc agagtgttag cagaaactta gtc | 33 |

<210> SEQ ID NO 349
<211> LENGTH: 21
<212> TYPE: DNA
<213> ORGANISM: Homo sapiens

<400> SEQUENCE: 349

| | |
|---|---|
| ggggcatcca ctagggccaa t | 21 |

<210> SEQ ID NO 350
<211> LENGTH: 24
<212> TYPE: DNA
<213> ORGANISM: Homo sapiens

<400> SEQUENCE: 350

| | |
|---|---|
| cagcagtata aaagctggcg gacg | 24 |

<210> SEQ ID NO 351
<211> LENGTH: 33
<212> TYPE: DNA
<213> ORGANISM: Homo sapiens

<400> SEQUENCE: 351

| | |
|---|---|
| cgggcaagtc agagcattag cagctattta aat | 33 |

<210> SEQ ID NO 352
<211> LENGTH: 21
<212> TYPE: DNA
<213> ORGANISM: Homo sapiens

<400> SEQUENCE: 352

| | |
|---|---|
| gctgcatcca gtttgcaaag t | 21 |

<210> SEQ ID NO 353
<211> LENGTH: 27
<212> TYPE: DNA
<213> ORGANISM: Homo sapiens

<400> SEQUENCE: 353

-continued

```
caacagagtt acagtacccc attcact                                      27

<210> SEQ ID NO 354
<211> LENGTH: 33
<212> TYPE: DNA
<213> ORGANISM: Homo sapiens

<400> SEQUENCE: 354
agggccagtc agagtgttag taggaattta gcc                               33

<210> SEQ ID NO 355
<211> LENGTH: 21
<212> TYPE: DNA
<213> ORGANISM: Homo sapiens

<400> SEQUENCE: 355
ggtgcatcca ccagggccac t                                            21

<210> SEQ ID NO 356
<211> LENGTH: 30
<212> TYPE: DNA
<213> ORGANISM: Homo sapiens

<400> SEQUENCE: 356
cagcagtata ataactggcc cacgtggacg                                   30

<210> SEQ ID NO 357
<211> LENGTH: 33
<212> TYPE: DNA
<213> ORGANISM: Homo sapiens

<400> SEQUENCE: 357
cgggcaagtc agggcattag aaatgattta ggc                               33

<210> SEQ ID NO 358
<211> LENGTH: 21
<212> TYPE: DNA
<213> ORGANISM: Homo sapiens

<400> SEQUENCE: 358
gctgcatcca gtttccaaag t                                            21

<210> SEQ ID NO 359
<211> LENGTH: 27
<212> TYPE: DNA
<213> ORGANISM: Homo sapiens

<400> SEQUENCE: 359
ctacagcata atagttaccc tccgacg                                      27

<210> SEQ ID NO 360
<211> LENGTH: 33
<212> TYPE: DNA
<213> ORGANISM: Homo sapiens

<400> SEQUENCE: 360
cgggcaagtc agggcattag aaatgattta ggc                               33

<210> SEQ ID NO 361
<211> LENGTH: 21
<212> TYPE: DNA
<213> ORGANISM: Homo sapiens
```

```
<400> SEQUENCE: 361
gctgcatcca gtttgcaaag t                                            21

<210> SEQ ID NO 362
<211> LENGTH: 27
<212> TYPE: DNA
<213> ORGANISM: Homo sapiens

<400> SEQUENCE: 362
ctacagcata aaagttaccc gctcact                                      27

<210> SEQ ID NO 363
<211> LENGTH: 33
<212> TYPE: DNA
<213> ORGANISM: Homo sapiens

<400> SEQUENCE: 363
cgggcaagtc agggcattag aaatgattta ggc                               33

<210> SEQ ID NO 364
<211> LENGTH: 21
<212> TYPE: DNA
<213> ORGANISM: Homo sapiens

<400> SEQUENCE: 364
gctgcatcca gtttgcaaag t                                            21

<210> SEQ ID NO 365
<211> LENGTH: 27
<212> TYPE: DNA
<213> ORGANISM: Homo sapiens

<400> SEQUENCE: 365
ctacagcata aaagttaccc gctcact                                      27

<210> SEQ ID NO 366
<211> LENGTH: 33
<212> TYPE: DNA
<213> ORGANISM: Homo sapiens

<400> SEQUENCE: 366
cgggcaagtc agggcattag aaatgattta ggc                               33

<210> SEQ ID NO 367
<211> LENGTH: 21
<212> TYPE: DNA
<213> ORGANISM: Homo sapiens

<400> SEQUENCE: 367
gctgcatcca gtttgcaaag t                                            21

<210> SEQ ID NO 368
<211> LENGTH: 27
<212> TYPE: DNA
<213> ORGANISM: Homo sapiens

<400> SEQUENCE: 368
ctacagcata agagttaccc gctcact                                      27

<210> SEQ ID NO 369
<211> LENGTH: 30
<212> TYPE: DNA
<213> ORGANISM: Homo sapiens
```

```
<400> SEQUENCE: 369
cgggcaagtc agggcattag aaatgattta                                          30

<210> SEQ ID NO 370
<211> LENGTH: 21
<212> TYPE: DNA
<213> ORGANISM: Homo sapiens

<400> SEQUENCE: 370
gctgcatcca gtttgcaaag t                                                   21

<210> SEQ ID NO 371
<211> LENGTH: 27
<212> TYPE: DNA
<213> ORGANISM: Homo sapiens

<400> SEQUENCE: 371
ctacagcata aaagttaccc gctcact                                             27

<210> SEQ ID NO 372
<211> LENGTH: 33
<212> TYPE: DNA
<213> ORGANISM: Homo sapiens

<400> SEQUENCE: 372
cgggcgagtc agggtattag gagctggtta gcc                                      33

<210> SEQ ID NO 373
<211> LENGTH: 21
<212> TYPE: DNA
<213> ORGANISM: Homo sapiens

<400> SEQUENCE: 373
gctgcatcca gtttgcaaag t                                                   21

<210> SEQ ID NO 374
<211> LENGTH: 27
<212> TYPE: DNA
<213> ORGANISM: Homo sapiens

<400> SEQUENCE: 374
caacaggcta acaatttccc tcggacg                                             27

<210> SEQ ID NO 375
<211> LENGTH: 33
<212> TYPE: DNA
<213> ORGANISM: Homo sapiens

<400> SEQUENCE: 375
agggccagtc agagtgttag cagcaactta gcc                                      33

<210> SEQ ID NO 376
<211> LENGTH: 21
<212> TYPE: DNA
<213> ORGANISM: Homo sapiens

<400> SEQUENCE: 376
ggtgcatcca ccagggccgc t                                                   21

<210> SEQ ID NO 377
<211> LENGTH: 30
<212> TYPE: DNA
```

```
<213> ORGANISM: Homo sapiens

<400> SEQUENCE: 377
cagcactata taaactggcc taagtggacg                                    30

<210> SEQ ID NO 378
<211> LENGTH: 33
<212> TYPE: DNA
<213> ORGANISM: Homo sapiens

<400> SEQUENCE: 378
agggccagtc agagtattag cagcagctta gcc                                33

<210> SEQ ID NO 379
<211> LENGTH: 21
<212> TYPE: DNA
<213> ORGANISM: Homo sapiens

<400> SEQUENCE: 379
ggtgcatcca ccagggccac t                                             21

<210> SEQ ID NO 380
<211> LENGTH: 27
<212> TYPE: DNA
<213> ORGANISM: Homo sapiens

<400> SEQUENCE: 380
cagcaatatg ataactggcc gctcact                                       27

<210> SEQ ID NO 381
<211> LENGTH: 48
<212> TYPE: DNA
<213> ORGANISM: Homo sapiens

<400> SEQUENCE: 381
aagtctagtc agagcctcct gcatagtgat ggaaagacct atttgtat                48

<210> SEQ ID NO 382
<211> LENGTH: 21
<212> TYPE: DNA
<213> ORGANISM: Homo sapiens

<400> SEQUENCE: 382
gaagtttcca cccggttctc t                                             21

<210> SEQ ID NO 383
<211> LENGTH: 27
<212> TYPE: DNA
<213> ORGANISM: Homo sapiens

<400> SEQUENCE: 383
atgcaaagta tacagcttcc gctcact                                       27

<210> SEQ ID NO 384
<211> LENGTH: 33
<212> TYPE: DNA
<213> ORGANISM: Homo sapiens

<400> SEQUENCE: 384
agggccagtc agagtgttag cagcaactta gcc                                33

<210> SEQ ID NO 385
<211> LENGTH: 21
```

```
<212> TYPE: DNA
<213> ORGANISM: Homo sapiens

<400> SEQUENCE: 385
gatgcatcca ccagggccac t                                           21

<210> SEQ ID NO 386
<211> LENGTH: 27
<212> TYPE: DNA
<213> ORGANISM: Homo sapiens

<400> SEQUENCE: 386
cagcagtatg ataactggcc gctcact                                     27

<210> SEQ ID NO 387
<211> LENGTH: 33
<212> TYPE: DNA
<213> ORGANISM: Homo sapiens

<400> SEQUENCE: 387
agggccagtc agagtgttag cagcaactta gcc                              33

<210> SEQ ID NO 388
<211> LENGTH: 21
<212> TYPE: DNA
<213> ORGANISM: Homo sapiens

<400> SEQUENCE: 388
gatgcatcca ccagggccgc t                                           21

<210> SEQ ID NO 389
<211> LENGTH: 27
<212> TYPE: DNA
<213> ORGANISM: Homo sapiens

<400> SEQUENCE: 389
cagcagtatg ataactggcc gctcact                                     27

<210> SEQ ID NO 390
<211> LENGTH: 33
<212> TYPE: DNA
<213> ORGANISM: Homo sapiens

<400> SEQUENCE: 390
agggccagtc agagtattag caccagctta gcc                              33

<210> SEQ ID NO 391
<211> LENGTH: 21
<212> TYPE: DNA
<213> ORGANISM: Homo sapiens

<400> SEQUENCE: 391
ggtacatcca ccagggccac t                                           21

<210> SEQ ID NO 392
<211> LENGTH: 27
<212> TYPE: DNA
<213> ORGANISM: Homo sapiens

<400> SEQUENCE: 392
caacagtatg atatctggcc gctcact                                     27

<210> SEQ ID NO 393
```

```
<211> LENGTH: 33
<212> TYPE: DNA
<213> ORGANISM: Homo sapiens

<400> SEQUENCE: 393
agggccagtc agagtgttag cagcaactta gcc                                    33

<210> SEQ ID NO 394
<211> LENGTH: 21
<212> TYPE: DNA
<213> ORGANISM: Homo sapiens

<400> SEQUENCE: 394
ggtgcatcca ccagggccac t                                                 21

<210> SEQ ID NO 395
<211> LENGTH: 27
<212> TYPE: DNA
<213> ORGANISM: Homo sapiens

<400> SEQUENCE: 395
cagcagtatg ataactggcc gctcact                                           27

<210> SEQ ID NO 396
<211> LENGTH: 51
<212> TYPE: DNA
<213> ORGANISM: Homo sapiens

<400> SEQUENCE: 396
aagaccagcc agagtgtttt atacagctcc aaaaacaaga acttcttagc t                51

<210> SEQ ID NO 397
<211> LENGTH: 21
<212> TYPE: DNA
<213> ORGANISM: Homo sapiens

<400> SEQUENCE: 397
tgggcatcta cccgggaatc c                                                 21

<210> SEQ ID NO 398
<211> LENGTH: 27
<212> TYPE: DNA
<213> ORGANISM: Homo sapiens

<400> SEQUENCE: 398
cagcaatatt atagtactcc attcact                                           27

<210> SEQ ID NO 399
<211> LENGTH: 33
<212> TYPE: DNA
<213> ORGANISM: Homo sapiens

<400> SEQUENCE: 399
agggccagtc agagtattag cagcaactta gcc                                    33

<210> SEQ ID NO 400
<211> LENGTH: 21
<212> TYPE: DNA
<213> ORGANISM: Homo sapiens

<400> SEQUENCE: 400
ggtgcatcca ccagggccac t                                                 21
```

```
<210> SEQ ID NO 401
<211> LENGTH: 27
<212> TYPE: DNA
<213> ORGANISM: Homo sapiens

<400> SEQUENCE: 401
cagcagtatg atacctggcc tctcact                                              27

<210> SEQ ID NO 402
<211> LENGTH: 33
<212> TYPE: DNA
<213> ORGANISM: Homo sapiens

<400> SEQUENCE: 402
cgggcgagtc agggcattag caattattta gcc                                       33

<210> SEQ ID NO 403
<211> LENGTH: 21
<212> TYPE: DNA
<213> ORGANISM: Homo sapiens

<400> SEQUENCE: 403
gctgcatcca ctttacaatc a                                                    21

<210> SEQ ID NO 404
<211> LENGTH: 27
<212> TYPE: DNA
<213> ORGANISM: Homo sapiens

<400> SEQUENCE: 404
caaaagtata accgtgcccc attcact                                              27

<210> SEQ ID NO 405
<211> LENGTH: 33
<212> TYPE: DNA
<213> ORGANISM: Homo sapiens

<400> SEQUENCE: 405
cgggcgagtc agggcattag caattattta gcc                                       33

<210> SEQ ID NO 406
<211> LENGTH: 21
<212> TYPE: DNA
<213> ORGANISM: Homo sapiens

<400> SEQUENCE: 406
gctgcatcca ctttgcaatc a                                                    21

<210> SEQ ID NO 407
<211> LENGTH: 27
<212> TYPE: DNA
<213> ORGANISM: Homo sapiens

<400> SEQUENCE: 407
caaaagtata accgtgcccc attcact                                              27

<210> SEQ ID NO 408
<211> LENGTH: 33
<212> TYPE: DNA
<213> ORGANISM: Homo sapiens

<400> SEQUENCE: 408
agggccagtc agagtgttag cagcaactta gcc                                       33
```

```
<210> SEQ ID NO 409
<211> LENGTH: 21
<212> TYPE: DNA
<213> ORGANISM: Homo sapiens

<400> SEQUENCE: 409
gatgcatcca ccagggccgc t                                              21

<210> SEQ ID NO 410
<211> LENGTH: 27
<212> TYPE: DNA
<213> ORGANISM: Homo sapiens

<400> SEQUENCE: 410
cagcagtatg ataactggcc gctcact                                        27

<210> SEQ ID NO 411
<211> LENGTH: 33
<212> TYPE: DNA
<213> ORGANISM: Homo sapiens

<400> SEQUENCE: 411
cgggcaagtc aggcattat aaatgattta ggc                                  33

<210> SEQ ID NO 412
<211> LENGTH: 21
<212> TYPE: DNA
<213> ORGANISM: Homo sapiens

<400> SEQUENCE: 412
gctgcatcca gtttgcaaag t                                              21

<210> SEQ ID NO 413
<211> LENGTH: 27
<212> TYPE: DNA
<213> ORGANISM: Homo sapiens

<400> SEQUENCE: 413
ctacagcata atagttaccc tccgacg                                        27

<210> SEQ ID NO 414
<211> LENGTH: 48
<212> TYPE: DNA
<213> ORGANISM: Homo sapiens

<400> SEQUENCE: 414
aggtctagtc aaagcctcgt atatagtgat ggacacacct gcttgaat                 48

<210> SEQ ID NO 415
<211> LENGTH: 21
<212> TYPE: DNA
<213> ORGANISM: Homo sapiens

<400> SEQUENCE: 415
aaggtttcta actgggactc t                                              21

<210> SEQ ID NO 416
<211> LENGTH: 30
<212> TYPE: DNA
<213> ORGANISM: Homo sapiens

<400> SEQUENCE: 416
atgcaaggta cacactggcc tctgtgcagt                                     30
```

<210> SEQ ID NO 417
<211> LENGTH: 48
<212> TYPE: DNA
<213> ORGANISM: Homo sapiens

<400> SEQUENCE: 417
aggtctagtc aaagcctcgt atatagtgat ggacacacct gcttgaat         48

<210> SEQ ID NO 418
<211> LENGTH: 21
<212> TYPE: DNA
<213> ORGANISM: Homo sapiens

<400> SEQUENCE: 418
aaggtttcta actgggactc t         21

<210> SEQ ID NO 419
<211> LENGTH: 30
<212> TYPE: DNA
<213> ORGANISM: Homo sapiens

<400> SEQUENCE: 419
atgcaaggta cacactggcc tctgtgcagt         30

<210> SEQ ID NO 420
<211> LENGTH: 33
<212> TYPE: DNA
<213> ORGANISM: Homo sapiens

<400> SEQUENCE: 420
cgggcgagtc aggccattag catttattta gcc         33

<210> SEQ ID NO 421
<211> LENGTH: 21
<212> TYPE: DNA
<213> ORGANISM: Homo sapiens

<400> SEQUENCE: 421
gctgcatcca gtttgcaaag t         21

<210> SEQ ID NO 422
<211> LENGTH: 27
<212> TYPE: DNA
<213> ORGANISM: Homo sapiens

<400> SEQUENCE: 422
caacagtata gtagttaccc tcggacg         27

<210> SEQ ID NO 423
<211> LENGTH: 33
<212> TYPE: DNA
<213> ORGANISM: Homo sapiens

<400> SEQUENCE: 423
agggccagtc agagtgttta cagcaactta gcc         33

<210> SEQ ID NO 424
<211> LENGTH: 21
<212> TYPE: DNA
<213> ORGANISM: Homo sapiens

<400> SEQUENCE: 424

```
ggtgcttcca ccagggccac t                                              21

<210> SEQ ID NO 425
<211> LENGTH: 27
<212> TYPE: DNA
<213> ORGANISM: Homo sapiens

<400> SEQUENCE: 425
cagcagtatt ataactggcc gtggacg                                        27

<210> SEQ ID NO 426
<211> LENGTH: 1409
<212> TYPE: DNA
<213> ORGANISM: Homo sapiens
<220> FEATURE:
<221> NAME/KEY: CDS
<222> LOCATION: (16)..(1398)

<400> SEQUENCE: 426
gtcgacgccg ccacc atg gag tgg acc tgg agg gtc ctt ttc ttg gtg gca    51
                 Met Glu Trp Thr Trp Arg Val Leu Phe Leu Val Ala
                  1               5                  10 gca gca aca ggt gcc cac tcc cag gtt cag ctg gtg cag tct gga gct    99
Ala Ala Thr Gly Ala His Ser Gln Val Gln Leu Val Gln Ser Gly Ala
            15                  20                  25 gag gtg aag aag cct ggg gcc tca gtg aag gtc tcc tgc aag gct tct   147
Glu Val Lys Lys Pro Gly Ala Ser Val Lys Val Ser Cys Lys Ala Ser
 30                  35                  40 ggt tac acc ttt acc aga tat ggt atc agc tgg gtg cga cag gcc cct   195
Gly Tyr Thr Phe Thr Arg Tyr Gly Ile Ser Trp Val Arg Gln Ala Pro
 45                  50                  55                  60 gga caa ggg ctt gag tgg atg gga tgg atc agc act tac agt ggt aac   243
Gly Gln Gly Leu Glu Trp Met Gly Trp Ile Ser Thr Tyr Ser Gly Asn
                 65                  70                  75 aca aac tat gca cag aag ctc cag ggc aga gtc acc atg acc aca gac   291
Thr Asn Tyr Ala Gln Lys Leu Gln Gly Arg Val Thr Met Thr Thr Asp
             80                  85                  90 aca tcc acg agc aca gcc tac atg gag ctg agg agc ctg aga tct gac   339
Thr Ser Thr Ser Thr Ala Tyr Met Glu Leu Arg Ser Leu Arg Ser Asp
         95                 100                 105 gac acg gcc gtg tat tac tgt gcg aga cgg cag ctt tac ttt gac tac   387
Asp Thr Ala Val Tyr Tyr Cys Ala Arg Arg Gln Leu Tyr Phe Asp Tyr
     110                 115                 120 tgg ggc cag gga acc ctg gtc acc gtc tca gct agc acc aag ggc        435
Trp Gly Gln Gly Thr Leu Val Thr Val Ser Ser Ala Ser Thr Lys Gly
125                 130                 135                 140 cca tcg gtc ttc ccc ctg gcg ccc tgc tcc agg agc acc tcc gag agc   483
Pro Ser Val Phe Pro Leu Ala Pro Cys Ser Arg Ser Thr Ser Glu Ser
                145                 150                 155 aca gcg gcc ctg ggc tgc ctg gtc aag gac tac ttc ccc gaa ccg gtg   531
Thr Ala Ala Leu Gly Cys Leu Val Lys Asp Tyr Phe Pro Glu Pro Val
            160                 165                 170 acg gtg tcg tgg aac tca ggc gct ctg acc agc ggc gtg cac acc ttc   579
Thr Val Ser Trp Asn Ser Gly Ala Leu Thr Ser Gly Val His Thr Phe
        175                 180                 185 cca gct gtc cta cag tcc tca gga ctc tac tcc ctc agc agc gtg gtg   627
Pro Ala Val Leu Gln Ser Ser Gly Leu Tyr Ser Leu Ser Ser Val Val
    190                 195                 200 acc gtg ccc tcc agc aac ttc ggc acc cag acc tac acc tgc aac gta   675
Thr Val Pro Ser Ser Asn Phe Gly Thr Gln Thr Tyr Thr Cys Asn Val
205                 210                 215                 220
```

```
gat cac aag ccc agc aac acc aag gtg gac aag aca gtt gag cgc aaa      723
Asp His Lys Pro Ser Asn Thr Lys Val Asp Lys Thr Val Glu Arg Lys
            225                 230                 235 tgt tgt gtc gag tgc cca ccg tgc cca gca cca cct gtg gca gga ccg      771
Cys Cys Val Glu Cys Pro Pro Cys Pro Ala Pro Pro Val Ala Gly Pro
            240                 245                 250 tca gtc ttc ctc ttc ccc cca aaa ccc aag gac acc ctc atg atc tcc      819
Ser Val Phe Leu Phe Pro Pro Lys Pro Lys Asp Thr Leu Met Ile Ser
            255                 260                 265 cgg acc cct gag gtc acg tgc gtg gtg gtg gac gtg agc cac gaa gac      867
Arg Thr Pro Glu Val Thr Cys Val Val Val Asp Val Ser His Glu Asp
            270                 275                 280 ccc gag gtc cag ttc aac tgg tac gtg gac ggc gtg gag gtg cat aat      915
Pro Glu Val Gln Phe Asn Trp Tyr Val Asp Gly Val Glu Val His Asn
285                 290                 295                 300 gcc aag aca aag cca cgg gag gag cag ttc aac agc acg ttc cgt gtg      963
Ala Lys Thr Lys Pro Arg Glu Glu Gln Phe Asn Ser Thr Phe Arg Val
                305                 310                 315 gtc agc gtc ctc acc gtt gtg cac cag gac tgg ctg aac ggc aag gag     1011
Val Ser Val Leu Thr Val Val His Gln Asp Trp Leu Asn Gly Lys Glu
                320                 325                 330 tac aag tgc aag gtc tcc aac aaa ggc ctc cca gcc ccc atc gag aaa     1059
Tyr Lys Cys Lys Val Ser Asn Lys Gly Leu Pro Ala Pro Ile Glu Lys
                335                 340                 345 acc atc tcc aaa acc aaa ggg cag ccc cga gaa cca cag gtg tac acc     1107
Thr Ile Ser Lys Thr Lys Gly Gln Pro Arg Glu Pro Gln Val Tyr Thr
            350                 355                 360 ctg ccc cca tcc cgg gag gag atg acc aag aac cag gtc agc ctg acc     1155
Leu Pro Pro Ser Arg Glu Glu Met Thr Lys Asn Gln Val Ser Leu Thr
365                 370                 375                 380 tgc ctg gtc aaa ggc ttc tac ccc agc gac atc gcc gtg gag tgg gag     1203
Cys Leu Val Lys Gly Phe Tyr Pro Ser Asp Ile Ala Val Glu Trp Glu
                385                 390                 395 agc aat ggg cag ccg gag aac aac tac aag acc aca cct ccc atg ctg     1251
Ser Asn Gly Gln Pro Glu Asn Asn Tyr Lys Thr Thr Pro Pro Met Leu
            400                 405                 410 gac tcc gac ggc tcc ttc ttc ctc tac agc aag ctc acc gtg gac aag     1299
Asp Ser Asp Gly Ser Phe Phe Leu Tyr Ser Lys Leu Thr Val Asp Lys
            415                 420                 425 agc agg tgg cag cag ggg aac gtc ttc tca tgc tcc gtg atg cat gag     1347
Ser Arg Trp Gln Gln Gly Asn Val Phe Ser Cys Ser Val Met His Glu
            430                 435                 440 gct ctg cac aac cac tac acg cag aag agc ctc tcc ctg tct ccg ggt     1395
Ala Leu His Asn His Tyr Thr Gln Lys Ser Leu Ser Leu Ser Pro Gly
445                 450                 455                 460 aaa tgagcggccg c                                                    1409
Lys

<210> SEQ ID NO 427
<211> LENGTH: 461
<212> TYPE: PRT
<213> ORGANISM: Homo sapiens

<400> SEQUENCE: 427

Met Glu Trp Thr Trp Arg Val Leu Phe Leu Val Ala Ala Ala Thr Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45
```

```
Thr Arg Tyr Gly Ile Ser Trp Val Arg Gln Ala Pro Gly Gln Gly Leu
 50                  55                  60

Glu Trp Met Gly Trp Ile Ser Thr Tyr Ser Gly Asn Thr Asn Tyr Ala
 65                  70                  75                  80

Gln Lys Leu Gln Gly Arg Val Thr Met Thr Thr Asp Thr Ser Thr Ser
                 85                  90                  95

Thr Ala Tyr Met Glu Leu Arg Ser Leu Arg Ser Asp Asp Thr Ala Val
            100                 105                 110

Tyr Tyr Cys Ala Arg Arg Gln Leu Tyr Phe Asp Tyr Trp Gly Gln Gly
            115                 120                 125

Thr Leu Val Thr Val Ser Ser Ala Ser Thr Lys Gly Pro Ser Val Phe
130                 135                 140

Pro Leu Ala Pro Cys Ser Arg Ser Thr Ser Glu Ser Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
            195                 200                 205

Ser Asn Phe Gly Thr Gln Thr Tyr Thr Cys Asn Val Asp His Lys Pro
210                 215                 220

Ser Asn Thr Lys Val Asp Lys Thr Val Glu Arg Lys Cys Cys Val Glu
225                 230                 235                 240

Cys Pro Pro Cys Pro Ala Pro Pro Val Ala Gly Pro Ser Val Phe Leu
                245                 250                 255

Phe Pro Pro Lys Pro Lys Asp Thr Leu Met Ile Ser Arg Thr Pro Glu
            260                 265                 270

Val Thr Cys Val Val Val Asp Val Ser His Glu Asp Pro Glu Val Gln
            275                 280                 285

Phe Asn Trp Tyr Val Asp Gly Val Glu Val His Asn Ala Lys Thr Lys
290                 295                 300

Pro Arg Glu Glu Gln Phe Asn Ser Thr Phe Arg Val Val Ser Val Leu
305                 310                 315                 320

Thr Val Val His Gln Asp Trp Leu Asn Gly Lys Glu Tyr Lys Cys Lys
                325                 330                 335

Val Ser Asn Lys Gly Leu Pro Ala Pro Ile Glu Lys Thr Ile Ser Lys
            340                 345                 350

Thr Lys Gly Gln Pro Arg Glu Pro Gln Val Tyr Thr Leu Pro Pro Ser
            355                 360                 365

Arg Glu Glu Met Thr Lys Asn Gln Val Ser Leu Thr Cys Leu Val Lys
370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Met Leu Asp Ser Asp Gly
                405                 410                 415

Ser Phe Phe Leu Tyr Ser Lys Leu Thr Val Asp Lys Ser Arg Trp Gln
            420                 425                 430

Gln Gly Asn Val Phe Ser Cys Ser Val Met His Glu Ala Leu His Asn
            435                 440                 445

His Tyr Thr Gln Lys Ser Leu Ser Leu Ser Pro Gly Lys
450                 455                 460
```

<210> SEQ ID NO 428
<211> LENGTH: 741
<212> TYPE: DNA
<213> ORGANISM: Homo sapiens
<220> FEATURE:
<221> NAME/KEY: CDS
<222> LOCATION: (24)..(725)

<400> SEQUENCE: 428

```
gtcgacgttt aaacgccgcc acc atg gaa gcg ccg gcg cag ctt ctc ttc ctc        53
                         Met Glu Ala Pro Ala Gln Leu Leu Phe Leu
                          1               5                  10 ctg cta ctc tgg ctc cca gat acc act gga gaa ata gtg atg acg cag         101
Leu Leu Leu Trp Leu Pro Asp Thr Thr Gly Glu Ile Val Met Thr Gln
             15                  20                  25 tct cca gcc acc ctg tct gtg tct cct ggg gaa aga gcc acc ctc tcc         149
Ser Pro Ala Thr Leu Ser Val Ser Pro Gly Glu Arg Ala Thr Leu Ser
 30                  35                  40 tgc agg gcc agt cag agt gtt agc agc aac tta gcc tgg ttc cag cag         197
Cys Arg Ala Ser Gln Ser Val Ser Ser Asn Leu Ala Trp Phe Gln Gln
             45                  50                  55 aaa cct ggc cag gct ccc agg ccc ctc atc tat gat gca tcc acc agg         245
Lys Pro Gly Gln Ala Pro Arg Pro Leu Ile Tyr Asp Ala Ser Thr Arg
 60                  65                  70 gcc act ggt gtc cca gcc agg ttc agt ggc agt ggg tct ggg aca gac         293
Ala Thr Gly Val Pro Ala Arg Phe Ser Gly Ser Gly Ser Gly Thr Asp
 75                  80                  85                  90 ttc act ctc acc atc agc agc ctg cag tct gaa gat ttt gca gtt tat         341
Phe Thr Leu Thr Ile Ser Ser Leu Gln Ser Glu Asp Phe Ala Val Tyr
                 95                 100                 105 tac tgt cag cag tat gat aac tgg ccg ctc act ttc ggc gga ggg acc         389
Tyr Cys Gln Gln Tyr Asp Asn Trp Pro Leu Thr Phe Gly Gly Gly Thr
             110                 115                 120 aag gtg gag atc aaa cgt acg gtg gct gca cca tct gtc ttc atc ttc         437
Lys Val Glu Ile Lys Arg Thr Val Ala Ala Pro Ser Val Phe Ile Phe
         125                 130                 135 ccg cca tct gat gag cag ttg aaa tct gga act gcc tct gtt gtg tgc         485
Pro Pro Ser Asp Glu Gln Leu Lys Ser Gly Thr Ala Ser Val Val Cys
140                 145                 150 ctg ctg aat aac ttc tat ccc aga gag gcc aaa gta cag tgg aag gtg         533
Leu Leu Asn Asn Phe Tyr Pro Arg Glu Ala Lys Val Gln Trp Lys Val
155                 160                 165                 170 gat aac gcc ctc caa tcg ggt aac tcc cag gag agt gtc aca gag cag         581
Asp Asn Ala Leu Gln Ser Gly Asn Ser Gln Glu Ser Val Thr Glu Gln
                175                 180                 185 gac agc aag gac agc acc tac agc ctc agc agc acc ctg acg ctg agc         629
Asp Ser Lys Asp Ser Thr Tyr Ser Leu Ser Ser Thr Leu Thr Leu Ser
            190                 195                 200 aaa gca gac tac gag aaa cac aaa gtc tac gcc tgc gaa gtc acc cat         677
Lys Ala Asp Tyr Glu Lys His Lys Val Tyr Ala Cys Glu Val Thr His
        205                 210                 215 cag ggc ctg agc tcg ccc gtc aca aag agc ttc aac agg gga gag tgt         725
Gln Gly Leu Ser Ser Pro Val Thr Lys Ser Phe Asn Arg Gly Glu Cys
    220                 225                 230 taggatccgc ggccgc                                                       741
```

<210> SEQ ID NO 429
<211> LENGTH: 234
<212> TYPE: PRT
<213> ORGANISM: Homo sapiens

```
<400> SEQUENCE: 429

Met Glu Ala Pro Ala Gln Leu Leu Phe Leu Leu Leu Trp Leu Pro
1               5                  10                  15

Asp Thr Thr Gly Glu Ile Val Met Thr Gln Ser Pro Ala Thr Leu Ser
            20                  25                  30

Val Ser Pro Gly Glu Arg Ala Thr Leu Ser Cys Arg Ala Ser Gln Ser
            35                  40                  45

Val Ser Ser Asn Leu Ala Trp Phe Gln Gln Lys Pro Gly Gln Ala Pro
        50                  55                  60

Arg Pro Leu Ile Tyr Asp Ala Ser Thr Arg Ala Thr Gly Val Pro Ala
65                  70                  75                  80

Arg Phe Ser Gly Ser Gly Ser Gly Thr Asp Phe Thr Leu Thr Ile Ser
                85                  90                  95

Ser Leu Gln Ser Glu Asp Phe Ala Val Tyr Tyr Cys Gln Gln Tyr Asp
            100                 105                 110

Asn Trp Pro Leu Thr Phe Gly Gly Gly Thr Lys Val Glu Ile Lys Arg
            115                 120                 125

Thr Val Ala Ala Pro Ser Val Phe Ile Phe Pro Pro Ser Asp Glu Gln
130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
            195                 200                 205

His Lys Val Tyr Ala Cys Glu Val Thr His Gln Gly Leu Ser Ser Pro
210                 215                 220

Val Thr Lys Ser Phe Asn Arg Gly Glu Cys
225                 230

<210> SEQ ID NO 430
<211> LENGTH: 866
<212> TYPE: PRT
<213> ORGANISM: Homo sapiens

<400> SEQUENCE: 430

Met Gly Ala Ala Arg Ser Pro Pro Ser Ala Val Pro Gly Pro Leu Leu
1               5                  10                  15

Gly Leu Leu Leu Leu Leu Leu Gly Val Leu Ala Pro Gly Gly Ala Ser
            20                  25                  30

Leu Arg Leu Leu Asp His Arg Ala Leu Val Cys Ser Gln Pro Gly Leu
            35                  40                  45

Asn Cys Thr Val Lys Asn Ser Thr Cys Leu Asp Asp Ser Trp Ile His
        50                  55                  60

Pro Arg Asn Leu Thr Pro Ser Ser Pro Lys Asp Leu Gln Ile Gln Leu
65                  70                  75                  80

His Phe Ala His Thr Gln Gln Gly Asp Leu Phe Pro Val Ala His Ile
                85                  90                  95

Glu Trp Thr Leu Gln Thr Asp Ala Ser Ile Leu Tyr Leu Glu Gly Ala
            100                 105                 110

Glu Leu Ser Val Leu Gln Leu Asn Thr Asn Glu Arg Leu Cys Val Arg
            115                 120                 125
```

-continued

Phe Glu Phe Leu Ser Lys Leu Arg His His Arg Arg Trp Arg Phe
        130                 135                 140

Thr Phe Ser His Phe Val Val Asp Pro Asp Gln Glu Tyr Glu Val Thr
145                     150                 155                 160

Val His His Leu Pro Lys Pro Ile Pro Asp Gly Asp Pro Asn His Gln
                165                 170                 175

Ser Lys Asn Phe Leu Val Pro Asp Cys Glu His Ala Arg Met Lys Val
            180                 185                 190

Thr Thr Pro Cys Met Ser Ser Gly Ser Leu Trp Asp Pro Asn Ile Thr
        195                 200                 205

Val Glu Thr Leu Glu Ala His Gln Leu Arg Val Ser Phe Thr Leu Trp
    210                 215                 220

Asn Glu Ser Thr His Tyr Gln Ile Leu Leu Thr Ser Phe Pro His Met
225                 230                 235                 240

Glu Asn His Ser Cys Phe Glu His Met His His Ile Pro Ala Pro Arg
                245                 250                 255

Pro Glu Glu Phe His Gln Arg Ser Asn Val Thr Leu Thr Leu Arg Asn
            260                 265                 270

Leu Lys Gly Cys Cys Arg His Gln Val Gln Ile Gln Pro Phe Phe Ser
        275                 280                 285

Ser Cys Leu Asn Asp Cys Leu Arg His Ser Ala Thr Val Ser Cys Pro
    290                 295                 300

Glu Met Pro Asp Thr Pro Glu Pro Ile Pro Asp Tyr Met Pro Leu Trp
305                 310                 315                 320

Val Tyr Trp Phe Ile Thr Gly Ile Ser Ile Leu Leu Val Gly Ser Val
                325                 330                 335

Ile Leu Leu Ile Val Cys Met Thr Trp Arg Leu Ala Gly Pro Gly Ser
            340                 345                 350

Glu Lys Tyr Ser Asp Asp Thr Lys Tyr Thr Asp Gly Leu Pro Ala Ala
        355                 360                 365

Asp Leu Ile Pro Pro Pro Leu Lys Pro Arg Lys Val Trp Ile Ile Tyr
    370                 375                 380

Ser Ala Asp His Pro Leu Tyr Val Asp Val Val Leu Lys Phe Ala Gln
385                 390                 395                 400

Phe Leu Leu Thr Ala Cys Gly Thr Glu Val Ala Leu Asp Leu Leu Glu
                405                 410                 415

Glu Gln Ala Ile Ser Glu Ala Gly Val Met Thr Trp Val Gly Arg Gln
            420                 425                 430

Lys Gln Glu Met Val Glu Ser Asn Ser Lys Ile Ile Val Leu Cys Ser
        435                 440                 445

Arg Gly Thr Arg Ala Lys Trp Gln Ala Leu Leu Gly Arg Gly Ala Pro
    450                 455                 460

Val Arg Leu Arg Cys Asp His Gly Lys Pro Val Gly Asp Leu Phe Thr
465                 470                 475                 480

Ala Ala Met Asn Met Ile Leu Pro Asp Phe Lys Arg Pro Ala Cys Phe
                485                 490                 495

Gly Thr Tyr Val Val Cys Tyr Phe Ser Glu Val Ser Cys Asp Gly Asp
            500                 505                 510

Val Pro Asp Leu Phe Gly Ala Ala Pro Arg Tyr Pro Leu Met Asp Arg
        515                 520                 525

Phe Glu Glu Val Tyr Phe Arg Ile Gln Asp Leu Glu Met Phe Gln Pro
    530                 535                 540

Gly Arg Met His Arg Val Gly Glu Leu Ser Gly Asp Asn Tyr Leu Arg

```
                    545                 550                 555                 560

Ser Pro Gly Gly Arg Gln Leu Arg Ala Ala Leu Asp Arg Phe Arg Asp
                565                 570                 575

Trp Gln Val Arg Cys Pro Asp Trp Phe Glu Cys Glu Asn Leu Tyr Ser
                580                 585                 590

Ala Asp Asp Gln Asp Ala Pro Ser Leu Asp Glu Glu Val Phe Glu Glu
                595                 600                 605

Pro Leu Leu Pro Pro Gly Thr Gly Ile Val Lys Arg Ala Pro Leu Val
                610                 615                 620

Arg Glu Pro Gly Ser Gln Ala Cys Leu Ala Ile Asp Pro Leu Val Gly
625                 630                 635                 640

Glu Glu Gly Gly Ala Ala Val Ala Lys Leu Glu Pro His Leu Gln Pro
                645                 650                 655

Arg Gly Gln Pro Ala Pro Gln Pro Leu His Thr Leu Val Leu Ala Ala
                660                 665                 670

Glu Glu Gly Ala Leu Val Ala Ala Val Glu Pro Gly Pro Leu Ala Asp
                675                 680                 685

Gly Ala Val Arg Leu Ala Leu Ala Gly Glu Gly Glu Ala Cys Pro
690                 695                 700

Leu Leu Gly Ser Pro Gly Ala Gly Arg Asn Ser Val Leu Phe Leu Pro
705                 710                 715                 720

Val Asp Pro Glu Asp Ser Pro Leu Gly Ser Ser Thr Pro Met Ala Ser
                725                 730                 735

Pro Asp Leu Leu Pro Glu Asp Val Arg Glu His Leu Glu Gly Leu Met
                740                 745                 750

Leu Ser Leu Phe Glu Gln Ser Leu Ser Cys Gln Ala Gln Gly Gly Cys
                755                 760                 765

Ser Arg Pro Ala Met Val Leu Thr Asp Pro His Thr Pro Tyr Glu Glu
                770                 775                 780

Glu Gln Arg Gln Ser Val Gln Ser Asp Gln Gly Tyr Ile Ser Arg Ser
785                 790                 795                 800

Ser Pro Gln Pro Pro Glu Gly Leu Thr Glu Met Glu Glu Glu Glu
                805                 810                 815

Glu Glu Gln Asp Pro Gly Lys Pro Ala Leu Pro Leu Ser Pro Glu Asp
                820                 825                 830

Leu Glu Ser Leu Arg Ser Leu Gln Arg Gln Leu Leu Phe Arg Gln Leu
                835                 840                 845

Gln Lys Asn Ser Gly Trp Asp Thr Met Gly Ser Glu Ser Glu Gly Pro
                850                 855                 860

Ser Ala
865

<210> SEQ ID NO 431
<211> LENGTH: 344
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 431

Met Gly Ala Ala Arg Ser Pro Pro Ser Ala Val Pro Gly Pro Leu Leu
1               5                   10                  15

Gly Leu Leu Leu Leu Leu Leu Gly Val Leu Ala Pro Gly Gly Ala Ser
                20                  25                  30
```

Leu Arg Leu Leu Asp His Arg Ala Leu Val Cys Ser Gln Pro Gly Leu
        35                  40                  45

Asn Cys Thr Val Lys Asn Ser Thr Cys Leu Asp Asp Ser Trp Ile His
 50                  55                  60

Pro Arg Asn Leu Thr Pro Ser Pro Lys Asp Leu Gln Ile Gln Leu
65                  70                  75                  80

His Phe Ala His Thr Gln Gln Gly Asp Leu Phe Pro Val Ala His Ile
                85                  90                  95

Glu Trp Thr Leu Gln Thr Asp Ala Ser Ile Leu Tyr Leu Glu Gly Ala
            100                 105                 110

Glu Leu Ser Val Leu Gln Leu Asn Thr Asn Glu Arg Leu Cys Val Arg
        115                 120                 125

Phe Glu Phe Leu Ser Lys Leu Arg His His Arg Arg Trp Arg Phe
    130                 135                 140

Thr Phe Ser His Phe Val Val Asp Pro Asp Gln Glu Tyr Glu Val Thr
145                 150                 155                 160

Val His His Leu Pro Lys Pro Ile Pro Asp Gly Asp Pro Asn His Gln
                165                 170                 175

Ser Lys Asn Phe Leu Val Pro Asp Cys Glu His Ala Arg Met Lys Val
            180                 185                 190

Thr Thr Pro Cys Met Ser Ser Gly Ser Leu Trp Asp Pro Asn Ile Thr
        195                 200                 205

Val Glu Thr Leu Glu Ala His Gln Leu Arg Val Ser Phe Thr Leu Trp
    210                 215                 220

Asn Glu Ser Thr His Tyr Gln Ile Leu Leu Thr Ser Phe Pro His Met
225                 230                 235                 240

Glu Asn His Ser Cys Phe Glu His Met His His Ile Pro Ala Pro Arg
                245                 250                 255

Pro Glu Glu Phe His Gln Arg Ser Asn Val Thr Leu Thr Leu Arg Asn
            260                 265                 270

Leu Lys Gly Cys Cys Arg His Gln Val Gln Ile Gln Pro Phe Phe Ser
        275                 280                 285

Ser Cys Leu Asn Asp Cys Leu Arg His Ser Ala Thr Val Ser Cys Pro
    290                 295                 300

Glu Met Pro Asp Thr Pro Glu Pro Ile Pro Asp Tyr Met Pro Leu Trp
305                 310                 315                 320

Glu Pro Arg Ser Gly Ser Ser Asp Tyr Lys Asp Asp Asp Lys Gly
                325                 330                 335

Ser Ser His His His His His His
            340

<210> SEQ ID NO 432
<211> LENGTH: 322
<212> TYPE: PRT
<213> ORGANISM: Mus musculus

<400> SEQUENCE: 432

Met Ala Ile Arg Arg Cys Trp Pro Arg Val Val Pro Gly Pro Ala Leu
1               5                   10                  15

Gly Trp Leu Leu Leu Leu Leu Asn Val Leu Ala Pro Gly Arg Ala Ser
            20                  25                  30

Pro Arg Leu Leu Asp Phe Pro Ala Pro Val Cys Ala Gln Glu Gly Leu
        35                  40                  45

Ser Cys Arg Val Lys Asn Ser Thr Cys Leu Asp Asp Ser Trp Ile His
    50                  55                  60

```
Pro Lys Asn Leu Thr Pro Ser Ser Pro Lys Asn Ile Tyr Ile Asn Leu
 65                  70                  75                  80

Ser Val Ser Ser Thr Gln His Gly Glu Leu Val Pro Val Leu His Val
                 85                  90                  95

Glu Trp Thr Leu Gln Thr Asp Ala Ser Ile Leu Tyr Leu Glu Gly Ala
            100                 105                 110

Glu Leu Ser Val Leu Gln Leu Asn Thr Asn Glu Arg Leu Cys Val Lys
        115                 120                 125

Phe Gln Phe Leu Ser Met Leu Gln His His Arg Lys Arg Trp Arg Phe
    130                 135                 140

Ser Phe Ser His Phe Val Val Asp Pro Gly Gln Glu Tyr Glu Val Thr
145                 150                 155                 160

Val His His Leu Pro Lys Pro Ile Pro Asp Gly Asp Pro Asn His Lys
                165                 170                 175

Ser Lys Ile Ile Phe Val Pro Asp Cys Glu Asp Ser Lys Met Lys Met
            180                 185                 190

Thr Thr Ser Cys Val Ser Ser Gly Ser Leu Trp Asp Pro Asn Ile Thr
        195                 200                 205

Val Glu Thr Leu Asp Thr Gln His Leu Arg Val Asp Phe Thr Leu Trp
    210                 215                 220

Asn Glu Ser Thr Pro Tyr Gln Val Leu Leu Glu Ser Phe Ser Asp Ser
225                 230                 235                 240

Glu Asn His Ser Cys Phe Asp Val Val Lys Gln Ile Phe Ala Pro Arg
                245                 250                 255

Gln Glu Glu Phe His Gln Arg Ala Asn Val Thr Phe Thr Leu Ser Lys
            260                 265                 270

Phe His Trp Cys Cys His His Val Gln Val Gln Pro Phe Phe Ser
        275                 280                 285

Ser Cys Leu Asn Asp Cys Leu Arg His Ala Val Thr Val Pro Cys Pro
    290                 295                 300

Val Ile Ser Asn Thr Thr Val Pro Lys Pro Val Ala Asp Tyr Ile Pro
305                 310                 315                 320

Leu Trp

<210> SEQ ID NO 433
<211> LENGTH: 344
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 433

Met Gly Ala Ala Arg Ser Pro Pro Ser Ala Val Pro Gly Pro Leu Leu
  1               5                  10                  15

Gly Leu Leu Leu Leu Leu Leu Gly Val Leu Ala Pro Gly Gly Ala Ser
                 20                  25                  30

Leu Arg Leu Leu Asp Phe Pro Ala Pro Val Cys Ala Gln Glu Gly Leu
            35                  40                  45

Ser Cys Arg Val Lys Asn Ser Thr Cys Leu Asp Asp Ser Trp Ile His
        50                  55                  60

Pro Arg Asn Leu Thr Pro Ser Ser Pro Lys Asp Leu Gln Ile Gln Leu
 65                  70                  75                  80

His Phe Ala His Thr Gln Gln Gly Asp Leu Phe Pro Val Ala His Ile
                 85                  90                  95
```

```
Glu Trp Thr Leu Gln Thr Asp Ala Ser Ile Leu Tyr Leu Glu Gly Ala
            100                 105                 110

Glu Leu Ser Val Leu Gln Leu Asn Thr Asn Glu Arg Leu Cys Val Arg
        115                 120                 125

Phe Glu Phe Leu Ser Lys Leu Arg His His Arg Arg Trp Arg Phe
    130                 135                 140

Thr Phe Ser His Phe Val Val Asp Pro Asp Gln Glu Tyr Glu Val Thr
145                 150                 155                 160

Val His His Leu Pro Lys Pro Ile Pro Asp Gly Asp Pro Asn His Gln
                165                 170                 175

Ser Lys Asn Phe Leu Val Pro Asp Cys Glu His Ala Arg Met Lys Val
            180                 185                 190

Thr Thr Pro Cys Met Ser Ser Gly Ser Leu Trp Asp Pro Asn Ile Thr
        195                 200                 205

Val Glu Thr Leu Glu Ala His Gln Leu Arg Val Ser Phe Thr Leu Trp
    210                 215                 220

Asn Glu Ser Thr His Tyr Gln Ile Leu Leu Thr Ser Phe Pro His Met
225                 230                 235                 240

Glu Asn His Ser Cys Phe Glu His Met His His Ile Pro Ala Pro Arg
                245                 250                 255

Pro Glu Glu Phe His Gln Arg Ser Asn Val Thr Leu Thr Leu Arg Asn
            260                 265                 270

Leu Lys Gly Cys Cys Arg His Gln Val Gln Ile Gln Pro Phe Phe Ser
        275                 280                 285

Ser Cys Leu Asn Asp Cys Leu Arg His Ser Ala Thr Val Ser Cys Pro
    290                 295                 300

Glu Met Pro Asp Thr Pro Glu Pro Ile Pro Asp Tyr Met Pro Leu Trp
305                 310                 315                 320

Glu Pro Arg Ser Gly Ser Ser Asp Tyr Lys Asp Asp Asp Lys Gly
                325                 330                 335

Ser Ser His His His His His His
            340

<210> SEQ ID NO 434
<211> LENGTH: 344
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 434

Met Gly Ala Ala Arg Ser Pro Pro Ser Ala Val Pro Gly Pro Leu Leu
1               5                   10                  15

Gly Leu Leu Leu Leu Leu Leu Gly Val Leu Ala Pro Gly Gly Ala Ser
            20                  25                  30

Leu Arg Leu Leu Asp His Arg Ala Leu Val Cys Ser Gln Pro Gly Leu
        35                  40                  45

Asn Cys Thr Val Lys Asn Ser Thr Cys Leu Asp Asp Ser Trp Ile His
    50                  55                  60

Pro Arg Asn Leu Thr Pro Ser Ser Pro Lys Asn Ile Tyr Ile Asn Leu
65                  70                  75                  80

Ser Val Ser Ser Thr Gln His Gly Glu Leu Val Pro Val Leu His Val
                85                  90                  95

Glu Trp Thr Leu Gln Thr Asp Ala Ser Ile Leu Tyr Leu Glu Gly Ala
```

```
                100                 105                 110
Glu Leu Ser Val Leu Gln Leu Asn Thr Asn Glu Arg Leu Cys Val Arg
            115                 120                 125

Phe Glu Phe Leu Ser Lys Leu Arg His His Arg Arg Trp Arg Phe
    130                 135                 140

Thr Phe Ser His Phe Val Val Asp Pro Asp Gln Glu Tyr Glu Val Thr
145                 150                 155                 160

Val His His Leu Pro Lys Pro Ile Pro Asp Gly Asp Pro Asn His Gln
                165                 170                 175

Ser Lys Asn Phe Leu Val Pro Asp Cys Glu His Ala Arg Met Lys Val
            180                 185                 190

Thr Thr Pro Cys Met Ser Ser Gly Ser Leu Trp Asp Pro Asn Ile Thr
        195                 200                 205

Val Glu Thr Leu Glu Ala His Gln Leu Arg Val Ser Phe Thr Leu Trp
        210                 215                 220

Asn Glu Ser Thr His Tyr Gln Ile Leu Leu Thr Ser Phe Pro His Met
225                 230                 235                 240

Glu Asn His Ser Cys Phe Glu His Met His His Ile Pro Ala Pro Arg
                245                 250                 255

Pro Glu Glu Phe His Gln Arg Ser Asn Val Thr Leu Thr Leu Arg Asn
            260                 265                 270

Leu Lys Gly Cys Cys Arg His Gln Val Gln Ile Gln Pro Phe Phe Ser
        275                 280                 285

Ser Cys Leu Asn Asp Cys Leu Arg His Ser Ala Thr Val Ser Cys Pro
    290                 295                 300

Glu Met Pro Asp Thr Pro Glu Pro Ile Pro Asp Tyr Met Pro Leu Trp
305                 310                 315                 320

Glu Pro Arg Ser Gly Ser Ser Asp Tyr Lys Asp Asp Asp Lys Gly
                325                 330                 335

Ser Ser His His His His His His
            340

<210> SEQ ID NO 435
<211> LENGTH: 344
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 435

Met Gly Ala Ala Arg Ser Pro Pro Ser Ala Val Pro Gly Pro Leu Leu
1               5                   10                  15

Gly Leu Leu Leu Leu Leu Leu Gly Val Leu Ala Pro Gly Gly Ala Ser
            20                  25                  30

Leu Arg Leu Leu Asp His Arg Ala Leu Val Cys Ser Gln Pro Gly Leu
        35                  40                  45

Asn Cys Thr Val Lys Asn Ser Thr Cys Leu Asp Asp Ser Trp Ile His
    50                  55                  60

Pro Arg Asn Leu Thr Pro Ser Ser Pro Lys Asp Leu Gln Ile Gln Leu
65                  70                  75                  80

His Phe Ala His Thr Gln Gln Gly Asp Leu Phe Pro Val Ala His Ile
                85                  90                  95

Glu Trp Thr Leu Gln Thr Asp Ala Ser Ile Leu Tyr Leu Glu Gly Ala
            100                 105                 110
```

```
Glu Leu Ser Val Leu Gln Leu Asn Thr Asn Glu Arg Leu Cys Val Lys
            115                 120                 125

Phe Gln Phe Leu Ser Met Leu Gln His His Arg Lys Arg Trp Arg Phe
130                 135                 140

Ser Phe Ser His Phe Val Val Asp Pro Gly Gln Glu Tyr Glu Val Thr
145                 150                 155                 160

Val His His Leu Pro Lys Pro Ile Pro Asp Gly Asp Pro Asn His Gln
                165                 170                 175

Ser Lys Asn Phe Leu Val Pro Asp Cys Glu His Ala Arg Met Lys Val
            180                 185                 190

Thr Thr Pro Cys Met Ser Ser Gly Ser Leu Trp Asp Pro Asn Ile Thr
            195                 200                 205

Val Glu Thr Leu Glu Ala His Gln Leu Arg Val Ser Phe Thr Leu Trp
    210                 215                 220

Asn Glu Ser Thr His Tyr Gln Ile Leu Leu Thr Ser Phe Pro His Met
225                 230                 235                 240

Glu Asn His Ser Cys Phe Glu His Met His His Ile Pro Ala Pro Arg
                245                 250                 255

Pro Glu Glu Phe His Gln Arg Ser Asn Val Thr Leu Thr Leu Arg Asn
            260                 265                 270

Leu Lys Gly Cys Cys Arg His Gln Val Gln Ile Gln Pro Phe Phe Ser
        275                 280                 285

Ser Cys Leu Asn Asp Cys Leu Arg His Ser Ala Thr Val Ser Cys Pro
    290                 295                 300

Glu Met Pro Asp Thr Pro Glu Pro Ile Pro Asp Tyr Met Pro Leu Trp
305                 310                 315                 320

Glu Pro Arg Ser Gly Ser Ser Asp Tyr Lys Asp Asp Asp Lys Gly
            325                 330                 335

Ser Ser His His His His His His
            340

<210> SEQ ID NO 436
<211> LENGTH: 344
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 436

Met Gly Ala Ala Arg Ser Pro Pro Ser Ala Val Pro Gly Pro Leu Leu
1               5                   10                  15

Gly Leu Leu Leu Leu Leu Leu Gly Val Leu Ala Pro Gly Gly Ala Ser
            20                  25                  30

Leu Arg Leu Leu Asp His Arg Ala Leu Val Cys Ser Gln Pro Gly Leu
        35                  40                  45

Asn Cys Thr Val Lys Asn Ser Thr Cys Leu Asp Asp Ser Trp Ile His
    50                  55                  60

Pro Arg Asn Leu Thr Pro Ser Ser Pro Lys Asp Leu Gln Ile Gln Leu
65                  70                  75                  80

His Phe Ala His Thr Gln Gln Gly Asp Leu Phe Pro Val Ala His Ile
                85                  90                  95

Glu Trp Thr Leu Gln Thr Asp Ala Ser Ile Leu Tyr Leu Glu Gly Ala
            100                 105                 110

Glu Leu Ser Val Leu Gln Leu Asn Thr Asn Glu Arg Leu Cys Val Arg
            115                 120                 125
```

-continued

```
Phe Glu Phe Leu Ser Lys Leu Arg His His His Arg Arg Trp Arg Phe
    130                 135                 140

Thr Phe Ser His Phe Val Val Asp Pro Asp Gln Glu Tyr Glu Val Thr
145                 150                 155                 160

Val His His Leu Pro Lys Pro Ile Pro Asp Gly Asp Pro Asn His Lys
                165                 170                 175

Ser Lys Ile Ile Phe Val Pro Asp Cys Glu Asp Ser Lys Met Lys Met
            180                 185                 190

Thr Thr Ser Cys Val Ser Ser Gly Ser Leu Trp Asp Pro Asn Ile Thr
        195                 200                 205

Val Glu Thr Leu Glu Ala His Gln Leu Arg Val Ser Phe Thr Leu Trp
    210                 215                 220

Asn Glu Ser Thr His Tyr Gln Ile Leu Leu Thr Ser Phe Pro His Met
225                 230                 235                 240

Glu Asn His Ser Cys Phe Glu His Met His His Ile Pro Ala Pro Arg
                245                 250                 255

Pro Glu Glu Phe His Gln Arg Ser Asn Val Thr Leu Thr Leu Arg Asn
            260                 265                 270

Leu Lys Gly Cys Cys Arg His Gln Val Gln Ile Gln Pro Phe Phe Ser
        275                 280                 285

Ser Cys Leu Asn Asp Cys Leu Arg His Ser Ala Thr Val Ser Cys Pro
    290                 295                 300

Glu Met Pro Asp Thr Pro Glu Pro Ile Pro Asp Tyr Met Pro Leu Trp
305                 310                 315                 320

Glu Pro Arg Ser Gly Ser Ser Asp Tyr Lys Asp Asp Asp Asp Lys Gly
                325                 330                 335

Ser Ser His His His His His His
            340

<210> SEQ ID NO 437
<211> LENGTH: 344
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 437

Met Gly Ala Ala Arg Ser Pro Pro Ser Ala Val Pro Gly Pro Leu Leu
1               5                   10                  15

Gly Leu Leu Leu Leu Leu Leu Gly Val Leu Ala Pro Gly Gly Ala Ser
                20                  25                  30

Leu Arg Leu Leu Asp His Arg Ala Leu Val Cys Ser Gln Pro Gly Leu
            35                  40                  45

Asn Cys Thr Val Lys Asn Ser Thr Cys Leu Asp Asp Ser Trp Ile His
        50                  55                  60

Pro Arg Asn Leu Thr Pro Ser Ser Pro Lys Asp Leu Gln Ile Gln Leu
65                  70                  75                  80

His Phe Ala His Thr Gln Gln Gly Asp Leu Phe Pro Val Ala His Ile
                85                  90                  95

Glu Trp Thr Leu Gln Thr Asp Ala Ser Ile Leu Tyr Leu Glu Gly Ala
            100                 105                 110

Glu Leu Ser Val Leu Gln Leu Asn Thr Asn Glu Arg Leu Cys Val Arg
        115                 120                 125

Phe Glu Phe Leu Ser Lys Leu Arg His His His Arg Arg Trp Arg Phe
```

```
            130                 135                 140
Thr Phe Ser His Phe Val Val Asp Pro Asp Gln Glu Tyr Glu Val Thr
145                 150                 155                 160

Val His His Leu Pro Lys Pro Ile Pro Asp Gly Asp Pro Asn His Gln
                165                 170                 175

Ser Lys Asn Phe Leu Val Pro Asp Cys Glu His Ala Arg Met Lys Val
                180                 185                 190

Thr Thr Pro Cys Met Ser Ser Gly Ser Leu Trp Asp Pro Asn Ile Thr
                195                 200                 205

Val Glu Thr Leu Asp Thr Gln His Leu Arg Val Asp Phe Thr Leu Trp
210                 215                 220

Asn Glu Ser Thr His Tyr Gln Ile Leu Leu Thr Ser Phe Pro His Met
225                 230                 235                 240

Glu Asn His Ser Cys Phe Glu His Met His His Ile Pro Ala Pro Arg
                245                 250                 255

Pro Glu Glu Phe His Gln Arg Ser Asn Val Thr Leu Thr Leu Arg Asn
                260                 265                 270

Leu Lys Gly Cys Cys Arg His Gln Val Gln Ile Gln Pro Phe Phe Ser
                275                 280                 285

Ser Cys Leu Asn Asp Cys Leu Arg His Ser Ala Thr Val Ser Cys Pro
                290                 295                 300

Glu Met Pro Asp Thr Pro Glu Pro Ile Pro Asp Tyr Met Pro Leu Trp
305                 310                 315                 320

Glu Pro Arg Ser Gly Ser Ser Asp Tyr Lys Asp Asp Asp Lys Gly
                325                 330                 335

Ser Ser His His His His His His
                340

<210> SEQ ID NO 438
<211> LENGTH: 346
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 438

Met Gly Ala Ala Arg Ser Pro Pro Ser Ala Val Pro Gly Pro Leu Leu
1               5                   10                  15

Gly Leu Leu Leu Leu Leu Leu Gly Val Leu Ala Pro Gly Gly Ala Ser
                20                  25                  30

Leu Arg Leu Leu Asp His Arg Ala Leu Val Cys Ser Gln Pro Gly Leu
                35                  40                  45

Asn Cys Thr Val Lys Asn Ser Thr Cys Leu Asp Asp Ser Trp Ile His
                50                  55                  60

Pro Arg Asn Leu Thr Pro Ser Ser Pro Lys Asp Leu Gln Ile Gln Leu
65                  70                  75                  80

His Phe Ala His Thr Gln Gln Gly Asp Leu Phe Pro Val Ala His Ile
                85                  90                  95

Glu Trp Thr Leu Gln Thr Asp Ala Ser Ile Leu Tyr Leu Glu Gly Ala
                100                 105                 110

Glu Leu Ser Val Leu Gln Leu Asn Thr Asn Glu Arg Leu Cys Val Arg
                115                 120                 125

Phe Glu Phe Leu Ser Lys Leu Arg His His His Arg Arg Trp Arg Phe
                130                 135                 140
```

Thr Phe Ser His Phe Val Val Asp Pro Asp Gln Glu Tyr Glu Val Thr
145                 150                 155                 160

Val His His Leu Pro Lys Pro Ile Pro Asp Gly Asp Pro Asn His Gln
            165                 170                 175

Ser Lys Asn Phe Leu Val Pro Asp Cys Glu His Ala Arg Met Lys Val
            180                 185                 190

Thr Thr Pro Cys Met Ser Ser Gly Ser Leu Trp Asp Pro Asn Ile Thr
        195                 200                 205

Val Glu Thr Leu Glu Ala His Gln Leu Arg Val Ser Phe Thr Leu Trp
    210                 215                 220

Asn Glu Ser Thr Pro Tyr Gln Val Leu Leu Glu Ser Phe Ser Asp Ser
225                 230                 235                 240

Glu Asn His Ser Cys Phe Asp Val Val Lys Gln Ile Phe Ala Pro Arg
                245                 250                 255

Gln Glu Glu Phe His Gln Arg Ala Asn Val Thr Phe Thr Leu Ser Lys
            260                 265                 270

Phe His Trp Cys Cys His His Val Gln Val Gln Pro Phe Phe Ser
        275                 280                 285

Ser Cys Leu Asn Asp Cys Leu Arg His Ala Val Thr Val Pro Cys Pro
        290                 295                 300

Val Ile Ser Asn Thr Thr Val Pro Lys Pro Val Ala Asp Tyr Ile Pro
305                 310                 315                 320

Leu Trp Glu Pro Arg Ser Gly Ser Ser Asp Tyr Lys Asp Asp Asp Asp
                325                 330                 335

Lys Gly Ser Ser His His His His His His
            340                 345

<210> SEQ ID NO 439
<211> LENGTH: 344
<212> TYPE: PRT
<213> ORGANISM: Artificial Sequence
<220> FEATURE:
<223> OTHER INFORMATION: Description of Artificial Sequence: Synthetic
    construct

<400> SEQUENCE: 439

Met Gly Ala Ala Arg Ser Pro Pro Ser Ala Val Pro Gly Pro Leu Leu
1               5                   10                  15

Gly Leu Leu Leu Leu Leu Leu Gly Val Leu Ala Pro Gly Gly Ala Ser
            20                  25                  30

Leu Arg Leu Leu Asp Phe Pro Ala Pro Val Cys Ala Gln Glu Gly Leu
        35                  40                  45

Ser Cys Arg Val Lys Asn Ser Thr Cys Leu Asp Asp Ser Trp Ile His
    50                  55                  60

Pro Arg Asn Leu Thr Pro Ser Ser Pro Lys Asp Leu Gln Ile Gln Leu
65                  70                  75                  80

His Phe Ala His Thr Gln Gln Gly Asp Leu Phe Pro Val Ala His Ile
                85                  90                  95

Glu Trp Thr Leu Gln Thr Asp Ala Ser Ile Leu Tyr Leu Glu Gly Ala
            100                 105                 110

Glu Leu Ser Val Leu Gln Leu Asn Thr Asn Glu Arg Leu Cys Val Arg
        115                 120                 125

Phe Glu Phe Leu Ser Lys Leu Arg His His Arg Arg Trp Arg Phe
    130                 135                 140

Thr Phe Ser His Phe Val Val Asp Pro Asp Gln Glu Tyr Glu Val Thr
145                 150                 155                 160

```
Val His His Leu Pro Lys Pro Ile Pro Asp Gly Asp Pro Asn His Gln
                165                 170                 175

Ser Lys Asn Phe Leu Val Pro Asp Cys Glu His Ala Arg Met Lys Val
            180                 185                 190

Thr Thr Pro Cys Met Ser Ser Gly Ser Leu Trp Asp Pro Asn Ile Thr
        195                 200                 205

Val Glu Thr Leu Asp Thr Gln His Leu Arg Val Asp Phe Thr Leu Trp
    210                 215                 220

Asn Glu Ser Thr His Tyr Gln Ile Leu Leu Thr Ser Phe Pro His Met
225                 230                 235                 240

Glu Asn His Ser Cys Phe Glu His Met His His Ile Pro Ala Pro Arg
                245                 250                 255

Pro Glu Glu Phe His Gln Arg Ser Asn Val Thr Leu Thr Leu Arg Asn
            260                 265                 270

Leu Lys Gly Cys Cys Arg His Gln Val Gln Ile Gln Pro Phe Phe Ser
        275                 280                 285

Ser Cys Leu Asn Asp Cys Leu Arg His Ser Ala Thr Val Ser Cys Pro
    290                 295                 300

Glu Met Pro Asp Thr Pro Glu Pro Ile Pro Asp Tyr Met Pro Leu Trp
305                 310                 315                 320

Glu Pro Arg Ser Gly Ser Ser Asp Tyr Lys Asp Asp Asp Lys Gly
                325                 330                 335

Ser Ser His His His His His His
            340
```

<210> SEQ ID NO 440
<211> LENGTH: 344
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 440

```
Met Gly Ala Ala Arg Ser Pro Pro Ser Ala Val Pro Gly Pro Leu Leu
1               5                   10                  15

Gly Leu Leu Leu Leu Leu Leu Gly Val Leu Ala Pro Gly Gly Ala Ser
            20                  25                  30

Leu Arg Leu Leu Asp His Arg Ala Leu Val Cys Ser Gln Pro Gly Leu
        35                  40                  45

Asn Cys Thr Val Lys Asn Ser Thr Cys Leu Asp Asp Ser Trp Ile His
    50                  55                  60

Pro Arg Asn Leu Thr Pro Ser Ser Pro Lys Asn Ile Tyr Ile Asn Leu
65                  70                  75                  80

Ser Val Ser Ser Thr Gln His Gly Glu Leu Val Pro Val Leu His Val
                85                  90                  95

Glu Trp Thr Leu Gln Thr Asp Ala Ser Ile Leu Tyr Leu Glu Gly Ala
            100                 105                 110

Glu Leu Ser Val Leu Gln Leu Asn Thr Asn Glu Arg Leu Cys Val Arg
        115                 120                 125

Phe Glu Phe Leu Ser Lys Leu Arg His His Arg Arg Trp Arg Phe
    130                 135                 140

Thr Phe Ser His Phe Val Val Asp Pro Asp Gln Glu Tyr Glu Val Thr
145                 150                 155                 160

Val His His Leu Pro Lys Pro Ile Pro Asp Gly Asp Pro Asn His Gln
```

```
                    165                 170                 175

Ser Lys Asn Phe Leu Val Pro Asp Cys Glu His Ala Arg Met Lys Val
            180                 185                 190

Thr Thr Pro Cys Met Ser Ser Gly Ser Leu Trp Asp Pro Asn Ile Thr
        195                 200                 205

Val Glu Thr Leu Asp Thr Gln His Leu Arg Val Asp Phe Thr Leu Trp
    210                 215                 220

Asn Glu Ser Thr His Tyr Gln Ile Leu Leu Thr Ser Phe Pro His Met
225                 230                 235                 240

Glu Asn His Ser Cys Phe Glu His Met His His Ile Pro Ala Pro Arg
                245                 250                 255

Pro Glu Glu Phe His Gln Arg Ser Asn Val Thr Leu Thr Leu Arg Asn
            260                 265                 270

Leu Lys Gly Cys Cys Arg His Gln Val Gln Ile Gln Pro Phe Phe Ser
        275                 280                 285

Ser Cys Leu Asn Asp Cys Leu Arg His Ser Ala Thr Val Ser Cys Pro
    290                 295                 300

Glu Met Pro Asp Thr Pro Glu Pro Ile Pro Asp Tyr Met Pro Leu Trp
305                 310                 315                 320

Glu Pro Arg Ser Gly Ser Ser Asp Tyr Lys Asp Asp Asp Asp Lys Gly
                325                 330                 335

Ser Ser His His His His His His
            340

<210> SEQ ID NO 441
<211> LENGTH: 344
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 441

Met Gly Ala Ala Arg Ser Pro Pro Ser Ala Val Pro Gly Pro Leu Leu
1               5                   10                  15

Gly Leu Leu Leu Leu Leu Leu Gly Val Leu Ala Pro Gly Gly Ala Ser
            20                  25                  30

Leu Arg Leu Leu Asp His Arg Ala Leu Val Cys Ser Gln Pro Gly Leu
        35                  40                  45

Asn Cys Thr Val Lys Asn Ser Thr Cys Leu Asp Asp Ser Trp Ile His
    50                  55                  60

Pro Arg Asn Leu Thr Pro Ser Ser Pro Lys Asp Leu Gln Ile Gln Leu
65                  70                  75                  80

His Phe Ala His Thr Gln Gln Gly Asp Leu Phe Pro Val Ala His Ile
                85                  90                  95

Glu Trp Thr Leu Gln Thr Asp Ala Ser Ile Leu Tyr Leu Glu Gly Ala
            100                 105                 110

Glu Leu Ser Val Leu Gln Leu Asn Thr Asn Glu Arg Leu Cys Val Lys
        115                 120                 125

Phe Gln Phe Leu Ser Met Leu Gln His His Arg Lys Arg Trp Arg Phe
    130                 135                 140

Ser Phe Ser His Phe Val Val Asp Pro Gly Gln Glu Tyr Glu Val Thr
145                 150                 155                 160

Val His His Leu Pro Lys Pro Ile Pro Asp Gly Asp Pro Asn His Gln
                165                 170                 175
```

```
Ser Lys Asn Phe Leu Val Pro Asp Cys Glu His Ala Arg Met Lys Val
            180                 185                 190

Thr Thr Pro Cys Met Ser Ser Gly Ser Leu Trp Asp Pro Asn Ile Thr
        195                 200                 205

Val Glu Thr Leu Asp Thr Gln His Leu Arg Val Asp Phe Thr Leu Trp
    210                 215                 220

Asn Glu Ser Thr His Tyr Gln Ile Leu Leu Thr Ser Phe Pro His Met
225                 230                 235                 240

Glu Asn His Ser Cys Phe Glu His Met His His Ile Pro Ala Pro Arg
                245                 250                 255

Pro Glu Glu Phe His Gln Arg Ser Asn Val Thr Leu Thr Leu Arg Asn
            260                 265                 270

Leu Lys Gly Cys Cys Arg His Gln Val Gln Ile Gln Pro Phe Phe Ser
        275                 280                 285

Ser Cys Leu Asn Asp Cys Leu Arg His Ser Ala Thr Val Ser Cys Pro
    290                 295                 300

Glu Met Pro Asp Thr Pro Glu Pro Ile Pro Asp Tyr Met Pro Leu Trp
305                 310                 315                 320

Glu Pro Arg Ser Gly Ser Ser Asp Tyr Lys Asp Asp Asp Lys Gly
                325                 330                 335

Ser Ser His His His His His His
            340
```

<210> SEQ ID NO 442
<211> LENGTH: 344
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 442

```
Met Gly Ala Ala Arg Ser Pro Pro Ser Ala Val Pro Gly Pro Leu Leu
1               5                   10                  15

Gly Leu Leu Leu Leu Leu Leu Gly Val Leu Ala Pro Gly Gly Ala Ser
            20                  25                  30

Leu Arg Leu Leu Asp His Arg Ala Leu Val Cys Ser Gln Pro Gly Leu
        35                  40                  45

Asn Cys Thr Val Lys Asn Ser Thr Cys Leu Asp Asp Ser Trp Ile His
    50                  55                  60

Pro Arg Asn Leu Thr Pro Ser Ser Pro Lys Asp Leu Gln Ile Gln Leu
65                  70                  75                  80

His Phe Ala His Thr Gln Gln Gly Asp Leu Phe Pro Val Ala His Ile
                85                  90                  95

Glu Trp Thr Leu Gln Thr Asp Ala Ser Ile Leu Tyr Leu Glu Gly Ala
            100                 105                 110

Glu Leu Ser Val Leu Gln Leu Asn Thr Asn Glu Arg Leu Cys Val Arg
        115                 120                 125

Phe Glu Phe Leu Ser Lys Leu Arg His His His Arg Arg Trp Arg Phe
    130                 135                 140

Thr Phe Ser His Phe Val Val Asp Pro Asp Gln Glu Tyr Glu Val Thr
145                 150                 155                 160

Val His His Leu Pro Lys Pro Ile Pro Asp Gly Asp Pro Asn His Lys
                165                 170                 175

Ser Lys Ile Ile Phe Val Pro Asp Cys Glu Asp Ser Lys Met Lys Met
            180                 185                 190
```

```
Thr Thr Ser Cys Val Ser Ser Gly Ser Leu Trp Asp Pro Asn Ile Thr
            195                 200                 205

Val Glu Thr Leu Asp Thr Gln His Leu Arg Val Asp Phe Thr Leu Trp
        210                 215                 220

Asn Glu Ser Thr His Tyr Gln Ile Leu Leu Thr Ser Phe Pro His Met
225                 230                 235                 240

Glu Asn His Ser Cys Phe Glu His Met His His Ile Pro Ala Pro Arg
                245                 250                 255

Pro Glu Glu Phe His Gln Arg Ser Asn Val Thr Leu Thr Leu Arg Asn
            260                 265                 270

Leu Lys Gly Cys Cys Arg His Gln Val Gln Ile Gln Pro Phe Phe Ser
        275                 280                 285

Ser Cys Leu Asn Asp Cys Leu Arg His Ser Ala Thr Val Ser Cys Pro
    290                 295                 300

Glu Met Pro Asp Thr Pro Glu Pro Ile Pro Asp Tyr Met Pro Leu Trp
305                 310                 315                 320

Glu Pro Arg Ser Gly Ser Ser Asp Tyr Lys Asp Asp Asp Asp Lys Gly
                325                 330                 335

Ser Ser His His His His His His
            340

<210> SEQ ID NO 443
<211> LENGTH: 346
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 443

Met Gly Ala Ala Arg Ser Pro Pro Ser Ala Val Pro Gly Pro Leu Leu
1               5                   10                  15

Gly Leu Leu Leu Leu Leu Leu Gly Val Leu Ala Pro Gly Gly Ala Ser
            20                  25                  30

Leu Arg Leu Leu Asp Phe Pro Ala Pro Val Cys Ala Gln Glu Gly Leu
        35                  40                  45

Ser Cys Arg Val Lys Asn Ser Thr Cys Leu Asp Asp Ser Trp Ile His
    50                  55                  60

Pro Arg Asn Leu Thr Pro Ser Ser Pro Lys Asp Leu Gln Ile Gln Leu
65                  70                  75                  80

His Phe Ala His Thr Gln Gln Gly Asp Leu Phe Pro Val Ala His Ile
                85                  90                  95

Glu Trp Thr Leu Gln Thr Asp Ala Ser Ile Leu Tyr Leu Glu Gly Ala
            100                 105                 110

Glu Leu Ser Val Leu Gln Leu Asn Thr Asn Glu Arg Leu Cys Val Arg
        115                 120                 125

Phe Glu Phe Leu Ser Lys Leu Arg His His Arg Arg Trp Arg Phe
    130                 135                 140

Thr Phe Ser His Phe Val Asp Pro Asp Gln Glu Tyr Glu Val Thr
145                 150                 155                 160

Val His His Leu Pro Lys Pro Ile Pro Asp Gly Asp Pro Asn His Gln
                165                 170                 175

Ser Lys Asn Phe Leu Val Pro Asp Cys Glu His Ala Arg Met Lys Val
            180                 185                 190

Thr Thr Pro Cys Met Ser Ser Gly Ser Leu Trp Asp Pro Asn Ile Thr
```

-continued

```
                195                 200                 205
Val Glu Thr Leu Glu Ala His Gln Leu Arg Val Ser Phe Thr Leu Trp
    210                 215                 220

Asn Glu Ser Thr Pro Tyr Gln Val Leu Glu Ser Phe Ser Asp Ser
225                 230                 235                 240

Glu Asn His Ser Cys Phe Asp Val Val Lys Gln Ile Phe Ala Pro Arg
                245                 250                 255

Gln Glu Glu Phe His Gln Arg Ala Asn Val Thr Phe Thr Leu Ser Lys
                260                 265                 270

Phe His Trp Cys Cys His His Val Gln Val Gln Pro Phe Phe Ser
            275                 280                 285

Ser Cys Leu Asn Asp Cys Leu Arg His Ala Val Thr Val Pro Cys Pro
    290                 295                 300

Val Ile Ser Asn Thr Thr Val Pro Lys Pro Val Ala Asp Tyr Ile Pro
305                 310                 315                 320

Leu Trp Glu Pro Arg Ser Gly Ser Ser Asp Tyr Lys Asp Asp Asp
                325                 330                 335

Lys Gly Ser Ser His His His His His His
                340                 345

<210> SEQ ID NO 444
<211> LENGTH: 346
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 444

Met Gly Ala Ala Arg Ser Pro Pro Ser Ala Val Pro Gly Pro Leu Leu
1               5                   10                  15

Gly Leu Leu Leu Leu Leu Leu Gly Val Leu Ala Pro Gly Gly Ala Ser
                20                  25                  30

Leu Arg Leu Leu Asp His Arg Ala Leu Val Cys Ser Gln Pro Gly Leu
            35                  40                  45

Asn Cys Thr Val Lys Asn Ser Thr Cys Leu Asp Asp Ser Trp Ile His
    50                  55                  60

Pro Arg Asn Leu Thr Pro Ser Ser Pro Lys Asn Ile Tyr Ile Asn Leu
65                  70                  75                  80

Ser Val Ser Ser Thr Gln His Gly Glu Leu Val Pro Val Leu His Val
                85                  90                  95

Glu Trp Thr Leu Gln Thr Asp Ala Ser Ile Leu Tyr Leu Glu Gly Ala
                100                 105                 110

Glu Leu Ser Val Leu Gln Leu Asn Thr Asn Glu Arg Leu Cys Val Arg
            115                 120                 125

Phe Glu Phe Leu Ser Lys Leu Arg His His Arg Arg Trp Arg Phe
        130                 135                 140

Thr Phe Ser His Phe Val Val Asp Pro Asp Gln Glu Tyr Glu Val Thr
145                 150                 155                 160

Val His His Leu Pro Lys Pro Ile Pro Asp Gly Asp Pro Asn His Gln
                165                 170                 175

Ser Lys Asn Phe Leu Val Pro Asp Cys Glu His Ala Arg Met Lys Val
            180                 185                 190

Thr Thr Pro Cys Met Ser Ser Gly Ser Leu Trp Asp Pro Asn Ile Thr
        195                 200                 205
```

```
Val Glu Thr Leu Glu Ala His Gln Leu Arg Val Ser Phe Thr Leu Trp
    210                 215                 220

Asn Glu Ser Thr Pro Tyr Gln Val Leu Leu Glu Ser Phe Ser Asp Ser
225                 230                 235                 240

Glu Asn His Ser Cys Phe Asp Val Val Lys Gln Ile Phe Ala Pro Arg
                245                 250                 255

Gln Glu Glu Phe His Gln Arg Ala Asn Val Thr Phe Thr Leu Ser Lys
            260                 265                 270

Phe His Trp Cys Cys His His Val Gln Val Gln Pro Phe Phe Ser
        275                 280                 285

Ser Cys Leu Asn Asp Cys Leu Arg His Ala Val Thr Val Pro Cys Pro
    290                 295                 300

Val Ile Ser Asn Thr Thr Val Pro Lys Pro Val Ala Asp Tyr Ile Pro
305                 310                 315                 320

Leu Trp Glu Pro Arg Ser Gly Ser Ser Asp Tyr Lys Asp Asp Asp Asp
                325                 330                 335

Lys Gly Ser Ser His His His His His His
            340                 345

<210> SEQ ID NO 445
<211> LENGTH: 346
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 445

Met Gly Ala Ala Arg Ser Pro Pro Ser Ala Val Pro Gly Pro Leu Leu
1               5                   10                  15

Gly Leu Leu Leu Leu Leu Leu Gly Val Leu Ala Pro Gly Gly Ala Ser
                20                  25                  30

Leu Arg Leu Leu Asp His Arg Ala Leu Val Cys Ser Gln Pro Gly Leu
            35                  40                  45

Asn Cys Thr Val Lys Asn Ser Thr Cys Leu Asp Asp Ser Trp Ile His
        50                  55                  60

Pro Arg Asn Leu Thr Pro Ser Ser Pro Lys Asp Leu Gln Ile Gln Leu
65                  70                  75                  80

His Phe Ala His Thr Gln Gln Gly Asp Leu Phe Pro Val Ala His Ile
                85                  90                  95

Glu Trp Thr Leu Gln Thr Asp Ala Ser Ile Leu Tyr Leu Glu Gly Ala
                100                 105                 110

Glu Leu Ser Val Leu Gln Leu Asn Thr Asn Glu Arg Leu Cys Val Lys
            115                 120                 125

Phe Gln Phe Leu Ser Met Leu Gln His His Arg Lys Arg Trp Arg Phe
        130                 135                 140

Ser Phe Ser His Phe Val Asp Pro Gly Gln Glu Tyr Glu Val Thr
145                 150                 155                 160

Val His His Leu Pro Lys Pro Ile Pro Asp Gly Asp Pro Asn His Gln
                165                 170                 175

Ser Lys Asn Phe Leu Val Pro Asp Cys Glu His Ala Arg Met Lys Val
            180                 185                 190

Thr Thr Pro Cys Met Ser Ser Gly Ser Leu Trp Asp Pro Asn Ile Thr
        195                 200                 205

Val Glu Thr Leu Glu Ala His Gln Leu Arg Val Ser Phe Thr Leu Trp
    210                 215                 220
```

Asn Glu Ser Thr Pro Tyr Gln Val Leu Leu Glu Ser Phe Ser Asp Ser
225                 230                 235                 240

Glu Asn His Ser Cys Phe Asp Val Val Lys Gln Ile Phe Ala Pro Arg
            245                 250                 255

Gln Glu Glu Phe His Gln Arg Ala Asn Val Thr Phe Thr Leu Ser Lys
                260                 265                 270

Phe His Trp Cys Cys His His Val Gln Val Gln Pro Phe Phe Ser
            275                 280                 285

Ser Cys Leu Asn Asp Cys Leu Arg His Ala Val Thr Val Pro Cys Pro
        290                 295                 300

Val Ile Ser Asn Thr Thr Val Pro Lys Pro Val Ala Asp Tyr Ile Pro
305                 310                 315                 320

Leu Trp Glu Pro Arg Ser Gly Ser Ser Asp Tyr Lys Asp Asp Asp Asp
                325                 330                 335

Lys Gly Ser Ser His His His His His His
            340                 345

<210> SEQ ID NO 446
<211> LENGTH: 346
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 446

Met Gly Ala Ala Arg Ser Pro Pro Ser Ala Val Pro Gly Pro Leu Leu
1               5                   10                  15

Gly Leu Leu Leu Leu Leu Leu Gly Val Leu Ala Pro Gly Gly Ala Ser
            20                  25                  30

Leu Arg Leu Leu Asp His Arg Ala Leu Val Cys Ser Gln Pro Gly Leu
        35                  40                  45

Asn Cys Thr Val Lys Asn Ser Thr Cys Leu Asp Asp Ser Trp Ile His
    50                  55                  60

Pro Arg Asn Leu Thr Pro Ser Ser Pro Lys Asp Leu Gln Ile Gln Leu
65                  70                  75                  80

His Phe Ala His Thr Gln Gln Gly Asp Leu Phe Pro Val Ala His Ile
                85                  90                  95

Glu Trp Thr Leu Gln Thr Asp Ala Ser Ile Leu Tyr Leu Glu Gly Ala
            100                 105                 110

Glu Leu Ser Val Leu Gln Leu Asn Thr Asn Glu Arg Leu Cys Val Arg
        115                 120                 125

Phe Glu Phe Leu Ser Lys Leu Arg His His Arg Arg Trp Arg Phe
    130                 135                 140

Thr Phe Ser His Phe Val Val Asp Pro Asp Gln Glu Tyr Glu Val Thr
145                 150                 155                 160

Val His His Leu Pro Lys Pro Ile Pro Asp Gly Asp Pro Asn His Lys
                165                 170                 175

Ser Lys Ile Ile Phe Val Pro Asp Cys Glu Asp Ser Lys Met Lys Met
            180                 185                 190

Thr Thr Ser Cys Val Ser Ser Gly Ser Leu Trp Asp Pro Asn Ile Thr
        195                 200                 205

Val Glu Thr Leu Glu Ala His Gln Leu Arg Val Ser Phe Thr Leu Trp
    210                 215                 220

Asn Glu Ser Thr Pro Tyr Gln Val Leu Leu Glu Ser Phe Ser Asp Ser

```
                225                 230                 235                 240
Glu Asn His Ser Cys Phe Asp Val Val Lys Gln Ile Phe Ala Pro Arg
                245                 250                 255

Gln Glu Glu Phe His Gln Arg Ala Asn Val Thr Phe Thr Leu Ser Lys
                260                 265                 270

Phe His Trp Cys Cys His His His Val Gln Val Gln Pro Phe Phe Ser
                275                 280                 285

Ser Cys Leu Asn Asp Cys Leu Arg His Ala Val Thr Val Pro Cys Pro
    290                 295                 300

Val Ile Ser Asn Thr Thr Val Pro Lys Pro Val Ala Asp Tyr Ile Pro
305                 310                 315                 320

Leu Trp Glu Pro Arg Ser Gly Ser Ser Asp Tyr Lys Asp Asp Asp Asp
                325                 330                 335

Lys Gly Ser Ser His His His His His His
                340                 345

<210> SEQ ID NO 447
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 447

Asp Tyr Lys Asp Asp Asp Asp Lys
1               5

<210> SEQ ID NO 448
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 448

Gly Gly Gly Ala Ala Ala Gly Gly Gly Ala Ala Ala
1               5                   10

<210> SEQ ID NO 449
<211> LENGTH: 88
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 449

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
                20                  25                  30

Leu Ala Trp Tyr Gln Gln Lys Pro Gly Gln Ala Pro Arg Leu Leu Ile
            35                  40                  45

Tyr Asp Ala Ser Thr Arg Ala Thr Gly Ile Pro Ala Arg Phe Ser Gly
        50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys
                85
```

<210> SEQ ID NO 450
<211> LENGTH: 88
<212> TYPE: PRT
<213> ORGANISM: Artificial Sequence
<220> FEATURE:
<223> OTHER INFORMATION: Description of Artificial Sequence: Synthetic construct

<400> SEQUENCE: 450

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Asp Ala Ser Thr Arg Ala Thr Gly Ile Pro Ala Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys
                85

<210> SEQ ID NO 451
<211> LENGTH: 88
<212> TYPE: PRT
<213> ORGANISM: Artificial Sequence
<220> FEATURE:
<223> OTHER INFORMATION: Description of Artificial Sequence: Synthetic construct

<400> SEQUENCE: 451

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Asp Ala Ser Thr Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys
                85

<210> SEQ ID NO 452
<211> LENGTH: 88
<212> TYPE: PRT
<213> ORGANISM: Artificial Sequence
<220> FEATURE:
<223> OTHER INFORMATION: Description of Artificial Sequence: Synthetic construct

<400> SEQUENCE: 452

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

```
Tyr Asp Ala Ser Thr Arg Ala Thr Gly Ile Pro Ala Arg Phe Ser Gly
         50                  55                  60

Ser Gly Pro Gly Thr Asp Phe Thr Leu Thr Ile Ser Ser Leu Glu Pro
 65              70                  75                  80

Glu Asp Phe Ala Val Tyr Tyr Cys
                 85

<210> SEQ ID NO 453
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Variable amino acid

<400> SEQUENCE: 453

Xaa Tyr Gly Ile Ser
 1               5

<210> SEQ ID NO 454
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Variable amino acid
<220> FEATURE:
<221> NAME/KEY: MOD_RES
<222> LOCATION: (3)..(3)
<223> OTHER INFORMATION: Variable amino acid
<220> FEATURE:
<221> NAME/KEY: MOD_RES
<222> LOCATION: (5)..(5)
<223> OTHER INFORMATION: Variable amino acid

<400> SEQUENCE: 454

Xaa Tyr Xaa Met Xaa
 1               5

<210> SEQ ID NO 455
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Variable amino acid

<400> SEQUENCE: 455

Ser Tyr Gly Met Xaa
 1               5

<210> SEQ ID NO 456
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (4)..(4)
<223> OTHER INFORMATION: Variable amino acid
<220> FEATURE:
<221> NAME/KEY: MOD_RES
<222> LOCATION: (6)..(6)
<223> OTHER INFORMATION: Variable amino acid
<220> FEATURE:
<221> NAME/KEY: MOD_RES
<222> LOCATION: (10)..(10)
<223> OTHER INFORMATION: Variable amino acid
<220> FEATURE:
<221> NAME/KEY: MOD_RES
<222> LOCATION: (14)..(15)
<223> OTHER INFORMATION: Variable amino acid

<400> SEQUENCE: 456

Trp Ile Ser Xaa Tyr Xaa Gly Asn Thr Xaa Tyr Ala Gln Xaa Xaa Gln
1               5                   10                  15

Gly

<210> SEQ ID NO 457
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: Variable amino acid
<220> FEATURE:
<221> NAME/KEY: MOD_RES
<222> LOCATION: (4)..(6)
<223> OTHER INFORMATION: Variable amino acid
<220> FEATURE:
<221> NAME/KEY: MOD_RES
<222> LOCATION: (8)..(8)
<223> OTHER INFORMATION: Variable amino acid
<220> FEATURE:
<221> NAME/KEY: MOD_RES
<222> LOCATION: (10)..(10)
<223> OTHER INFORMATION: Variable amino acid

<400> SEQUENCE: 457

Xaa Xaa Ser Xaa Xaa Xaa Ser Xaa Ile Xaa Tyr Ala Asp Ser Val Lys
1               5                   10                  15

Gly

<210> SEQ ID NO 458
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(8)
<223> OTHER INFORMATION: Variable amino acid
<220> FEATURE:
<221> NAME/KEY: MOD_RES
<222> LOCATION: (10)..(10)
<223> OTHER INFORMATION: Variable amino acid

<400> SEQUENCE: 458

Val Ile Trp Tyr Asp Gly Xaa Xaa Lys Xaa Tyr Ala Asp Ser Val Lys
1               5                   10                  15

Gly
```

```
<210> SEQ ID NO 459
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Variable amino acid
<220> FEATURE:
<221> NAME/KEY: MOD_RES
<222> LOCATION: (4)..(5)
<223> OTHER INFORMATION: Variable amino acid

<400> SEQUENCE: 459

Xaa Gln Leu Xaa Xaa Asp Tyr
1               5

<210> SEQ ID NO 460
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Variable amino acid
<220> FEATURE:
<221> NAME/KEY: MOD_RES
<222> LOCATION: (4)..(4)
<223> OTHER INFORMATION: Variable amino acid

<400> SEQUENCE: 460

Xaa Gln Leu Xaa Phe Asp Tyr
1               5

<210> SEQ ID NO 461
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Variable amino acid
<220> FEATURE:
<221> NAME/KEY: MOD_RES
<222> LOCATION: (7)..(9)
<223> OTHER INFORMATION: Variable amino acid
<220> FEATURE:
<221> NAME/KEY: MOD_RES
<222> LOCATION: (11)..(11)
<223> OTHER INFORMATION: Variable amino acid

<400> SEQUENCE: 461

Arg Ala Ser Gln Xaa Ile Xaa Xaa Xaa Leu Xaa
1               5                   10

<210> SEQ ID NO 462
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (6)..(9)
<223> OTHER INFORMATION: Variable amino acid

<400> SEQUENCE: 462

Arg Ala Ser Gln Ser Xaa Xaa Xaa Xaa Leu Ala
1               5                   10

<210> SEQ ID NO 463
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(8)
<223> OTHER INFORMATION: Variable amino acid
<220> FEATURE:
<221> NAME/KEY: MOD_RES
<222> LOCATION: (11)..(11)
<223> OTHER INFORMATION: Variable amino acid

<400> SEQUENCE: 463

Arg Ala Ser Gln Ser Val Xaa Xaa Asn Leu Xaa
1               5                   10

<210> SEQ ID NO 464
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Variable amino acid

<400> SEQUENCE: 464

Ala Ala Ser Ser Xaa Gln Ser
1               5

<210> SEQ ID NO 465
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Variable amino acid

<400> SEQUENCE: 465

Ala Ala Ser Xaa Leu Gln Ser
1               5

<210> SEQ ID NO 466
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
```

```
<223> OTHER INFORMATION: Variable amino acid
<220> FEATURE:
<221> NAME/KEY: MOD_RES
<222> LOCATION: (7)..(7)
<223> OTHER INFORMATION: Variable amino acid

<400> SEQUENCE: 466

Xaa Xaa Ser Thr Arg Ala Xaa
1               5

<210> SEQ ID NO 467
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Variable amino acid
<220> FEATURE:
<221> NAME/KEY: MOD_RES
<222> LOCATION: (7)..(8)
<223> OTHER INFORMATION: Variable amino acid

<400> SEQUENCE: 467

Leu Gln His Xaa Ser Tyr Xaa Xaa Thr
1               5

<210> SEQ ID NO 468
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(6)
<223> OTHER INFORMATION: Variable amino acid
<220> FEATURE:
<221> NAME/KEY: MOD_RES
<222> LOCATION: (8)..(8)
<223> OTHER INFORMATION: Variable amino acid

<400> SEQUENCE: 468

Gln Xaa Xaa Xaa Xaa Xaa Pro Xaa Thr
1               5

<210> SEQ ID NO 469
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Variable amino acid

<400> SEQUENCE: 469

Gln Gln Tyr Asp Xaa Trp Pro Leu Thr
1               5

<210> SEQ ID NO 470
<211> LENGTH: 10
<212> TYPE: PRT
<213> ORGANISM: Artificial Sequence
<220> FEATURE:
```

```
-continued

<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Variable amino acid
<220> FEATURE:
<221> NAME/KEY: MOD_RES
<222> LOCATION: (4)..(5)
<223> OTHER INFORMATION: Variable amino acid
<220> FEATURE:
<221> NAME/KEY: MOD_RES
<222> LOCATION: (7)..(9)
<223> OTHER INFORMATION: Variable amino acid

<400> SEQUENCE: 470

Gln Xaa Tyr Xaa Xaa Trp Xaa Xaa Xaa Thr
1               5                   10
```